United States Patent
Gephart et al.

(10) Patent No.: US 12,232,782 B2
(45) Date of Patent: Feb. 25, 2025

(54) MINIMALLY INVASIVE SURGICAL SYSTEM

(71) Applicant: Xtant Medical Holdings, Inc., Belgrade, MT (US)

(72) Inventors: Matthew P. Gephart, Marquette, MI (US); Matthew N. Songer, Marquette, MI (US); Ernest N. Corrao, Bethel, CT (US); Phillip J. Berman, Jacksonville, FL (US)

(73) Assignee: Xtant Medical Holdings, Inc., Belgrade, MT (US)

( * ) Notice: Subject to any disclaimer, the term of this patent is extended or adjusted under 35 U.S.C. 154(b) by 0 days.

(21) Appl. No.: 17/397,199

(22) Filed: Aug. 9, 2021

(65) Prior Publication Data

US 2022/0071668 A1     Mar. 10, 2022

Related U.S. Application Data

(63) Continuation of application No. 16/229,719, filed on Dec. 21, 2018, now Pat. No. 11,116,553, which is a
(Continued)

(51) Int. Cl.
    *A61B 17/70*      (2006.01)
    *A61B 17/00*      (2006.01)
    (Continued)

(52) U.S. Cl.
    CPC .... *A61B 17/7083* (2013.01); *A61B 17/00234* (2013.01); *A61B 17/3421* (2013.01);
(Continued)

(58) Field of Classification Search
    CPC ............ A61B 17/7083; A61B 17/0024; A61B 17/3421; A61B 17/70; A61B 17/7002;
(Continued)

(56) References Cited

U.S. PATENT DOCUMENTS

| | | | |
|---|---|---|---|
| 3,844,291 A | 10/1974 | Moen | |
| 5,020,519 A | 6/1991 | Hayes | |

(Continued)

FOREIGN PATENT DOCUMENTS

| | | |
|---|---|---|
| EP | 1858422 | 11/2007 |
| WO | 2004017847 A2 | 3/2004 |

(Continued)

OTHER PUBLICATIONS

"Universal Spinal System (USS) Technique Guide", Synthes Spine, Jun. 1997.
(Continued)

*Primary Examiner* — Eduardo C Robert
*Assistant Examiner* — Tara Rose E Carter
(74) *Attorney, Agent, or Firm* — Sheridan Ross P.C.

(57) ABSTRACT

A multi-stage minimally invasive surgical procedure and associated instruments are disclosed. First, the surgical site is prepared. After preparation, the bone screws or anchors are attached to the bone. Subsequent to insertion of the screws, a rod or connecting member is positioned within the yoke portion of the bone screw. Caps are then placed in a pre-lock position within the yokes. The bone screws may be compressed together or distracted along the rod or connecting member, thereby setting the final spacing of the bones or bone segments. Finally the caps are moved to a final lock position to fix the screws to the rod or connecting member to maintain the bones in position relative to each other.

19 Claims, 141 Drawing Sheets

Related U.S. Application Data continuation of application No. 15/644,563, filed on Jul. 7, 2017, now Pat. No. 10,194,959, which is a continuation of application No. 14/713,962, filed on May 15, 2015, now Pat. No. 9,730,738, which is a continuation of application No. 14/144,020, filed on Dec. 30, 2013, now Pat. No. 9,033,988, which is a continuation of application No. 13/083,347, filed on Apr. 8, 2011, now Pat. No. 8,641,719, which is a continuation-in-part of application No. 12/438,538, filed as application No. PCT/US2007/076687 on Aug. 23, 2007, now Pat. No. 8,551,141, said application No. 13/083,347 is a continuation-in-part of application No. 11/844,265, filed on Aug. 23, 2007, now Pat. No. 7,922,727, which is a continuation of application No. PCT/US2006/006684, filed on Feb. 23, 2006.

(60) Provisional application No. 60/839,895, filed on Aug. 23, 2006, provisional application No. 60/722,604, filed on Sep. 29, 2005, provisional application No. 60/655,983, filed on Feb. 23, 2005.

(51) Int. Cl.
  *A61B 17/02* (2006.01)
  *A61B 17/34* (2006.01)
  *A61B 90/00* (2016.01)

(52) U.S. Cl.
  CPC .......... *A61B 17/70* (2013.01); *A61B 17/7002* (2013.01); *A61B 17/7011* (2013.01); *A61B 17/7013* (2013.01); *A61B 17/7032* (2013.01); *A61B 17/7035* (2013.01); *A61B 17/7037* (2013.01); *A61B 17/7043* (2013.01); *A61B 17/708* (2013.01); *A61B 17/7085* (2013.01); *A61B 17/7086* (2013.01); *A61B 17/7091* (2013.01); *A61B 2017/0256* (2013.01); *A61B 17/3472* (2013.01); *A61B 17/7004* (2013.01); *A61B 17/701* (2013.01); *A61B 2090/034* (2016.02)

(58) Field of Classification Search
  CPC ............ A61B 17/7011; A61B 17/7013; A61B 17/7032; A61B 17/7035; A61B 17/7037; A61B 17/7043; A61B 17/708; A61B 17/7085; A61B 17/7086; A61B 17/7091
  USPC ........................................ 606/250–279, 86 A
  See application file for complete search history.

(56) References Cited

U.S. PATENT DOCUMENTS

| | | |
|---|---|---|
| 5,092,866 A | 3/1992 | Breard |
| 5,171,279 A | 12/1992 | Mathews |
| 5,242,443 A | 9/1993 | Kambin |
| 5,258,005 A | 11/1993 | Christian |
| 5,480,440 A | 1/1996 | Kambin |
| 5,507,772 A | 4/1996 | Shutt |
| 5,584,887 A | 12/1996 | Kambin |
| 5,683,392 A | 11/1997 | Richelsoph |
| 5,720,751 A | 2/1998 | Jackson |
| 5,782,833 A | 7/1998 | Haider |
| 5,863,293 A | 1/1999 | Richelsoph |
| 5,941,885 A | 8/1999 | Jackson |
| 5,954,635 A | 9/1999 | Foley et al. |
| 5,964,760 A | 10/1999 | Richelsoph |
| 5,964,761 A | 10/1999 | Kambin |
| 6,010,503 A | 1/2000 | Richelsoph |
| 6,090,111 A | 7/2000 | Nichols |
| 6,096,044 A | 8/2000 | Boyd |
| 6,132,432 A | 10/2000 | Richelsoph |
| 6,174,311 B1 | 1/2001 | Branch |
| 6,226,548 B1 | 5/2001 | Foley |
| 6,287,313 B1 | 9/2001 | Sasso |
| 6,308,423 B1 | 10/2001 | Ono |
| 6,355,040 B1 | 3/2002 | Richelsoph |
| 6,440,133 B1 | 8/2002 | Beale |
| 6,485,491 B1 | 11/2002 | Farris |
| 6,485,591 B1 | 11/2002 | Nakao |
| 6,530,929 B1 | 3/2003 | Justis |
| 6,565,565 B1 | 5/2003 | Yuan |
| 6,648,888 B1 | 11/2003 | Shluzas |
| 6,660,006 B2 | 12/2003 | Markworth |
| 6,666,866 B2 | 12/2003 | Martz |
| 6,749,614 B2 | 6/2004 | Teitelbaum |
| 6,755,829 B1 | 6/2004 | Bono |
| 6,793,656 B1 | 9/2004 | Mathews |
| 6,875,212 B2 | 4/2005 | Shaolian |
| 6,951,538 B2 | 10/2005 | Ritland |
| 6,964,667 B2 | 11/2005 | Shaolian |
| 7,011,660 B2 | 3/2006 | Sherman |
| 7,081,117 B2 | 7/2006 | Bono |
| 7,083,621 B2 | 8/2006 | Shaolian |
| 7,090,674 B2 | 8/2006 | Doubler |
| 7,125,426 B2 | 10/2006 | Moumene |
| 7,141,051 B2 | 11/2006 | Janowski |
| 7,476,240 B2 * | 1/2009 | Raymond .......... A61B 17/7085 606/279 |
| 7,918,878 B2 | 4/2011 | Songer |
| 7,922,727 B2 | 4/2011 | Songer |
| 8,192,439 B2 | 6/2012 | Songer |
| 8,551,141 B2 | 10/2013 | Gephart |
| 8,641,719 B2 | 2/2014 | Gephart |
| 9,033,988 B2 | 5/2015 | Gephart et al. |
| 9,730,738 B2 | 8/2017 | Gephart |
| 10,194,959 B2 | 2/2019 | Gephart |
| 11,116,553 B2 | 9/2021 | Gephart |
| 2002/0120272 A1 | 8/2002 | Yuan |
| 2002/0161368 A1 | 10/2002 | Foley |
| 2003/0004519 A1 | 1/2003 | Torode |
| 2003/0060826 A1 | 3/2003 | Foley |
| 2003/0073998 A1 | 4/2003 | Pagliuca |
| 2003/0125742 A1 | 7/2003 | Yuan |
| 2003/0208203 A1 | 11/2003 | Lim |
| 2003/0225408 A1 | 12/2003 | Nichols |
| 2003/0229347 A1 | 12/2003 | Sherman |
| 2003/0236447 A1 | 12/2003 | Ritland |
| 2004/0039384 A1 | 2/2004 | Boehm |
| 2004/0059333 A1 | 3/2004 | Carl |
| 2004/0082960 A1 | 4/2004 | Davison |
| 2004/0092952 A1 | 5/2004 | Newton |
| 2004/0133201 A1 | 7/2004 | Shluzas et al. |
| 2004/0138662 A1 | 7/2004 | Landry |
| 2004/0143265 A1 | 7/2004 | Landry |
| 2004/0147937 A1 | 7/2004 | Dunbar |
| 2004/0172022 A1 | 9/2004 | Landry |
| 2004/0215190 A1 | 10/2004 | Nguyen |
| 2004/0230100 A1 | 11/2004 | Shluzas |
| 2004/0230191 A1 | 11/2004 | Frey |
| 2005/0004519 A1 | 1/2005 | Vanjaarsveldt |
| 2005/0004593 A1 | 1/2005 | Simonson |
| 2005/0021030 A1 | 1/2005 | Pagliuca |
| 2005/0021031 A1 | 1/2005 | Foley |
| 2005/0033297 A1 | 2/2005 | Davison |
| 2005/0033299 A1 | 2/2005 | Shluzas |
| 2005/0065516 A1 | 3/2005 | Jahng |
| 2005/0065517 A1 | 3/2005 | Chin |
| 2005/0075540 A1 | 4/2005 | Shluzas |
| 2005/0075644 A1 | 4/2005 | DiPoto |
| 2005/0080418 A1 | 4/2005 | Simonson |
| 2005/0085813 A1 | 4/2005 | Spitler |
| 2005/0090822 A1 | 4/2005 | DiPoto |
| 2005/0090824 A1 | 4/2005 | Shluzas |
| 2005/0090833 A1 | 4/2005 | DiPoto |
| 2005/0090899 A1 | 4/2005 | DiPoto |
| 2005/0107789 A1 | 5/2005 | Sweeney |
| 2005/0131408 A1 | 6/2005 | Sicvol |
| 2005/0131419 A1 | 6/2005 | McCord |
| 2005/0131420 A1 | 6/2005 | Techiera |
| 2005/0131421 A1 | 6/2005 | Anderson |

(56) References Cited

U.S. PATENT DOCUMENTS

| | | |
|---|---|---|
| 2005/0131422 A1 | 6/2005 | Anderson |
| 2005/0137593 A1 | 6/2005 | Gray |
| 2005/0149022 A1 | 7/2005 | Shaolian |
| 2005/0149036 A1 | 7/2005 | Varieur |
| 2005/0149053 A1 | 7/2005 | Varieur |
| 2005/0154389 A1 | 7/2005 | Selover |
| 2005/0159651 A1 | 7/2005 | Raymond et al. |
| 2005/0171540 A1 | 8/2005 | Lim |
| 2005/0171551 A1 | 8/2005 | Sukovich |
| 2005/0192570 A1 | 9/2005 | Jackson |
| 2005/0192579 A1 | 9/2005 | Jackson |
| 2005/0192589 A1 | 9/2005 | Raymond |
| 2005/0215999 A1 | 9/2005 | Birkmeyer |
| 2005/0216002 A1 | 9/2005 | Simonson |
| 2005/0228380 A1 | 10/2005 | Moore |
| 2005/0228400 A1 | 10/2005 | Chao |
| 2005/0234449 A1 | 10/2005 | Aferzon |
| 2005/0245942 A1 | 11/2005 | DiPoto |
| 2005/0251192 A1 | 11/2005 | Shluzas |
| 2005/0273131 A1 | 12/2005 | Shluzas |
| 2005/0273132 A1 | 12/2005 | Shluzas |
| 2005/0273133 A1 | 12/2005 | Shluzas |
| 2005/0288671 A1 | 12/2005 | Yuan |
| 2006/0036244 A1 | 2/2006 | Spitler |
| 2006/0074445 A1 | 4/2006 | Gerber et al. |
| 2006/0089651 A1 | 4/2006 | Trudeau |
| 2006/0111714 A1 | 5/2006 | Foley |
| 2006/0155278 A1 | 7/2006 | Warnick |
| 2006/0173456 A1 | 8/2006 | Hawkes |
| 2006/0200135 A1 | 9/2006 | Sherman |
| 2006/0229614 A1 | 10/2006 | Foley |
| 2006/0235393 A1 | 10/2006 | Bono |
| 2006/0241600 A1 | 10/2006 | Ensign |
| 2006/0247630 A1 | 11/2006 | Iott |
| 2006/0247636 A1 | 11/2006 | Yuan |
| 2006/0264962 A1 | 11/2006 | Chin |
| 2006/0276791 A1 | 12/2006 | Shluzas |
| 2006/0276792 A1 | 12/2006 | Ensign |
| 2007/0055235 A1 | 3/2007 | Janowski |
| 2007/0078460 A1 | 4/2007 | Frigg |
| 2007/0093817 A1 | 4/2007 | Barrus |
| 2007/0093826 A1 | 4/2007 | Hawkes |
| 2007/0093827 A1 | 4/2007 | Warnick |
| 2007/0185491 A1 | 8/2007 | Foley |
| 2007/0198015 A1 | 8/2007 | Foley |
| 2007/0213714 A1 | 9/2007 | Justis |
| 2007/0225711 A1 | 9/2007 | Ensign |
| 2007/0288004 A1 | 12/2007 | Alvarez |
| 2008/0039840 A1 | 2/2008 | Songer |
| 2008/0051821 A1 | 2/2008 | Gephart |
| 2008/0154277 A1 | 6/2008 | Machalk |
| 2008/0195155 A1 | 8/2008 | Hoffman |
| 2008/0228233 A1 | 9/2008 | Hoffman |
| 2009/0228054 A1 | 9/2009 | Hoffman |
| 2010/0160977 A1 | 6/2010 | Gephart |
| 2015/0245856 A1 | 9/2015 | Gephart |
| 2017/0319245 A1 | 11/2017 | Gephart |

FOREIGN PATENT DOCUMENTS

| | | |
|---|---|---|
| WO | 2004047650 | 6/2004 |
| WO | 2004071339 | 8/2004 |
| WO | 2006091863 | 8/2006 |
| WO | 2008024937 | 2/2008 |

OTHER PUBLICATIONS

Aebi, M. et al., AO ASIF Principles in Spine Surgery, pp. 119-120, Dec. 23, 1997.
B.W. Cunningham et al., "Video-Assisted Thopacoscopic Surgery Versus Open Thoracotomy for Anterior Thoracic Spinal Fusion", Spine, vol. 23, No. 12, pp. 1333-1340, Nov. 1998.
Buhren et al., "Minimal-Invasive Ventral Spondylodesen bei Verletzungen der Brust-und Lendenwirbelsaule (Minimally Invasive Ventral Spondylodesis for Injuries of the Thoracic and Lumbar Spine)", Der Chirug. 68, pp. 1076-1084, 1997.
Callahan, J. et al., "Percutaneous Lumber Discectomy: A New Adjunct Open Surgery" Indiana Medicine, 84(3), pp. 188-190, Mar. 1991.
Ditsworth, D., "Comprehensive Percutaneous Endoscopic Spinal Surgery" AANS 1995 Annual Meeting, Abstract, Apr. 1995.
Foley, M.D., Kevin T., Schwender, MD., James D., and Rouben, MD., David P., PyrametriX.RTM. Advance: Instrument Set Technique, surgical brochure provided by manufacturer Medtronic Sofamor Danek, Inc., 2005, (25 pages).
Globus Medical, "Pivot Minimally Invasive Stablization System Surgical Technique", Globus Medical, Jun. 27, 2008.
Globus Medical, "Pivot System", Minimally Invasive Products, Copyright 2005 Globus Medical, www.globusmedical.com.
Harrington, P., "Treatment of Scoliosis: Correction and Internal Fixation by Spine Instrumentation", Journal of Bone and Joint Surgery Am, 44:591-634, 1962.
I. L. Fedder et al., "Video-Assisted Spinal Surgery: Laboratory Protocol" General Principles of Thoracoscopy and Laparoscopy—Atlas of Endoscopic Spine Surgery, Quality Medical Publishing, Inc. pp. 18-26, 1995.
International Search Report and Written Opinion for PCT/US2006/06684, dated Sep. 20, 2007.
International Search Report and Written Opinion for PCT/US2007/76687, dated Sep. 22, 2008.
Kambin, P., "Arthroscopic Fusion of the Lumbosacral Spine," Lumbosacral and Spinopelvic Fixation, 1996.
Kambin, P., "Posterolateral Percutaneous Lumbar Discectomy and Decompression: Arthroscopic Microdicectomy," Arthroscopic Microdiscectomy, Ch 6, 1991.
Lowery et al., "Posterior Percutaneous Spine Instrumentation", Eur. Spine J. (2000), 9(Supp. 1), S-126.S130 Sep. 3, 1999.
Mahvi et al., "A Prospective Study of Laparoscopic Spinal Fusion", Annals of Surgery, vol. 224, No. 1, pp. 85-90, 1996.
Mathews, H. H., "Percutaneous Interbody Fusions," Othopedic Clinics of North America, vol. 29, No. 4, Oct. 1998.
Matthews, MD, Hallett, Evens, MD, Martin, Molligan, MD, Harry J., Long, RN,MS, Brenda H., Laparoscopic Discectomy With Anterior Lumbar Interbody Fusion, A Preliminary Review, Spine vol. 20, No. 16, pp. 1797-1802, 1995, (6 pages).
McAfee et al., "The Incidence of Complications in Endoscopic Anterior Thoracolumbar Spinal Reconstructive Surgery", Spine, vol. 20, No. 14, pp. 1624-1632, 1995.
McAfee et al., "Anterior Thoracic Corpectomy for Spinal Cord Decompression Performed Endoscopically", Surgical Laparoscopy and Endoscopy, vol. 5, No. 5, pp. 339-348, 1995.
Moran, J. M. et al., "Transpedicular Screw Fixation," Journal Orthepedic Research, vol. 7, pp. 107-114, 1989.
Regan, J. et al., "Endoscopic Techniques in Spinal Surgery", Clinical Orthopaedics and Related Research, No. 335, pp. 122-139, Feb. 1997.
Rosenthal, D. et al., "Newer Applications of Spinal Instrumentation," in, Atlas of Endoscopic Spine Surgery, Regan, J. F., et al., Eds., Quality Medical Publishing, Inc., St. Louis, pp. 333-337, 1995.
Sofamor Danek (as described by Simmons, Edward H. et al.,) The Spine Specialist, "TSRH Pedicle Screw Spinal System, Severe Spondylolisthese of L5-S1 Grade 3 & 4", Surgical Technique, 1997.
Supplementary European Search Report issued in the counterpart European Application No. EP06736091.7 dated Nov. 25, 2011, 8 pages.
Zindrick, M. R., "The Role of Transpedicular Fixation Systems for Stabilization of the Lumbar Spine," Orthopedic Clinics of North America, vol. 22, No. 2, Apr. 1991.
Zucherman et al., "Instrumented Laparoscopic Spinal Fusion: Preliminary Results", Spine, vol. 20, No. 18, pp. 2029-2035, 1995.
Amendment, filed Aug. 30, 2010, in related U.S. Appl. No. 11/844,265 (10 pages).
Amendment, filed Jan. 18, 2010, in related U.S. Appl. No. 11/844,265 (14 pages).
Synthes Spine, "The Universal Spinal System: Surgical Technique Guide for the Correction of Scoliosis", 1994.

(56) References Cited

OTHER PUBLICATIONS

Official Action for U.S. Appl. No. 11/844,277, dated Nov. 27, 2009, 19 pages.
Ex Parte Quayle Action for U.S. Appl. No. 11/844,277, dated Aug. 6, 2010, 6 pages.
Notice of Allowance for U.S. Appl. No. 11/844,277, dated Nov. 18, 2010, 6 pages.
Official Action for U.S. Appl. No. 11/844,265, dated Sep. 17, 2009, 17 pages.
Official Action for U.S. Appl. No. 11/844,265, dated Apr. 28, 2010, 20 pages.
Notice of Allowance for U.S. Appl. No. 11/844,265, dated Dec. 9, 2010, 4 pages.
Official Action for U.S. Appl. No. 11/844,259, dated Nov. 12, 2009, 14 pages.
Official Action for U.S. Appl. No. 11/844,259, dated Jul. 21, 2010, 8 pages.
Notice of Allowance for U.S. Appl. No. 11/844,259, dated Feb. 9, 2012, 7 pages.
Official Action for U.S. Appl. No. 12/438,538, dated Sep. 17, 2012, 5 pages.
Notice of Allowance for U.S. Appl. No. 12/438,538, dated Jun. 6, 2013, 6 pages.
Official Action for U.S. Appl. No. 13/083,347, dated Mar. 11, 2013, 7 pages.
Notice of Allowance for U.S. Appl. No. 13/083,347, dated Sep. 12, 2013, 6 pages.
Official Action for U.S. Appl. No. 14/144,020, dated Apr. 9, 2014, 5 pages.
Notice of Allowance for U.S. Appl. No. 14/144,020, dated Jan. 16, 2015, 6 pages.
Official Action for U.S. Appl. No. 14/713,962, dated Sep. 23, 2016, 6 pages.
Notice of Allowance for U.S. Appl. No. 14/713,962, dated Apr. 6, 2017, 7 pages.
Official Action for U.S. Appl. No. 15/644,563, dated Apr. 4, 2018, 12 pages.
Notice of Allowance for U.S. Appl. No. 15/644,563, dated Sep. 21, 2018, 8 pages.
Supplemental Notice of Allowance for U.S. Appl. No. 15/644,563, dated Nov. 8, 2018, 5 pages.
Official Action for U.S. Appl. No. 16/229,719, dated Jun. 29, 2020, 24 pages.
Official Action for U.S. Appl. No. 16/229,719, dated Dec. 31, 2020, 21 pages.
Notice of Allowance for U.S. Appl. No. 16/229,719, dated May 17, 2021, 5 pages.
Corrected Notice of Allowance for U.S. Appl. No. 16/229,719, dated Jun., 2 pages.

* cited by examiner

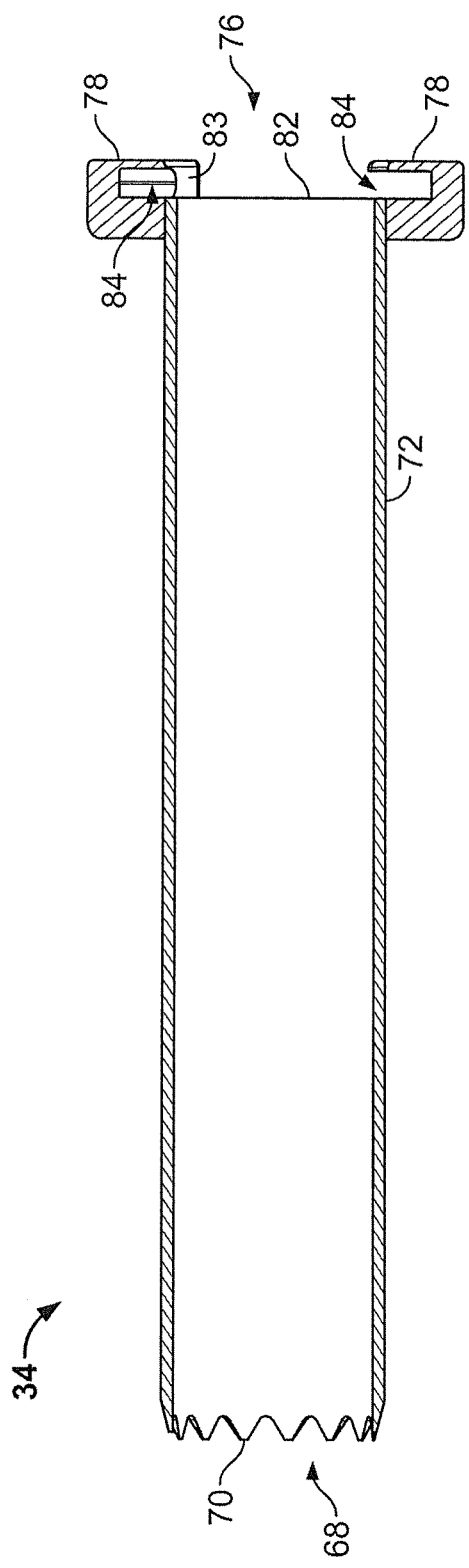
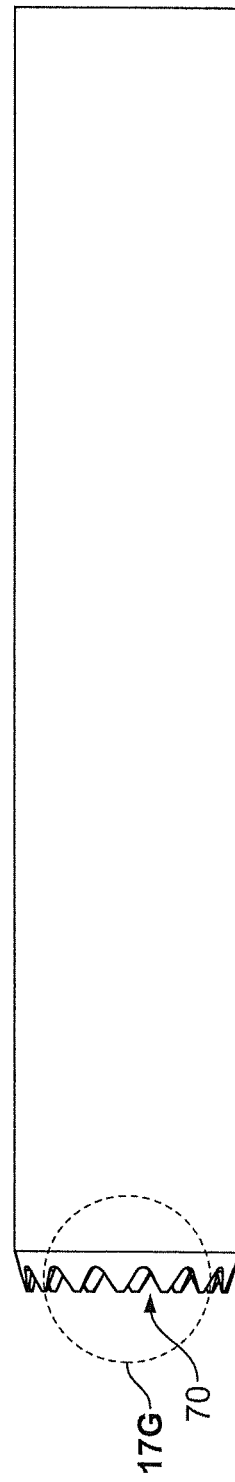
FIG. 17D
FIG. 17E

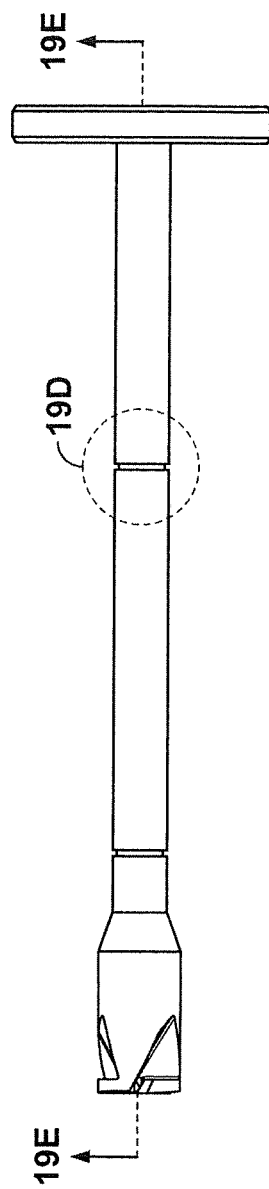
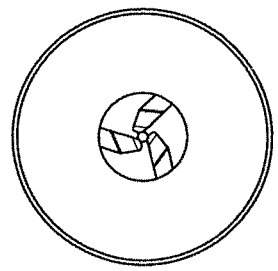
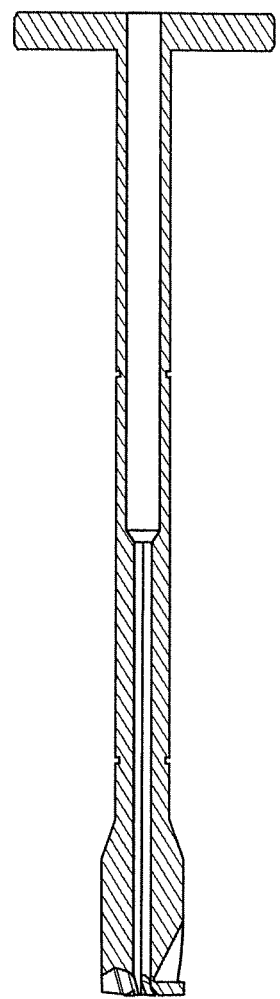
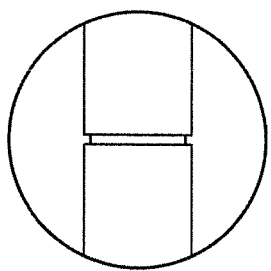
FIG. 19C
FIG. 19E
FIG. 19B
FIG. 19D

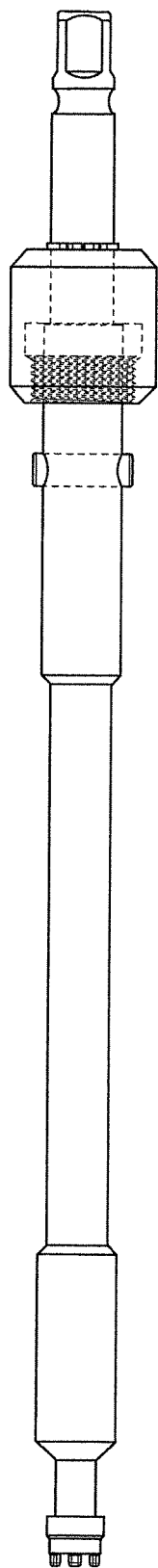
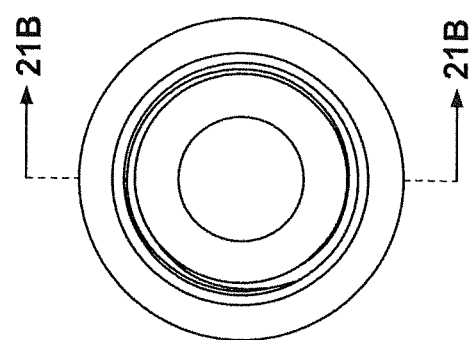
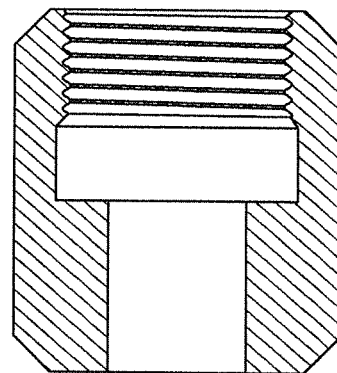
FIG. 21A
FIG. 21C
FIG. 21B

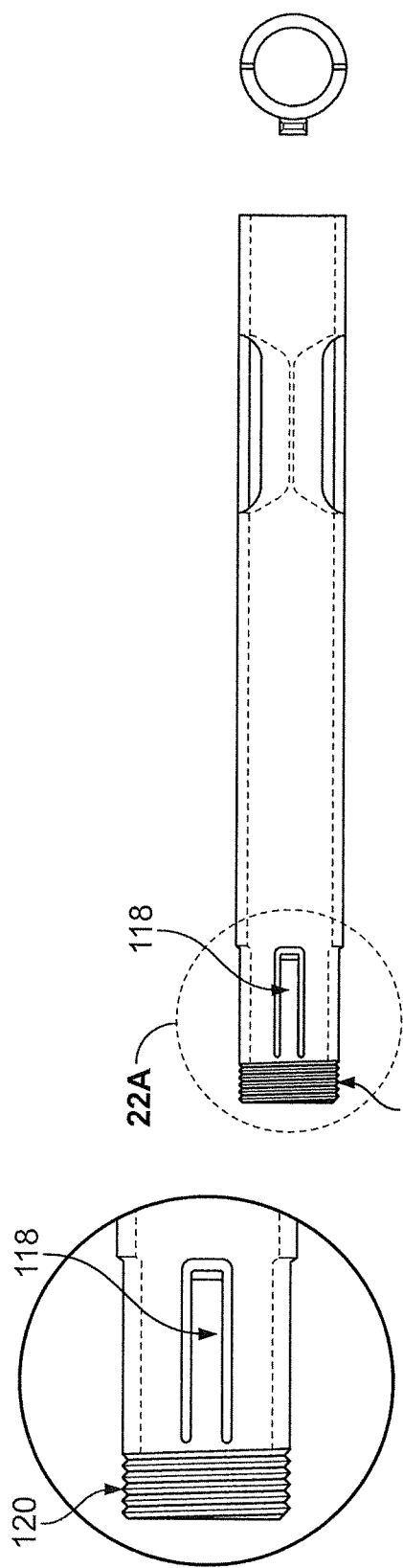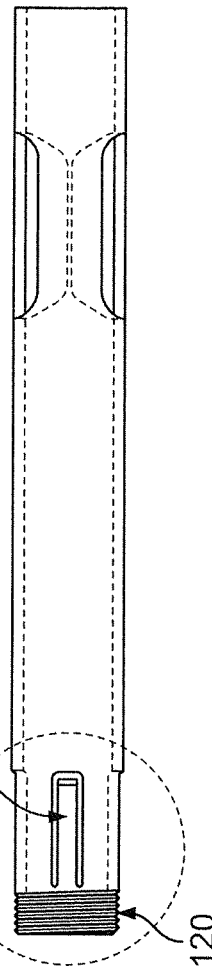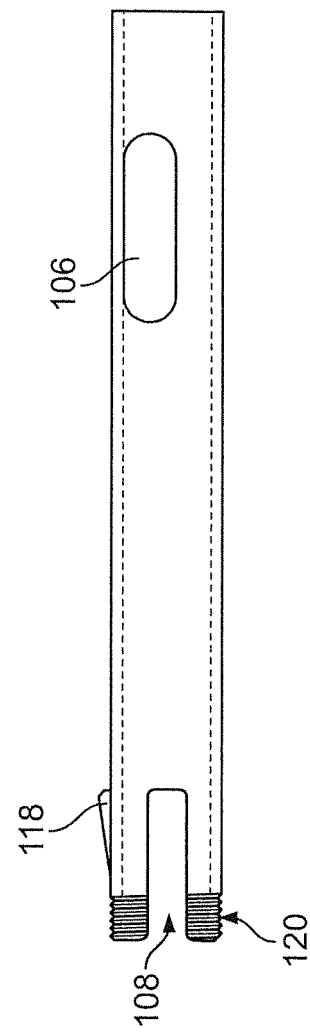
FIG. 22C
FIG. 22B
FIG. 22D
FIG. 22A

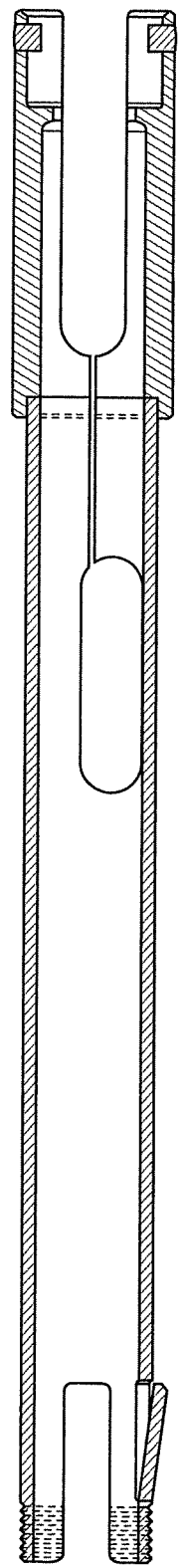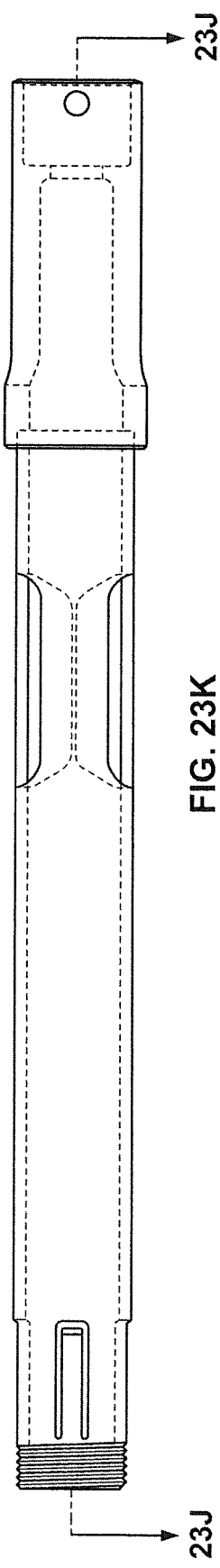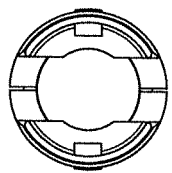
FIG. 23J
FIG. 23K
FIG. 23L

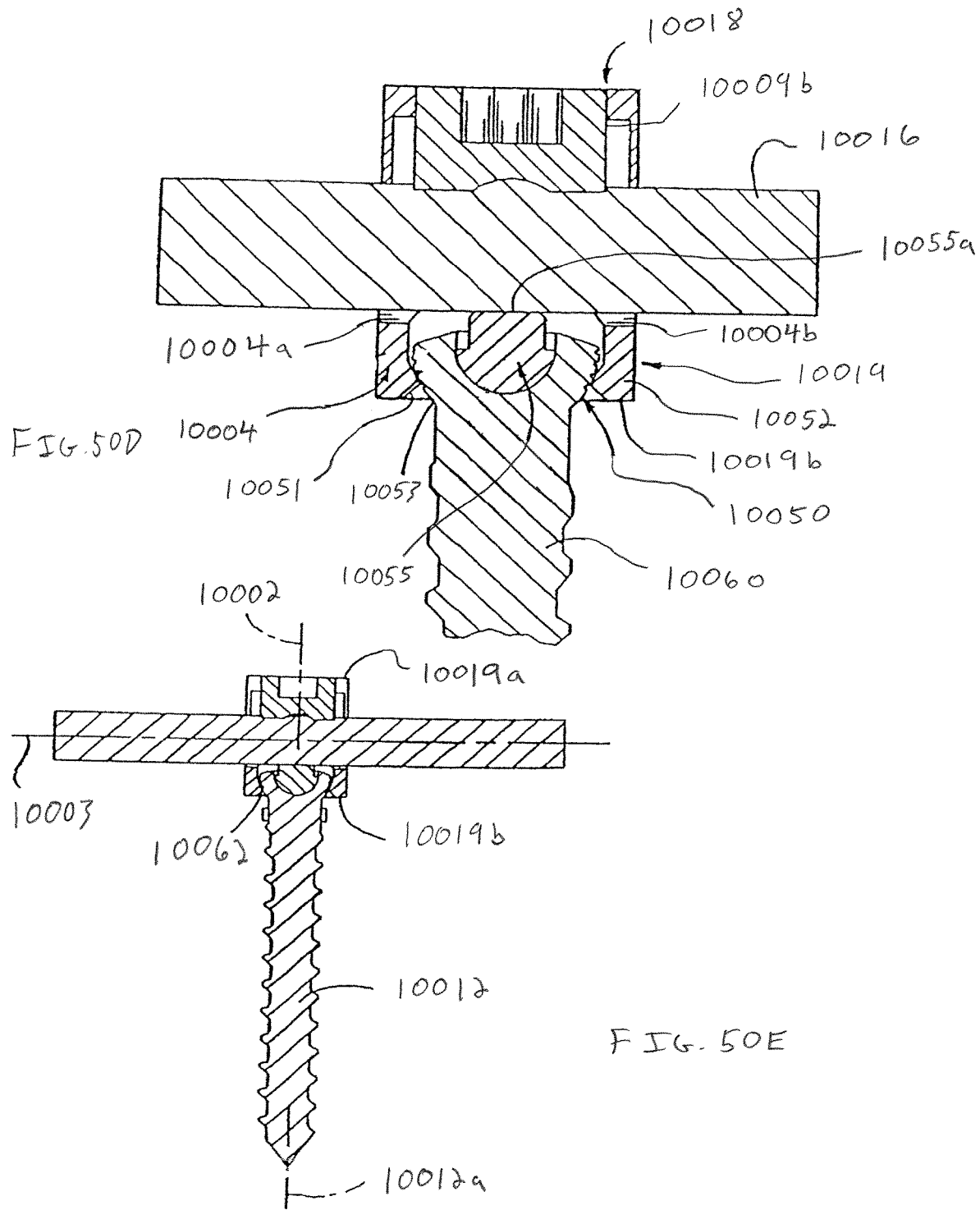

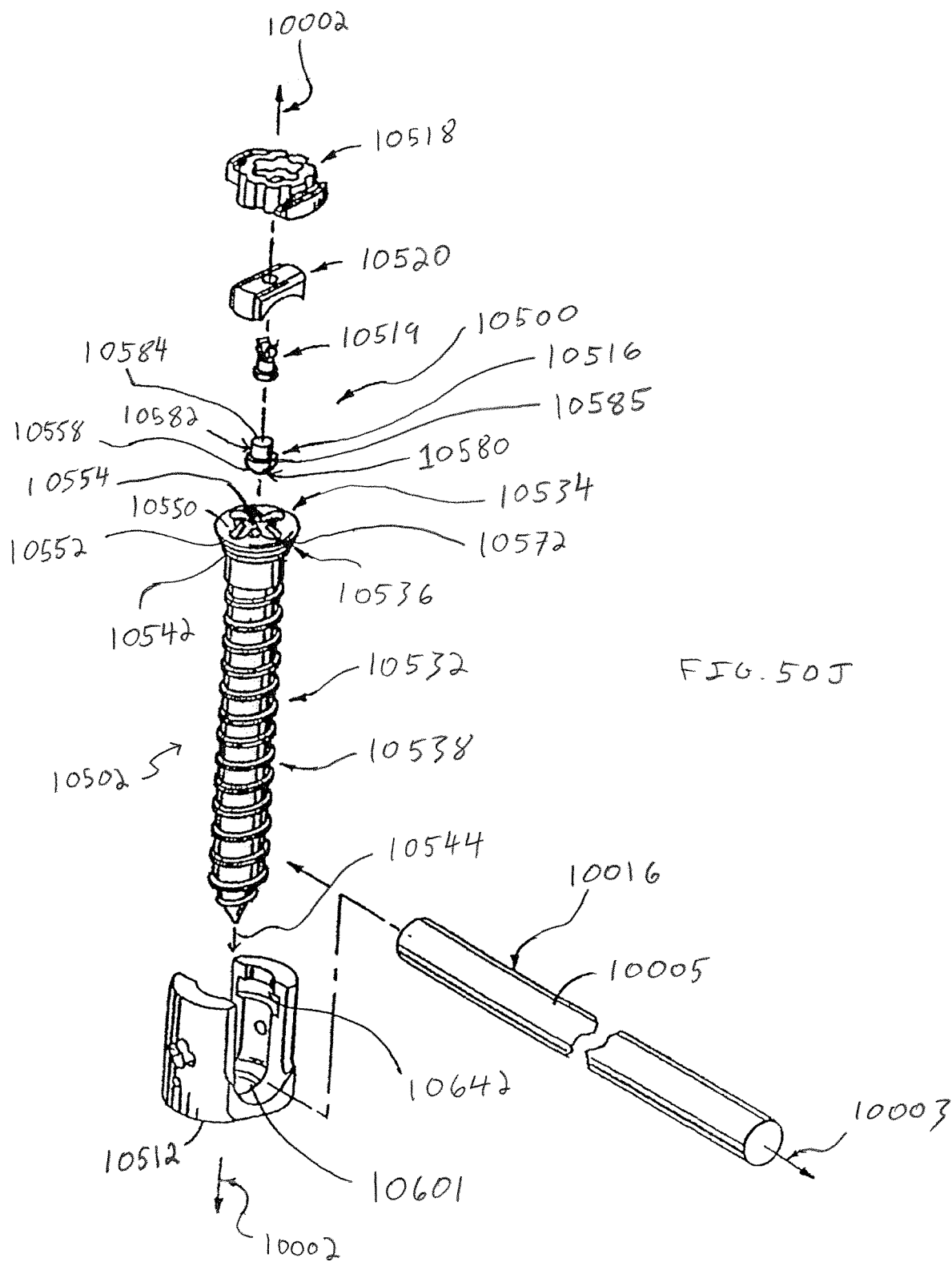

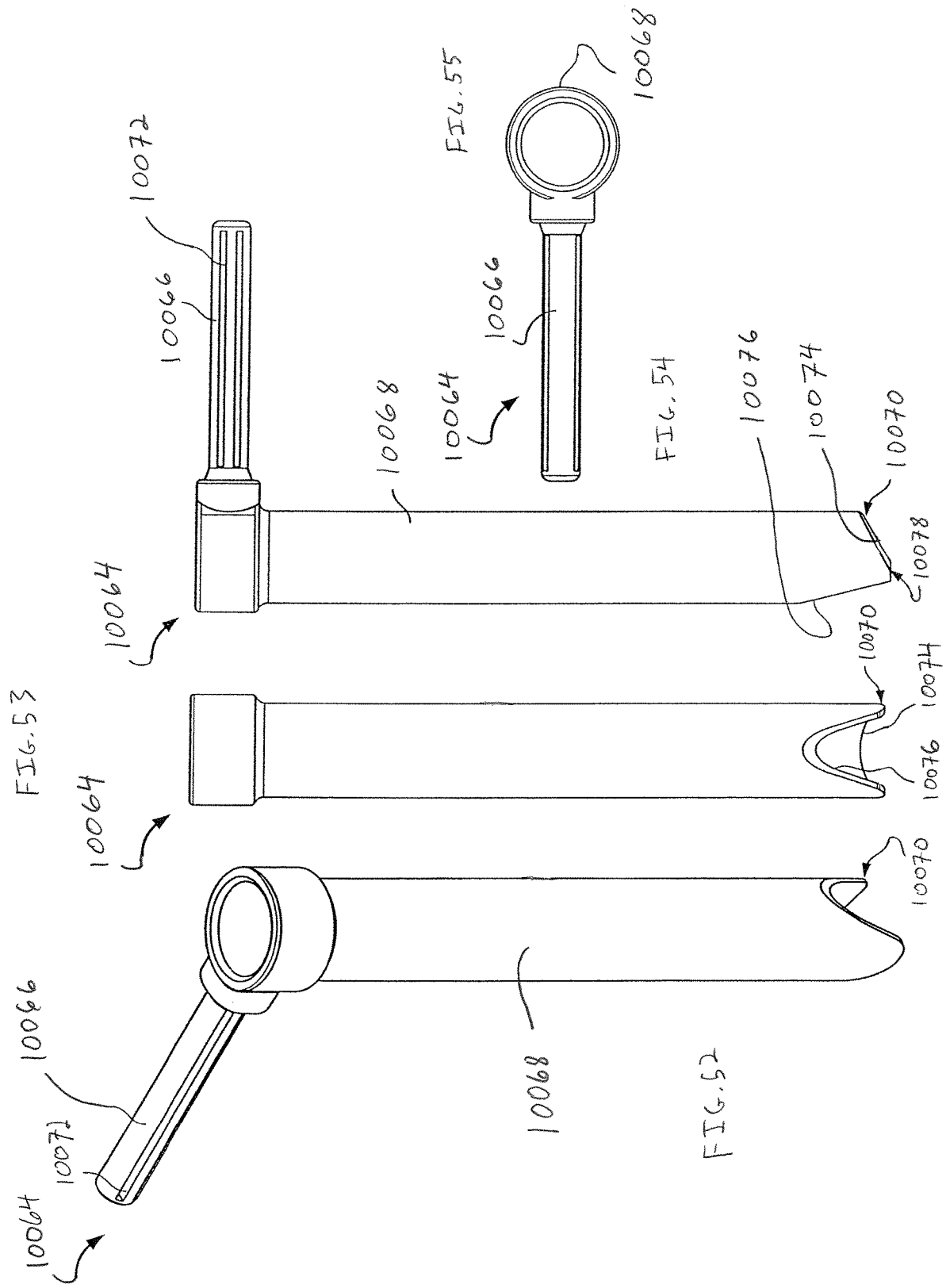

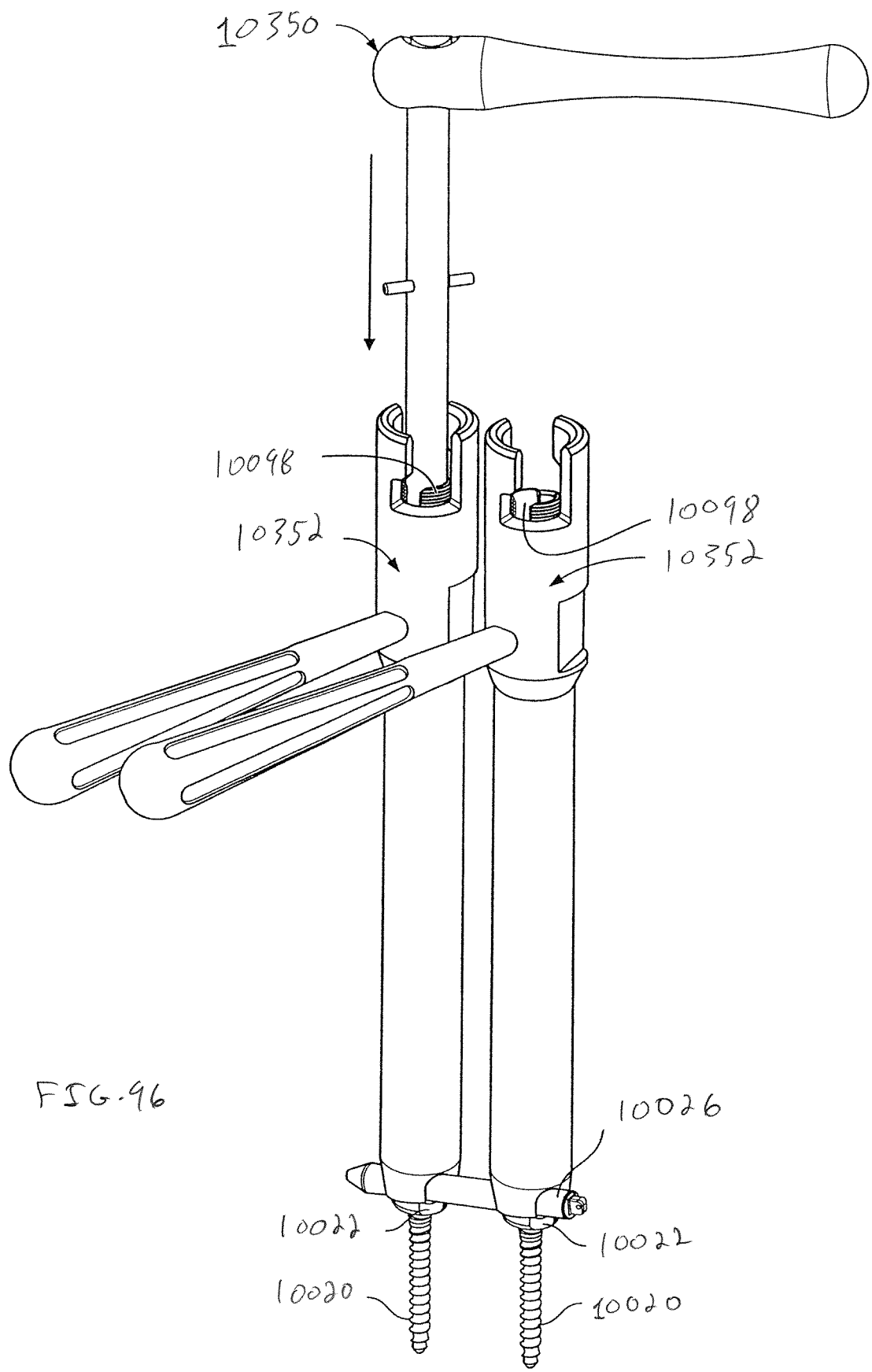

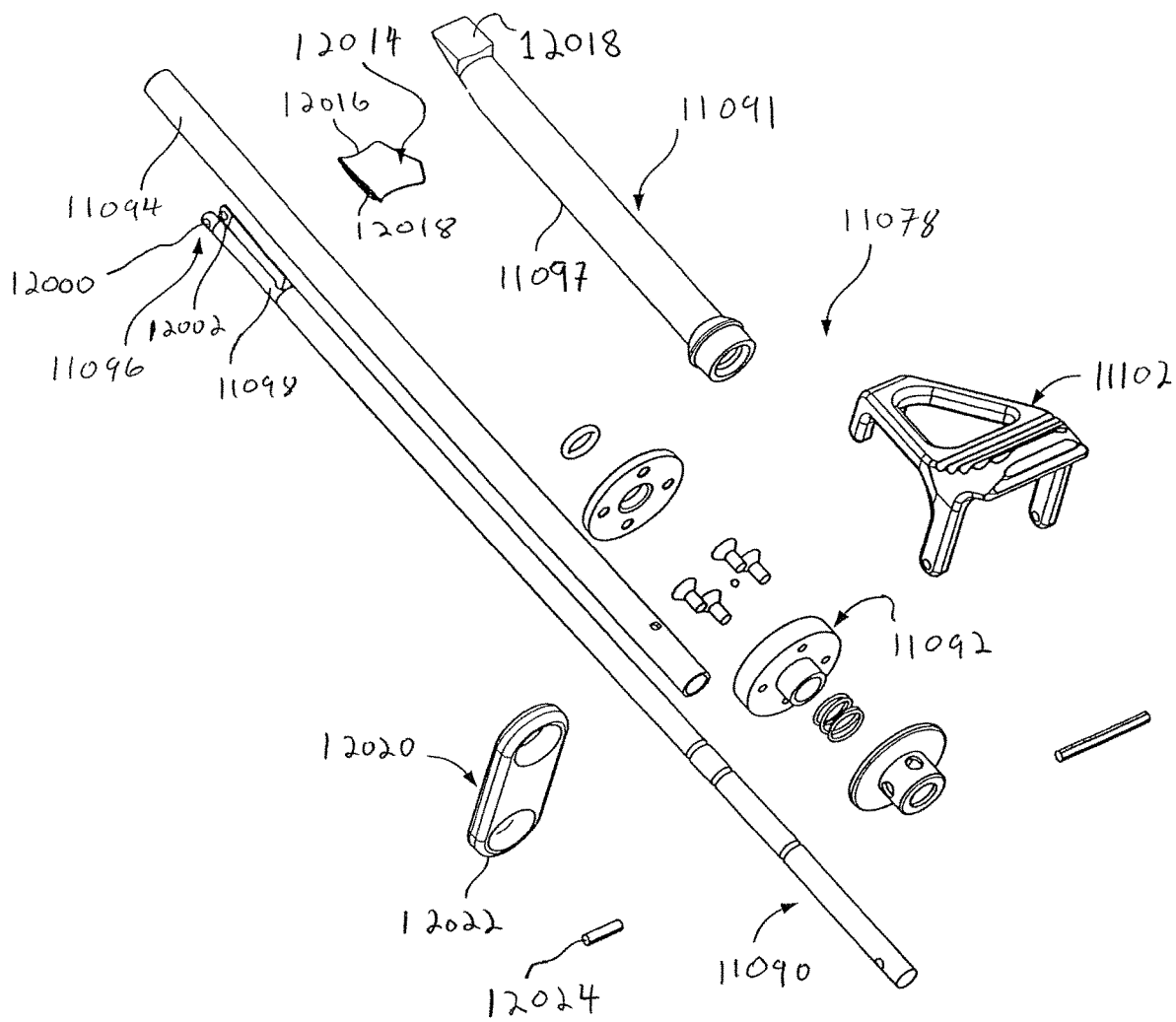
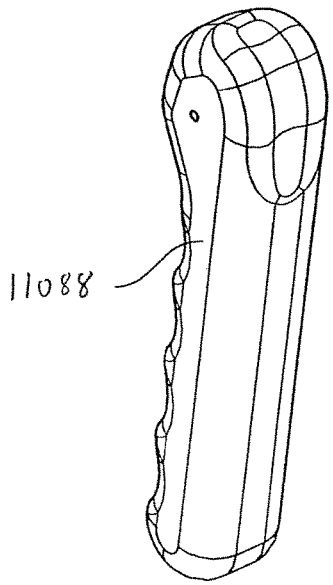
FIG. 97C

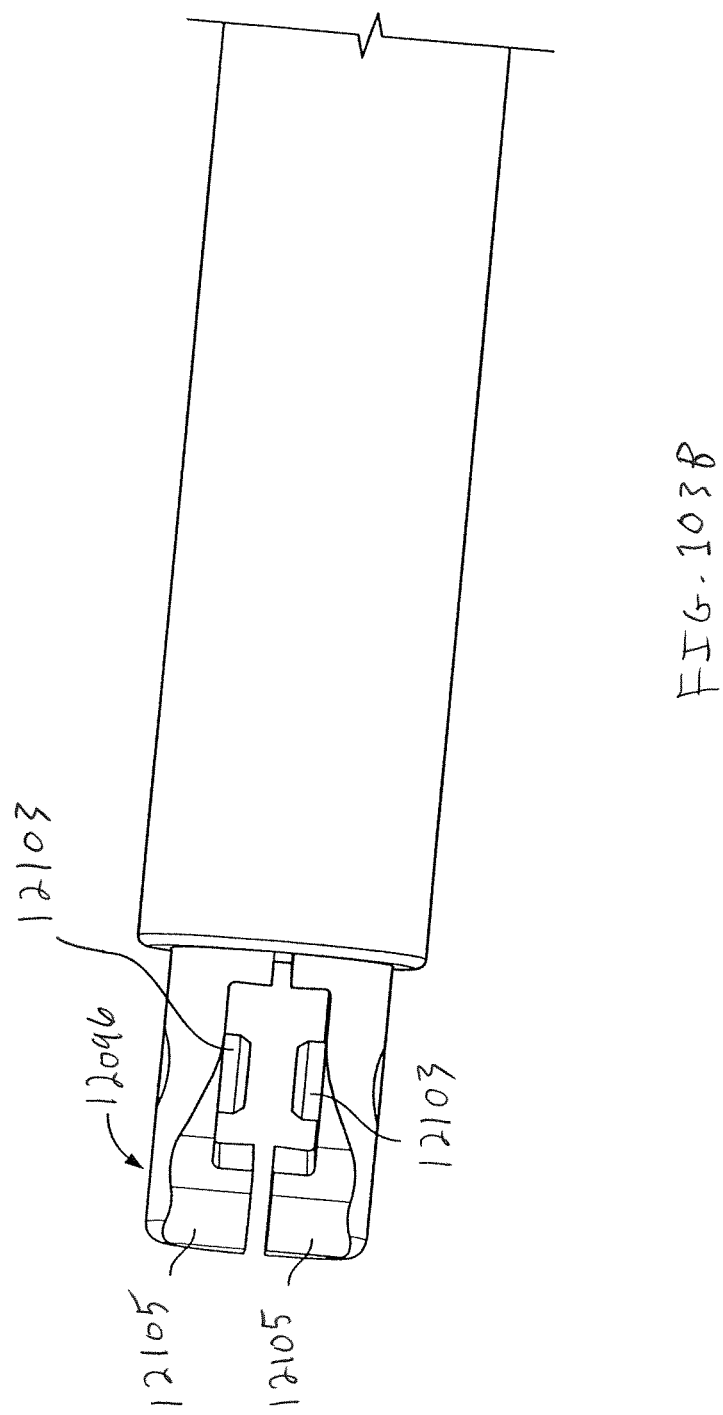

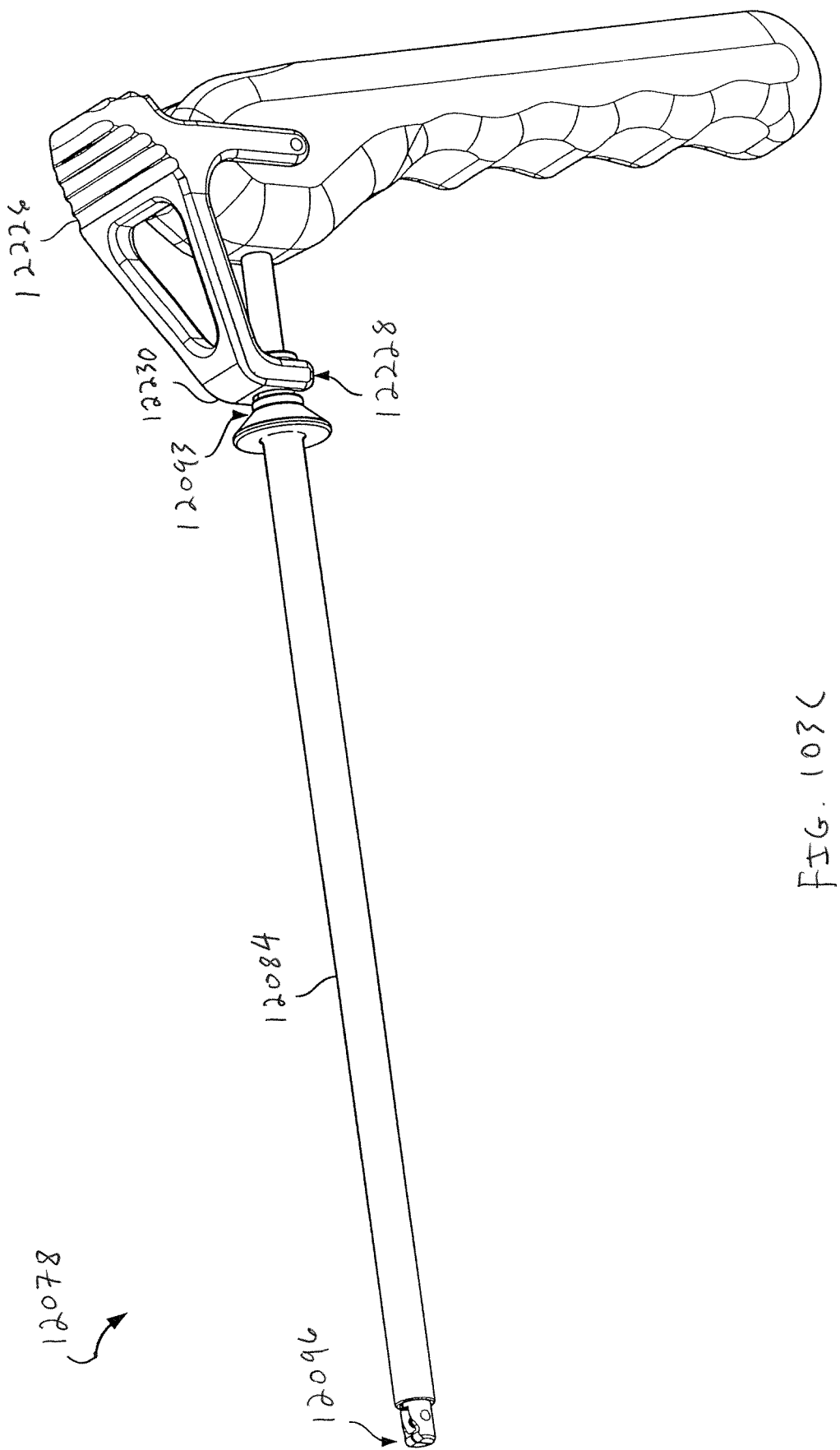

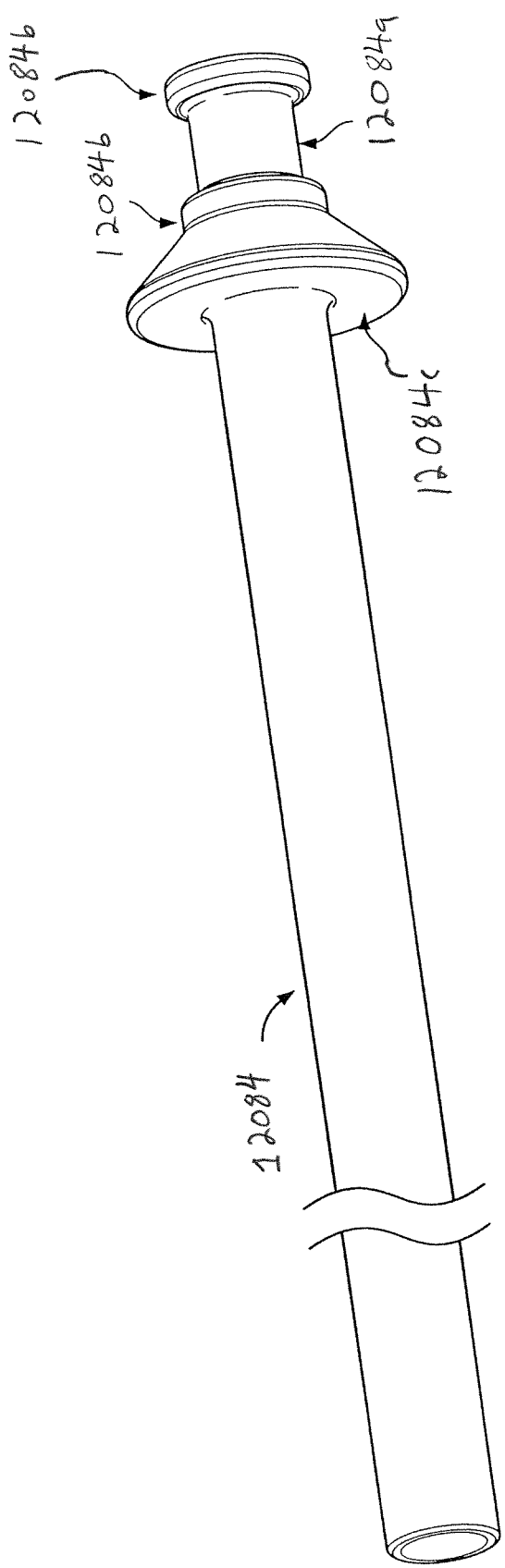

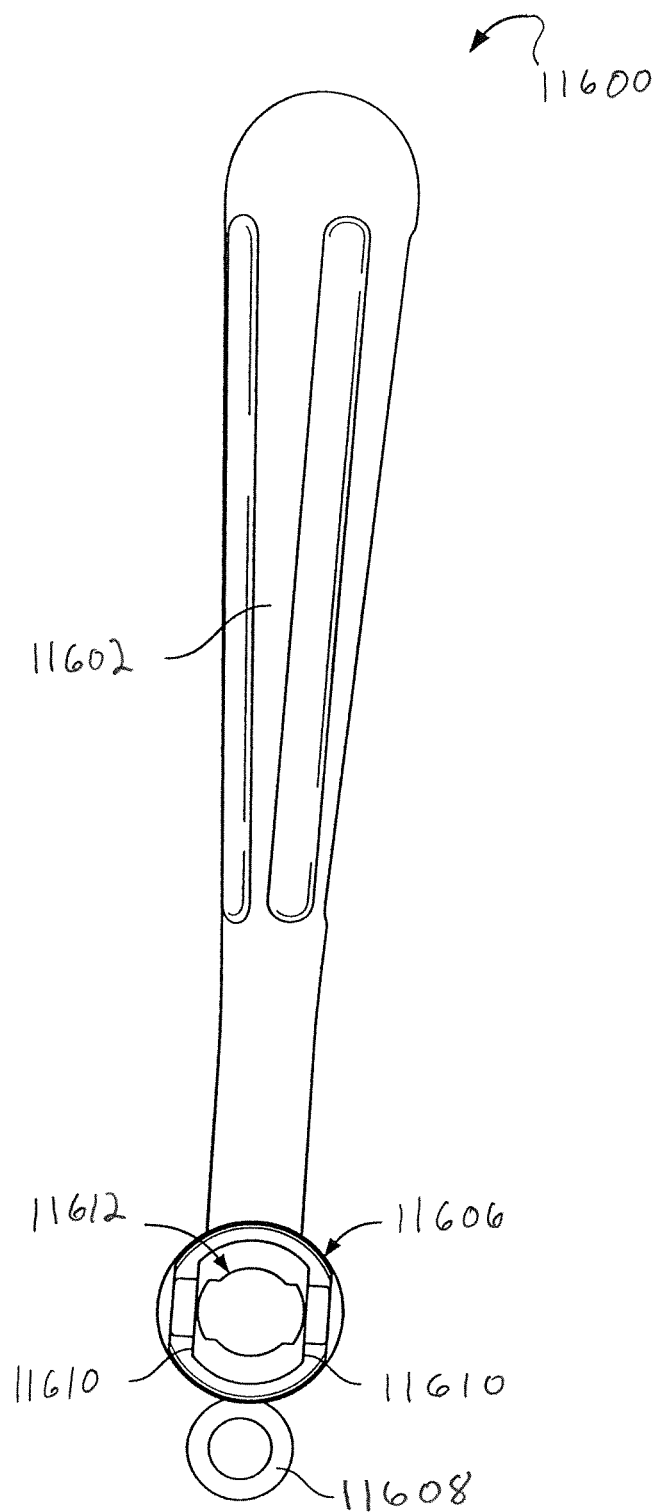
FIG. 1058

MINIMALLY INVASIVE SURGICAL SYSTEM

CROSS-REFERENCE TO RELATED APPLICATIONS

This application is a continuation of U.S. patent application Ser. No. 16/229,719, filed Dec. 21, 2018, which is a continuation of U.S. patent application Ser. No. 15/644,563, filed Jul. 7, 2017, which issued as U.S. Pat. No. 10,194,959 on Feb. 5, 2019, which is a continuation of U.S. patent application Ser. No. 14/713,962, filed May 15, 2015, which issued as U.S. Pat. No. 9,730,738 on Aug. 15, 2017, which is a continuation of U.S. patent application Ser. No. 14/144,020, filed Dec. 30, 2013, which issued as U.S. Pat. No. 9,033,988 on May 19, 2015, which is a continuation of U.S. patent application Ser. No. 13/083,347, filed Apr. 8, 2011, which issued as U.S. Pat. No. 8,641,719 on Feb. 4, 2014, which is a continuation-in-part of U.S. patent application Ser. No. 11/844,265, filed Aug. 23, 2007, which issued as U.S. Pat. No. 7,922,727 on Apr. 12, 2011, which is a continuation of PCT Application No. PCT/US06/06684, filed Feb. 23, 2006, which claims the benefit of U.S. Provisional Application No. 60/722,604, filed Sep. 29, 2005 and U.S. Provisional Application No. 60/655,983, filed Feb. 23, 2005, the contents of which are all hereby incorporated by reference in their entireties. The Ser. No. 13/083,347 is also a continuation-in-part of U.S. patent application Ser. No. 12/438,538, having a 35 U.S.C. § 371(c) date of Aug. 23, 2010 and which issued as U.S. Pat. No. 8,551,141 on Oct. 8, 2013, which is a U.S. National Stage Application filed under 35 U.S.C. § 371 of International Application No. PCT/US07/76687, filed Aug. 23, 2007, which claims the benefit of U.S. Provisional Application No. 60/839,895, filed Aug. 23, 2006, the contents of which are all hereby incorporated by reference in their entireties.

FIELD OF THE INVENTION

This invention relates generally to apparatus and methods for surgically implanting bone fixation devices, and more particularly, to surgical instruments and surgical methods that secure bone or bone segments relative to one another with minimal invasion into the surrounding body tissue.

BACKGROUND OF THE INVENTION

Implant devices secured to bone or bone segments are utilized to promote the healing and repair of various parts of the human body. In some cases, the implant devices are secured to the bone or bone segments such that the bones themselves heal, fuse, or stabilize relative to one another. In other cases, implant or fixation devices are used to secure bones or bone fragments so that the surrounding soft tissue may heal without disruption by relative movement of the bones.

During the surgical procedure to implant the fixation devices, a plurality of bone screws or other fixations elements are secured to a plurality of respective bones. Then, each of the bone screws is secured relative to the others with an additional apparatus, such as a connecting member or rod.

For example, spinal rods that immobilize vertebral bones of the spinal column are typically anchored to the vertebrae via bone screws that extend through the pedicle into the vertebral bodies or by hooks that engage about the vertebrae. The spinal rods are connected to the screws or anchor members by coupling members, which may be yoke-shaped. Such coupling members may be integral with the anchor member head or separate components from the anchor member.

While incisions are required during such surgical procedures in order to gain access to the site where the implant is secured, such incisions can cause damage, injury, and trauma to the patient's body. To avoid causing unnecessary damage, it is preferable to make the incisions as small and few as possible.

One prior approach to implanting a bony structure stabilization device uses an installation instrument with a pivoting brace inserter. To implant the connecting element, extensions are attached to the anchors and the installation instrument with the pivoting brace inserter being rigidly attached to the extensions. The pivoting brace inserter employs a fixed geometric relationship to guide the connecting element into position. The installation instrument mounts to the bone anchors extension and holds the connecting element such that when the instrument's pivoting arm is pivoted, the connecting element follows a direct predetermined path into position about the anchor. As the connecting element is swung into position, the element enters the body through the skin at a remote location removed from the surgical incisions made to attach the bone anchors.

This approach can be problematic because another incision or opening is made through the skin, in addition to the openings required to insert the two screws. This additional opening allows for insertion of the brace or rod. Further, because of the fixed path, such a system is unable to direct the connecting element along a path of least resistance through the soft tissues and thereby causes tissue trauma that could otherwise be avoided by the surgeon variably moving the connecting element around and between these tissues. In addition, if the patient's vertebrae are misaligned the surgeon can encounter difficulty when inserting the brace along predetermined path because the predetermined path may not account for the various vertebrae locations.

Another approach to the minimally invasive system utilizes the same pathway that is used to insert the spinal anchors to also insert the connecting element. The connecting element is then manipulated such that it shifts to a perpendicular orientation to the insertion pathway in order to connect the anchors. Positioning of the connecting element can be assisted by a manipulation tool but nonetheless remains relatively unguided relying significantly on surgeon skill and patience.

Accordingly, there is a need for a minimally invasive surgical system that limits the number and size of the incisions, minimizes trauma to the soft tissues, and also provides physicians with control to efficiently and effectively implant necessary devices.

SUMMARY OF THE INVENTION

In accordance with one aspect of the present invention, a Minimally Invasive Surgical System (MISS) apparatus and method are disclosed that secure bone or bone fragments together. To this end, the apparatus and method utilize a plurality of bone anchors and a connecting rod. The bone anchors are fixed to the bone and the connecting member is secured to the bone anchors such that the bones are substantially fixed relatively to one another. To implant the anchors and connecting member, the system utilizes a number of tools or instruments that provide the surgeon with accurate and precise implant insertion, while limiting the number and extent of the incisions required. While the MISS can be used to secure various bones and bone fragments relative to one another, a pedicle screw assembly with a spinal rod is described herein as an example.

In accordance with one aspect of the present invention, a minimally invasive surgical (MIS) system and method are disclosed that secure bone or bone fragments together, such as vertebrae. To this end, the apparatus and methods utilize a plurality of pedicle screw assemblies and a connecting member. The bone anchors are fixed to the bone and the connecting member or rod is secured to the bone anchors by a yoke, such that the bones are substantially fixed relative to one another. To implant the anchors and connecting member, the system utilizes a number of tools or instruments that provide the surgeon with accurate and precise implant insertion, while limiting the number and the size of the incisions required. While the MIS system can be used to secure various bones and bone fragments relative to one another, a pedicle screw assembly with a spinal rod is described herein as an example.

The preferred MISS implant includes at least two pedicle anchors or screws, yokes, closure caps, and a connecting member. In addition, in a preferred form, the system may include a dilation tool, docking sleeves, yoke manipulators, restraints that engage the yoke manipulators, a rod inserter, and optionally a guide. To begin the procedure, a surgeon percutaneously inserts a Jamshidi needle over the posterior spinal anatomy creating a small incision the Jamshidi holds the guidewire and is used to percutaneously force in the guidewire. A surgeon can determine through tactile feedback, where the implants and various tools should be inserted. The guidewire is driven to a predetermined depth into the target pedicle bone of the selected vertebral segment. After the guidewire is secured, the surrounding tissue is stretched using various dilation techniques. The surrounding tissue may also be incised to provide passage of the MISS tools. Subsequent to tissue dilation and/or incision a docking sleeve is inserted into the percutaneous opening.

The preferred MIS implant includes at least two pedicle anchors or screws, yokes, caps, and a connecting member, although three or more screw assemblies can also be used. Ensuring proper anchor placement is generally necessary for a successful procedure. Therefore, a number of tools can be utilized to correctly position the implant. In a preferred form, the system may include a dilation tool, docking ports, yoke manipulators, restraints that engage the yoke manipulators, a rod inserter, and optionally a guide bar. Some or all of these tools may be used during a procedure, depending upon the needs of the patient and the preferences of the surgeon.

The docking sleeve is the minimally invasive surgical portal through which the surgery is performed. In one form, the docking sleeve has docking fasteners such that the docking sleeve can be fixed to the bone during the surgical procedure. After the docking sleeve is secured in position, the surgeon can prepare the bone for receiving the anchor. A facing tool is sometimes used to resurface the bone to a more desired contour such as concave, dome, flat, or other beneficial shape. Before the anchor is inserted, an awl or other instrument can be used to create a depression or opening on the bone surface at the location where the anchor will be set. To aid the surgeon in attaching the anchors, yoke manipulators are employed to assist in the insertion. The yoke manipulators, anchors, and restraint are advanced down the docking sleeve with a screw driver that rotates the anchor into position on the pedicle bone. At this point the docking sleeve may be removed.

Before insertion of the connecting member, the surgeon must repeat the procedure and insert the other bone anchor (s). After the bone anchors are inserted, the yoke manipulators remain attached to the anchors to facilitate insertion of the connecting member. At least one of the yoke manipulators includes slots on each side that allow for the passage of connecting member. Another yoke manipulator has at least one slot allowing for insertion of the connecting member. The connecting member is fed between the yoke manipulators by a rod inserter. Therefore, the yoke manipulators allow for the connecting member to be inserted into position without requiring another opening or incision into the body than the openings used to attach the anchors. After the connecting member is positioned in the anchor yokes, a closure cap is inserted into the yoke and rotated such that the connecting member is fixedly secured into position. The yoke manipulators may now be removed from the bone anchors along with any other tools and instruments such as the docking sleeve. After removal of the tools, the surgeon closes the wound. The MISS allows for insertion of an implant with out unnecessary trauma to the body and more particularly to the surrounding tissue. Further, the system provides the surgeon with guidance during the procedure without being unduly rigid.

Therefore, a minimally invasive surgery system (MISS), described herein, is used to implant bone fixation devices. An MISS system is particularly useful during spinal and neurosurgical procedures because the surgeon must have access to location deep within the body and such access requires the surgeon to reposition or avoid vital tissues.

An MISS is useful for performing a spinal surgery, but can be effectively used for non-spinal applications in humans and other mammals. The implants described herein are preferred models, however, this minimally invasive instrumentation may be used with a variety of implant forms, spinal and non-spinal, in many cases with minimal or no modification. For example, the docking sleeve described herein may be used for repairs of the hip as well as for repairs of the spine. It may be used to implant bone screws, fusion devices, and many other prosthetic and non-prosthetic implants, or to perform non-implant repair.

The disclosed MISS accommodates both cannulated and non-cannulated implant placement. This allows the system to be tailored to a particular surgeon's preferences. For example, when employing a guidewire, a cannulated pedicle bone screw along with cannulated tools are utilized. However, many surgeons find cannulated instruments to be less effective due to the movement constraints resulting from the presence of the guidewire. Therefore, surgeons can tailor the system to accommodate their preferences for guidewire use.

In one form, the MIS procedure is performed in stages. First, the surgical site is prepared. After preparation, the pedicle screw assemblies are attached to the bone. Subsequent to insertion of the screws, a rod or connecting member is positioned within the yoke portion of the pedicle screw assembly. The caps are then placed in either a pre-lock or final-lock position within the yokes. When only one of the caps is in the final-lock configuration, the bone screws may be compressed together or distracted along the rod or connecting member, thereby setting the final spacing of the bones or bone segments. Finally, the remaining caps are moved to the final lock configuration to fix the screws to the rod or connecting member to maintain the bones in a desired position relative to one another.

A surgical procedure typically begins by preparing the surgical site. Preparation may require a number of steps, including, but not limited to creating an incision, stretching the tissue surrounding the incision, and smoothing or otherwise preparing the surface of the bone. Next, the screws or bone anchors, along with the yoke, are inserted into the site and driven into the bone. After the bone anchors have been driven into the bone, the rod or connecting member is seated within the yoke of each bone anchor and spans between each bone anchor. A cap is seated within the yoke to secure the connecting member within the yoke. After the cap is inserted into the yoke, the cap is advanced to the pre-lock position. With one cap in the pre-lock position, the spacing between the bone anchors can be adjusted to ensure proper spacing of the vertebra by permitting the bone anchors to translate along the connecting member. After proper spacing is achieved, the caps are moved to a final locking position to fix the bone anchors to the connecting member. After final locking, the various tools used to complete the procedure can be removed from the surgical site and the incisions can be closed.

To begin the preparation step of the procedure, an opening or incision, such as a stab wound, is made at the surgical site. This may be done with a scalpel or possibly a self-cutting, self-tapping guide wire. The opening is then stretched or dilated to accommodate the tools needed to implant the device. Such dilation may be accomplished by a number of tools, such as series dilators, a multi-stage telescoping tissue dilator, or obturators. After the surrounding tissue is sufficiently stretched, a docking port is positioned in the opening and functions as the access window through which the rest of the procedure is conducted. After the docking port is secured in the opening, such as by using an articulating arm, such as an iron intern an example of which is disclosed in U.S. Pat. No. 6,308,423, the vertebrae can be prepared by using an awl or facing tool such that the bone anchors can be readily attached to the vertebrae.

After the surgical site has been prepared, the bone anchors are driven into the vertebrae. This stage of the procedure begins by attaching the bone anchors to the yoke manipulators. The bone anchors typically have a yoke attached or include a yoke portion integral with the anchor. Each yoke manipulator is positioned about a yoke before being inserted. Following attachment of the yoke to the yoke manipulator, the bone anchor, yoke, and yoke manipulator can together be advanced through the docking port to the surgical site where the anchor will be seated. A screw driver, separate from the yoke manipulator, can be used to advance the bone anchors into the bone. The screw driver can be mated with the head of the bone anchor before or after the yoke manipulator, anchor, and yoke are positioned at the surgical site through the docking port. After the anchor has been seated in the bone, the screw driver is removed.

After each of the bone anchors has been driven into to the vertebrae, the rod or connecting member is positioned within the yokes. To begin this stage of the procedure, a guide bar can be employed to align the openings in the yoke manipulators. The guide bar may be attached to the upper ends of the yoke manipulators and may permit selective locking of each relative to the guide bar. After the manipulator openings are aligned, the rod inserter, having the connecting member attached to one end, can be advanced through one of the yoke manipulators. The rod inserter is maneuvered to position the connecting member in the yokes, beginning with the yoke opposite the incision into which the rod inserter is located. Once the connecting member is positioned in the opposite yoke, the rod inserter is used to manipulate the connecting member into the yoke associated with the incision in which the rod manipulator is located. The connecting member can move relative to the rod inserter in different arrangements to facilitate insertion of the connecting member into the yokes. For example, the rod inserter can be configured to securely hold the connecting member such that there is no relative movement between the inserter and the connecting member. In another configuration, the connecting member is allowed to rotate relative to the rod inserter. In a preferred embodiment, the rotation only occurs in one limited direction. In another configuration, the connecting member is released from the inserter. Slots may be provided in the yoke manipulators to facilitate insertion of the rod into the yokes. Before the connecting member is completely released, the inserter is maneuvered such that the connecting member is fed into the other manipulator and into the yoke. After the connecting member is positioned in the yokes and one cap is in the pre-lock position so as to prevent rotation, the inserter is removed from the incision.

Subsequent to the positioning of the connecting member into the yokes, a cap is inserted into each of the yokes to secure the member therewith. The cap may be inserted in two steps: pre-lock and final-lock. In the pre-lock stage, the cap is rotated about its rotary axis so that a portion of the cap is advanced axially to a predetermined position or depth on the yoke such that there is adequate spacing between the cap and the head of the bone anchor or insert to allow the connecting member to be adjusted along the axis thereof in the yokes. The pre-lock configuration allows for the adjustment of the spacing of the bone anchors and vertebrae. It is often desirable to fully lock one of the caps in a system with two or more bone anchors and pre-lock the other cap or caps to allow the vertebral spacing to be adjusted. A cap inserter or rod persuader may be employed to pre-lock the caps. The cap inserter is typically used for the first cap that is seated in its respective yoke. The rod persuader, which can provide a mechanical advantage for seating the rod in the yoke, is typically used for the subsequent cap insertion after the first cap is seated. After the caps are pre-locked and the desired spacing of the vertebrae is accomplished, a final locking instrument is used to tighten the caps into the final-lock position.

Depending on the patient's anatomy, the device implanted, or the preferences of the surgeon, the procedure may be customized by employing various instruments alternative to those previously discussed or by using a different combination of tools. Thus, a number of tools are disclosed below having various configurations that may be suited to particular situations. The various tools can provide surgeons with flexibility to accommodate different patients and may also allow the surgeon to employ tools more suited to the surgeon's preferences.

One such alternative tool is an alternative rod inserter, which functions similar to the previously discussed rod inserter. The alternative rod inserter further includes structure in the form of a latch to limit movement of the members of the shaft assembly to thereby prevent accidental release of the connecting member from the alternative rod inserter. The alternative rod inserter also includes structure configured to engage the yoke manipulators during portions of the insertion procedure to verify correct positioning of the connecting member despite the lack of visual indication.

Another alternative tool is the convincing tool that provides a surgeon with another option for customization. The convincing tool is positioned around the yoke manipulators in order to seat or position the connecting member within the yokes of the pedicle screw assemblies. The convincing tool may be employed to position the rod in a procedure separate from the cap insertion procedure. A counter torque tube may also provide the surgeon with structure to move the connecting member down relative to the yoke of the pedicle screw in order to thereby seat the connecting member.

In addition to the MIS system, a number of the instruments described herein may also be used for a minimally open procedure (mini-open). During a MIS implantation, the implant is typically, though not necessarily, inserted through two or more expanded stab wounds. By comparison, the mini-open procedure can employ a slit opening that spans the distance between the vertebrae where the bone anchors will be seated. A retractor can be used with a mini-open procedure to expand the slit to provide the surgeon sufficient clearance to perform the procedure and, therefore, the instruments used for such a procedure are preferably sized and designed to fit easily within the opening created by the retractor. While the mini-open procedure can be more invasive than a typical MIS procedure, the mini-open procedure may be preferable depending on the patient's anatomy or the surgeon's preferences.

In one aspect of the methods disclosed herein for securing a spinal rod to a vertebral bone, a relatively small incision can be formed at a surgical site adjacent a first vertebral bone. A guideway can be confined through the small incision through which a tool or tools can be used to manipulate a pedicle screw assembly and spinal rod. During such manipulation, the tools can obstruct viewing of the pedicle screw assembly and the spinal rod through the confined guideway. A driving tool extending in the confined guideway can be used to turn a locking device of the pedicle screw assembly secured to the vertebral bone. During such turning, tactile feedback can be generated upon turning of the locking device to a predetermined rotary position in order to indicate that the spinal rod is clamped so that viewing of the locking device and spinal rod through the obstructed guideway to determine the clamping of the spinal rod is unnecessary.

In a further aspect, the turning of the locking device in order to clamp the spinal rod may include stopping rotation of the locking device at the predetermined rotary position at which the tactile feedback is generated. The stopping of the rotation of the locking device may include abutting a lower rod engaging portion against a stop of a turned upper portion of the locking device. The turning of the locking device for clamping the spinal rod includes driving a lower rod engaging portion of the locking device into clamping engagement with the spinal rod.

In another aspect of the system disclosed herein for positioning a spinal rod relative to two or more pedicle screws, a rod insertion tool is provided that includes an inner shaft having an end portion adapted to pivotably engage a spinal rod about a pivot axis and an outer control sleeve surrounding at least a portion of the inner shaft and having an end portion shiftable between a blocking position covering the pivot axis to restrict pivoting of the spinal rod about the pivot axis and an unblocking position spaced from the pivot axis to permit pivoting of the spinal rod about the pivot axis. A spinal rod can be pivotably connected to an end portion of the inner shaft about the pivot axis. The outer control sleeve can be positioned in a blocking position over the pivot axis to prevent pivoting of the spinal rod about the pivot axis. A first portion of the spinal rod can be inserted into a yoke of a first pedicle screw. The outer control sleeve can be moved to the unblocking position away from the pivot axis to permit pivoting of the spinal rod about the pivot axis and a second portion of the spinal rod can be inserted into a yoke of a second pedicle screw by pivoting the spinal rod about the pivot axis. Then the spinal rod can be disconnected from the end portion of the inner shaft.

The rod insertion tool may include a shaft assembly having a longitudinal axis, an inner elongate rod holding member of the shaft assembly extending along the axis of the shaft assembly, an outer shaft member of the shaft assembly extending along the axis of the shaft assembly, and a pivot connection of the rod holding member for pivotally connecting the spinal rod thereto. The outer shaft member of the shaft assembly can be moveable relative to the inner elongate rod member to block the pivot connection to prevent pivoting of the spinal rod.

In another aspect of the system disclosed herein for inserting a cap having a drive recess, into a yoke of a pedicle screw assembly, the cap inserter including an outer shaft having a drive end for insertion into the bore of the cap. The drive end of the outer shaft can have a plurality of prongs. An inner shaft can be disposed within the outer shaft. A cam interface is located between the drive end of the outer shaft and the inner shaft. The inner shaft is shiftable into a biasing position biasing the prongs outwardly for frictionally engaging inner surfaces of the drive recess of the cap in order to securely hold the cap.

In another aspect of the system disclosed herein for inserting a cap having a drive recess into a yoke of a pedicle screw, the cap inserter has an outer cylindrical shaft having a drive end for insertion into the drive recess of the cap. The drive end has a plurality of moveable prongs with a bore between the moveable prongs. The prongs may have internal cam surfaces. The cap inserter further includes an inner cylindrical shaft disposed within the outer shaft and having external cam surfaces. The cam surfaces of the inner shaft are axially shiftable toward the cam surfaces of the outer cylindrical shaft to urge the prongs outwardly for frictionally engaging inner surfaces of the drive recess of the cap in order to securely hold the cap.

In another aspect of the method disclosed herein for gripping a cap having a drive recess insertable into a yoke of a pedicle screw, a split drive end can be inserted into the drive recess of the cap and shifted in a transverse direction into tight engagement with the drive recess of the cap.

In another aspect of the system disclosed herein for inserting a cap having a drive recess into a yoke of a pedicle screw, the cap inserter has a shaft assembly with an elongate drive member having a split drive end configured for engaging the drive recess of the cap. An actuator of the shaft assembly is operable to shift the split drive end of the elongate drive member into tight engagement with the drive recess of the cap for securing the cap to the elongate drive member.

In another aspect of the method disclosed herein for inserting a spinal rod into the yokes of at least two pedicle screw assemblies, a first yoke manipulator can be placed around a yoke of a first pedicle screw assembly. The first yoke manipulator has an axial entrance slot aligned with one of the side openings in the yoke of the first pedicle screw assembly and an axial exit slot aligned with the opposing side opening. A second yoke manipulator can be placed around a yoke of a second pedicle screw assembly. The second yoke manipulator may have an axial entrance slot aligned with one of the side opening in the yoke of the second pedicle screw assembly and an axial exit slot aligned with the opposing side opening. The slots may have a length longer than a depth of the side opening. A spinal rod inserter can be provided having a spinal rod connected thereto about a pivot axis. A distal end portion of the spinal rod can be passed through the entrance and exit slots of the first yoke manipulator to position the pivot axis between the entrance slots of the first and second yoke manipulators. The distal end portion of the spinal rod can then be passed through at least the entrance slot of the second yoke manipulator to a position in the side opening of the yoke of the second pedicle screw assembly. The proximate end portion of the spinal rod may then be positioned in the side opening of the yoke of the first pedicle screw assembly.

In another aspect of the method disclosed here in for positioning a spinal rod between a pair of pedicle screw assemblies, a first yoke manipulator can be positioned around one of the pair of pedicle screw assemblies and a second yoke manipulator can be positioned around the other of the pair of pedicle screw assemblies. Each of the first and second yoke manipulators may have a pair of opposing slots aligned with side opening in yokes of the pair of pedicle screw assemblies. A spinal rod can be provided that connects to an insertion tool about a pivot axis. The spinal rod can be passed through the first yoke manipulator to position the pivot axis between the first and second yoke manipulators. The spinal rod can be freely orientated in the side opening of the yoke of the pedicle screw assembly in the second yoke manipulator. The spinal rod can then be pivoted relative to the insertion tool about the pivot axis to shift the pivot axis from between the first and second yoke manipulators to an opposite side of the first yoke manipulator to position the spinal rod in the side opening of the pedicle screw assembly in the first yoke manipulator.

The minimally invasive surgical system may include a pedicle screw assembly having an anchor for engaging the vertebral bone, a yoke for receiving the spinal rod and a locking device for clamping the spinal rod in the yoke. An elongate tubular member is provided for extending through an incision to allow for tool access to the vertebral bone. A tool is adapted to fit through the tubular member and to turn the locking device until reaching a stop that keeps the tool from turning the locking device by more than a predetermined amount.

The minimally invasive surgical system may include a pedicle screw assembly having an anchor for engaging the vertebral bone, a yoke for receiving the spinal rod, and a non-threaded locking device for clamping the spinal rod in the yoke. An elongate tubular member may extend through an incision to allow for tool access to the pedicle screw assembly anchored to the vertebral bone. A tool is provided and configured to fit through the tubular member and to turn the non-threaded locking device for clamping of the spinal rod in the yoke.

In another aspect of the method disclosed herein for securing a spinal rod to a vertebral bone, a relatively small incision can be formed at a surgical site adjacent a first vertebral bone. A pedicle screw assembly and spinal rod can be manipulated with surgical tools via the small incision. The pedicle screw assembly can be secured to the first vertebral bone and a locking device of the pedicle screw assembly can be turned to a first predetermined rotary position in a yoke of the pedicle screw assembly. The turning of the locking device can be restricted beyond the first predetermined rotary position. The spinal rod received in the yoke can be adjusted in the yoke of the pedicle screw assembly with the locking device at the first predetermined rotary position. The locking device can then be turned beyond the first predetermined rotary position to clamp the spinal rod in the yoke once the spinal rod has been adjusted. A guideway is confined through the small incision through which tools manipulate the pedicle screw assembly and the spinal rod with viewing of the pedicle screw assembly and spinal rod during manipulation being obstructed by the confined guideway and tool or tools therein.

BRIEF DESCRIPTION OF THE DRAWINGS

FIG. 16 A is a side view of the obturator of FIG. 16;

FIG. 16 B is another side view of the obturator of FIG. 16;

FIG. 16 C is a cross section of the obturator of FIG. 16B along line A-A;

FIG. 16 D includes various plan views of portions of the obturator of FIG. 16;

FIG. 17 A is a top plan view of the docking sleeve of FIG. 17;

FIG. 17 B is a front view of the docking sleeve of FIG. 17;

FIG. 17 C is a side view of the docking sleeve of FIG. 17;

FIG. 17 D is a cross section of the docking sleeve of FIG. 17;

FIG. 17 E is a side view of a receiver of the docking sleeve of FIG. 17;

FIG. 17 F is an end view of the docking sleeve of FIG. 17;

FIG. 17 G is a magnified view of a portion of the docking sleeve of FIG. 17;

FIG. 17 H is a side view of a retainer;

FIG. 17 I is a cross section of a the retainer of FIG. 17H;

FIG. 19 A is a side view of the facing tool of FIG. 19;

FIG. 19 B is a top view of the facing tool of FIG. 19;

FIG. 19 C is a side view of the facing tool of FIG. 19;

FIG. 19 D is a magnified view of a portion of FIG. 19 C;

FIG. 19 E is a cross section view of a facing tool of FIG. 19;

FIG. 19 F is a side view of a portion of the facing tool of FIG. 19;

FIG. 19 G is a top plan view of a portion of the facing tool of FIG. 19 F;

FIG. 21 A is a side view of a screw driver of FIG. 21;
FIG. 21 B is a cross section view along line A-A of a portion of the screw driver of FIG. 21;
FIG. 21 C is a top view of a portion of the screw driver of FIG. 21;
FIG. 21 D is a bottom plan view of the screw driver of FIG. 21;
FIG. 21 E is a side view of the screw driver of FIG. 21;
FIG. 21 F is a cross section view of a portion of the screw driver of FIG. 21;
FIG. 21 G is a bottom plan view of the screw driver of FIG. 21;
FIG. 21 H is a side view of a portion of the screw driver of FIG. 21;
FIG. 22 A is a side view of a portion of the yoke manipulator of FIG. 22;
FIG. 22 B is a side view of the yoke manipulator of FIG. 22;
FIG. 22 C is a top plan view of the yoke manipulator of FIG. 22;
FIG. 22 D is another side view of the yoke manipulator of FIG. 22;
FIGS. 23F-23L are various views of portions of the yoke manipulator of FIG. 22.

FIG. 44 B is another perspective view of a cap inserter;
FIG. 50D is a cross-sectional view of the spinal fixation device showing a recess formed in the screw head in which a low profile anvil insert is received for clamping of the spinal rod thereagainst;
FIG. 50E is a cross-sectional view similar to FIG. 50D showing the relative sizes of the various components of the spinal fixation device;
FIG. 50J is an exploded perspective view of another form of the spinal fixation system showing a bone screw and a coupling device including a coupling member, a cam lock member, a spring clip connector member, a clamping member, and an insert for securing a spinal rod relative to the bone screw;
FIG. 52 is a perspective view of a docking port;
FIG. 53 is a front view of the docking port of FIG. 52;
FIG. 54 is a side elevation view of the docking port of FIG. 52;
FIG. 55 is a top view of the docking port of FIG. 52.

FIG. 65A is a top view of a portion of the guide bar of FIG. 65;

FIG. 96 is a perspective view of two yoke manipulators with the yokes and bone anchors mated therewith, and a final locker;

FIG. 97C is an exploded view of the rod inserter of FIG. 97A showing the components of the rod inserter;

FIG. 103B is a perspective view of an end portion of the alternative rod inserter of FIG. 103A showing the structure for connecting the spinal rod to the rod inserter;

FIG. 103C is a perspective view of the alternative rod inserter of FIG. 103A;

FIG. 103D is a perspective view of a locking sleeve of the alternative rod inserter of FIG. 103A;

FIG. 105B is a bottom plan view of the stabilization tube of FIG. 105a showing the internal geometry of the stabilization tube.

The elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements may not be depicted in order to facilitate a less obstructed view of the various structures. It will further be appreciated that certain actions and/or steps may be described or depicted in a particular order of occurrence while those skilled in the art will understand that such steps can be performed in different orders and that certain steps may be omitted, depending upon patient need and/or surgeon preference.

DETAILED DESCRIPTION OF THE PREFERRED EMBODIMENTS

Figure 1:
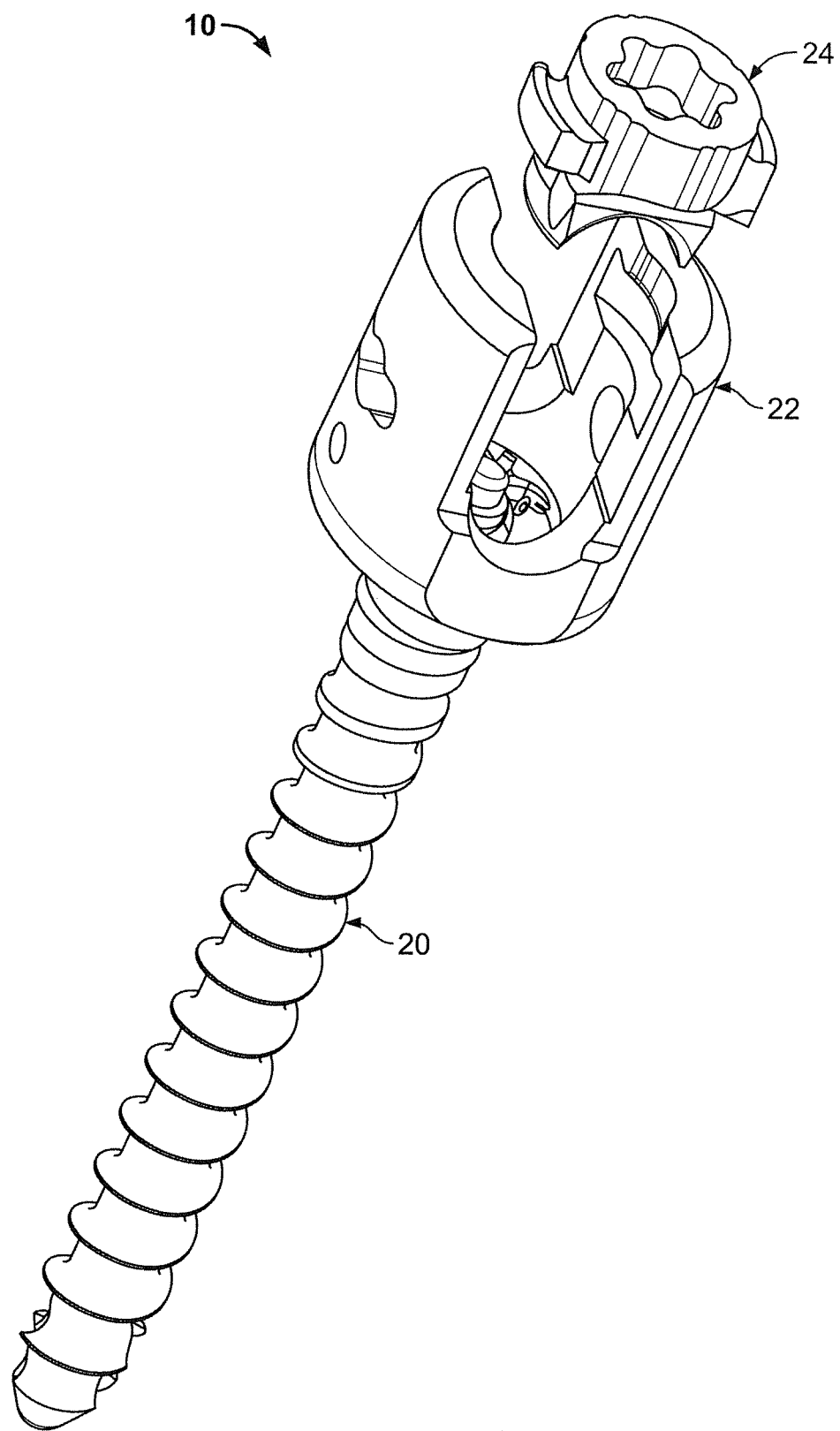
FIG. 1 is a perspective view of a bone anchor, yoke, and closure cap.
Figure 2:
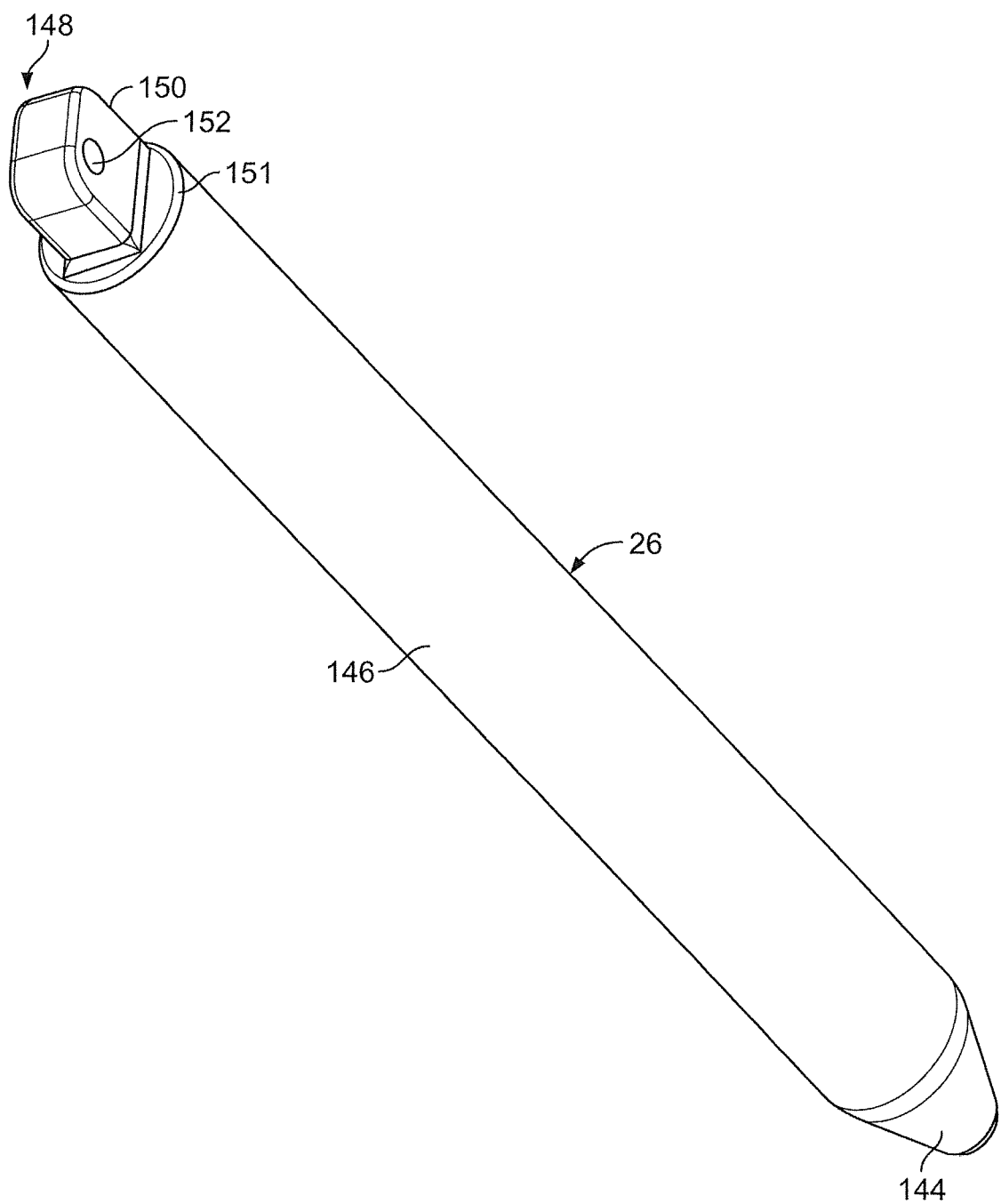
FIG. 2 is a perspective view of a MISS connecting member.
Figure 3:
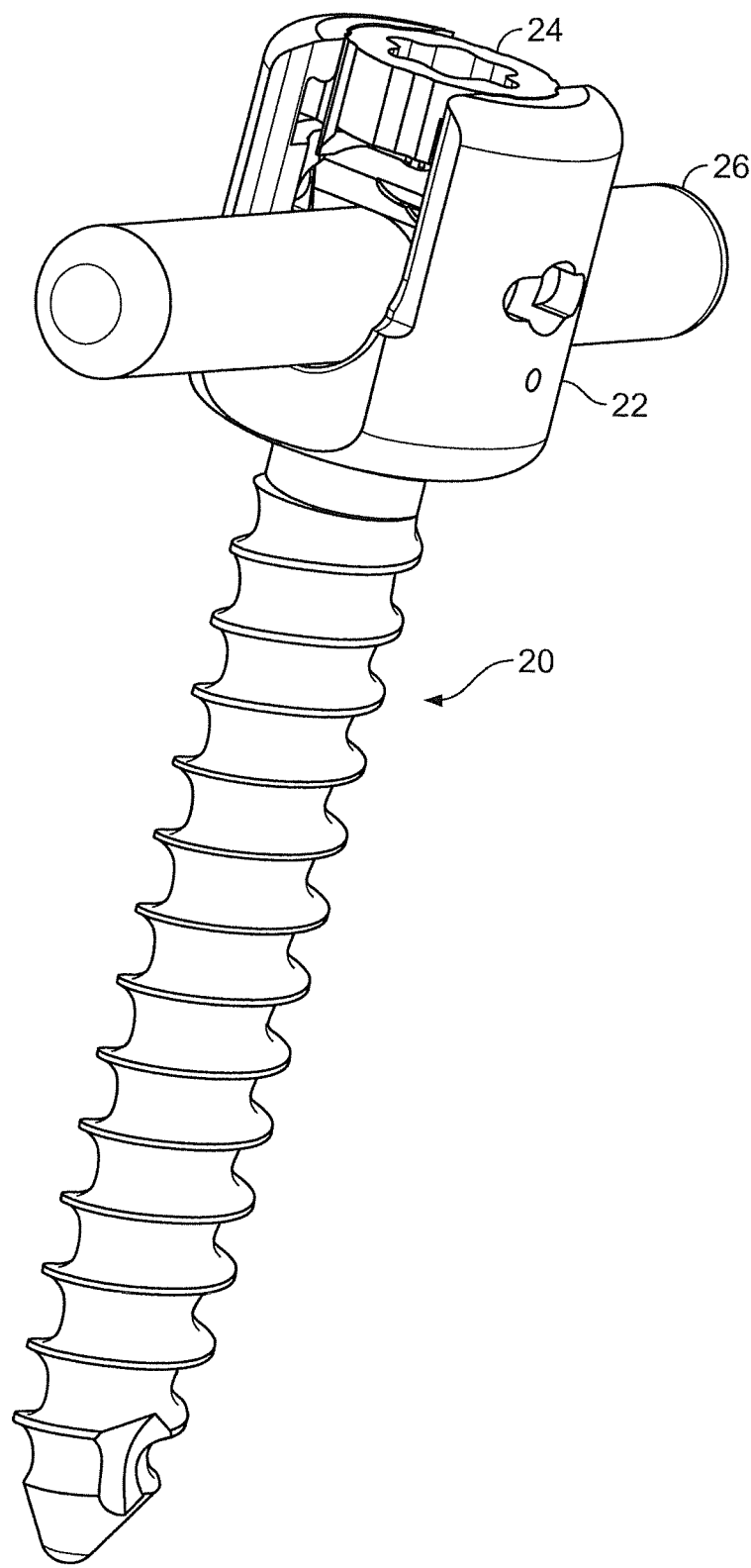
FIG. 3 is a perspective view of a portion of a connecting rod, a bone anchor, a yoke, and a closure cap.
Figure 4:
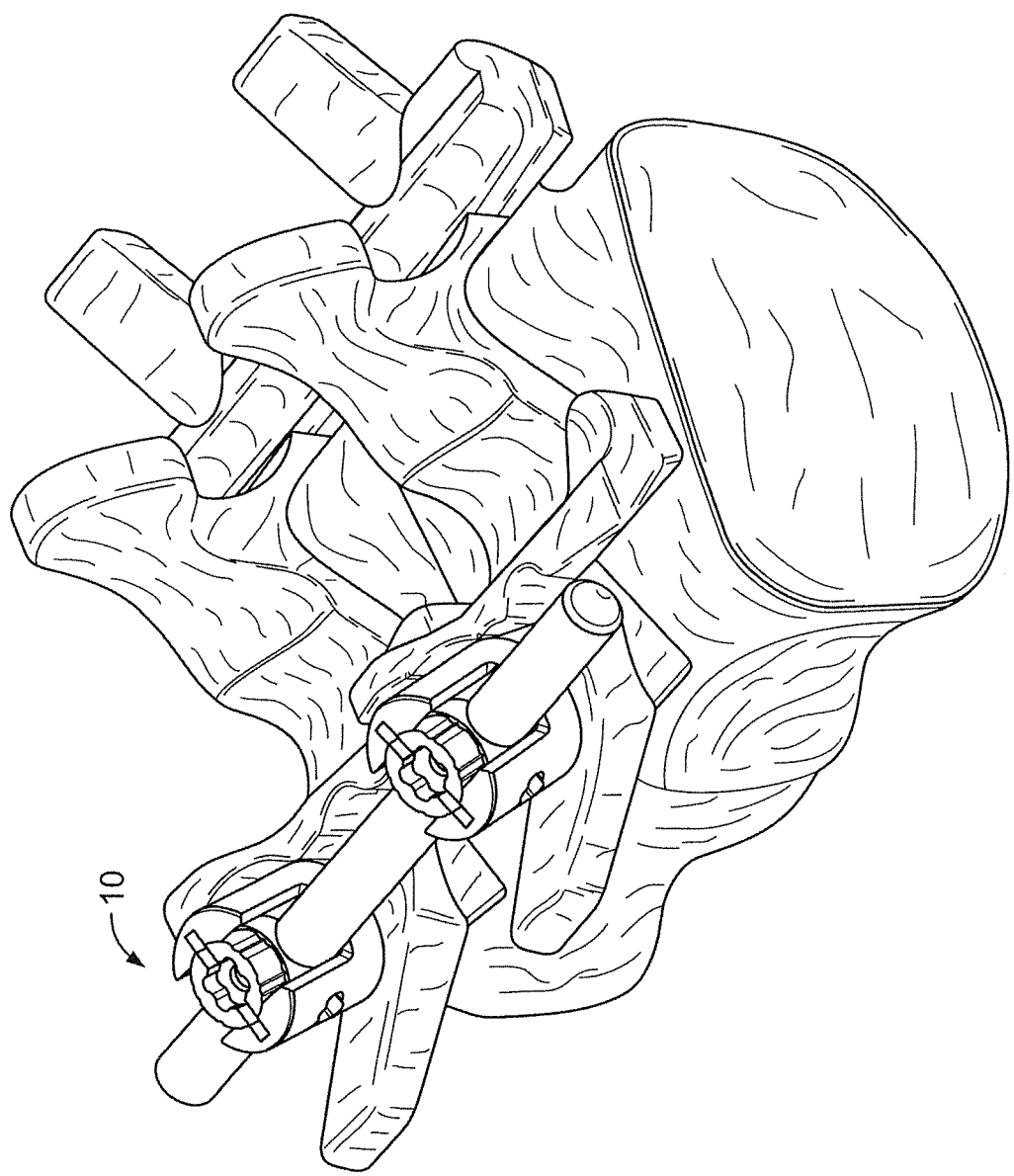
FIG. 4 is a perspective view of an MISS implant.

In the preferred embodiment, the MISS is utilized to implant a fixation device. In FIG. 1, the device 10 is shown as including a bone anchor or screw 20, a yoke 22 and a closure cap 24. While the cap 24 is preferably non-threaded, a threaded embodiment is also contemplated. The cap 24 locks into the anchor yoke 22 such that a spinal rod or connecting member 26 is fixedly held into position. The connecting member 26 is illustrated in FIG. 2. FIG. 3 shows a portion of a connecting rod 26 seated into the yoke 22. One embodiment of the implant, illustrated in FIG. 4, includes two anchors, and a connecting rod 26. For example, a similar system is disclosed in applicants' assignee's co-pending application PCT/US2004/003605 and U.S. patent application Ser. No. 10/973,659. Both of which are hereby incorporated in their entirety. Since the bone anchor 20, yoke 22, closure cap 24, and connecting member 26 are implanted into the body it is preferably that they be constructed of biocompatible material.

Figure 5:
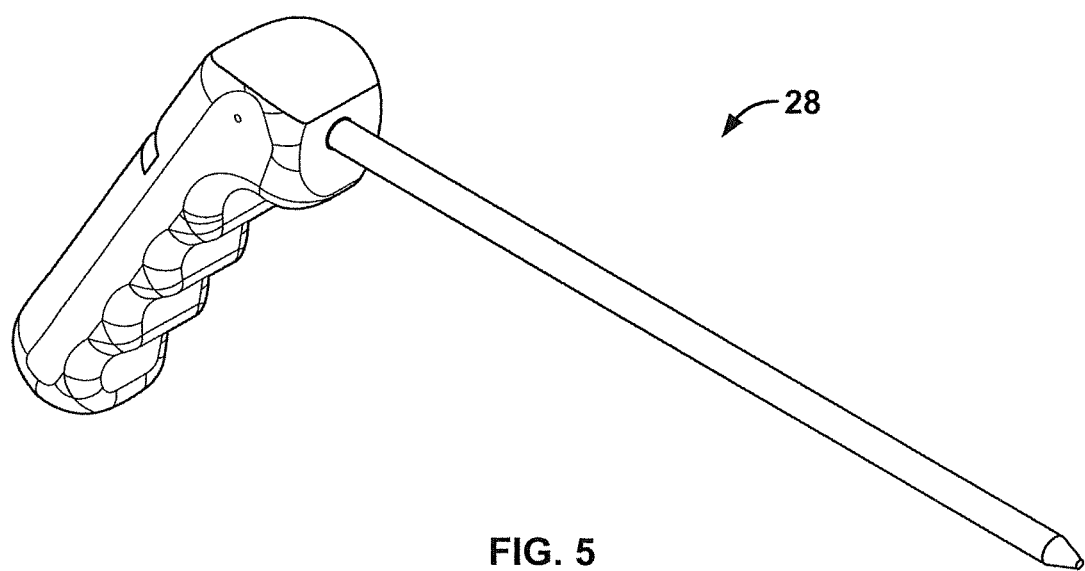
FIG. 5 is a perspective view of a Jamshidi needle without a guidewire inserted therein.
Figure 6:
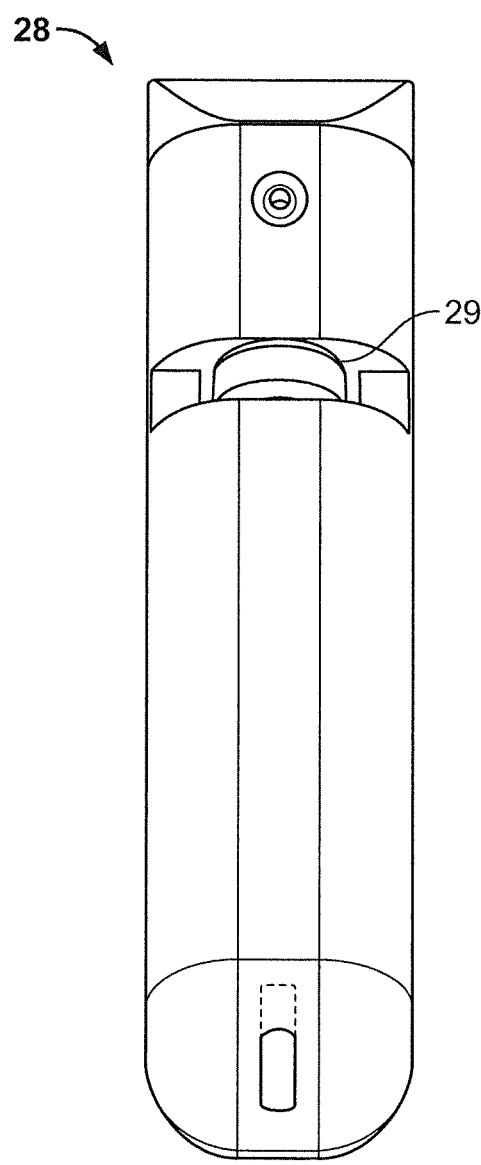
FIG. 6 is a rear plan view of the handle of the Jamshidi needle of FIG. 5.
Figure 7:
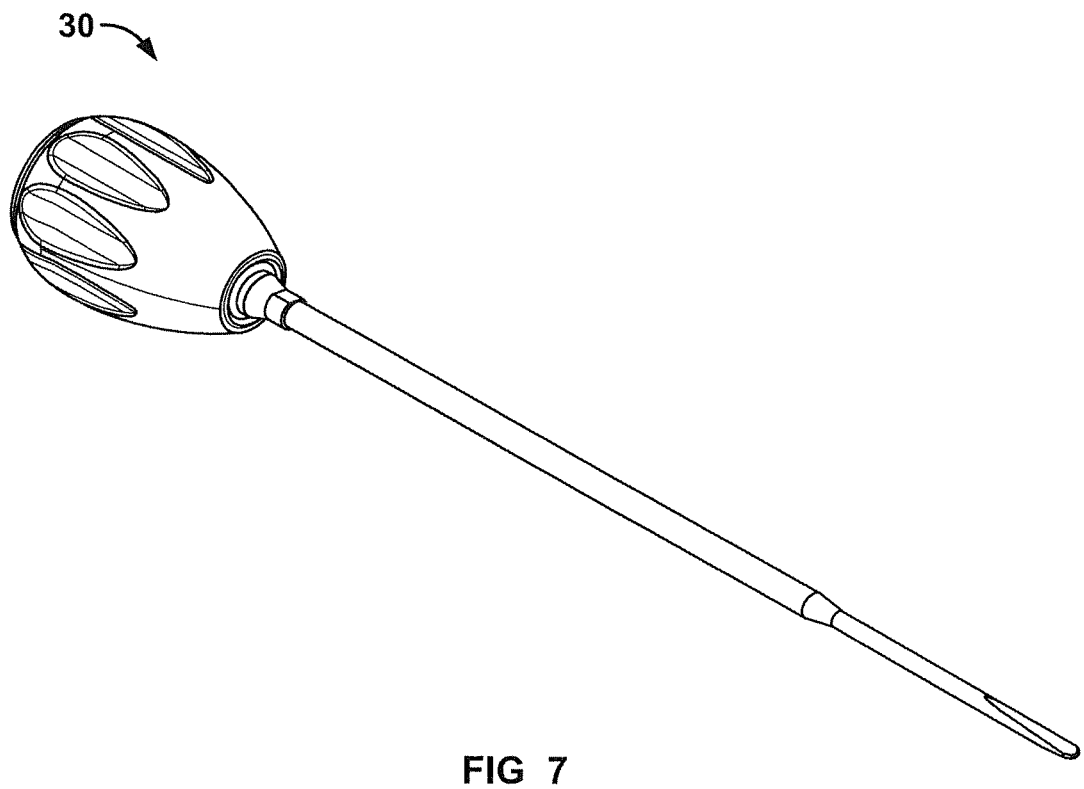
FIG. 7 is a perspective view of a pedicle finder.
Figure 8:
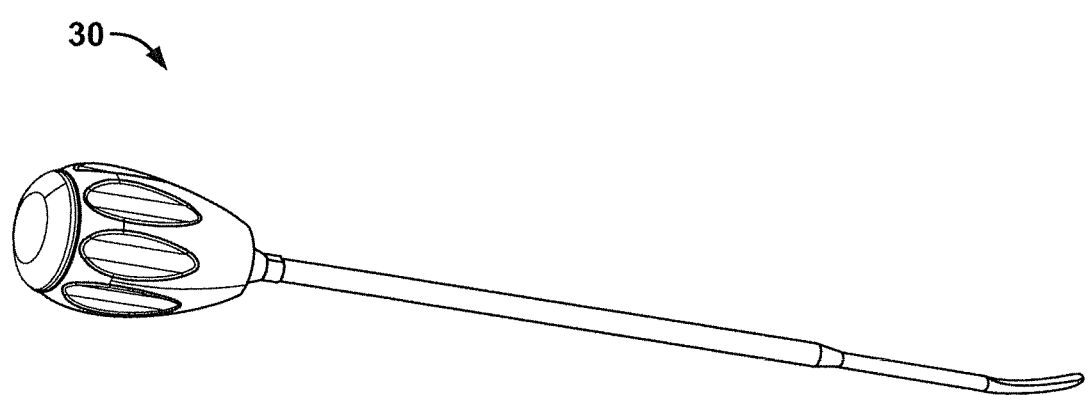
FIG. 8 is a perspective view of a pedicle finder having a curved insertion end.

Starting with proper implant placement is generally necessary for a successful procedure. The surgeon needs to identify the pedicle anatomy to determine anchor 20 placement. To begin, a surgeon may percutaneously insert a Jamshidi needle 28 over the posterior spinal anatomy. FIG. 5 illustrates the Jamshidi needle 28. The Jamshidi needle 28 is typically coupled with a guidewire 32. The handle of the Jamshidi needle 28 includes a clickwheel 29. The clickwheel 29, as shown in FIG. 6, is turned until the guidewire 32 is held firmly into position. After the needle 28 and guidewire 32 are coupled together, the assembly is then advanced into the patient. Guidance radio-imagery may be used. Gaining access using the needle 28 provides the surgeon tactile feedback regarding boney landmarks. At this time, a surgeon may also employ a pedicle finder 30, shown in FIGS. 7 and 8, to help identify the spinal anatomy. Alternatively, if the guidewire 32 was not inserted with the Jamshidi needle 28, it can be entered into the surgical site after the needle.

After entering through the skin, the guidewire 32 is then driven to a predetermined depth until secure. Wherever the guidewire 32 placed is typically the general target location for one of the bone anchors 20. Throughout the procedure, a fluoroscopic or other imaging device may be used to assure accurate placement of the guidewire 32, implant, and/or other tools. Using such an imaging tool, prevents placing the tools incorrectly or driving the instruments or implants in the wrong location, or too deeply into the body tissue as this could harm vital body tissue such as vascular or nerve tissue.

The guidewire 32 is preferred to have a self-cutting and self-tapping thread, however, the thread type and insertion means vary by surgeon preference. Alternatively, the guidewire 32 may have a non-threaded sharpened end for advancement through soft tissue and piercing the bone. Such a guidewire 32 is preferably constructed of biocompatible metals or alloys such as stainless steel, titanium, or nitinol.

Once the guidewire 32 has been positioned at the surgical site, the surrounding tissue may be stretched and/or incised to provide passage of additional MISS tools. To stretch the tissue, a number of series dilators 33 or open ended sleeves, can be slid down the guidewire 32 one on top of another. As shown in FIG. 11 A-11 H, the series dilators 33 are tubes with one end having a sloped nose 35 to allow for easy insertion into the tissue. Each dilator expands slightly in diameter and thereby expands the tissue as the dilator is slid down the guidewire 32 into the surgical site. After the series dilators have sufficiently stretched the tissue, a docking sleeve 34 may be slid down the series dilators. The docking sleeve 34, discussed in more detail below, provides a window to the surgical site. The docking sleeve 34 may be slid down a dilator with a slightly smaller diameter than the docking sleeve 34.

Figure 12:
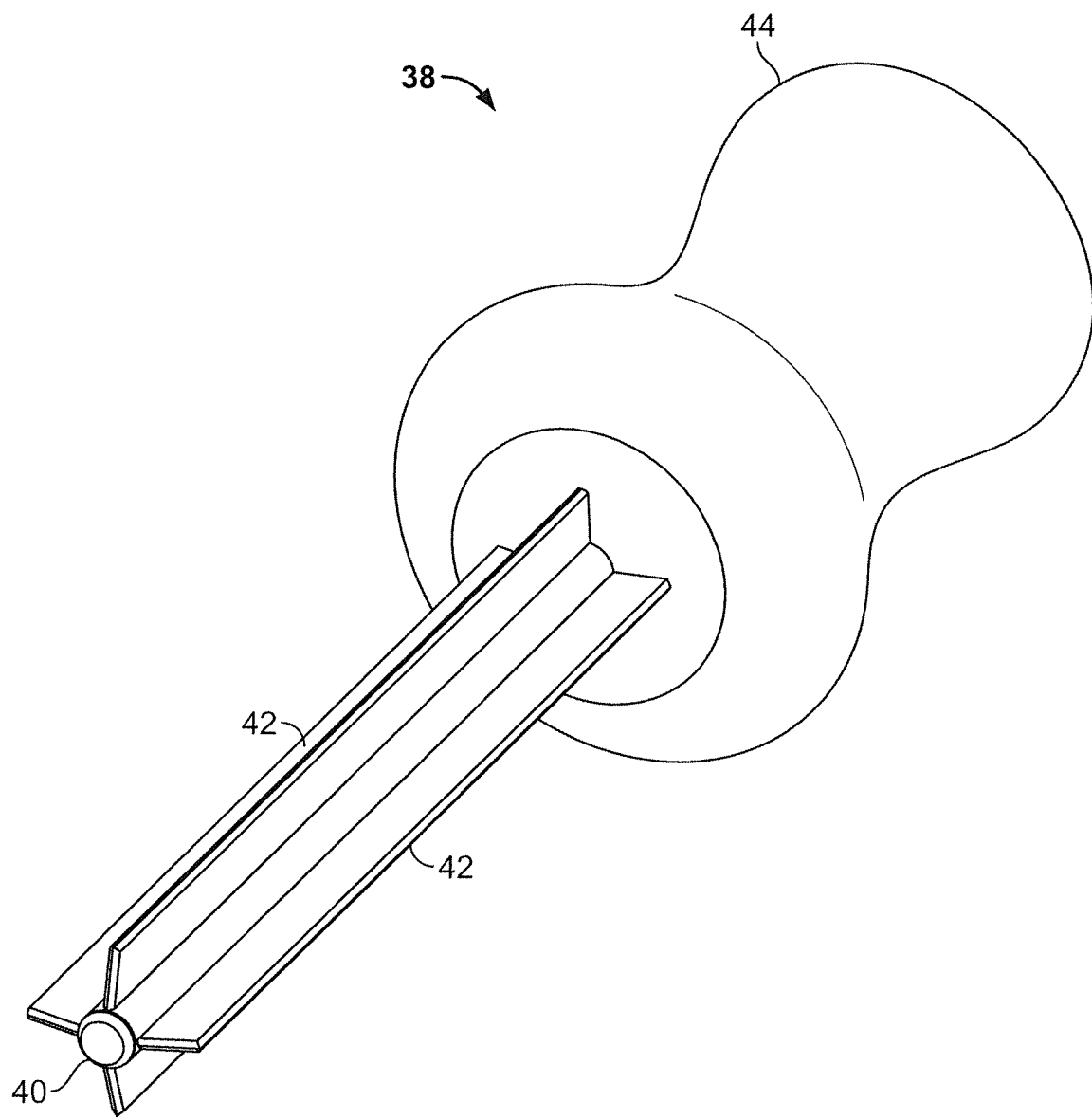
FIG. 12 is a perspective view of a cannulated cutting instrument.

Alternatively, the surgeon could use a scalpel or another cutting instrument such as the cannulated cutting tool 38 of FIG. 12 to incise the tissue along a path generally following the guidewire to gain increased access to the surgical site. The cannulated cutting tool 38 may have a tube or guide portion 40, a plurality of fin portions 42 that may be used to precisely create an opening of the tissue, and a handle portion 44.

Figure 13:
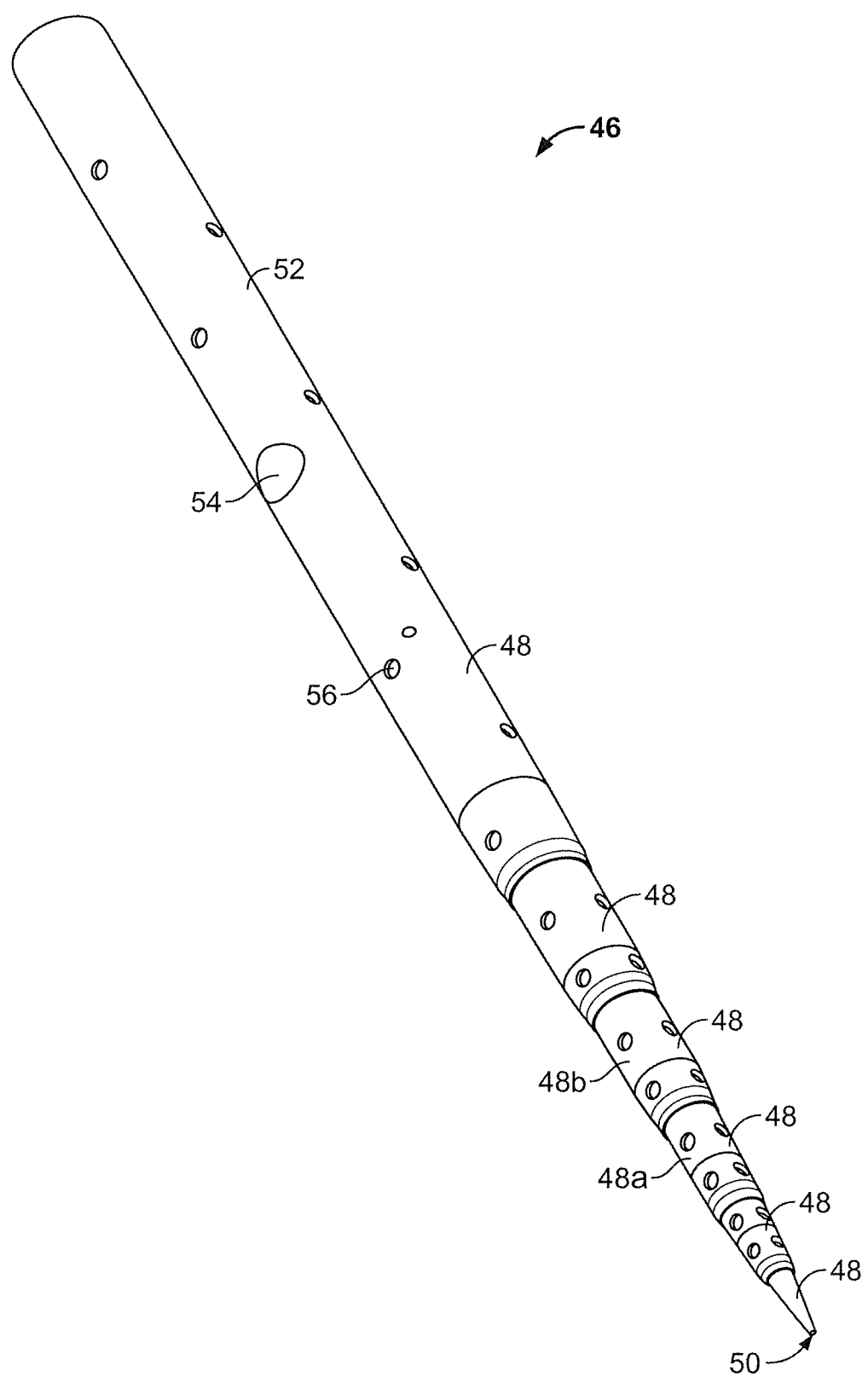
FIG. 13 is a perspective view of a harpoon dilator in an extended configuration.

Various other dilation tools may also be employed. For example instead of the series dilators, a surgeon may use a harpoon dilator 46, shown in FIGS. 13, 14, and 15. The harpoon dilator 46 is spring biased to a fully extended position shown in FIG. 13. The harpoon dilator 46 comprises a series of progressively larger spring loaded interdependent cylinder portions 48. Each interdependent cylinder 48 is preferably biased away from the next cylinder by a series of springs. Such springs have a progressively higher spring constant as the diameter of the independent cylinder portions 48 increases. The dilator 46 may further include a reduced diameter nose 50 that is cannulated to allow for passage of the guidewire 32.

Figure 14:
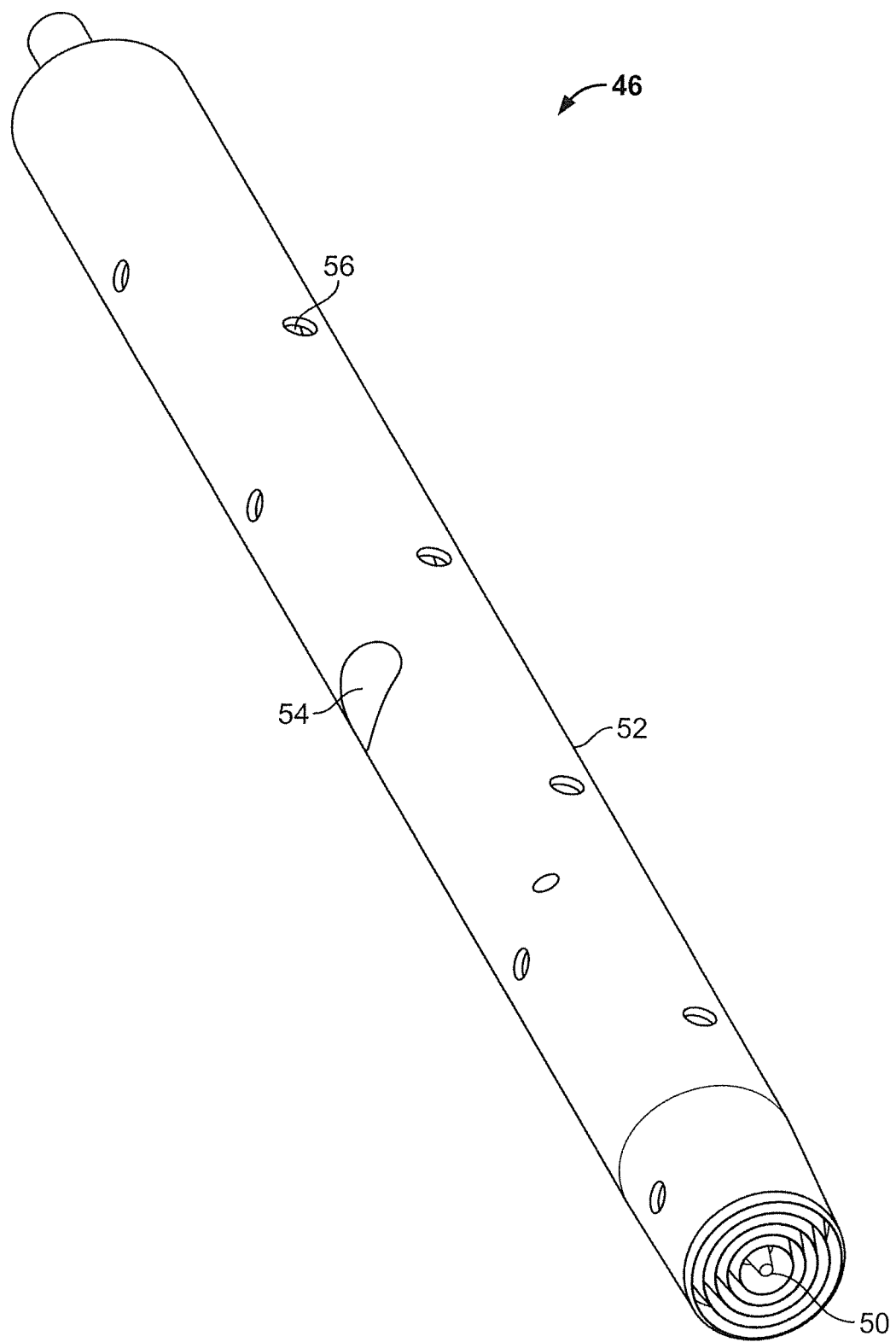
FIG. 14 is a perspective view of a harpoon dilator in a collapsed configuration.
Figure 15:
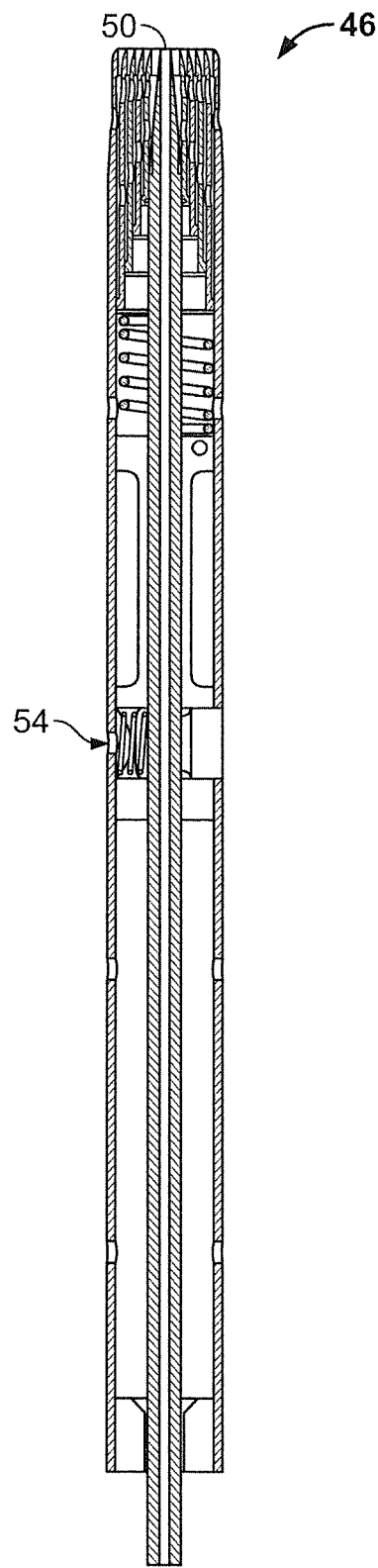
FIG. 15 is a cross sectional view of the harpoon dilator of FIG. 14.

The harpoon dilator 46 is placed over the guidewire 32 by placing the end of the guidewire 32 into the cannulated nose 50. The dilator 46 may then be slid down the guidewire 32 until the nose 50 contacts the bone surface. The surgeon then drives the extended dilator toward the bone, progressively dilating the soft tissue by pushing a smaller diameter cylinder 48a into an adjacent, larger diameter cylinder 48b. When the final cylinder 52, which is also the largest, has been pushed into contact with the surrounding soft tissue and contacts or closely approximates the bone, the surrounding tissue has been stretched to the diameter of the largest cylinder 52. When the harpoon dilator has been fully collapsed it automatically locks into this configuration as shown in FIGS. 14 and 15. To extend the harpoon dilator to its original configuration, a release button 54 may be engaged.

The harpoon dilator 46 can be removed from the system either in the collapsed or extended position by sliding it back off the guidewire 32. While the harpoon dilator 46 can be used alone, it may also be sized to cooperate with the docking sleeve 34 or the yoke manipulator assembly 141 to assist the introduction of these tools into the soft tissue. In addition, the harpoon dilator 46 could be configured to stretch the tissue without the assistance of the guidewire 32. The dilator 46 may include cleansing holes 56 for instrument sanitation.

Figure 16:
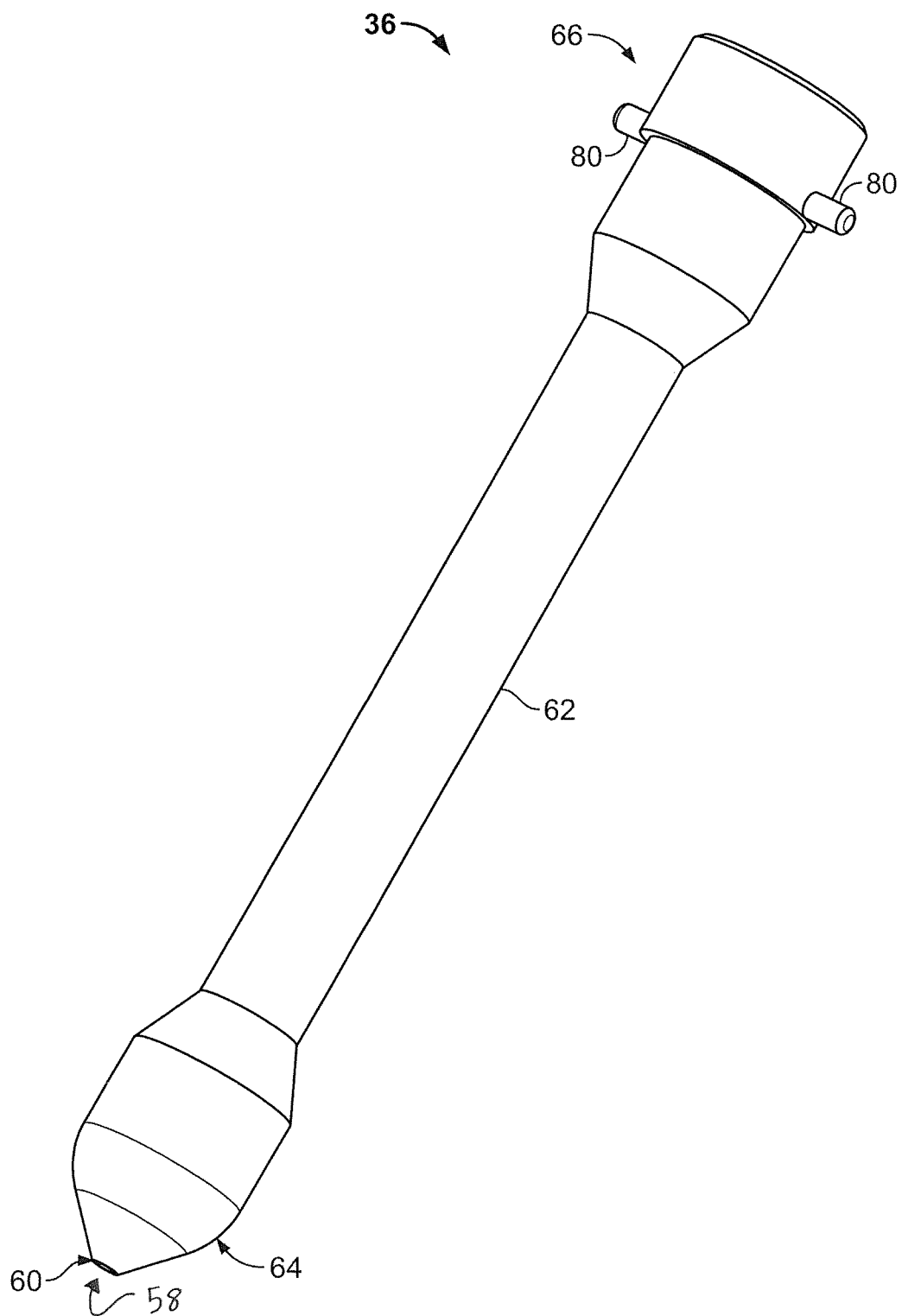
FIG. 16 is a perspective view of an obturator.
Figure 16A:
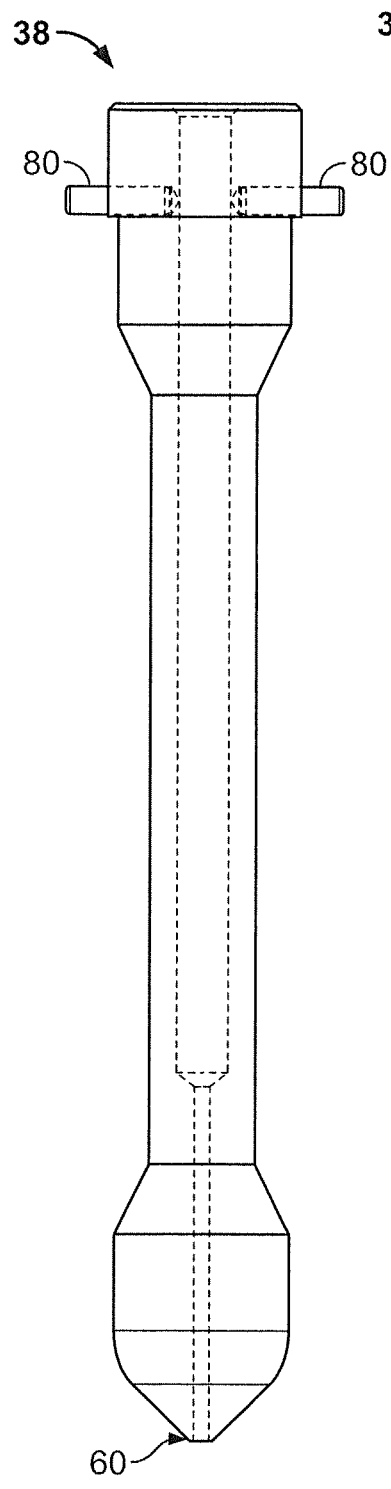
Figure 16B:
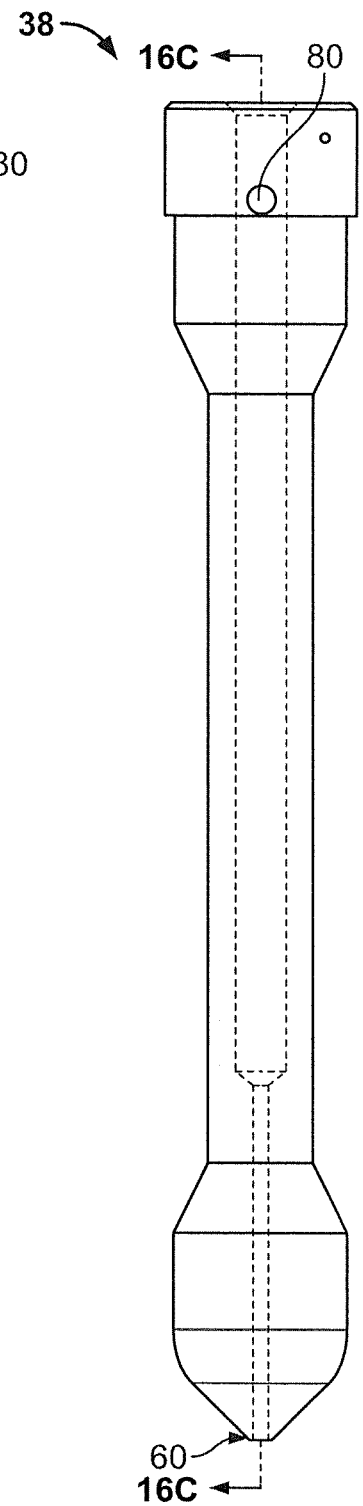
Figure 16C:
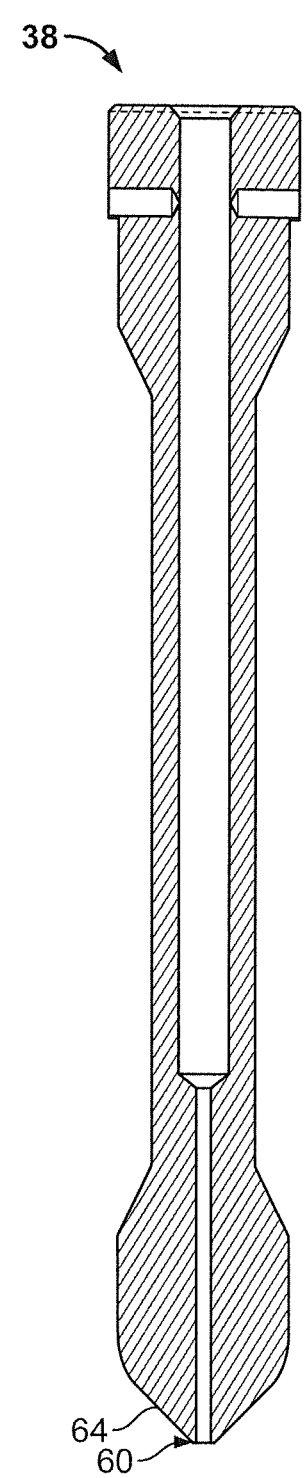
Figure 16D:
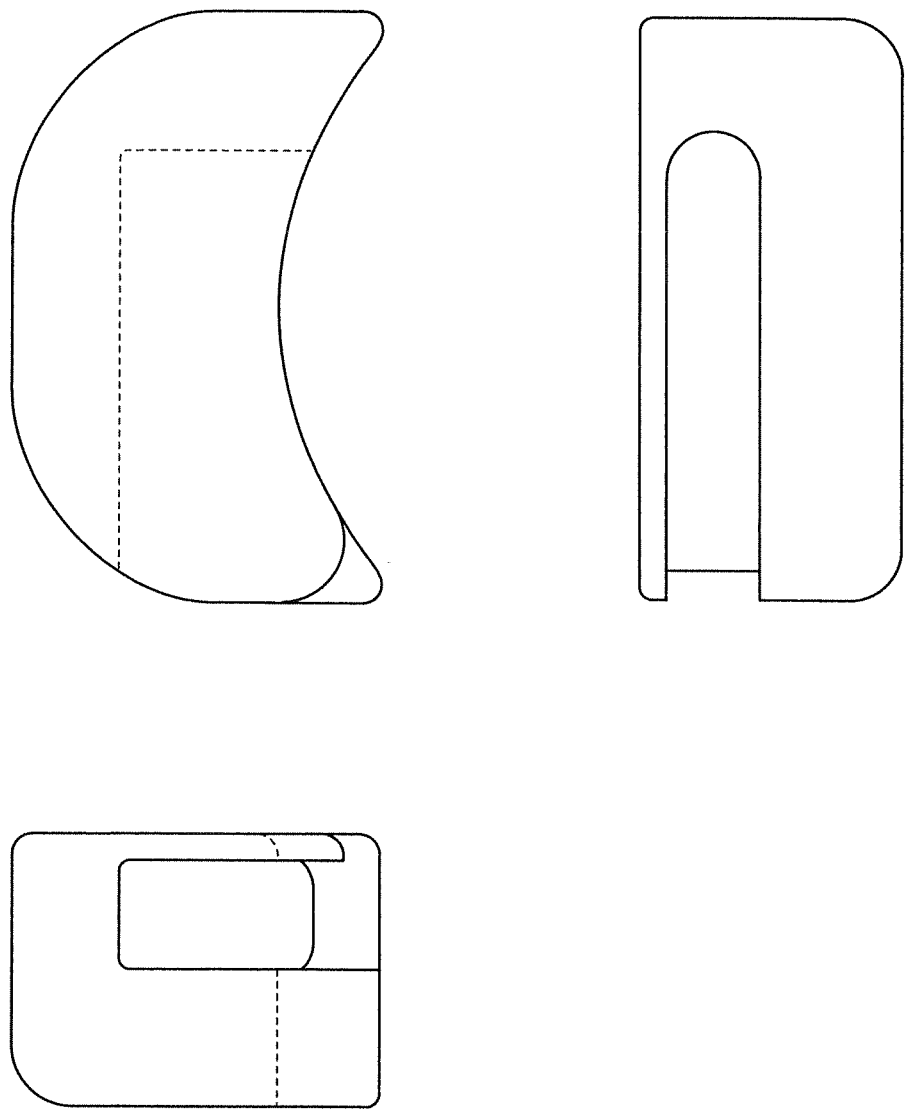

A single obturator 36, shown in FIG. 16, or set of obturators 36 may also be used to dilate the tissue surrounding the surgical site. The obturators 36 may be used in conjunction with or instead of incising the tissue along the guidewire 32. When a set of obturators 36 is employed, the surgeon uses obturators 36 with progressively larger diameters. By using the cannulated opening 58 in the obturators 36, the tool is advanced down the guidewire 32. After the obturator 36 has been advanced down the guidewire 32 and the tissue stretched, the first obturator 36 may be removed and another larger obturator 36 then inserted. Utilizing such tools stretches the surrounding tissue to accommodate the obturator's increasing size. This process continues until the surgeon has employed an obturator 36 with a sufficiently large enough diameter to create sufficient stretching of the surrounding tissue.

Figure 9:
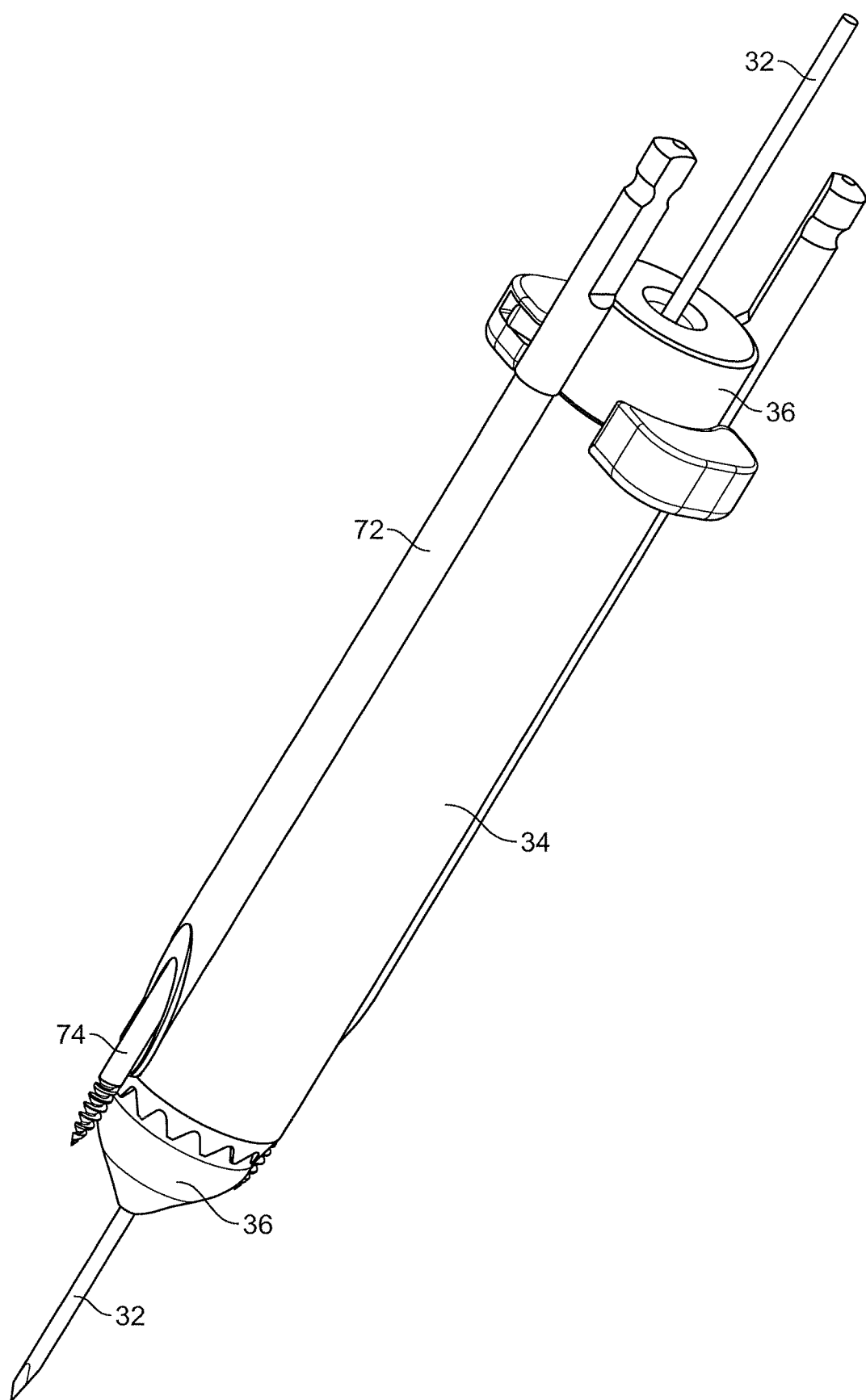
FIG. 9 is a perspective view of an assembly of a docking sleeve with retainers, and fasteners located therein, and a guidewire and an obturator.
Figure 10:
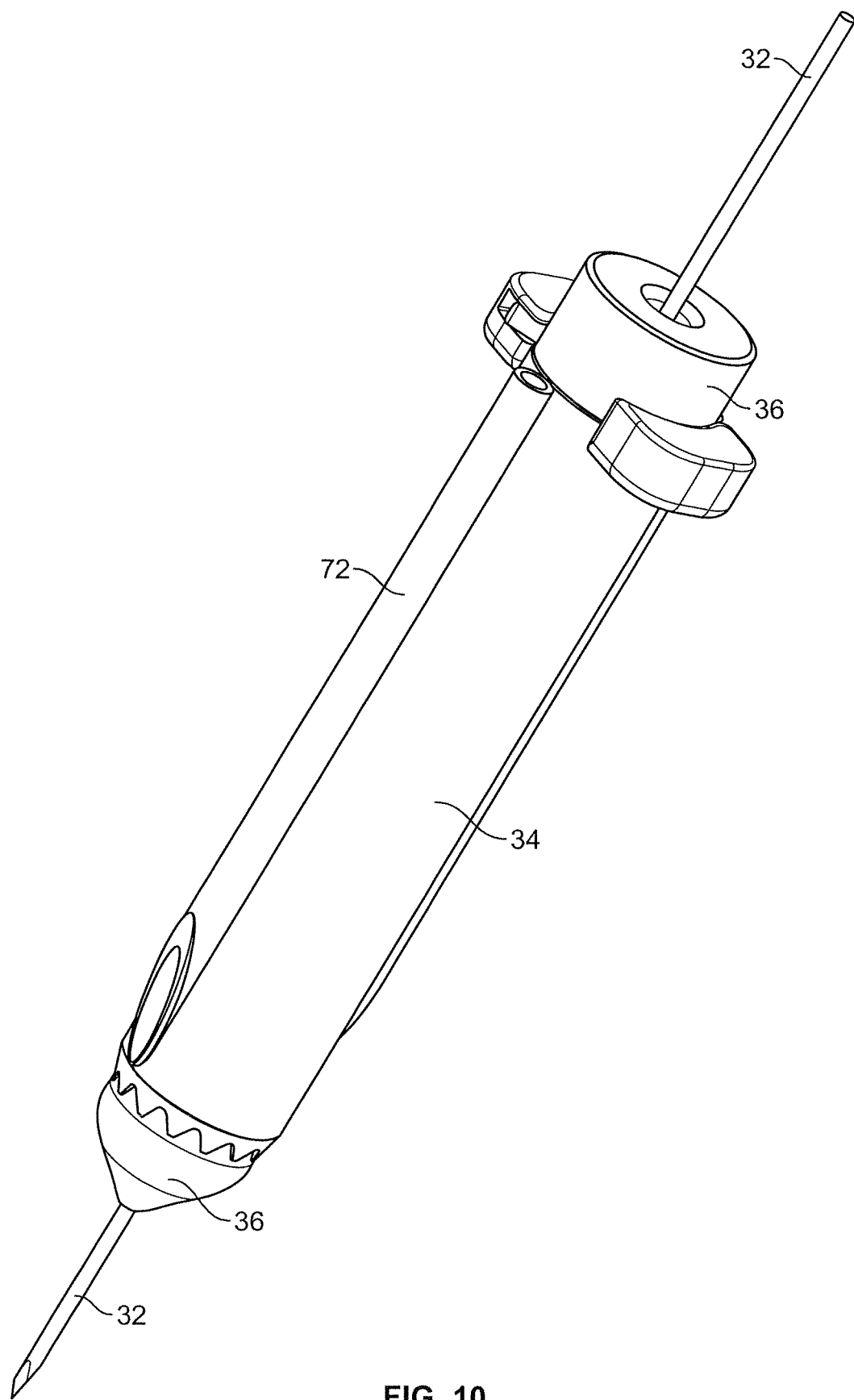
FIG. 10 is a perspective view of an assembly of a docking sleeve with retainers, without fasteners, a guidewire, and an obturator.
Figure 11A:
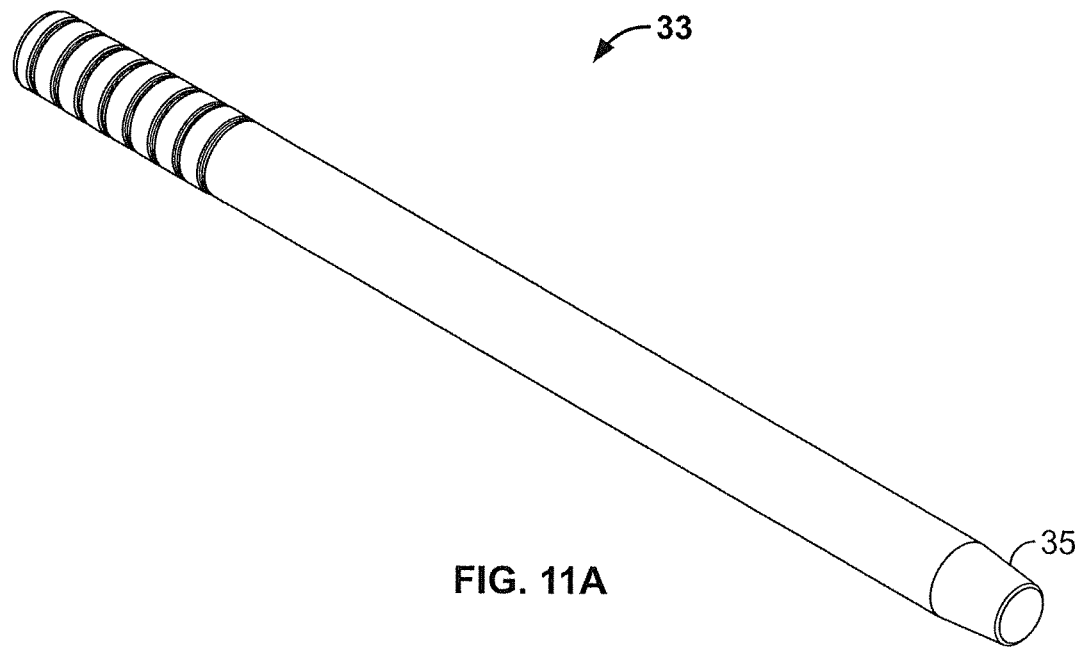
FIGS. 11 A-11H depict series dilators.
Figure 11B:
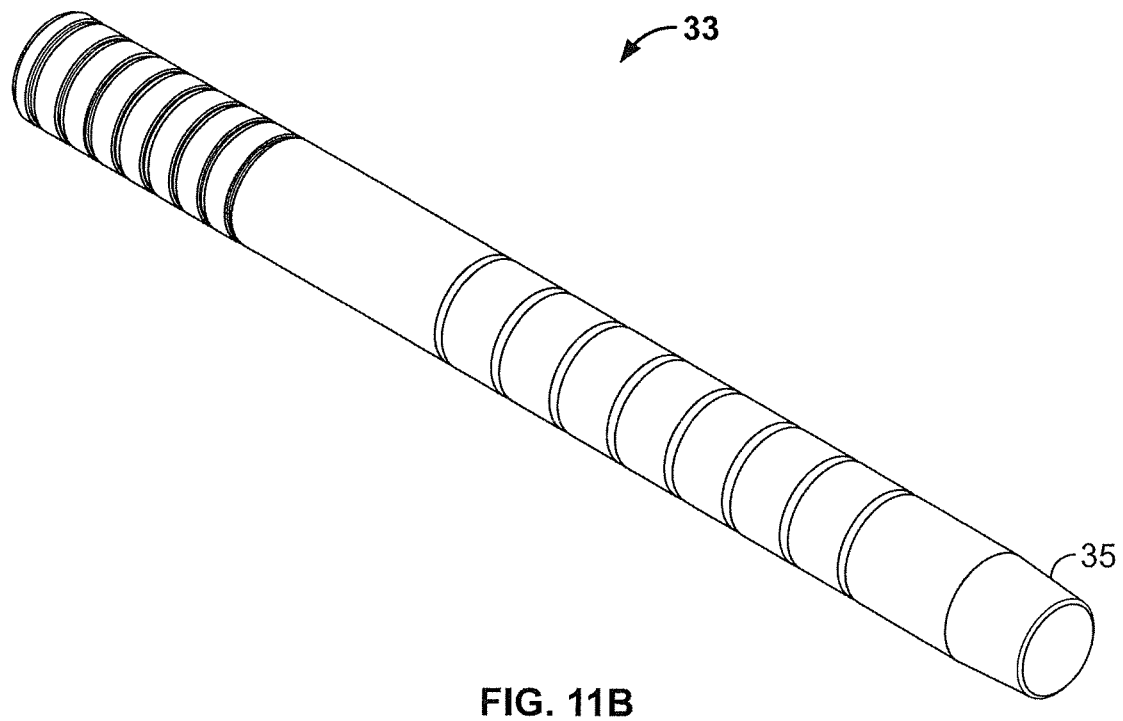
Figure 11C:
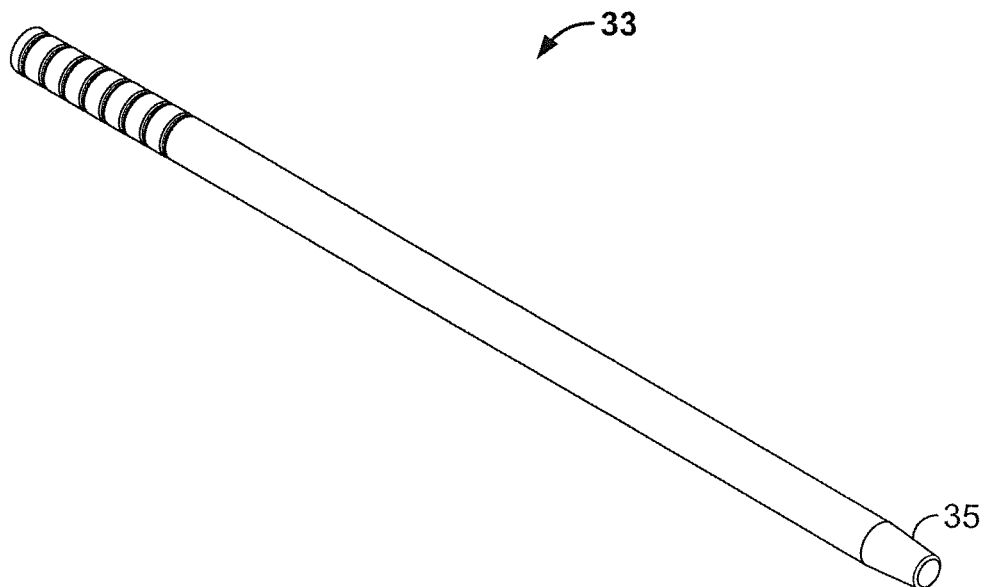
Figure 11D:
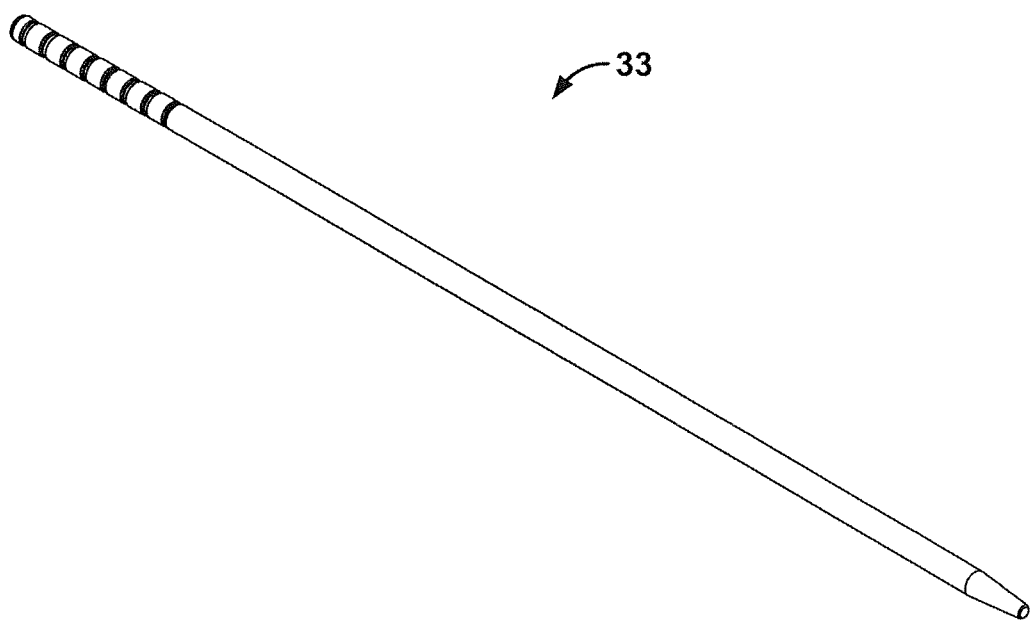
Figure 11E:
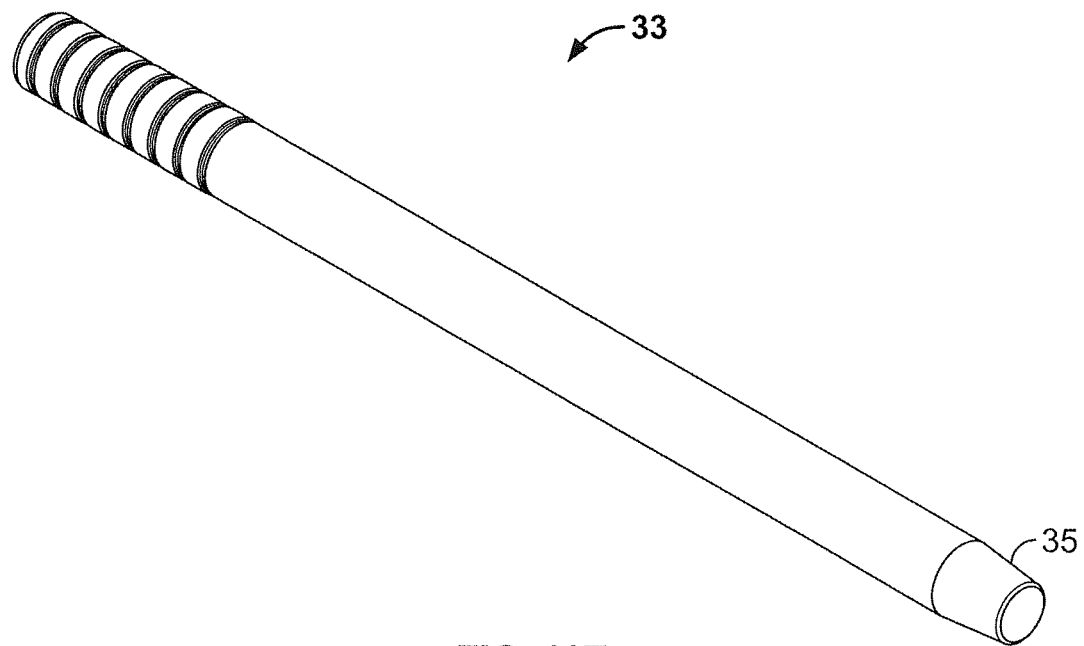
Figure 11F:
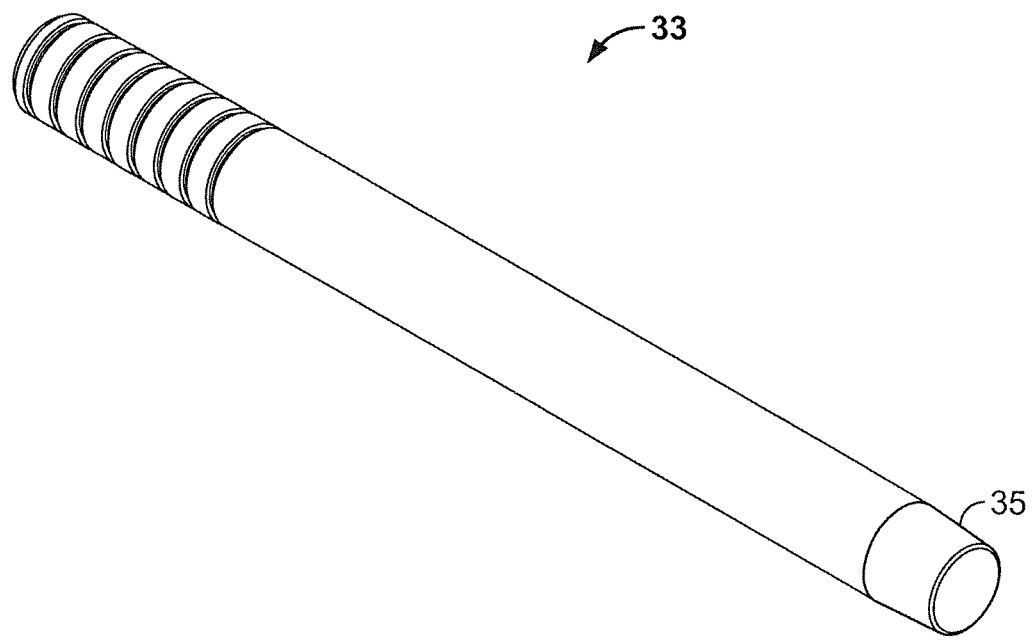
Figure 11G:
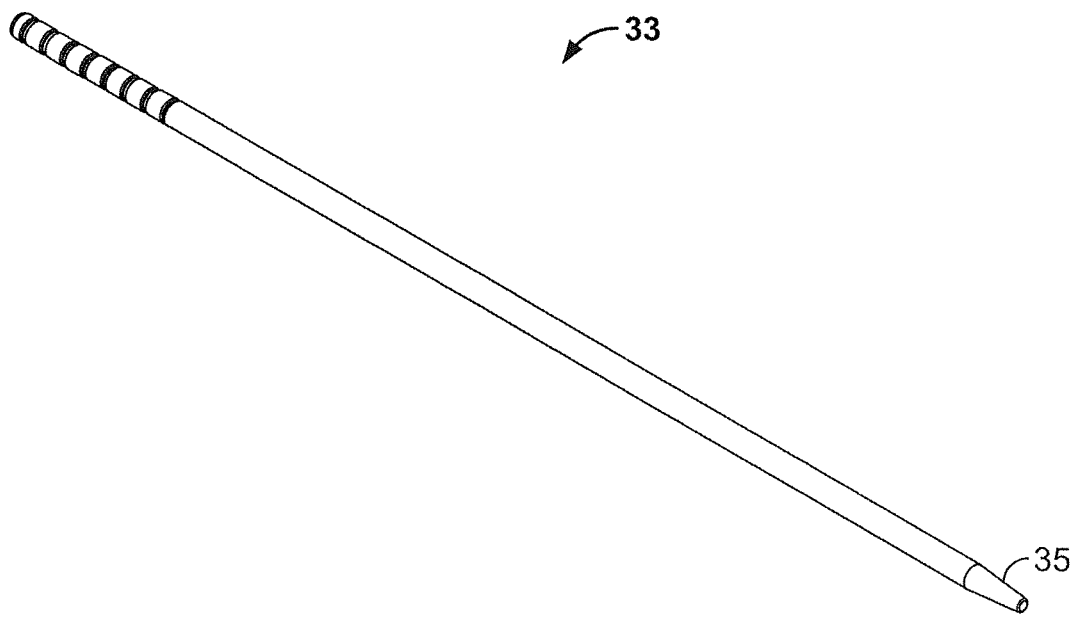
Figure 11H:
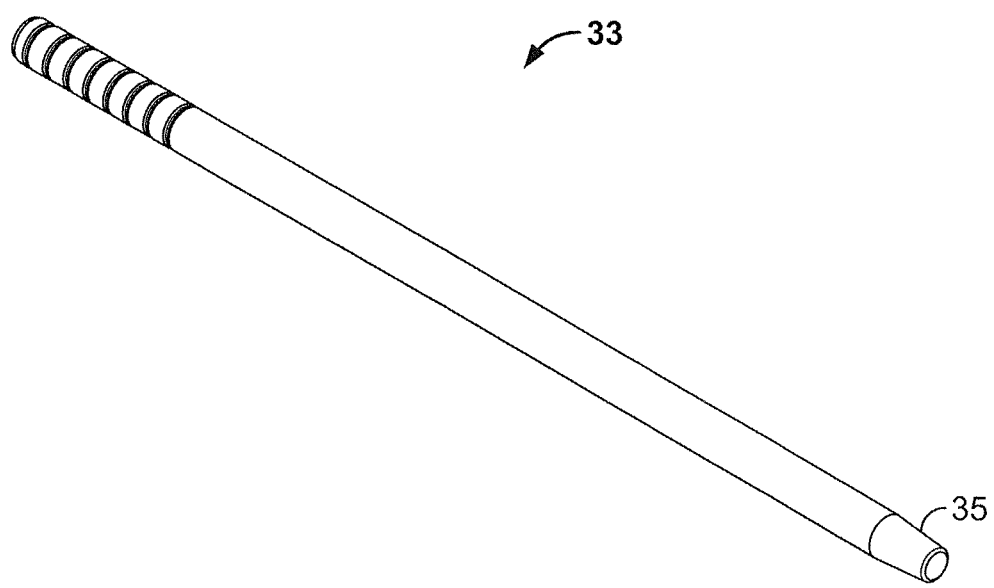

It is preferred that the obturator(s) 36 have a nose 60 that is sloped, curved, or otherwise well-suited for dilating tissue from a smaller diameter to a larger diameter as the obturator 36 is fed down the guidewire 32. The shaft 62 of the obturator 36 may be the same, reduced, or enlarged in diameter, compared to the nose 60. However, transitional sloped or radiused portions 64 are preferred to ease retraction of the device. The obturator 36 may include locking pins, boss, flange, threads or other structure to lock the obturator 36 into position. The proximal end of the obturator 36 may have a handle 66 or other area suited for improving the grip such that the instrument may be advanced into the opening in a controlled fashion by the surgeon. Optimally, the ergonomic handle will improve grip, minimize slippage and surgeon discomfort. After the obturator(s) 36 have been used to stretch the tissue, the docking sleeve 34 can be advanced into the surgical site. FIGS. 9 and 10 illustrate how the docking sleeve 34 and obturator 36 would be advanced down the guidewire 32.

By sufficiently stretching the soft tissue, the force required to insert and position the bone anchors 20 and/or the docking sleeves 34 is reduced while also minimizing the potential damages to the soft tissues. This reduces the difficulty of the insertion procedure. After sufficiently stretching the incision through utilization of various dilation tools, the surgeon may then insert the docking sleeve 34, however, the bone anchors 20 may be inserted without the docking sleeves 34 in place. In this instance, it is preferred that the anchors are cannulated and follow the pre-positioned guidewire path, however surgeons may still choose to use non-cannulated anchors.

The docking sleeve 34 (FIG. 17) is the minimally invasive surgical portal through which at least the initial portion of the surgery may be performed. Depending on factors such as incision size and tissue elasticity, the surgeon may choose among several techniques to advance the docking sleeve 34 through the soft tissue toward the bone. For example, after the surgeon dilates the soft tissue using series dilators, obturator(s) 36 or the harpoon dilator 46 as discussed above, a final obturator 36, pre-loaded and housed within the docking sleeve 34, is advanced down the guidewire 32 together with the docking sleeve 34 toward the bone. If the obturator 36 and docking sleeve are advanced together, the obturator 36, after reaching the bone, may then be disengaged from the docking sleeve 34 such that the docking sleeve 34 then continues to advance until it contact the bone surface.

Another option for stretching the tissue and advancing the docking sleeve, combines several tools discussed previously. A smaller diameter obturator 36 may be advanced down the guidewire 32 to the site of the bone and one or more series dilators or open ended sleeves of larger diameter may then be guided over the initial obturator 36 until the desired tissue dilation is achieved. At that point in time, the docking sleeve 34 may then be advanced over the final expansion sleeve.

In another alternative, the docking sleeve 34 may be introduced over an obturator 36 by sliding the docking sleeve 34 over the final obturator 36. For example, the final obturator 36 may have a diameter slightly smaller than the internal diameter of the docking sleeve 34. In addition, the docking sleeve 34 could be introduced into the wound after the obturator 36 or expansion sleeves are removed by inserting a removable positioning plug. The plug keeps the docking sleeve generally centered over the guidewire 32.

Figure 17:
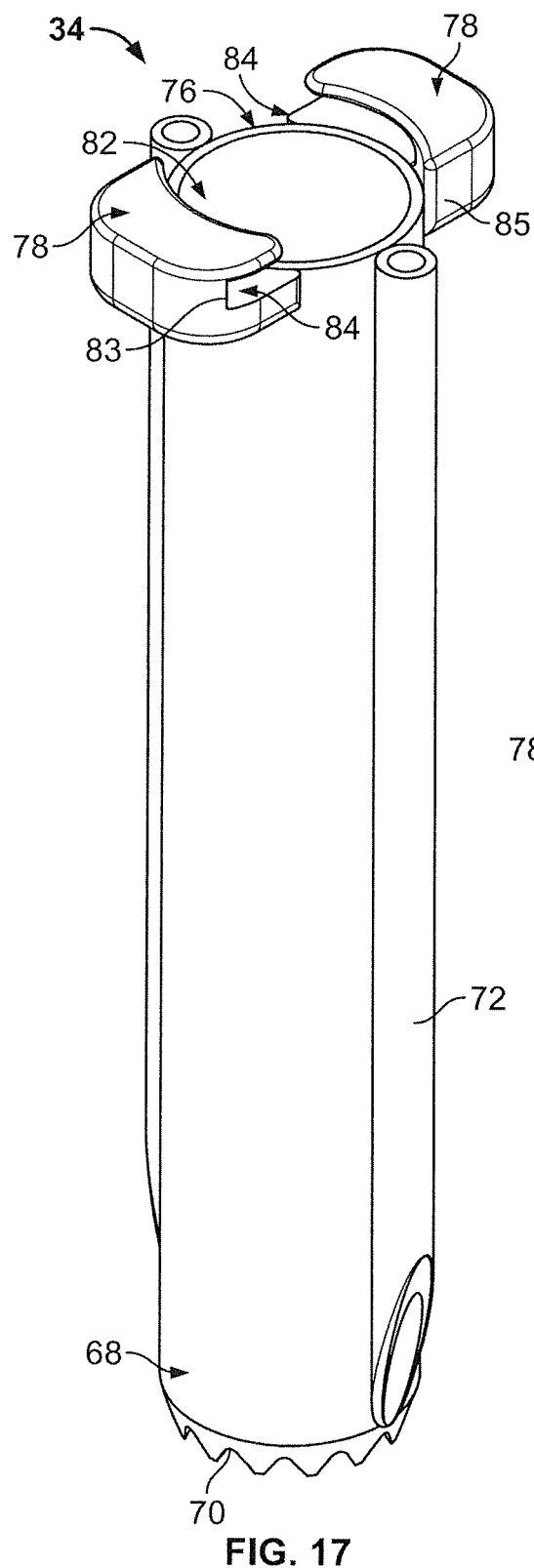
FIG. 17 is a perspective view of a docking sleeve.
Figure 17A:
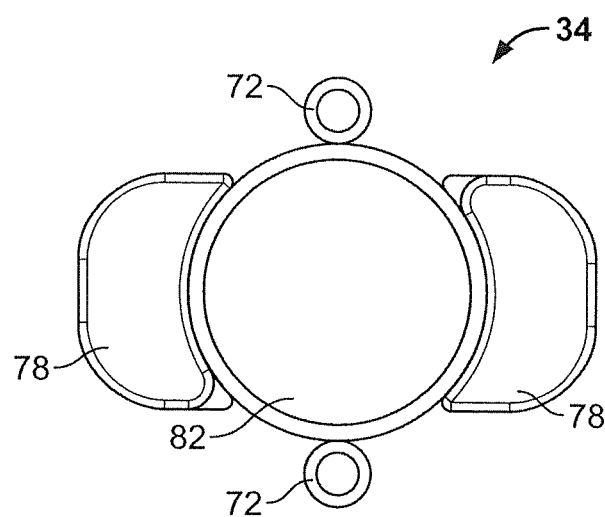
Figure 17B:
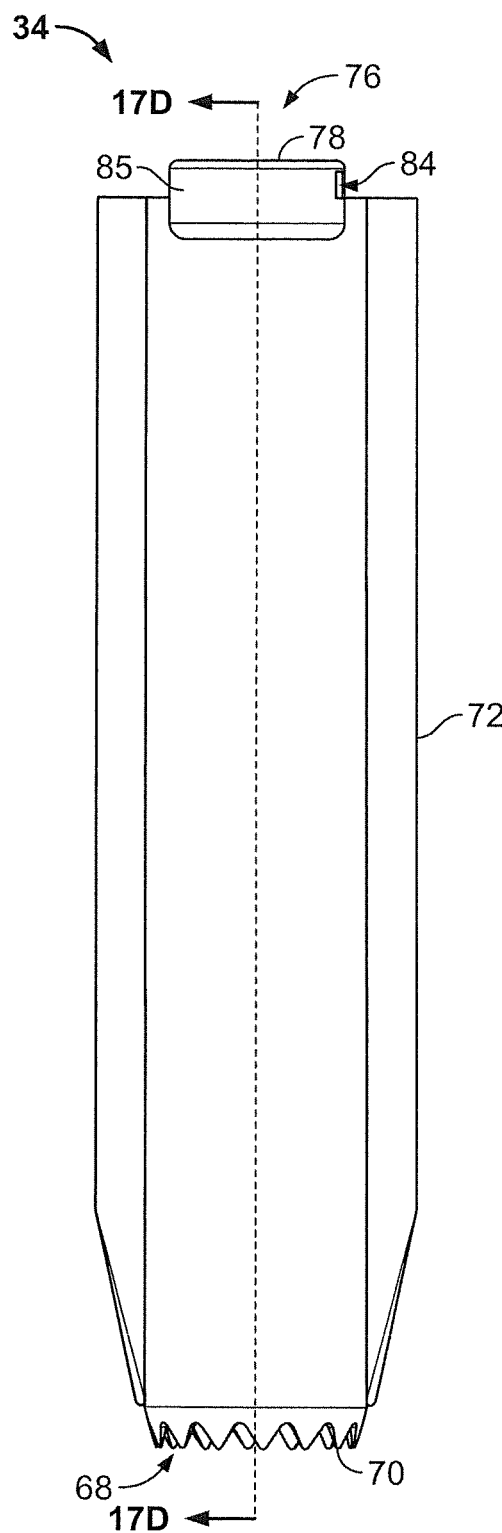
Figure 17C:
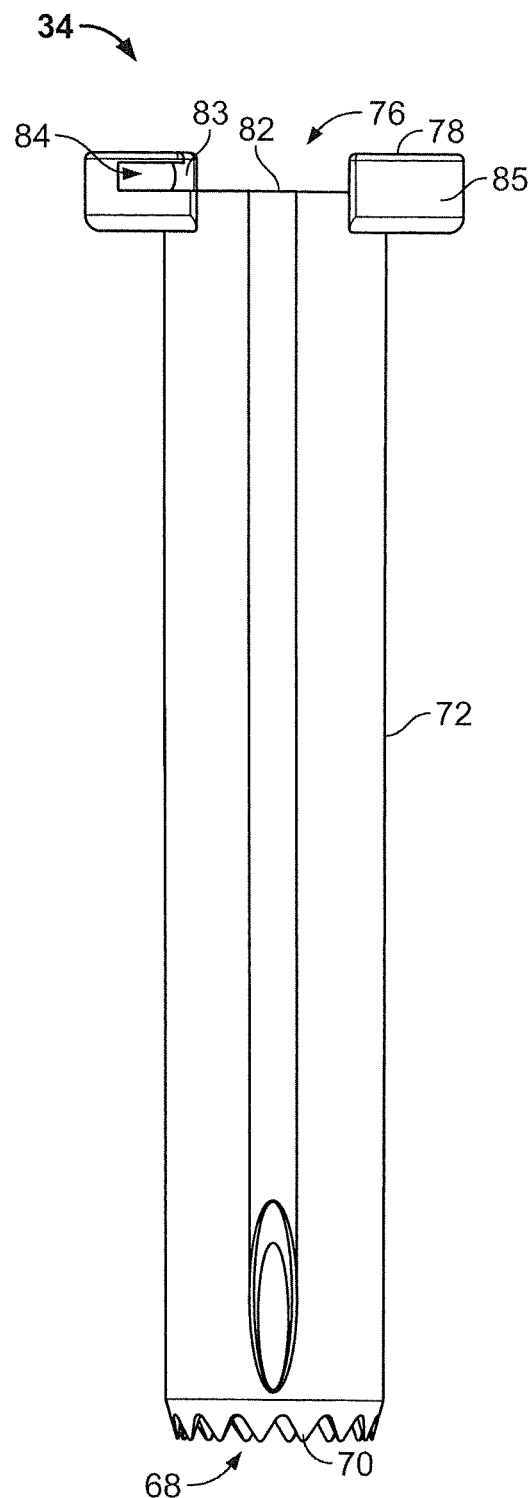
Figure 17G:
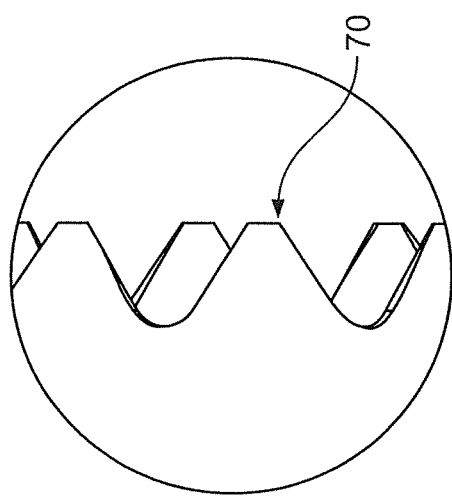
Figure 17F:
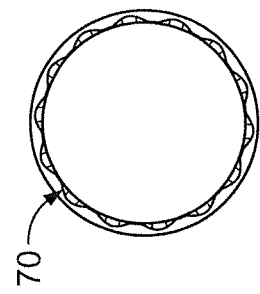
Figure 17H:
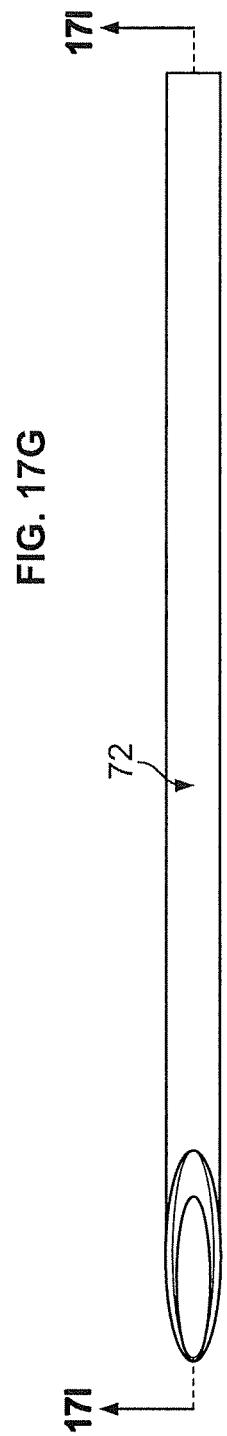
Figure 17I:
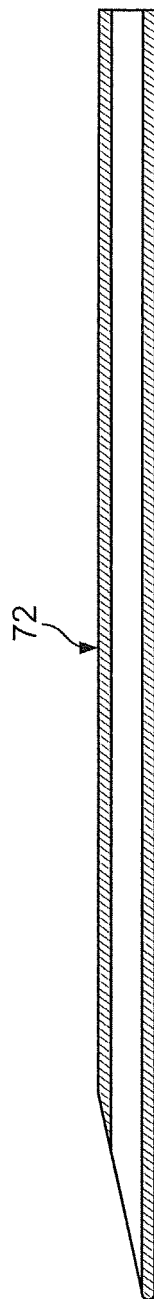
Figure 18:
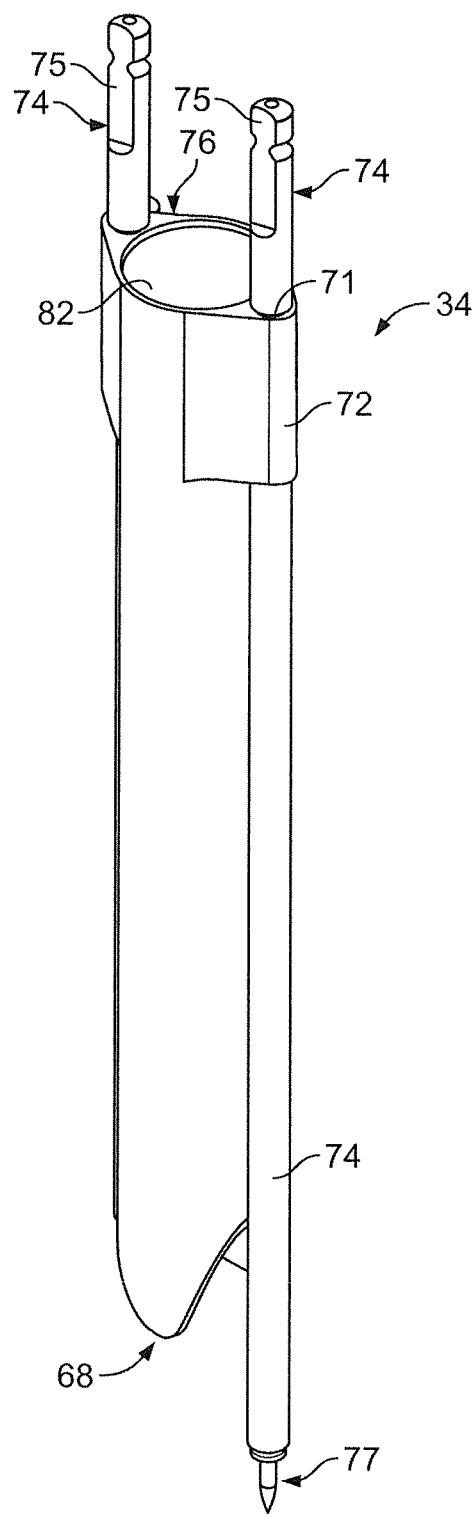
FIG. 18 is perspective view of another embodiment of a docking sleeve.

As illustrated in FIG. 17, the distal or bone engaging end 68 of the docking sleeve 34, preferably has an anti-skid portion 70 such as teeth, penetrating pins, or another non-smooth surface to retain the desired position of the sleeve on the bone. The anti-skid portion 70 prevents slippage across the bone surface. The distal, bone-facing end 68 may also include contouring as shown in FIG. 18. The contouring of the docking sleeve 34 allows it to sit generally flush against the adjacent non-flat bone surface. For example, one side of the proximal end 68 of the docking sleeve 34 is contoured to fit adjacent transverse process whereas the other side of the docking sleeve is contoured to fit adjacent the facet joint. The contouring may therefore vary from one side of the docking sleeve to another.

The docking sleeve 34 may also include one or more receivers 72 to house one or more fasteners 74 (FIGS. 17 and 18). Preferably, the receivers 72 are tubes or channels integrated or otherwise attached to the docking sleeve 34. (FIG. 17). Alternatively, the receiver(s) 72 may also be a small ring, snap, wire, or another retaining type fastener to guide and secure the docking fasteners 74. (FIG. 18). The receivers 72, as shown in both FIGS. 17 and 18, are located adjacent the cylindrical surface of the tubular wall of the docking sleeve 34, however, they could also be located adjacent or spaced from the inside wall surface. If the receivers 72 are placed on the inside wall surface of the docking sleeve 34 adjustments may be required to provide clearance for the implant and tools.

FIG. 17 illustrates how the receivers 72 may be sloped, radiused, chamfered, or sharpened near the proximal, bone-facing end to improve advancement of the sleeve 34 through the soft tissue. Further, the distal end of the docking fasteners 74 can also be so sloped, radiused, chamfered, or sharpened to improve insertion of the fasteners 74.

The proximal end 76 of the docking sleeve 34 may further include retainer 78. The retainer 78 cooperates with a locking pin, a boss, flange, thread, or other structure which could lock or temporarily secure the obturator 36 within the docking sleeve 34. The retainer 78 may also be used in cooperation with other instrumentation for other surgical procedures performed through the docking sleeve. The preferred retainer 78 shown is formed to house a locking pin 80 located on the obturator 36. The obturator 36 is slid into a window or bore 82 of the docking sleeve 34. After the obturator has been inserted, it is then rotated until the pin 80 is received in a circumferentially extending slot 84 of the retainer 78 through an open end 83. The opposite end 85 of the retainer slot 84 is closed so that the obturator 36 is stopped from further rotation with the pin 80 engaged by the closed end 85 of the retainer slot 84.

Preferably, the docking fastener(s) 74 are in the form of roughly 1-5 mm diameter pins and may have a self drilling auger type thread, although other fastener types may be used such as those having expanding heads. The fasteners 74 may be threaded or non-threaded, or the surgeon could use a threaded and a non-threaded fastener. The fasteners 74 are preferably AO standardized. While both manual and power tool advancement is possible, manual advancement is preferred. This can provide tactile feedback. To allow for more control of the fastener 74 and for the use of a driving tool such as a handle or ratchet, the proximal end of the fastener located remote from the surgical site may have a non-circular driver attachment portion 75.

In addition, the docking fastener(s) 74 may include a depth limiting feature, such as a collar, or depth guide, to prevent the pin from being drilled to deeply into the bone. Another option for the fastener(s) 74 is for each to have a proximal face 71 that is adapted to engage the docking sleeve 34 and the retainer 78 with the distal end 77 screwed into the bone thereby further securing the docking sleeve 34 relative to the bone.

In another embodiment, the anti-skid portion 70 of the docking sleeve 34 is adequate to hold the docking sleeve 34 into position on the skeletal anatomy. If the anti-skid portion secures the docking sleeve, the fastener(s) 74 may be unnecessary.

The window or bore 82 of the docking sleeve 34 is sized to provide space to perform the surgery and pass the desired implants into the surgical site. While the bore 82 of the docking sleeve 34 illustrated here is generally circular in cross-section, other shapes and sizes may be employed. The shape and size may be influence by the underlying anatomy, implants, and tools required for the surgery.

The docking sleeve 34 may be constructed of biocompatible materials, however, radiolucent materials such as polymers or carbon fiber may be preferred for better radiographic imaging of the area.

As previously described, the obturator 36 and the docking sleeve 34 are advanced down the guidewire 32, through the soft tissue until the nose 60 of the obturator meets the bone. At this point, the obturator 36 may be released by derotating or otherwise unlocking it from the retainer 78. By derotating the obturator 36, the locking pin 80 is disengaged from the slot 84 located on the docking sleeve retainer 78. After the obturator 36 and docking sleeve 34 are no longer mated together, the obturator can be pulled out of the sleeve 34. After the obturator 36 is removed, the docking sleeve 34 can then continue advancing to the bone surface. The obturator 36, along with any other tissue expansion tools, may be fully removed at any time after the docking sleeve 34 is advanced down to the bone.

Once the docking sleeve 34 reaches the bone surface, the sleeve 34 is securely attached to the bone. The docking fastener(s) 74 may be preloaded into the receivers 72 or may be loaded during or after advancement of the docking sleeve 34. To secure the sleeve 34 to the bone surface, the docking fasteners 74 may be advanced into the bone thereby positionally securing the docking sleeve 34 against the bone. If the docking sleeve 34 is not employing the fasteners 74, but instead utilizing the anti-skid portion 70 to secure the sleeve 34, the sleeve 34 may need to be rotated or pushed into the bone. Either way, the docking sleeve 34 is left secured to the bone by the docking fastener(s) 74, the anti-skid portion 70, or both. After the docking sleeve 34 is secured into position, the obturators 36 or other various dilation tools are removed.

Figure 19:
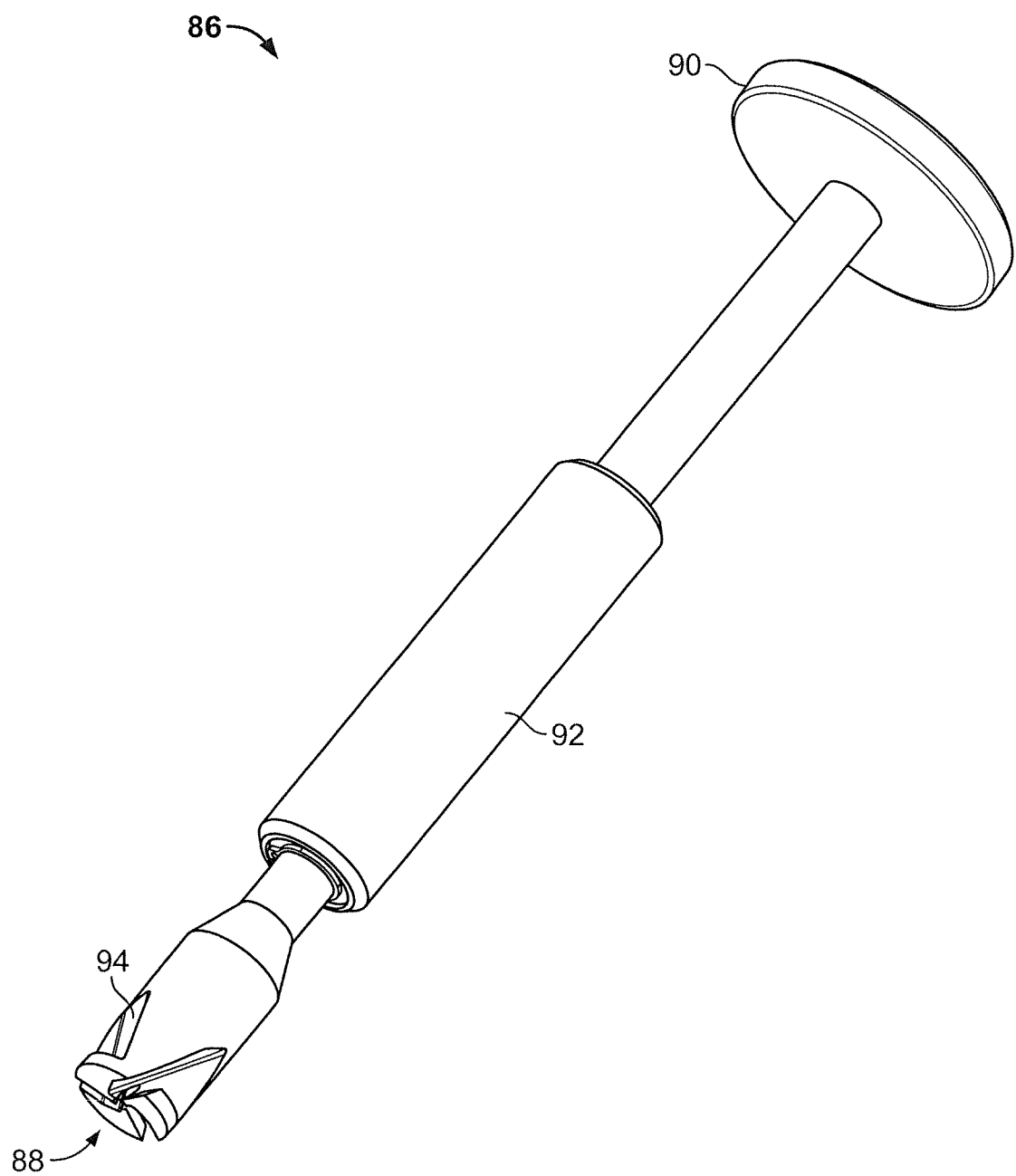
FIG. 19 is a perspective view of a facing tool.
Figure 19A:
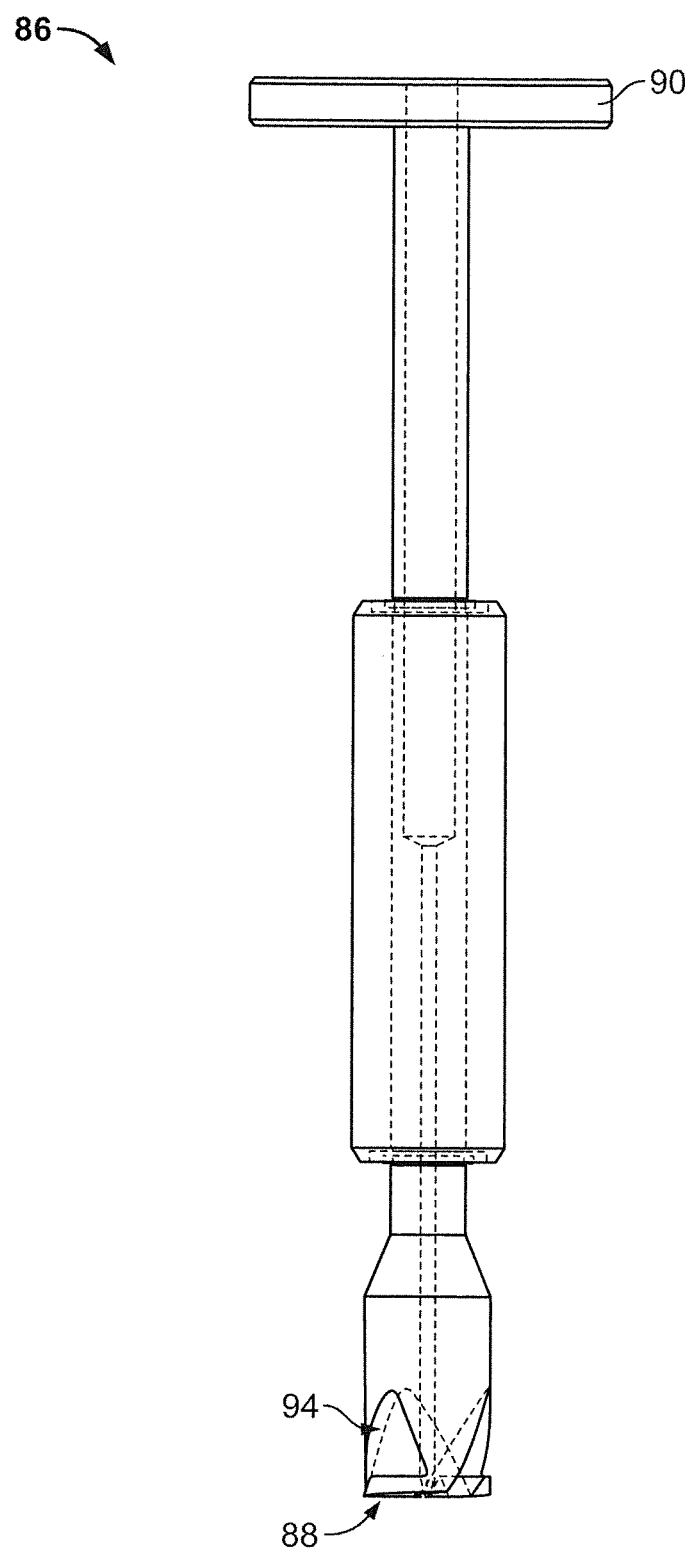
Figure 19G:
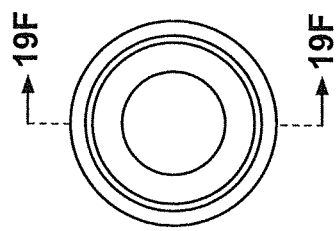
Figure 19F:
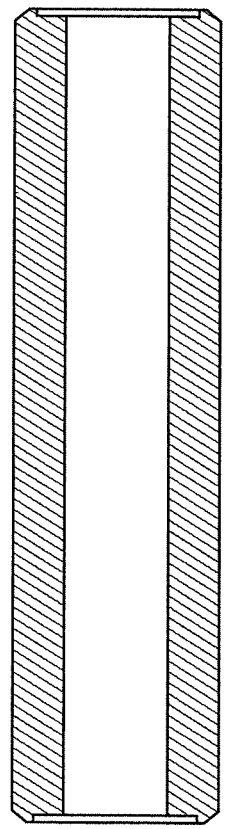

After creating a porthole to the surgical site via the docking sleeve 34, the surgeon may desire to prepare the bone by reshaping the surface. For example, if there is anything in the way such as an osteophyte overlying the area where the anchor 20 will be seated a surgeon can remove potentially interfering structures using a facing tool 86. The facing tool 86 (FIG. 19) may be used to refine bone surface and create a flattened area suitable for seating implants. The facing tool 86 may be cannulated and utilize the guidewire 32 for positioning within the docking sleeve 34 or may be non-c annulated and guided by the inside wall of the sleeve 34 in which case the guidewire 32 is not used or previously removed.

The facing tool 86 preferably includes a generally flat cutting portion 88. The cutting portion 88 removes, flattens, and cuts away the surface of the bone as the tool 86 is rotated. Alternatively, the tool 86 may include a shaped cutting portion 88 to shave the bone in a contour such as a concave, dome or another shape beneficial to inserting various implants. The facing tool 86 may include a handle portion 90 and a depth stop 91, in the form of a stop collar located to engage the top of the docking sleeve 34. Such a depth stop generally avoids having the tool advanced too far into the bone. A centering portion 92 on tool 86 may be sized to the inside diameter of the docking sleeve 34. The centering portion 92 may keep the tool generally centered in the docking station 34 to keep the cutting portion 88 from wearing against the sides of the docking sleeve window 82. In addition, a bone chip reservoir 94 that may be a space or opening near the cutting portion 88. This reservoir 94 may accumulate the bone chips being removed from the bone surface as the tool is rotated.

Figure 20:
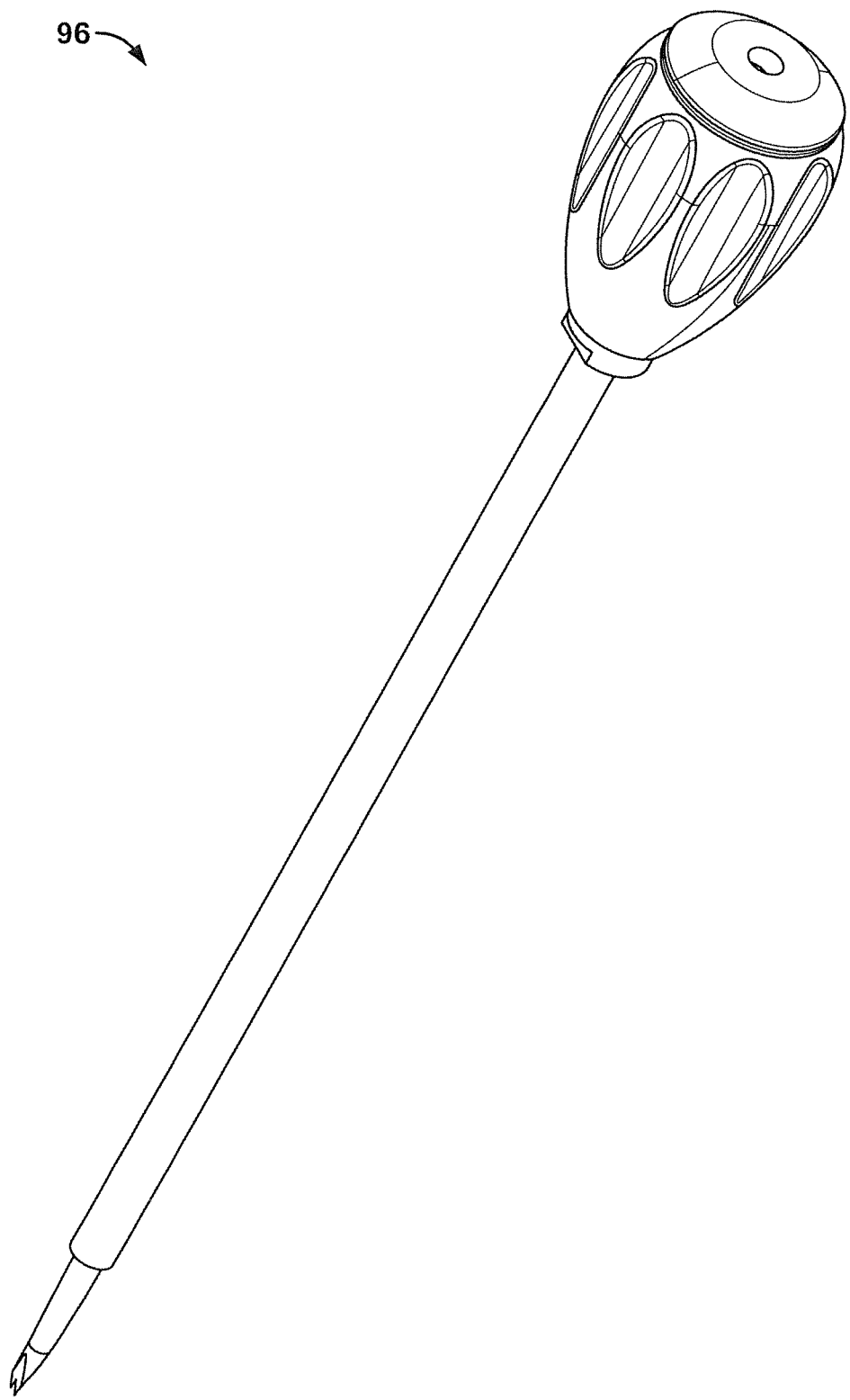
FIG. 20 is a perspective view of a cannulated awl.

Before attaching the bone anchor 20, a cannulated awl 96 may be used to perforate the cortex of the bone overlying the pedicle. The cannulated awl 96, shown in FIG. 20, may slide down the guide wire and then be driven into the bone by tapping on the proximal or upper end projecting out from the docking sleeve 34 with a mallet. After the cortex of the bone is breached and a depression or opening is made, the awl 96 can be removed. The depression can also be created by rotating or otherwise manipulating the cannulated awl 96. Alternatively, if the guidewire 32 is not being used or has previously been removed, the awl 96 can be visually placed at the bone site with the surgeon looking through the docking bore 82 for this purpose. Another option is to have a collar on the shaft of the awl tool that guides the awl 96 down the docking sleeve 34 toward the bone site.

If a guidewire 32 is still inserted into the wound, the surgeon may choose to remove it at this time. After which, the pedicle finder 30 or another drilling tool may be advanced down the docking sleeve 34 toward the bone where the pedicle finder 30 may create a pilot hole of suitable and safe depth for the bone anchor 20. Whether or not the surgeon wishes to tap a pilot hole often depends on the anchor type and surgeon preference. Further, the surgeon may also wish to use a probe to assess the position of the hole and ensure that it has not veered into an unintended or unsafe direction. When a pilot hole or tap is made, it is appropriately sized to the bone anchor that will implanted.

Verifying the hole position can be difficult in guidewire 32 dependent systems because the implants and instruments are usually constrained to the guidewire 32. In such cases, the implant follows where the guidewire 32 is directed and if a guidewire 32 is improperly placed the implant placement can be improper and potentially harmful. Therefore, it is preferred that the guidewire 32 eventually be removed, if used at the beginning of the procedure.

Figure 21:
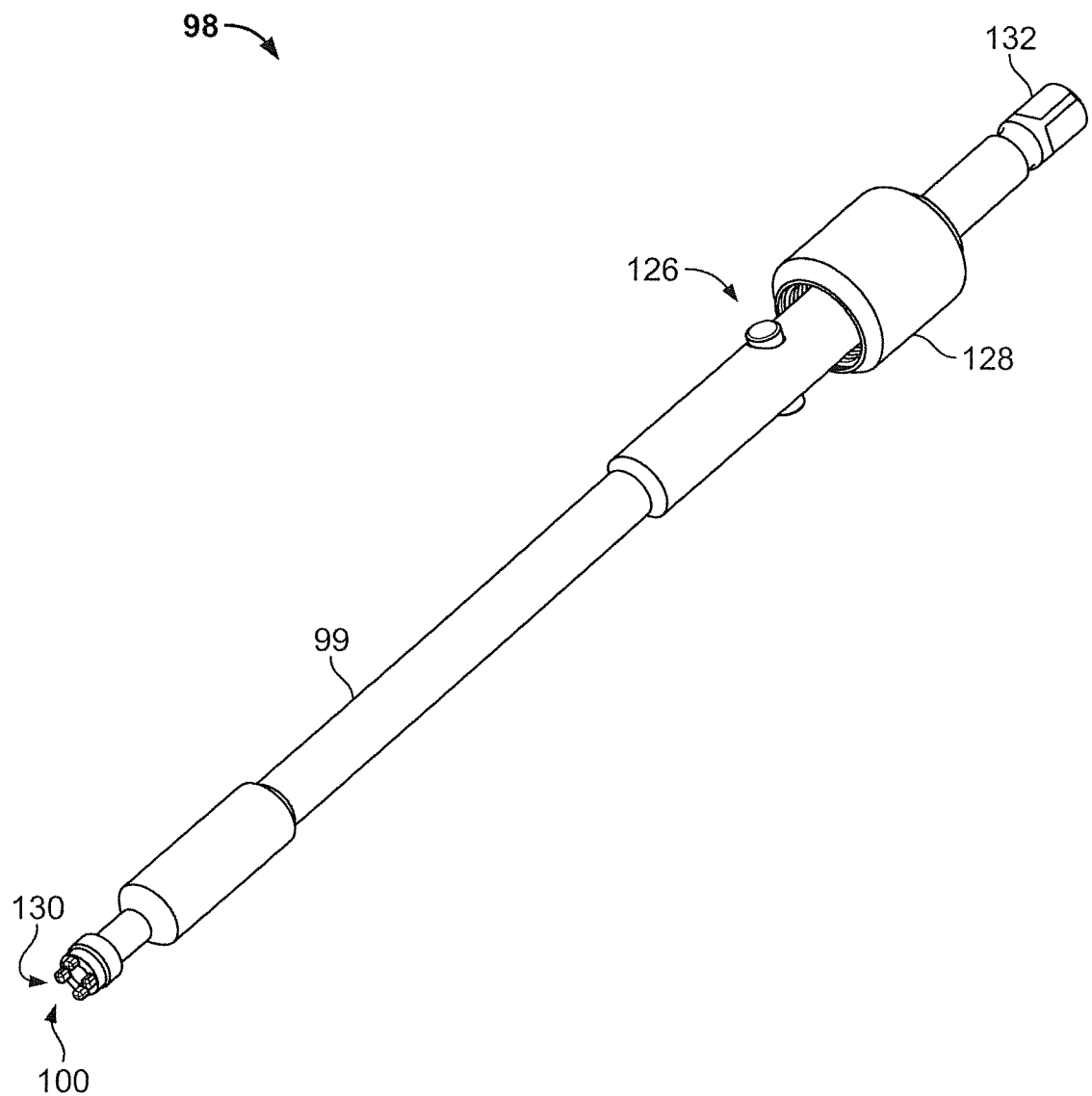
FIG. 21 is a perspective view of a screw driver.
Figure 21E:
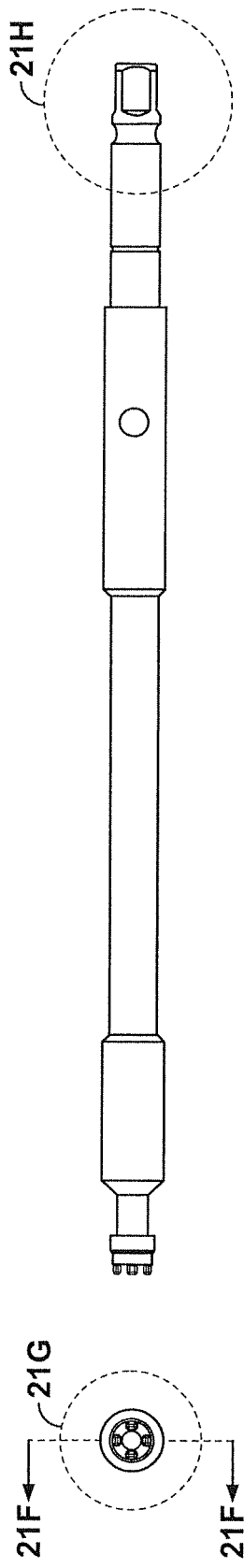
Figure 21H:
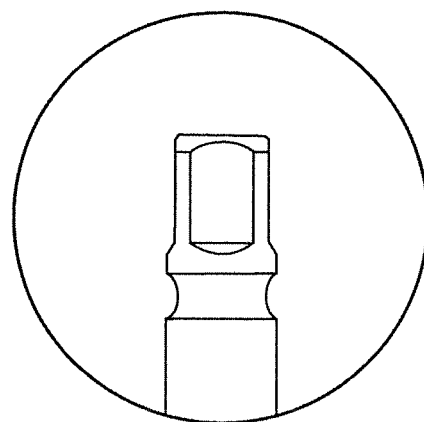
Figure 21G:
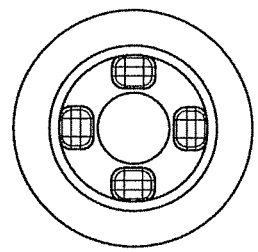
Figure 21F:
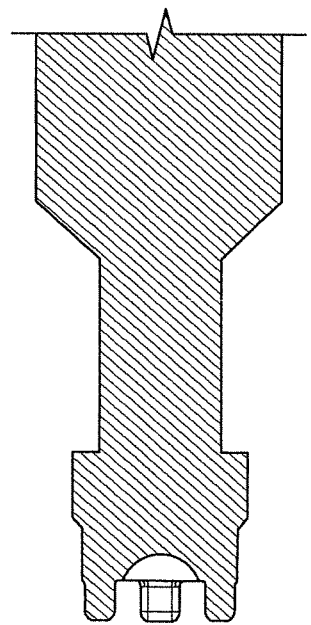
Figure 21D:
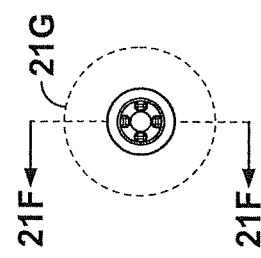

Then, with the guidewire 32 removed, the placement of the pilot hole verified, the surgeon may now advance the anchor 20 and a screw driver 98 assembly down the docking sleeve 34. Then, the anchor 20 can be driven into the bone through the prepared pilot hole by rotating the screw driver. As shown in FIG. 21, the screw driver 98 has a first end with a set of prongs 100 that mate with a proximal end of the anchor such that when the screw driver 98 is rotated, the anchor advances into the bone.

There are several preferred methods of delivering the bone anchors into the surgical site. Therefore, numerous instruments are disclosed to assist in insertion of the implant. The instruments can be used in varying combination and a few examples are disclosed herein.

Figure 22:
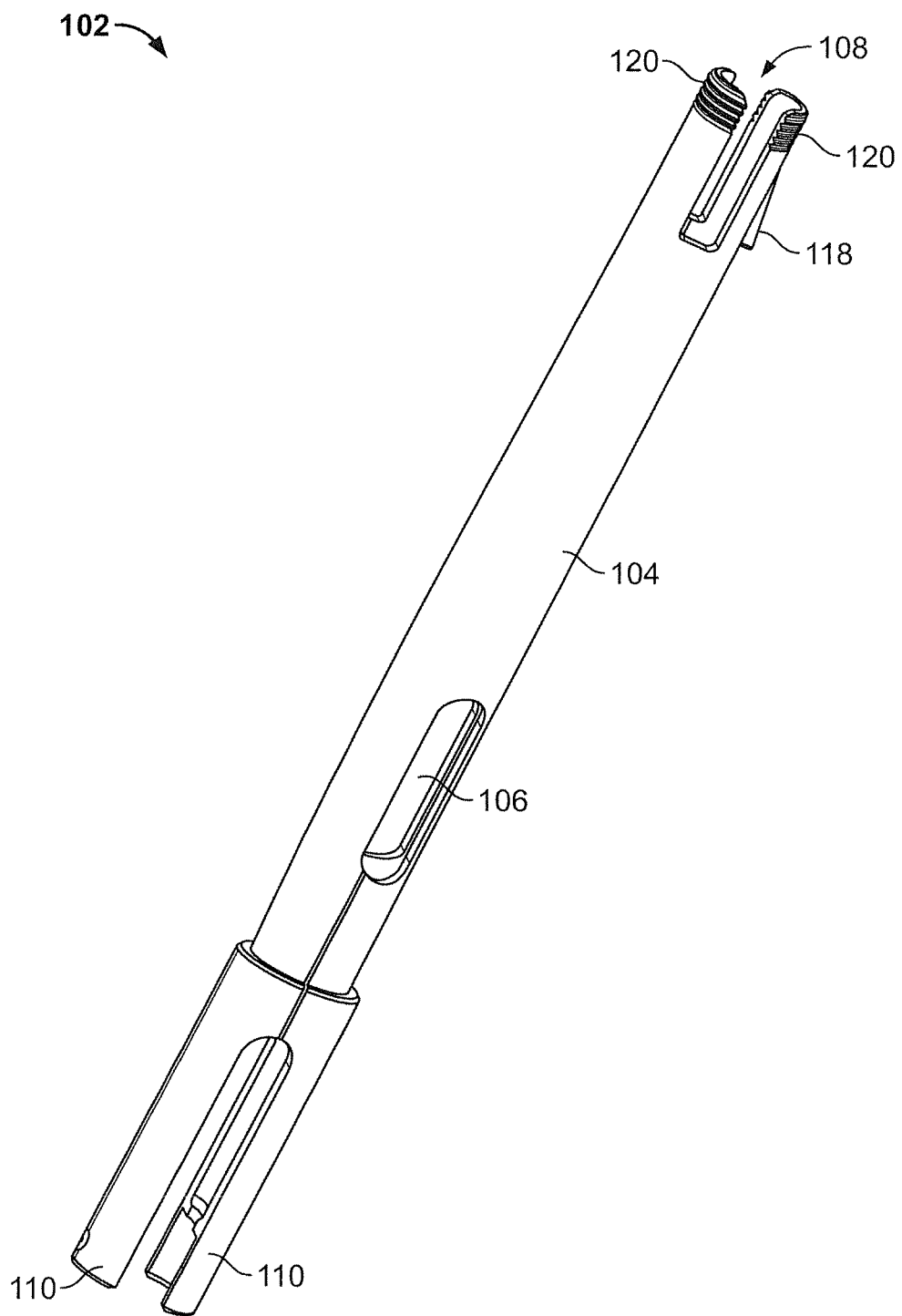
FIG. 22 is a perspective view of a yoke manipulator.
Figure 23:
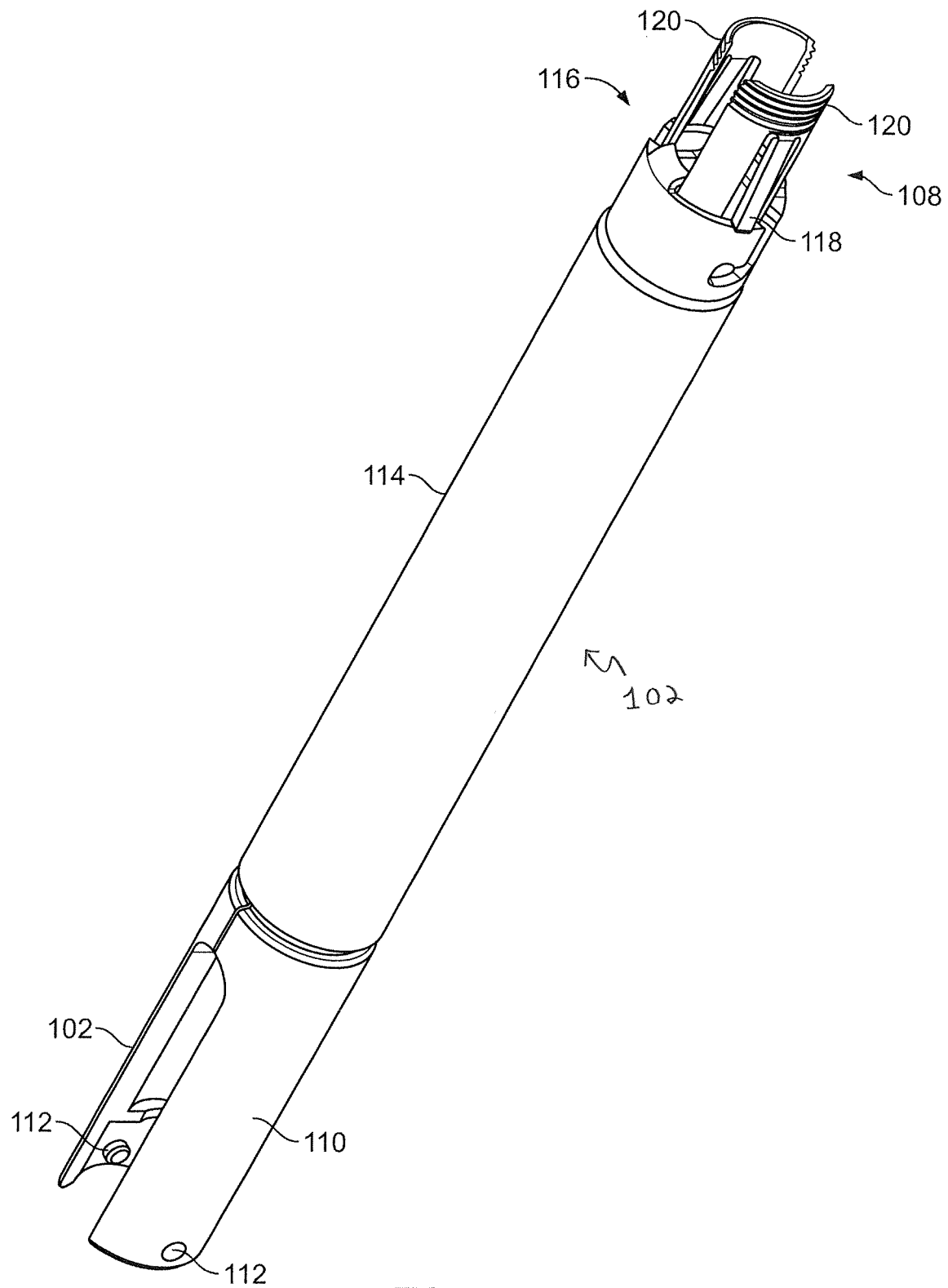
FIG. 23 is a perspective view of a yoke manipulator with a restraint.
Figure 23A:
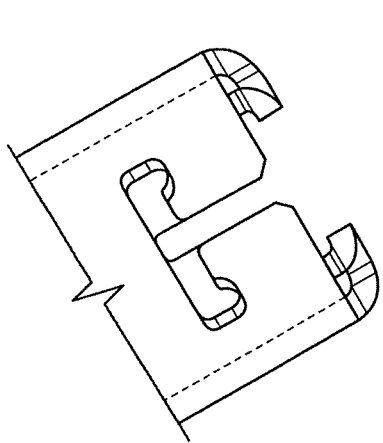
FIGS. 23A-23E are various view of the restraint of FIG. 23.
Figure 23B:
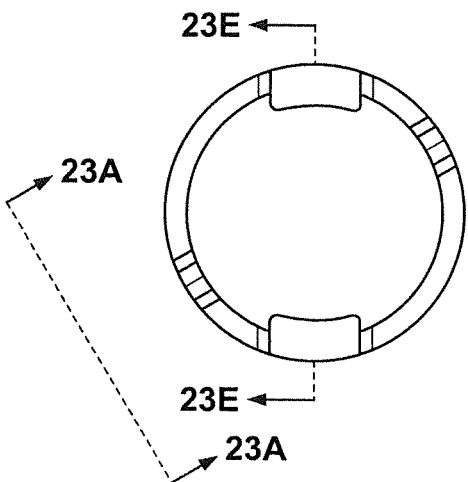
Figure 23C:
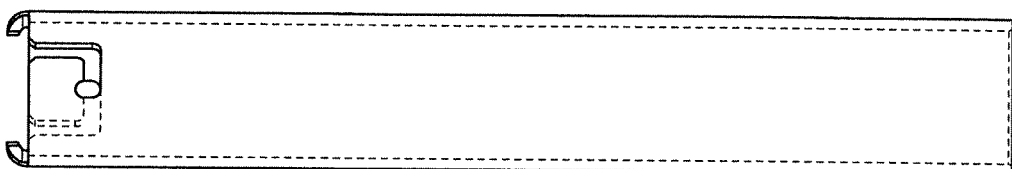
Figure 23D:
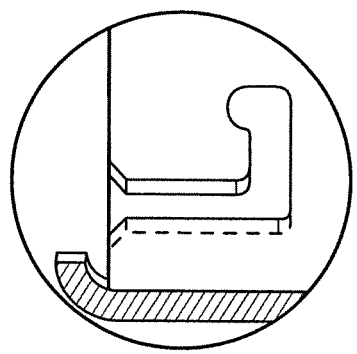
Figure 23E:
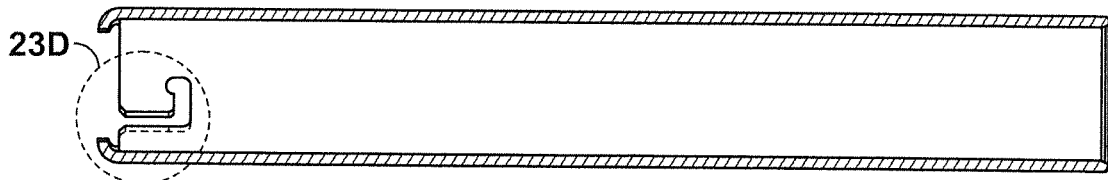
Figure 23G:
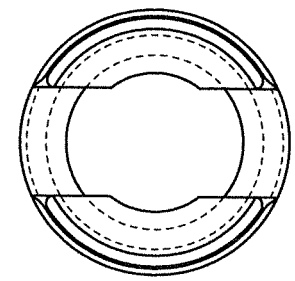
Figure 23I:
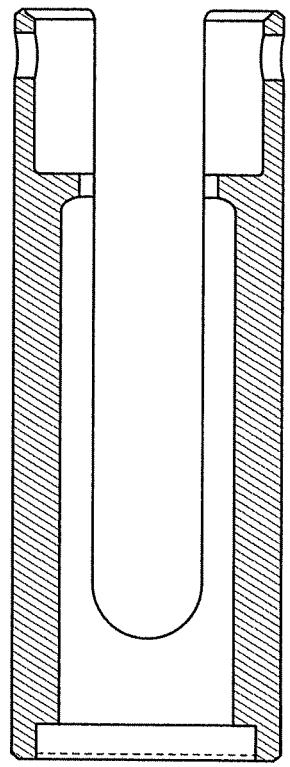
Figure 23F:
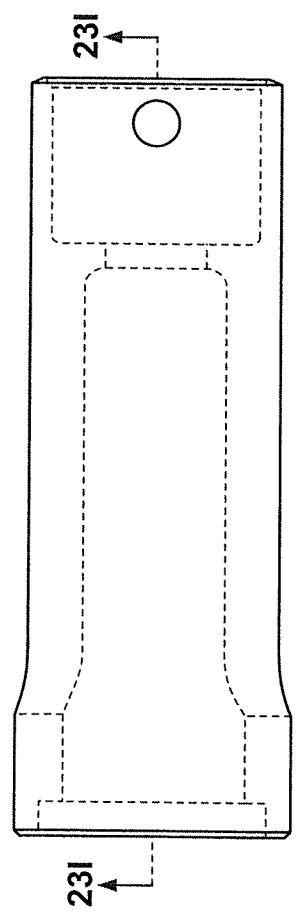
Figure 23H:
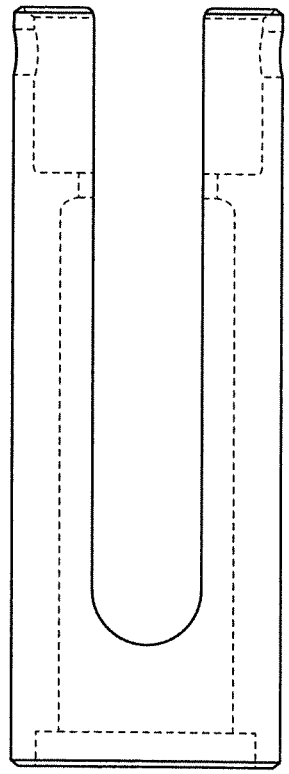

A yoke manipulator 102 is shown in FIG. 22. The manipulator is mated to the yoke 22 and thereby the anchors 20. The yoke manipulator 102 has at least a shaft 104, a slot 106, and manipulator end 108. The yoke manipulator 102 may be used to manipulate and help insert the anchor 20 and yoke 22 into the bone by attaching and holding the yoke 22 within one or more manipulator arms 110 at the distal end of the manipulator. At least one of the arms 110 is flexible and may preferably spring outward to a resting position wherein the inner diameter between the two arms is greater than the diameter of the yoke 22. Alternatively, one or more of the arms 110 may flex only when the yoke 22 is inserted between the arm portions. The arms 110 may include a boss, recess, flange, or other retainer to engage a complementary structure on the yoke 22. As shown in FIG. 23, the retainer 112 is a pair of bosses located on each arm on the inside of the manipulator shaft. Such an engagement retains the yoke 22 in predetermined alignment with the yoke manipulator 102. Such a structure also prevents the yoke from prematurely separating from the manipulator arms 110. The bosses seat in corresponding slots on the anchor yoke 22.

The yoke manipulator 102 may include a slot, cut, or space defining each arm portion 110. The manipulator shaft 104 may be recessed to accommodate a restraint 114 such as a locking sleeve, collar, or outer sheath shown disposed over the yoke manipulator in FIG. 23. The restraint 114 prevents or limits outward expansion of one or more of the arms 110. The restraint 114, depicted as a locking sleeve in FIG. 23, extends over a portion of the arms 110 to securely capture the anchor yoke 22. For example, the arms 110 are positioned around the yoke 22 and since the arms 110 have some flexibility, the restraint 114 is slid down the manipulator 102 to strengthen the connection. The restraint may also include a positioner 116 to orient the restraint 114 to the yoke manipulator 102. The positioner 116, for example, may be in the form of a flange, boss, recess, or other structure complementary to the yoke manipulator 102 for alignment. The restraint 116 may also include retraction structure 122, such as a slot, flange, boss, or recess for engagement of a tool handle to remove the restraint 114.

The manipulator end 108, opposite the arms 110, further includes a positioner 116. The positioner 116 is preferably in the form of a slot, boss, or flange that may orient the locking restraint 114 on the yoke manipulator 102 and/or to align each bone anchor 20 relative one another for passage of the connecting member 26. The yoke manipulator 102 may also include a releasable stop 118 to temporarily hold the restraint 114 over the arms 110. Connecting structure 120 such as threads, flanges, slots, or bosses may be present to connect an instrument such as the screw drive assembly.

One of the yoke manipulators used in the system may be a long slot yoke manipulator 124. The long slot manipulator 124 includes a shaft 104, slot 106, and arms 110, like the short slot manipulator 102, however, the slot 106 on the long slot manipulator is generally longer than on the short slot manipulator 102. For example, as shown in FIG. 2, the short slot is generally less than half the length of the long slot. The long slot manipulator 124 provides the surgeon with additional clearance during the insertion of the connecting member 26 as is more fully explained below. The long slot manipulator 124 may incorporate most of the features of the short slot manipulator 102. It is contemplated that the slots in the manipulators be of different lengths. In fact, as long as one of the manipulators has enough clearance for the connecting member 26 to be inserted, the other manipulator may include a smaller slot or may include a slot on only one side. As discussed below, the long slot manipulator 124 is proximate to the rod inserter 140 to provide the sufficient clearance. Preferably, the MISS having two bone anchors with have one long slot manipulator 124 and one short slot manipulator 102. If the implant has three bone anchors, the MISS will include two long slot manipulators 124 and one short slot manipulator 102. It is preferred that a system not include more than one short slot manipulator 102 because additional short slot manipulators 102 may interfere with insertion of the connecting rod 26. In any event, whether the slots are short or long, they must provide suitable access to pass the connecting member into the yokes.

The number of yoke manipulators 102, 124 preferably corresponds to the number of bone anchors 20. It is also preferred that each manipulator should generally be aligned relative to one another. This alignment may be done by placing a strut or guide 142 between the positioners 116 on each of the manipulators as discussed below. After the manipulators 102, 124 are in position, the docking sleeves 34 may be removed although typically the docking sleeves cannot be removed if a strut or guide is located between the manipulators. The shafts 104 manipulators 102, 124 are hollow thereby providing access to the anchor 20 and manipulator 22.

As mentioned above, the screw driver assembly or inserter 98 advances the anchor into the bone. The driver 98 is sized to fit within the yoke manipulators 102 and 124. The driver 98 includes a shaft 99 and a positioning structure 126, preferably in the form of a pin, boss, flange, or other structure complementary to the positioner 116 on the yoke manipulator 102, 124 for orienting the screw driver 98 to the yoke manipulators 102, 124. The driver 98 may also include a removable capture 128 for capturing the screw driver 98 in the yoke manipulator 102, 124 and holding the screw drive surface 130 tight within the head of bone anchor 20. In this embodiment, the removable capture 128 on the driver 98 and the connecting structure 120 on the yoke manipulator 102, 124 are inter-mating threads, but other connections such as a bayonet style connection could be used. Such an association ensures that the driver 98 engages the anchor 20 while the manipulator 102, 124 engages the yoke 22. Opposite the screw drive surface 130, the driver 98 may include an engagement end 132 for non-rotatable engagement with a removable handle, ratchet, or fixed handle. In addition, the driver 98 may include one or more guide surfaces 134 that have an outer diameter generally similar to the inner diameter of the yoke manipulators 102, 124 such that the screw driver 98 remains centered within the manipulator. After the driver 98 is mated with the anchor 20, the driver 98 and manipulator 102 or 124 are both turned at the same rate, such that there is no relative motion between the anchor 20 and the yoke 22. After the anchor has been inserted, the driver 98 may be removed.

Figure 27:
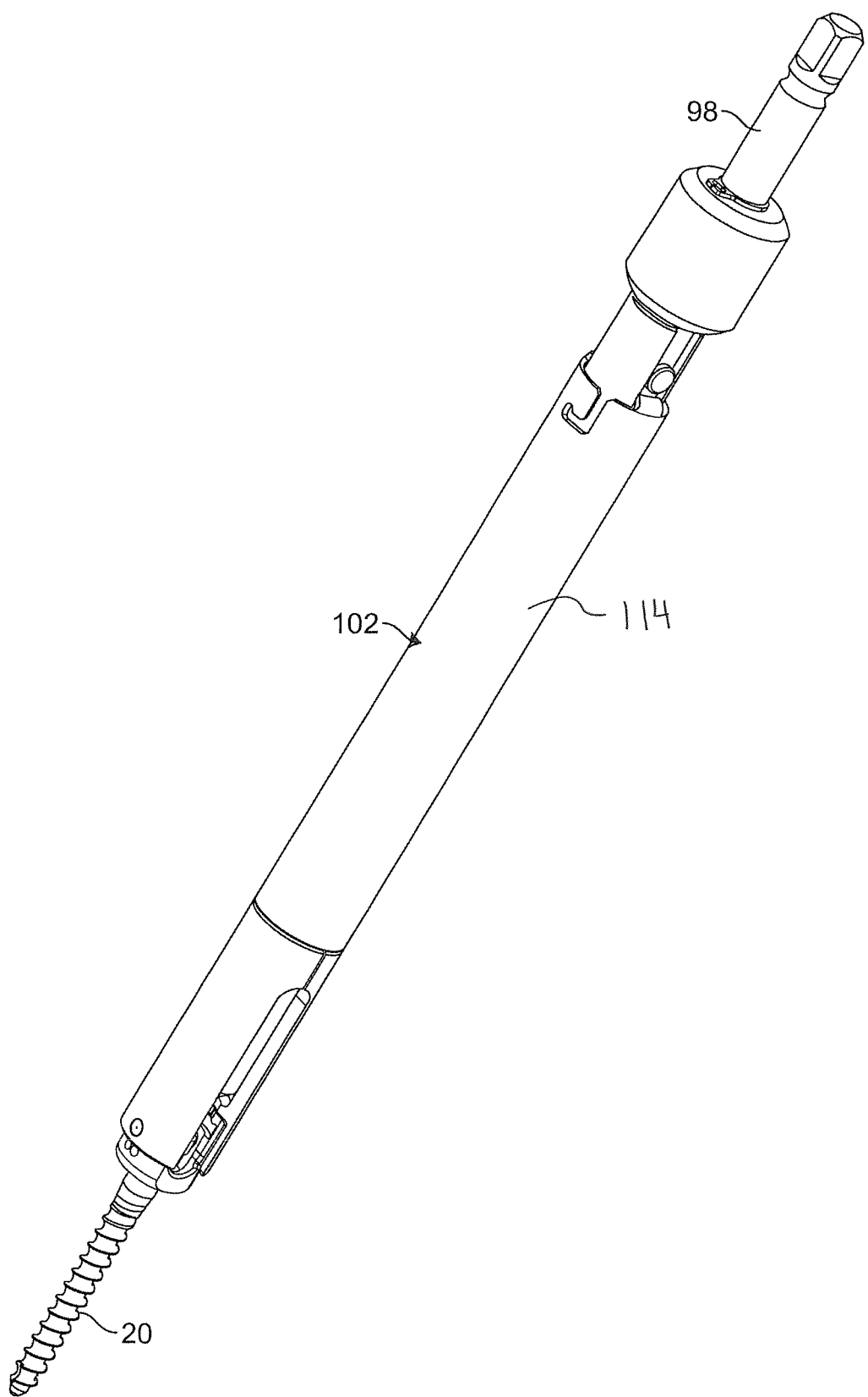
FIG. 27 is a perspective view of an assembly of the anchor, yoke manipulator, and screw driver.
Figure 28:
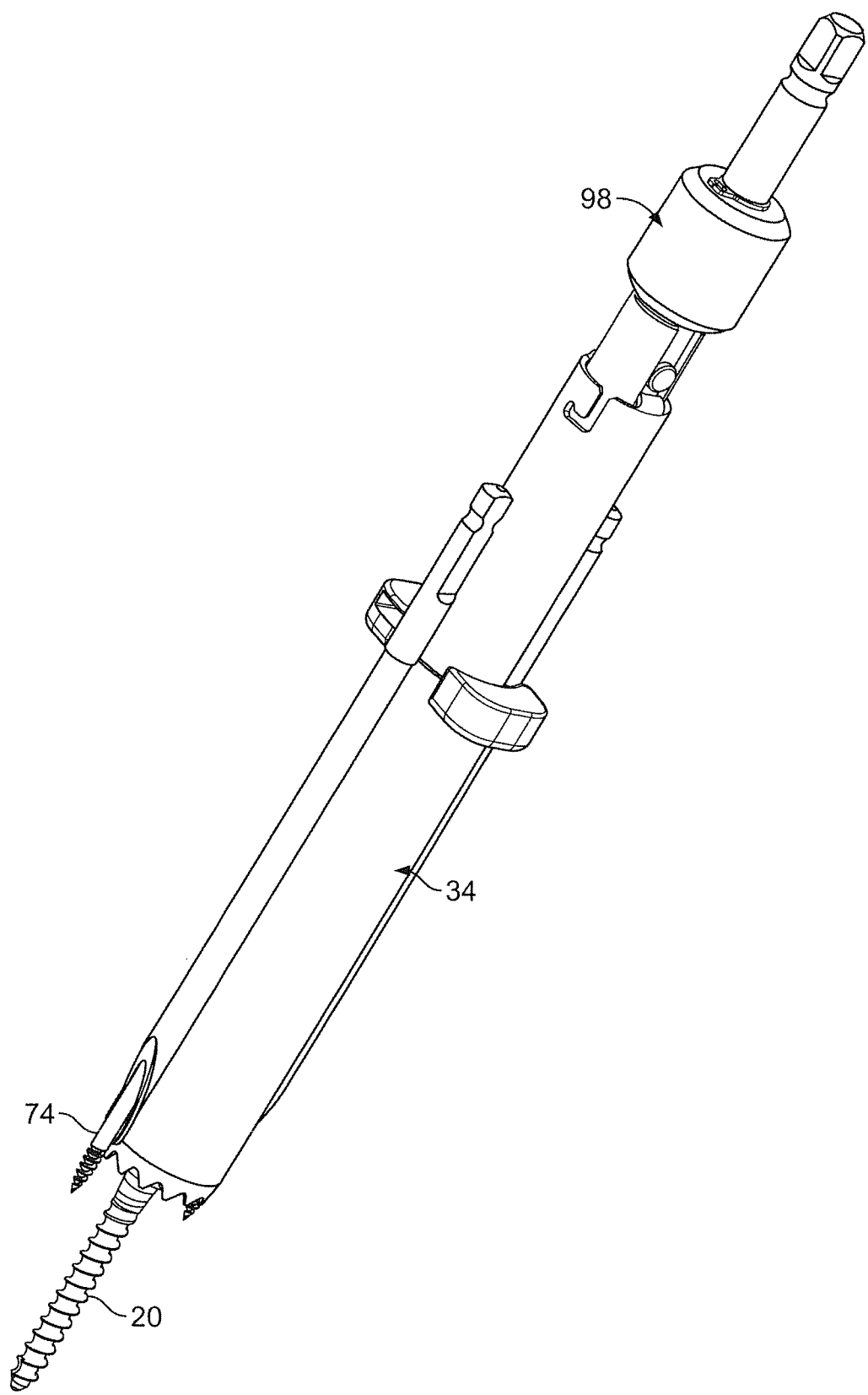
FIG. 28 is a perspective view of an assembly of the anchor, docking sleeve with fasteners; yoke manipulator; and screw driver.

FIG. 27 illustrates a screw driver 98, yoke manipulator 102, restraint 114, and a bone anchor 20 as an assembly in operable relation to each other. This preferred assembly is advanced through the window or bore 82 of the docking sleeve 34. As the assembly illustrates, the bone anchor 20 and yoke 22 may be loaded into a yoke manipulator 102 or 124 and captured between the arms 110 prior to loading the assembly into the docking sleeve 34. The retainer 112 engages a pair of recesses 136 on the opposing walls 23 of the yoke 22. The manipulator restraint 114 is slid over the shaft of the manipulator 102, 124 securing the yoke manipulator arms 110 around the yoke 22. The restraint 114 aligns with the positioner slot 116 on the yoke manipulator. The releasable stop 118 axially secures the restraint 114 onto the yoke manipulator 102, 124. After assembly, the instrumentation may now be fed into the docking sleeve 34. Alternatively, as shown in FIG. 22 the screw driver 98 may also be added to the assembly before insertion into the sleeve 34.

If the screw driver 98 is fed down the center of the manipulator 102, 124 after the anchor 20 has been advanced down the manipulator, the driver 98 advances until the screw drive surface 130 engages the anchor sockets 138. The positioner 126 of the driver 98 aligns with the positioner 116 of the manipulator for full engagement of the drive surfaces. The guide surface 134 will center the driver 98 within the manipulator 102, 124. The driver 98 is secured to the manipulator 102, 124 by threaded engagement of the internally threaded removable capture nut 128 to the thread connector 120 at the proximal end of the manipulators.

As mentioned above, the assembly shown in FIG. 27 is moved down the docking sleeve 34 until the tip of the bone anchor 20 falls into the pilot hole. The surgeon rotates the assembly by the drive handle until the anchor 20 is fed down the pilot hole and satisfactorily inserted or driven into the bone, after which the driver 98 may be removed. This procedure may be repeated as needed to set the needed number of anchors at the required locations.

Figure 29:
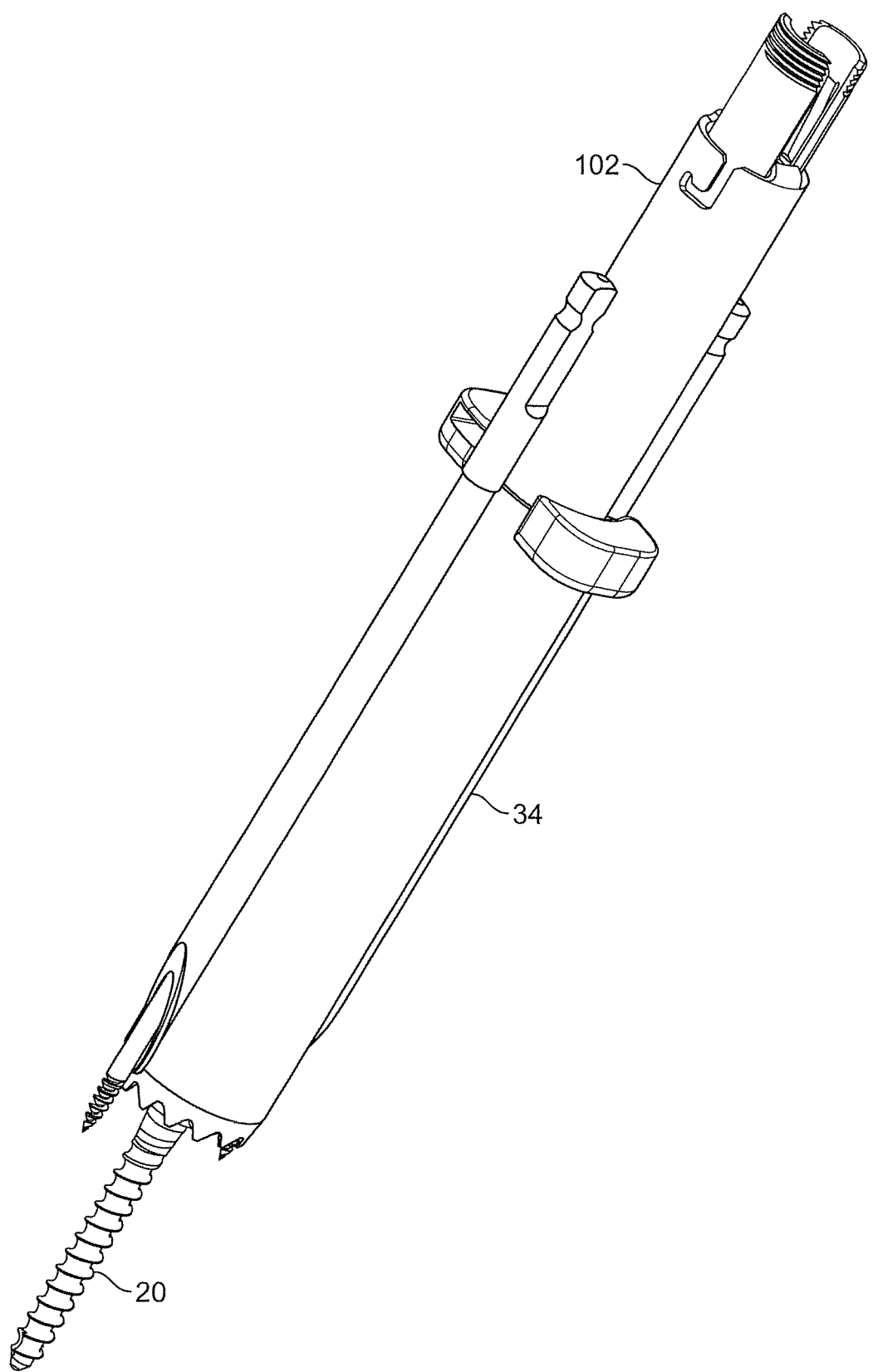
FIG. 29 is a perspective view of an assembly of the anchor, docking sleeve with fasteners; and yoke manipulator.

The assembly shown in FIG. 29 (screw inserter drive handle not shown) is moved down the docking sleeve 34 until the tip of the anchor falls into the pilot hole. The surgeon rotates the assembly by the drive handle until the anchor is fed down the pilot hole and satisfactorily inserted into the bone. The screw driver 98 may now be removed. This procedure may be repeated as needed for placement of additional anchors 20 at other locations.

Once at least two anchors 20 have been set, a connecting member or spinal rod 26 may be fed between the yokes 22. After the inserting procedure that positions the connecting member 26, detailed below, an instrument preferably operated through the yoke manipulator 102, 124 is driven to compress the closure cap 24 and connecting member 26 into the yoke 22. The connecting member 26 may be pre-bent or bent by surgery staff to the surgeon's specifications. The preferred bend of the member 26 is approximately 7 degrees. Once adequately seated, the closure cap 24 is rotated to a locked position. This process is repeated until the connecting member 26 is fully locked down.

Figure 30:
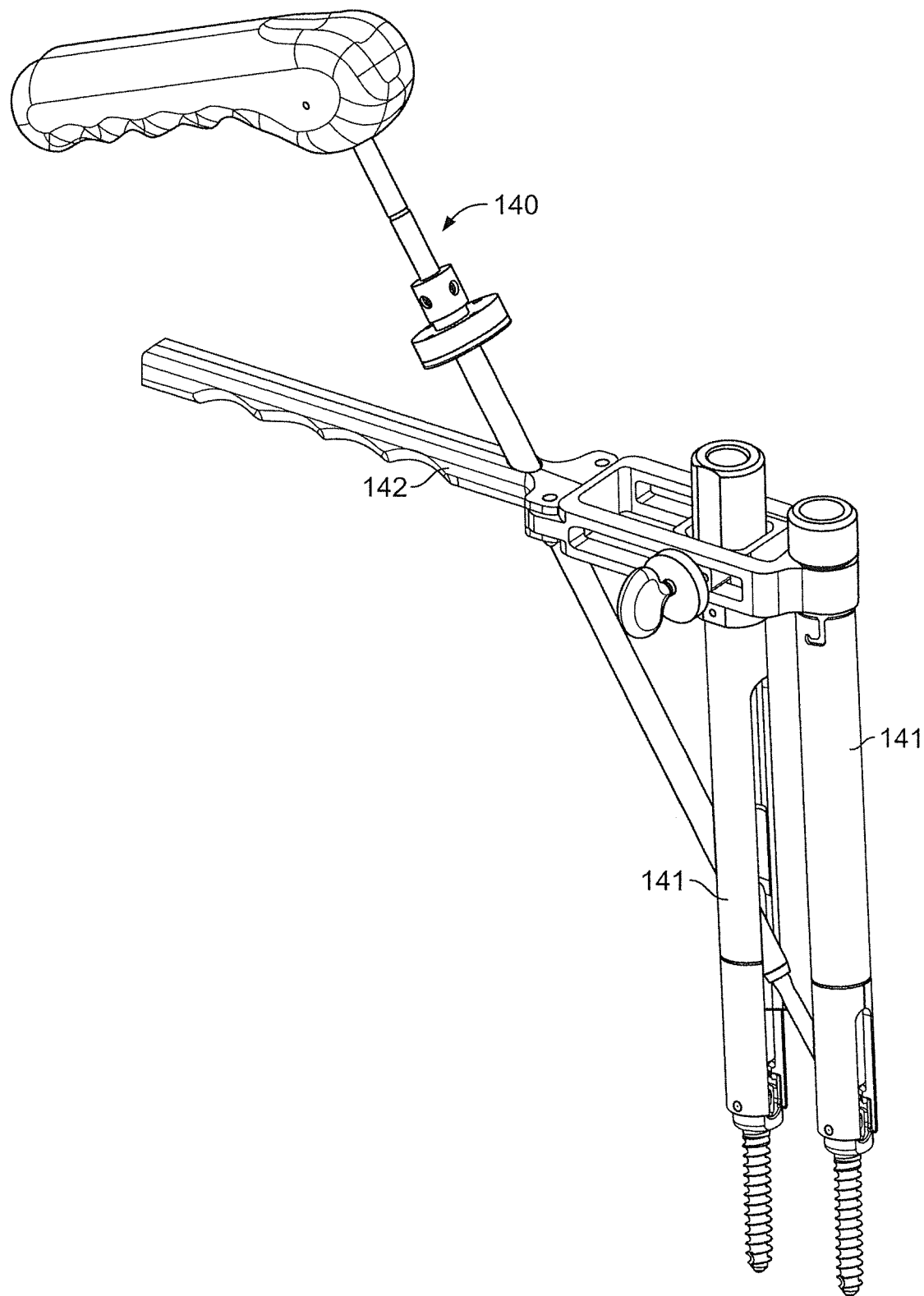
FIG. 30 is a perspective view of a MISS.

To assist in the insertion, guidance, and lockdown of the connecting rod member 26, a rod inserter 140, and a guide 142 along with the yoke manipulators assemblies 141 are employed (FIG. 30). In this embodiment, the connecting member 26 may include features that enable optimal insertion. As shown in FIG. 2, the connecting member 26 may include a nose portion 144 with a rounded, chamfered, or reduced diameter tip. The nose 144 is shaped to ease the passage of the rod through the soft tissue, the yoke manipulators, or other MISS instrumentation, and into the yoke 22. The main body portion 146 of the connecting member 26 is preferably round having a 5.5 mm constant diameter. Alternatively, the rod body 146 may have a non-circular diameter. Further, the member 26 may be straight or preferably has a pre-bent profile. To initially create a path through the tissues, a muscle splitter in a reduced diameter or profile of that of the connecting member may first be driven through the soft tissues to create a path for the connecting member 26.

The rod member 26 has an attachment end 148 used to attach, hold, or steer the member 26 into position within the yoke 22. The end 148 may have a boss 150 which may include two flat portions further having a capture 152 located therein. The capture 152 is illustrated in FIG. 2 as a hole. The capture may be a hole, bore, recess, boss, groove, or other structure that would provide a distinct point of capture for holding the connecting member 26 in the rod inserter 140. This attachment end 148 is secured to the rod inserter 140 during the insertion procedure. Further, the end 148 may include a ridge portion 156 or other structure that limits the range of movement of the connecting member 26 relative to the rod inserter 140 during insertion as will be described hereinafter.

Figure 33:
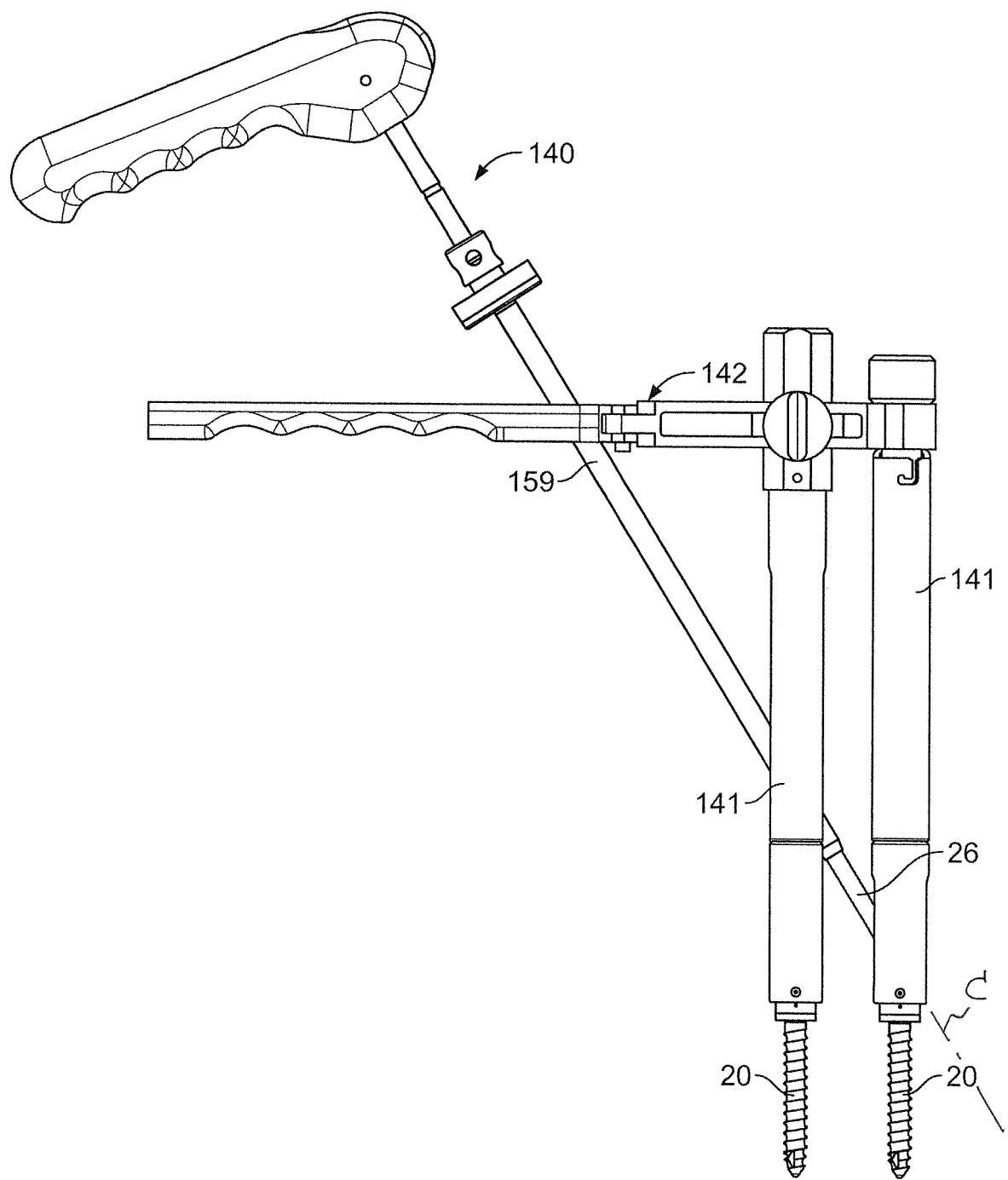
FIG. 33 is a side view of the MISS having the rod inserter in a first position.

A portion of the rod inserter 140 is fed transversally through the yoke manipulator 124 via the slot 106, as shown in FIG. 33. The manipulator assembly 141 nearest to the handle of the rod inserter 140 has the longer slot 106 since that assembly will require greater clearance because the connecting member 26 is passed into a farther, more distally positioned yoke manipulator assembly 141. Preferably the slots 106 in manipulators 102, 124 are also slightly wider than the diameter of the connecting member 26. As stated previously the positioner 116 located on the manipulators 102, 124 may cooperate to properly orient the manipulators 102, 124 and slots 106. As can be seen in FIG. 33, the cooperation between the yoke manipulators and rod inserter 140 ensures clearance of the connecting member 26 so that it can be properly seated in yoke 22.

Figure 31:
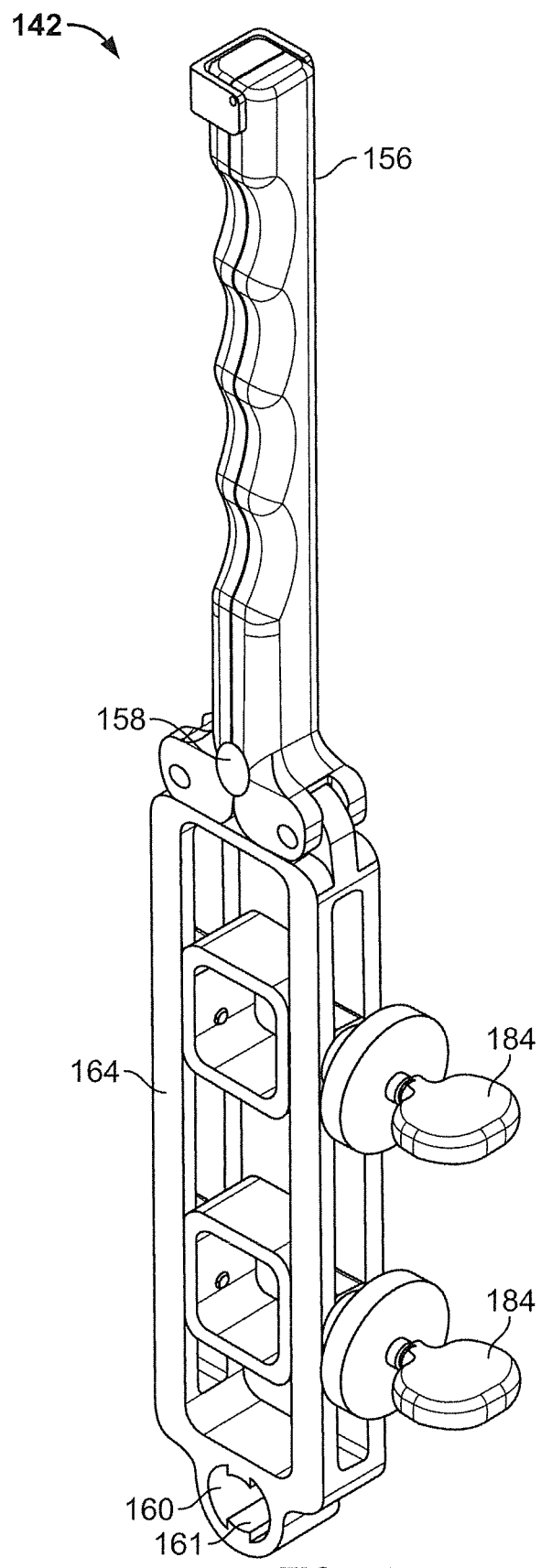
FIG. 31 is a perspective view of a guide.
Figure 32:
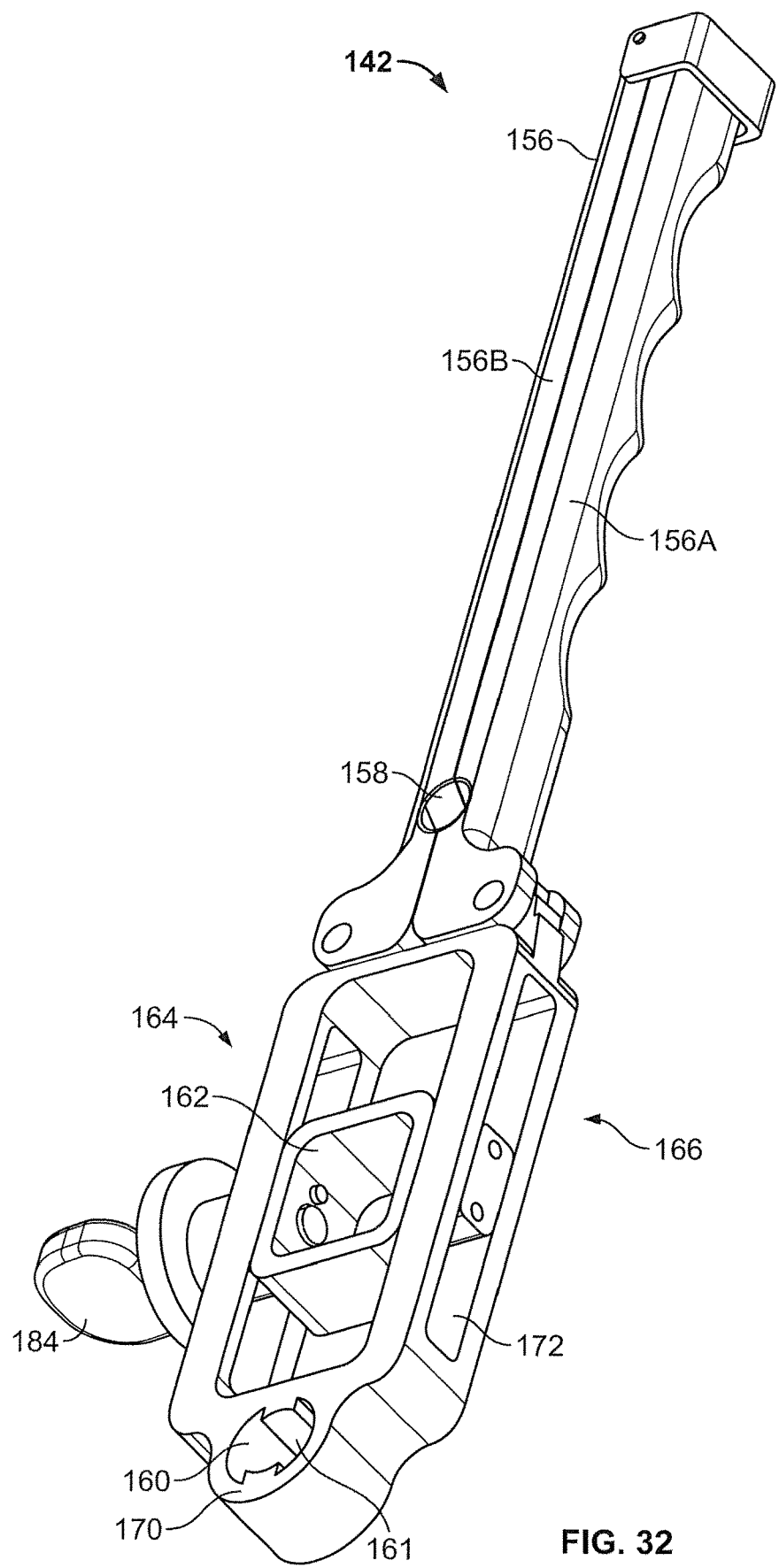
FIG. 32 is a perspective view of another embodiment of a guide.

To assist in directing the rod inserter 140 into position, a guide device 142 may be employed although the surgeon may choose to use the rod inserter 140 in the absence of the guide 142. After the manipulators are positioned inside the body as previously described, the guide 142 is attached to the manipulators 102, 124. The guide 142 moves the yoke manipulators 102, 124 generally parallel to one another for passage of the connecting member 26. The guide 142, as illustrated in FIGS. 31 and 32, may include a handle portion 156 to permit operator control over the guide 142, a rod inserter aperture 158 to permit control over the rod inserter 142, a distal holder 160 with opening 161 to permit control over the distal yoke manipulator assembly 141, a proximal holder 162 with opening 163 to permit control over the proximal yoke manipulator assembly 141, and a guide body portion 164. The handle portion 156 is preferably sized and shaped to ergonomically fit into the surgeon's hand. For example, the handle 156 may be scalloped for an improved finger grasp.

As shown in FIGS. 31 and 32, the handle portion 156 is pivotally attached to the guide body 164. The pivot elements may be a pivot pin or rivet through the handle and body, or another joint such as a hinge, or ball and socket among other options. The handle portion 156 may include two halves, A and B. When the handle portions are closed together, the rod inserter aperture 158 is formed and the shaft 159 of the rod inserter 140 can be fed through the aperture 158 and the slot 106 in the manipulators 124. This aperture is preferably circular although non-circular shapes are contemplated, such as an elongated slot, provided the opening is sized to accept the rod inserter 140. Having the aperture 158 created by pivoting halves gives the rod inserter 140 more freedom of movement. For example, after the rod inserter 140 has positioned the connecting member 26, the inserter 140 does not need to be backed out of the guide 142 through aperture 158, but instead can be more easily removed by opening up the two halves. The surgeon may not wish to employ the guide 140, but may instead use the rod inserter 140 independent of the guide 142.

FIG. 33 illustrates, how the rod inserter aperture 158 is angled along a trajectory leading toward the yoke 22. More specifically, the surface of the aperture 158 is canted as it extends through the handle portion 156 so that an axis C extending there through extends transverse or obliquely to the axes of the manipulators in which the yokes are retained or held.

Figure 24:
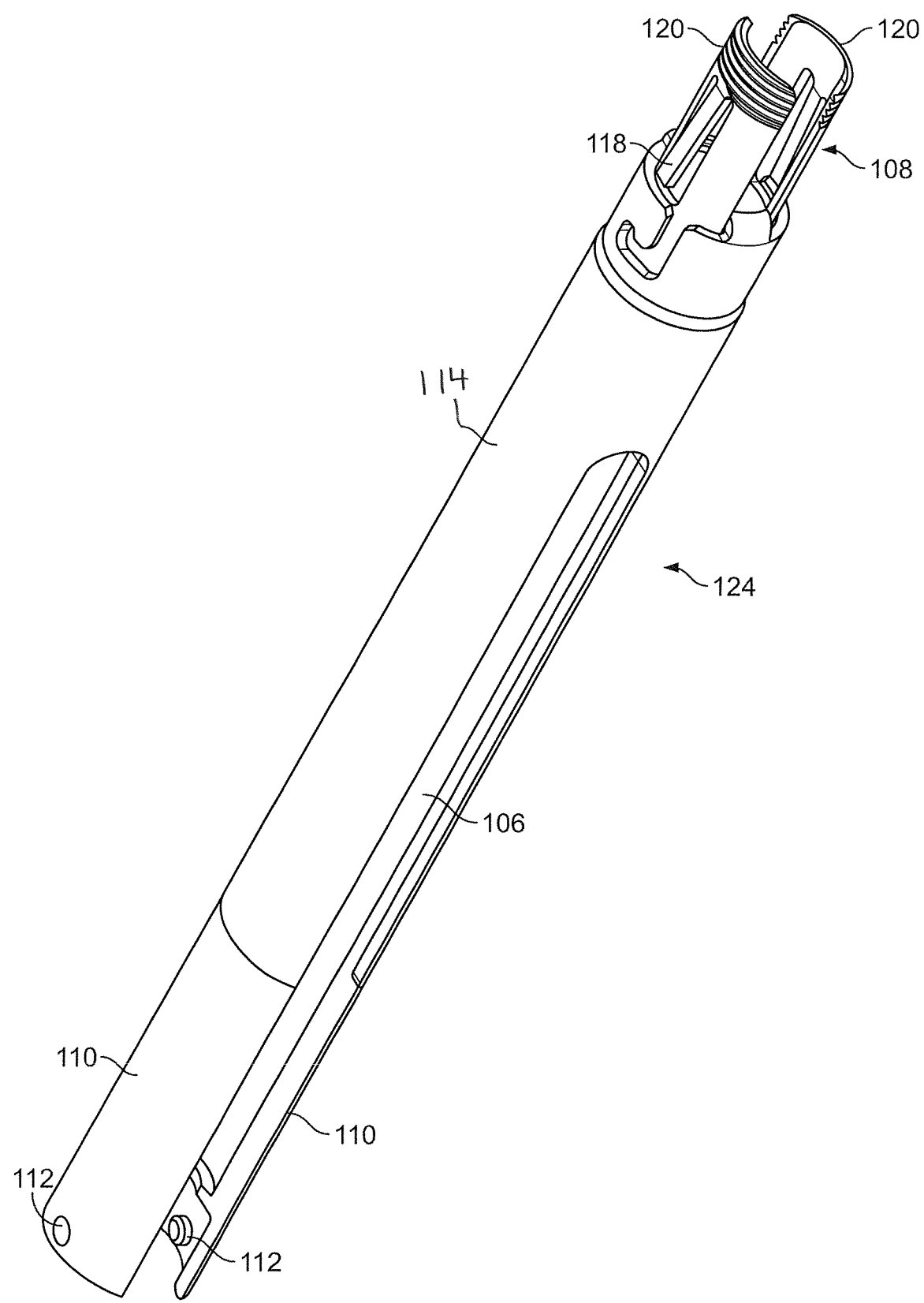
FIG. 24 is a perspective view of another yoke manipulator.
Figure 25:
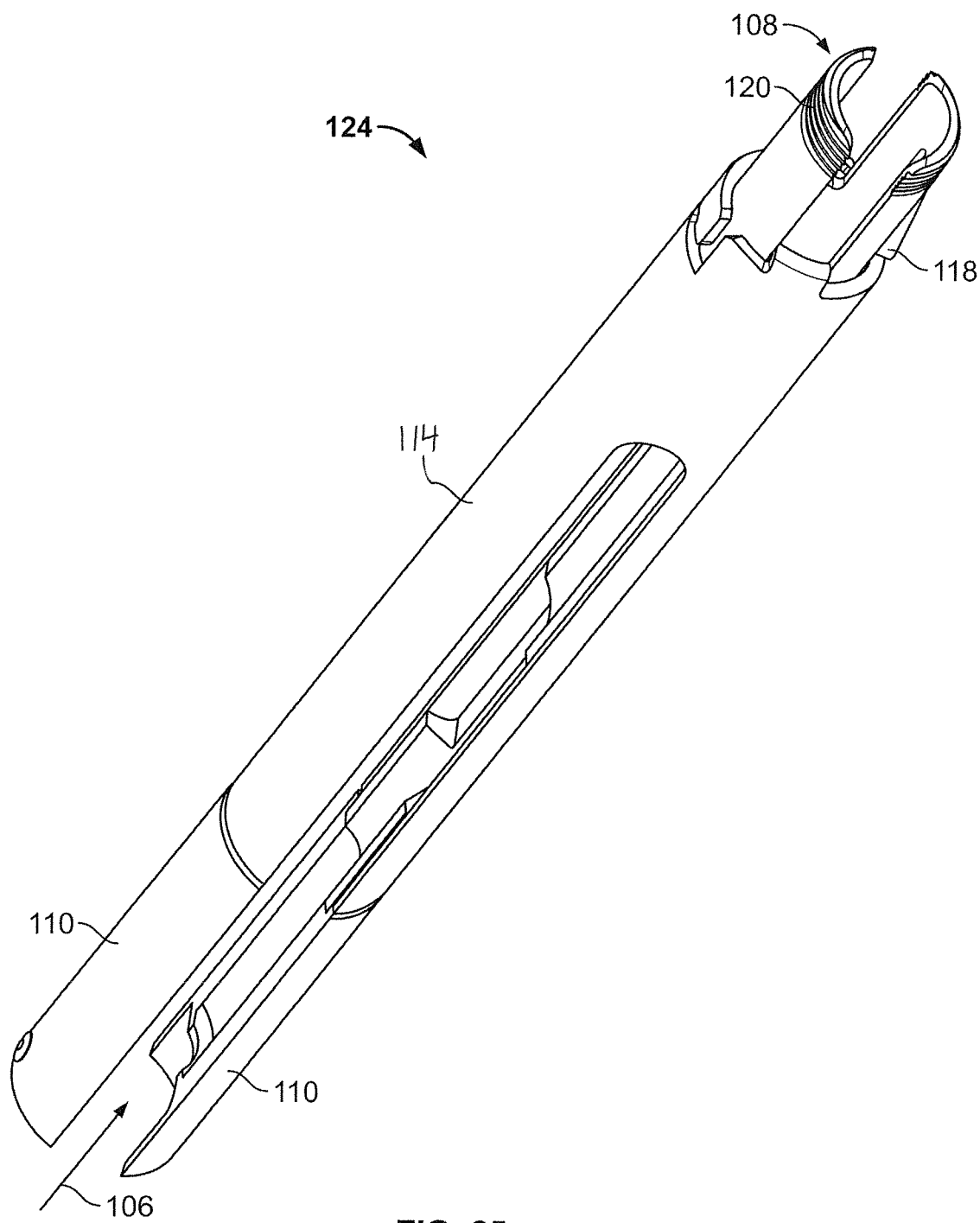
FIG. 25 is another perspective view of the yoke manipulator of FIG. 25.
Figure 26:
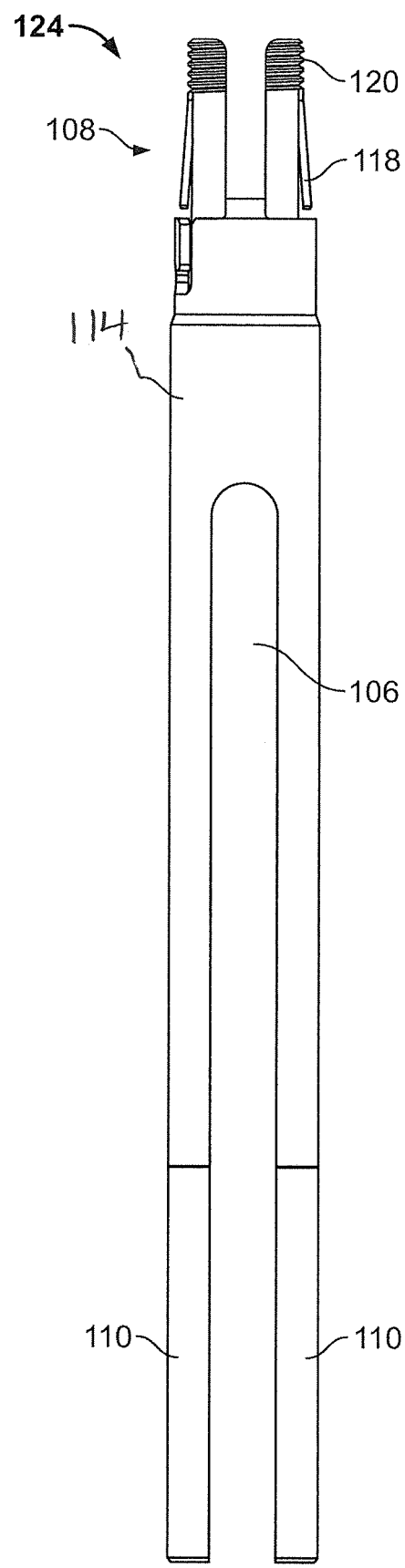
FIG. 26 is a side plan view of the yoke manipulator of FIG. 25.

The guide body 164 serves as the primary mechanical structure to which other major guide portions attach. For example, in FIG. 24, the body 164 includes a handle pod 168 for cooperation with the handle portion 156. On the distal end, the guide body 164 may include the distal holder 160 for housing the distally positioned yoke manipulator assembly 141. It is preferred that the distal holder 160 be formed to cooperate with the yoke manipulator assembly 141 for correct positioning of the connecting member 26. Further, the distal holder 160 may include one or more directional locators 170. The locators 170 are small nub projections extending in the holder opening 161 that mate with the positioner 116 on the manipulators 102, 124. The depth of the positioner 116 may be adjusted to cooperate with the directional locators 170 such that the connecting structure 120 is held in a predetermined position with respect to the guide body 164.

The guide body 164 may also house the proximal holder 162 to permit control over the proximally positioned yoke manipulator assembly 141. It is preferred that the proximal holder 162 include a groove, ridge, track, or other structure to make it positionally adjustable within the guide body 164. For example, in FIG. 32, the body 164 includes a proximator guide 172, illustrated as a groove which adjustably guides the proximal holder 162 by way of the holder guide 174, towards and away from the distal holder 160. Such an adjustment is helpful to account for the variation in spacing of boney landmarks between one patient and another thereby making the MISS useful for patients of varying sizes. The holder guide 186 in the embodiment shown in FIG. 27, is in the form of a boss but could take many forms that complement the proximator guide 172 for the function of guiding the proximal opening yoke within the body 164.

More particularly, the guide body 164 includes a pair of generally parallel rail portions 166 extending along either side of the main opening 169 formed in the body 164. The rail portions 166 each have elongate slots 171 formed therein, and the proximal holder 162 has a generally square configuration with side walls 173 adjacent the rails 166. The sidewalls 173 have a slide member 175 attached thereto, sized to fit in the slots for sliding therein. To fix the adjustable, proximal holder 162 in the guide body opening 169, a releasable lock 184 such as in the form of a threaded nut is utilized, as will be described more fully herein after.

Figure 34:
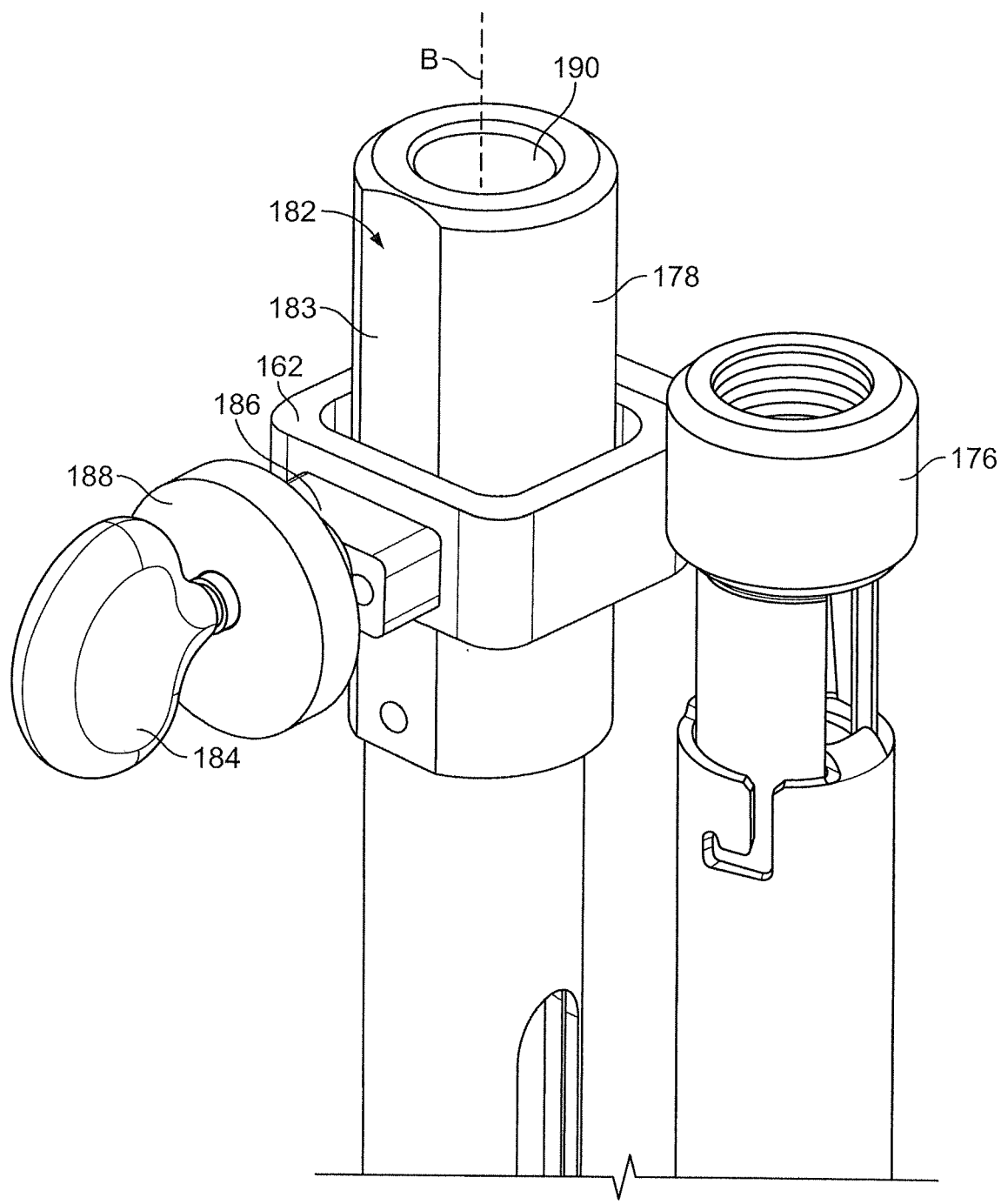
FIG. 34 is an enlarged perspective view of portions of the guide attached to the yoke manipulator.
Figure 35:
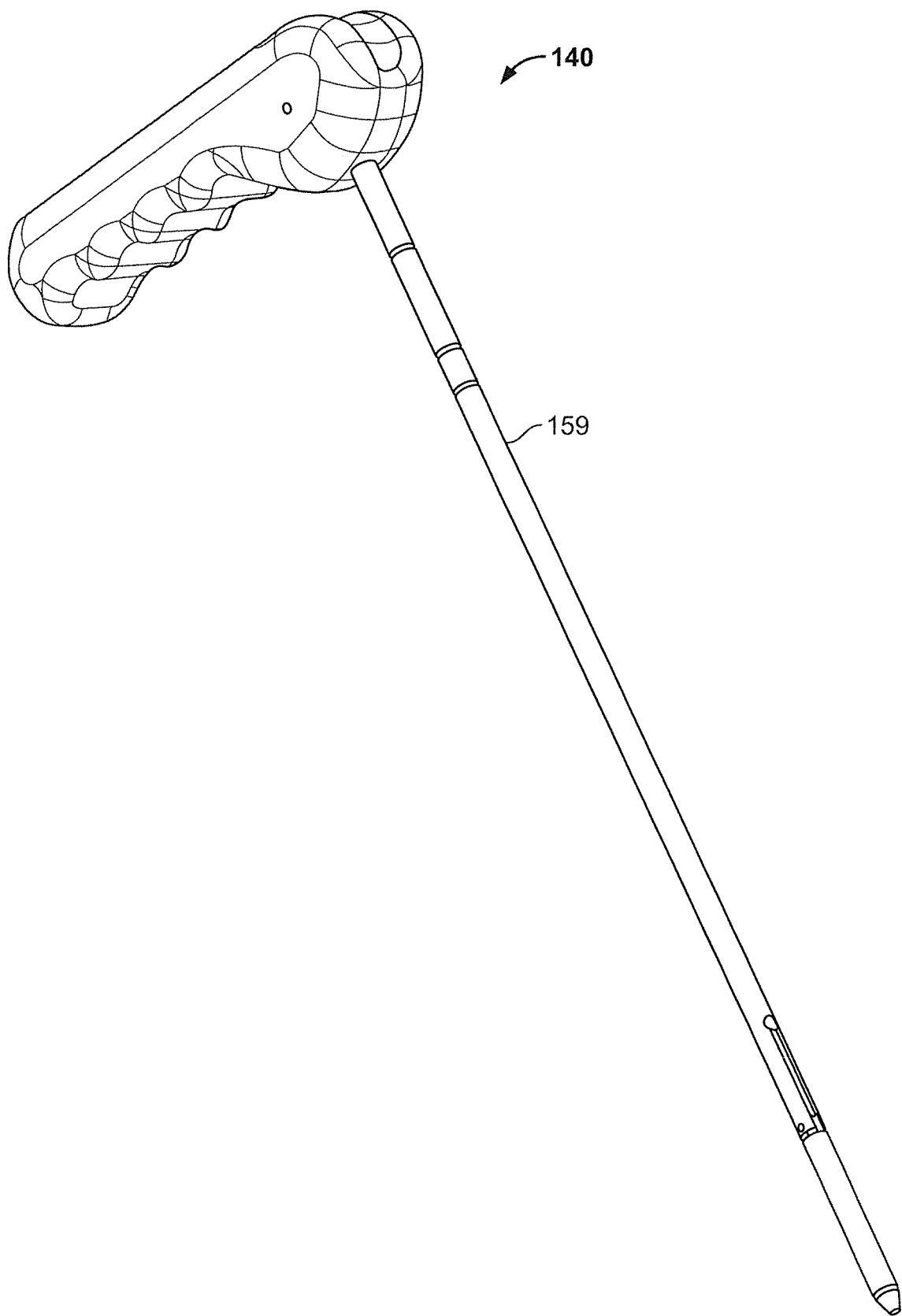
FIG. 35 is a perspective view of the rod inserter with an attached connecting member with the locking sleeve removed.

The proximal end of the yoke manipulator assembly 141, include a locking cap 176 or guide cap 178. The locking cap 176 is a structure intended for securing the yoke manipulator assembly 141 within the distal holder 160. For example, as shown in FIG. 34, the locking cap 176 may be in the form of a threaded nut mating with complementary connecting structure 120, which is illustrated as external threads at the proximal end of the manipulator. Alternatively, other connections may be used such as a bayonet connection, a set screw, or a ball detent.

The guide cap 178 may also use these alternative connections, however the bayonet style connection is preferred. A locator boss 180 formed or fixed within the guide cap 178 may serve to position, with respect to the yoke manipulator assembly 141, and hold the guide cap 178 within the retraction structure when applied in a push and twist manner.

As illustrated, the guide cap 178 and long slot manipulator bayonet attachment includes a J-shaped slot at the promixal end of the outer shaft or restraint 114 of the manipulator in which the boss 180 is linearly advanced before bottoming out. Thereafter, the cap 178 is turned so that the cap 178 cannot be pulled axially of the manipulator absent rotation thereof in the opposite direction. The cap 178 may have a bayonet attachment, a lock press fit, among others. Further, the cap 178 has tabs on the inside to resist torque. The cap 178 may include a positioner portion 182 serving to position the guide cap 178, and thus the yoke manipulator assembly 141, within the proximal holder 162 such that the slot 106 in the yoke manipulator assembly 141 is properly oriented for passage of the connecting rod 26. In the embodiment shown in FIG. 27, the positioner portion 182 is in the form of a flat surface 183 on the guide cap 178 thereby permitting fit of the guide cap 178 in only a predetermined orientation within the proximal holder 162. The positioner 182 could also be in the form of a boss, ridge, groove, or other structure to maintain positional orientation. It is preferred that the positioner 182 is formed to also permit the guide cap 178 to be adjustable generally along the axis B of the manipulator to again accommodate the variation in skeletal bone structure between patients. In this manner, guide cap 178 and therefore the yoke manipulator assembly 141 may be adjusted along axis B then locked in a desired position with manipulator lock 184 with respect to proximal holder 162.

The proximal holder 162 may also include a manipulator lock 184 for releasably locking the guide cap 178 or yoke manipulator assembly 141 in the proximal holder 162. Mis lock feature is illustrated in FIG. 34 in the form of a thumb screw, threaded into the body of the proximal holder 162, which upon rotation jams against the flat positioner 182. The guide 142 may also include a proximator lock 188 for locking the proximal holder 162 a predetermined distance from the distal holder 160. Again this distance is generally dependent on the anatomy of the patient. In this embodiment, the proximator lock 188 is in the form of a threaded nut wherein rotation of the nut on the threads of the thumbscrew will jam the nut against the guide body 164, and specifically adjacent side rail 166 thereof, to lock the proximal holder 162 in position. Alternatively, this lock 184 could be in the form of a cam, a ball detent, a spring pin, or other structure to lock the proximal holder 162 at a desired location within the opening 169 of the body 164. It is preferred that the proximal holder 162 is not permitted to pivot. For example, the holder guide 186 has a rectangular or block shape to prevent rotation when seated within the proximator guide 172. Both the locking cap 176 and the guide cap 178 preferably have an open center useful as a viewport 190 to permit the user to look down the yoke manipulator 102, 124 and view the connecting rod 26 entering the yoke 22 during operation.

Figure 40:
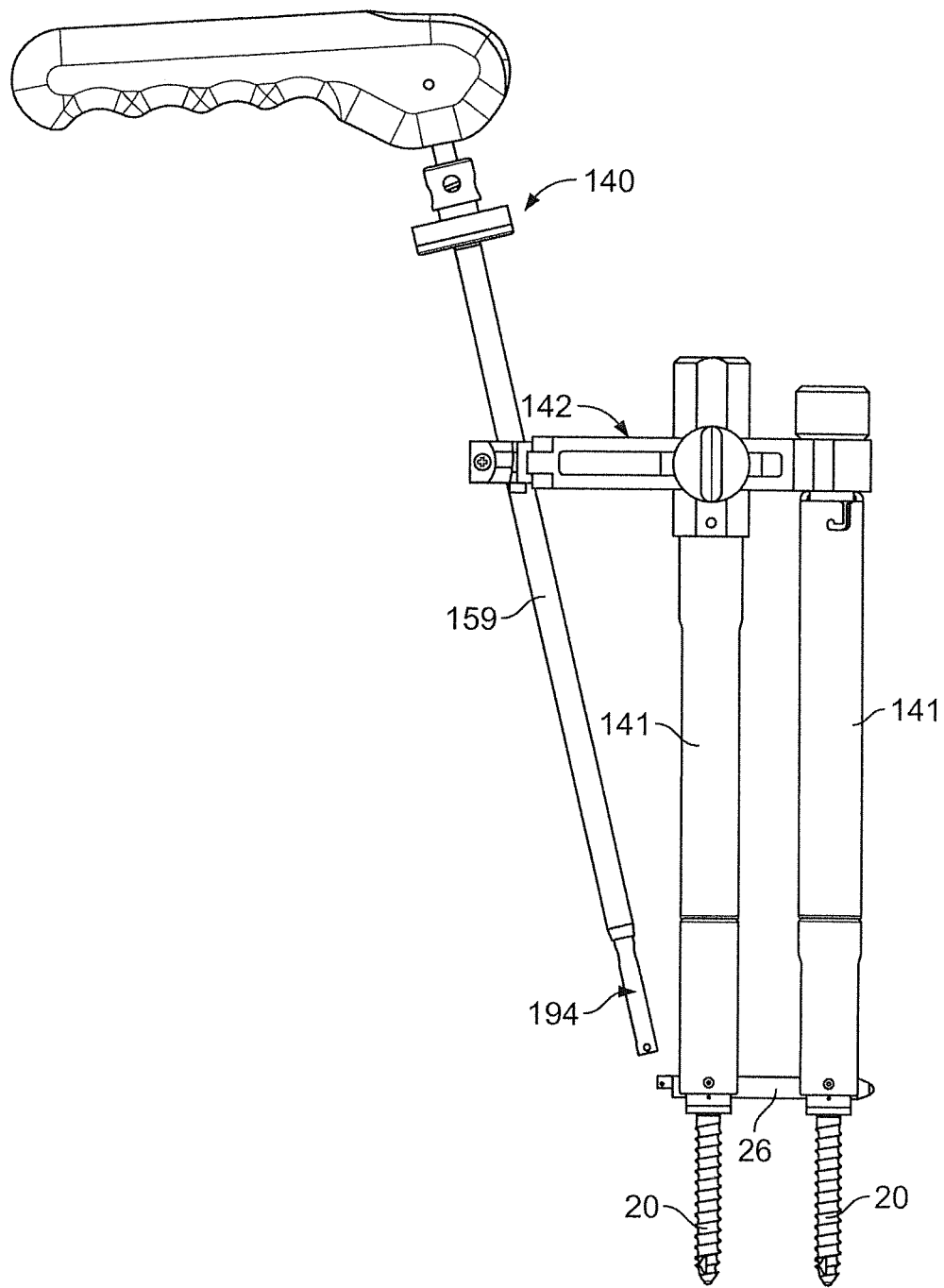
FIG. 40 is a side view of the MISS having a rod inserter in a third position.
Figure 41:
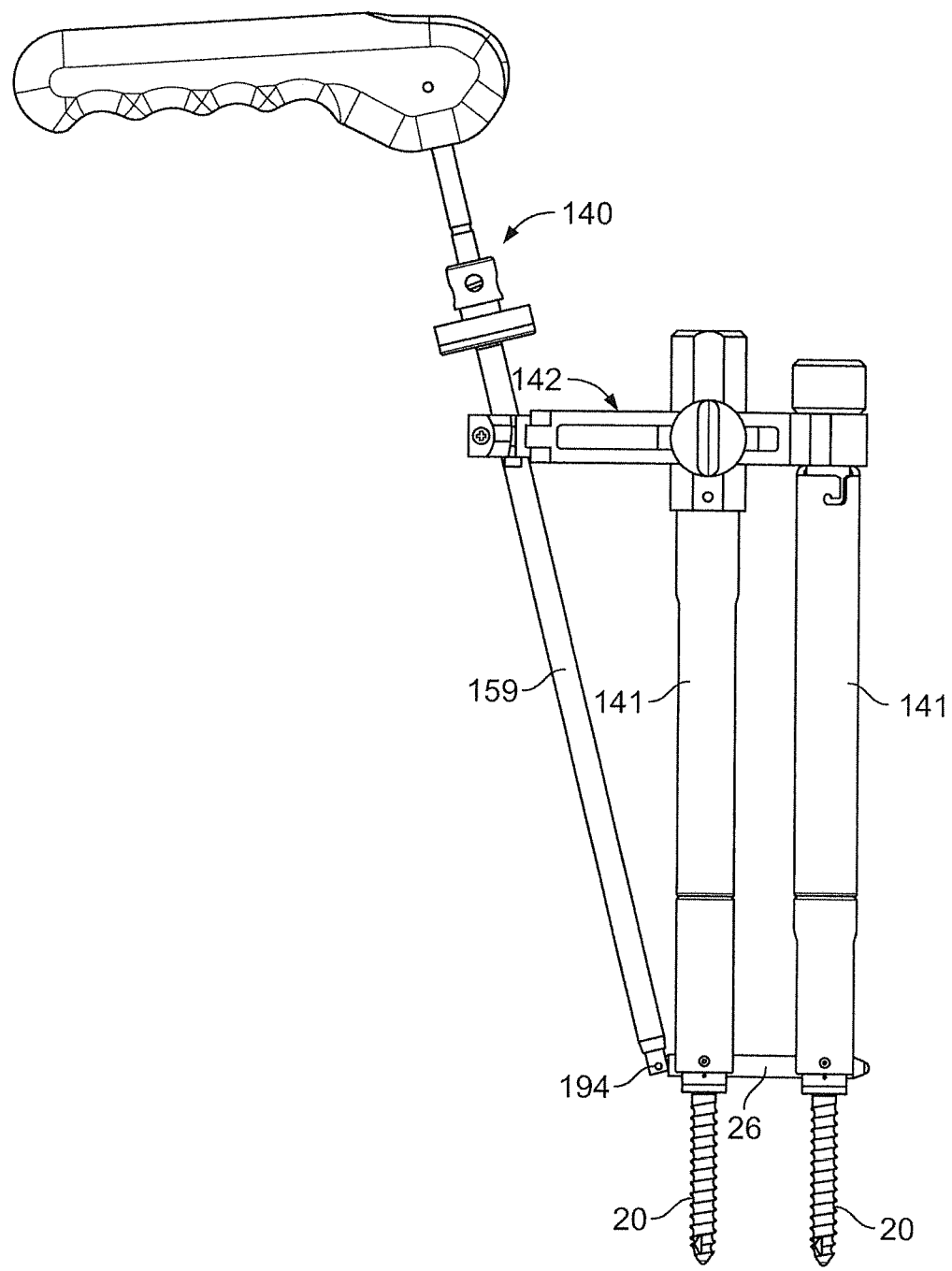
FIG. 41 is a side view of the MISS having a rod inserter in a second position.

A preferred embodiment of the rod inserter 140 is illustrated in FIGS. 33, 40, and 41. The rod inserter 140 functions to hold and guide the connecting rod 26 into a predetermined position within the yoke 22 of the pedicle screw implant assembly. The inserter 140 may include a clamping bar portion 192 having a deflectable clamp arm portion 194 at its distal end for grasping of the connecting member 26. The clamp 194 may be comprised of two or more clamp arms 196 formed by a cut or slot at the distal end of the clamping bar 192. Each clamp arm 196 may include one or more clamp bosses 198 to mate within the control capture 152 of the connecting rod 26. The clamp arms 196 are preferably spaced by a sufficient distance for acceptance of the control boss 150 on the connecting rod 26. The clamp slot is preferably of adequate length wherein the clamp arms 196 are flexible. In this manner, the end boss 150 of the connecting rod 26 may be cammed or otherwise fit between the arms and clamp bosses 198 thereof until the bosses 150 are aligned and received in the control capture 152 in the form of recesses or openings in the end thereof.

The proximal end of the clamping bar 192 is fixed within the handle by a fixation pin, however use of a compression fit, bonding or other adhesives, screw threads or other fixation methods are acceptable. The handle 157 is preferably mounted generally perpendicular to the clamping bar 192 and is preferably sized and shaped for control by an operator's hand.

Figure 36:
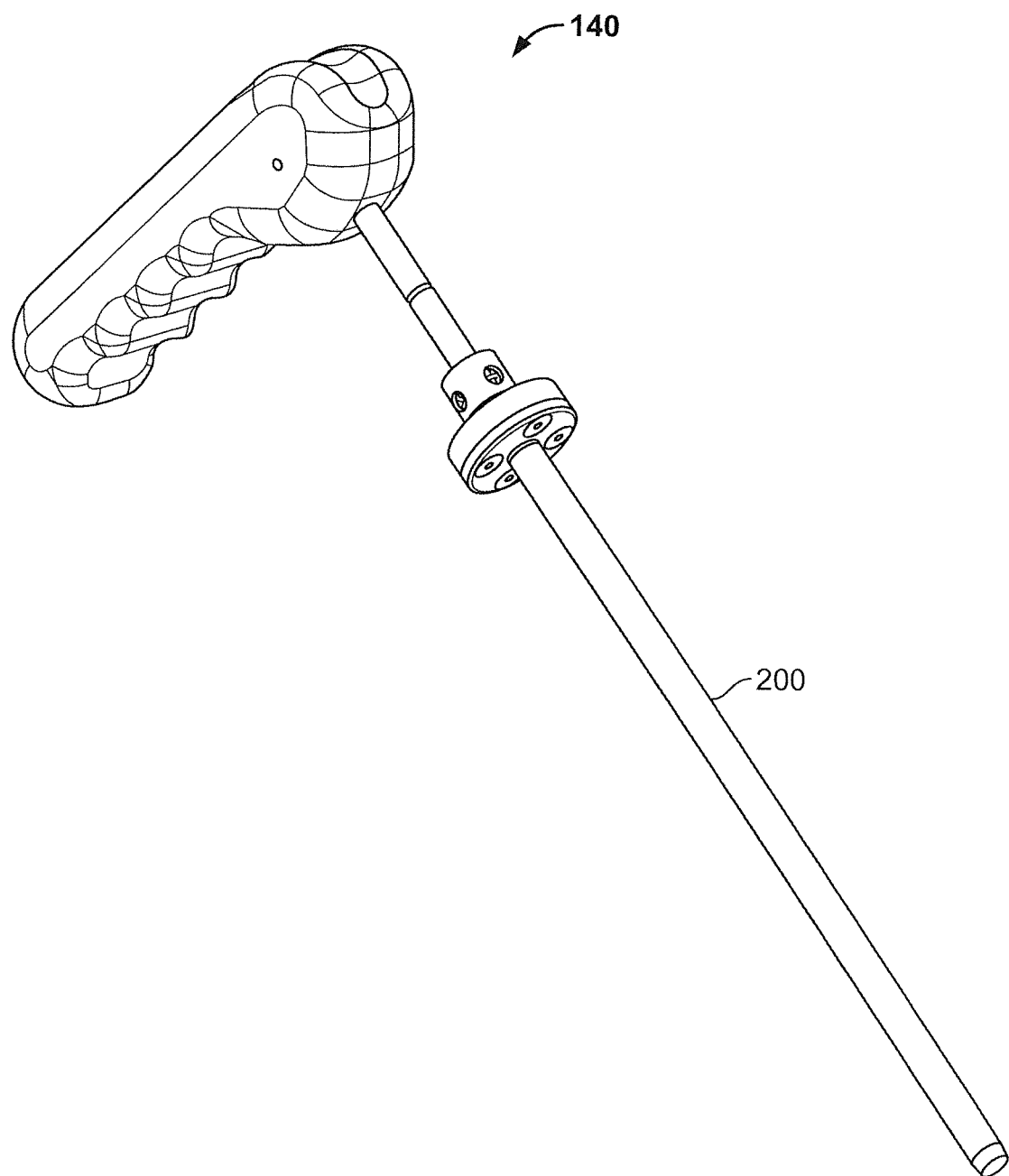
FIG. 36 is a perspective view of the rod inserter.
Figure 37:
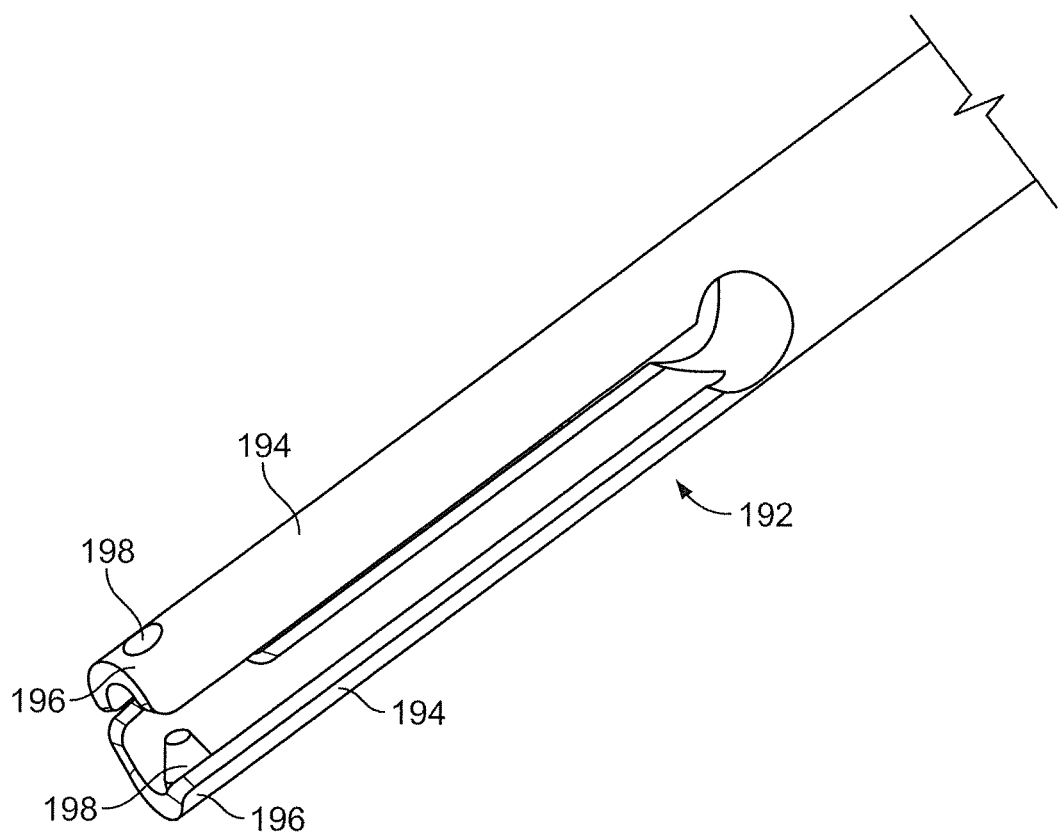
FIG. 37 is an enlarged view of the rod inserter clamp.
Figure 38:
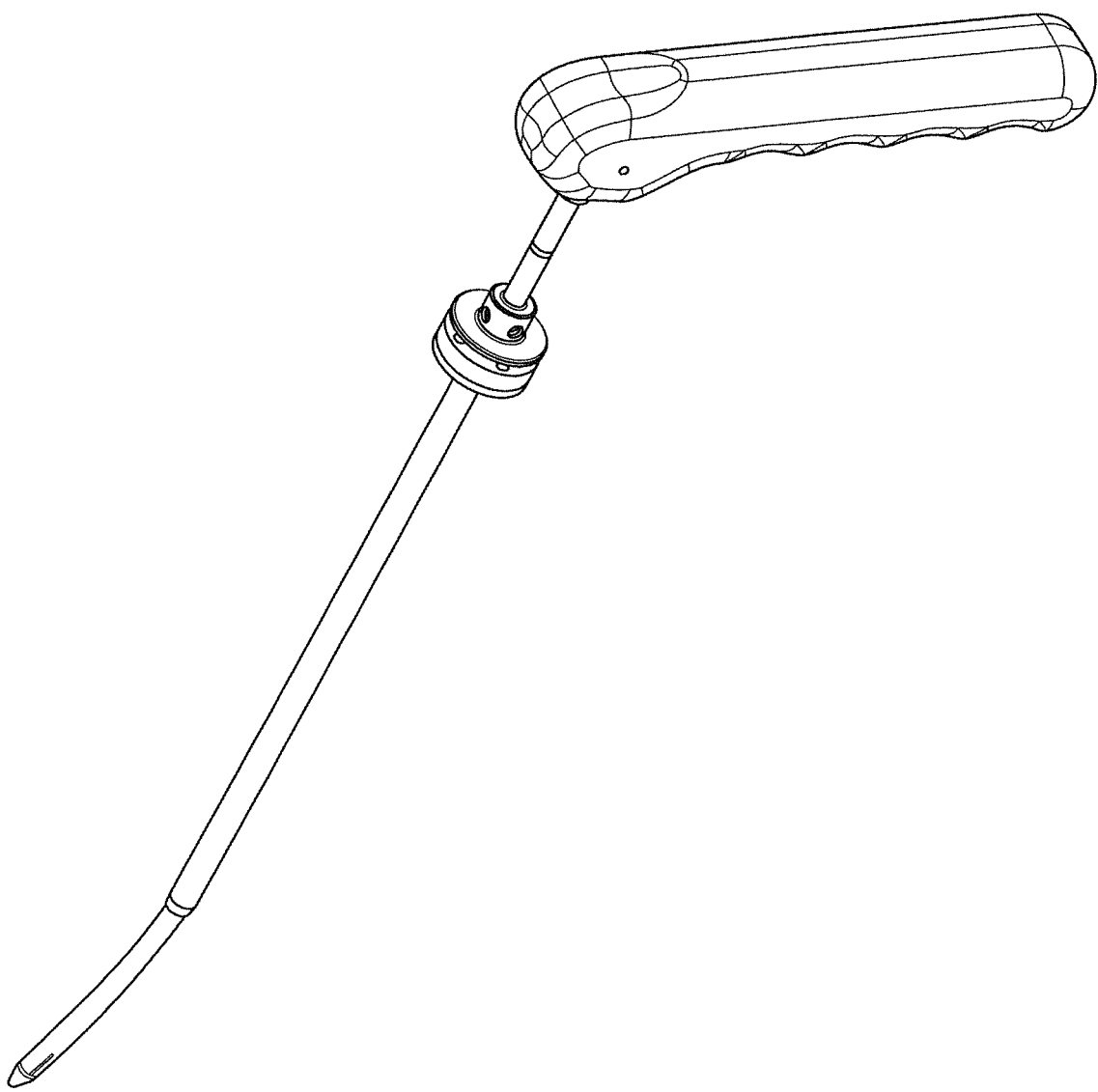
FIG. 38 is a perspective view of another embodiment of the rod inserter having a bent connecting member attached to the inserter clamp.

FIG. 36 illustrates a rod inserter 140 with a locking sleeve 200 and a positional lock 202 removed and the connecting rod 26 held within the clamp 194. The clamping bar 192 may include positional recess 204 which works in conjunction with the positional lock 202. The positional lock 202 may be in the form of a ball detent mechanism as shown in FIG. 39, a radial spring, a boss in groove, or other mechanism which provides releasable positioning of the locking sleeve 200 on the clamping bar 192.

It is preferred that the positional lock 202 defines three locking sleeve positions. In this regard, the lock 202 is connected with the sleeve, as described hereinafter. The three locking sleeve positions correlate to different insertion positions or orientations of the connecting rod 26. In "position 1" the connecting member 26 is firmly grasped within the clamp 194, such that the member 26 cannot move independent of the inserter 140. In "position 2" the connecting member is grasped in the clamp 194 such that the member 26 can pivot with respect to the inserter 140. In "position 3" the clamp 194 releases the connecting member 26.

In the present embodiment, when the positional lock 202 is in a positional recess 204a nearest the handle, "position 3" (FIG. 40), the locking sleeve annulus is positioned behind or clear of the clamp 194 wherein the clamp arms 196 are free to deflect and the connecting rod 26 is free to be inserted or released from the clamp arms 196. When the positional lock 202 is in the middle positional recess 204b, "position 2" (FIG. 41), the locking sleeve annulus is positioned partially over the clamp arms 196 thereby locking the connecting rod 26 within the arms 196 yet permitting the connecting rod 26 to pivot about the clamp bosses 198 in a range allowed by stops such as the control ridge 154. In position 2, the connecting member 26 is able to angulate 90 degrees up from collinear of the inserter 140 and specifically the bar thereof, but cannot angulate down. When the positional lock 202 is in the distal positional recess 204c, "position 1" (FIG. 33), the locking sleeve annulus is positioned over the clamp 194 and partially over the rod body 146 so that the connecting rod 26 is held within and generally in line with the axis of the locking sleeve 200.

Figure 39:
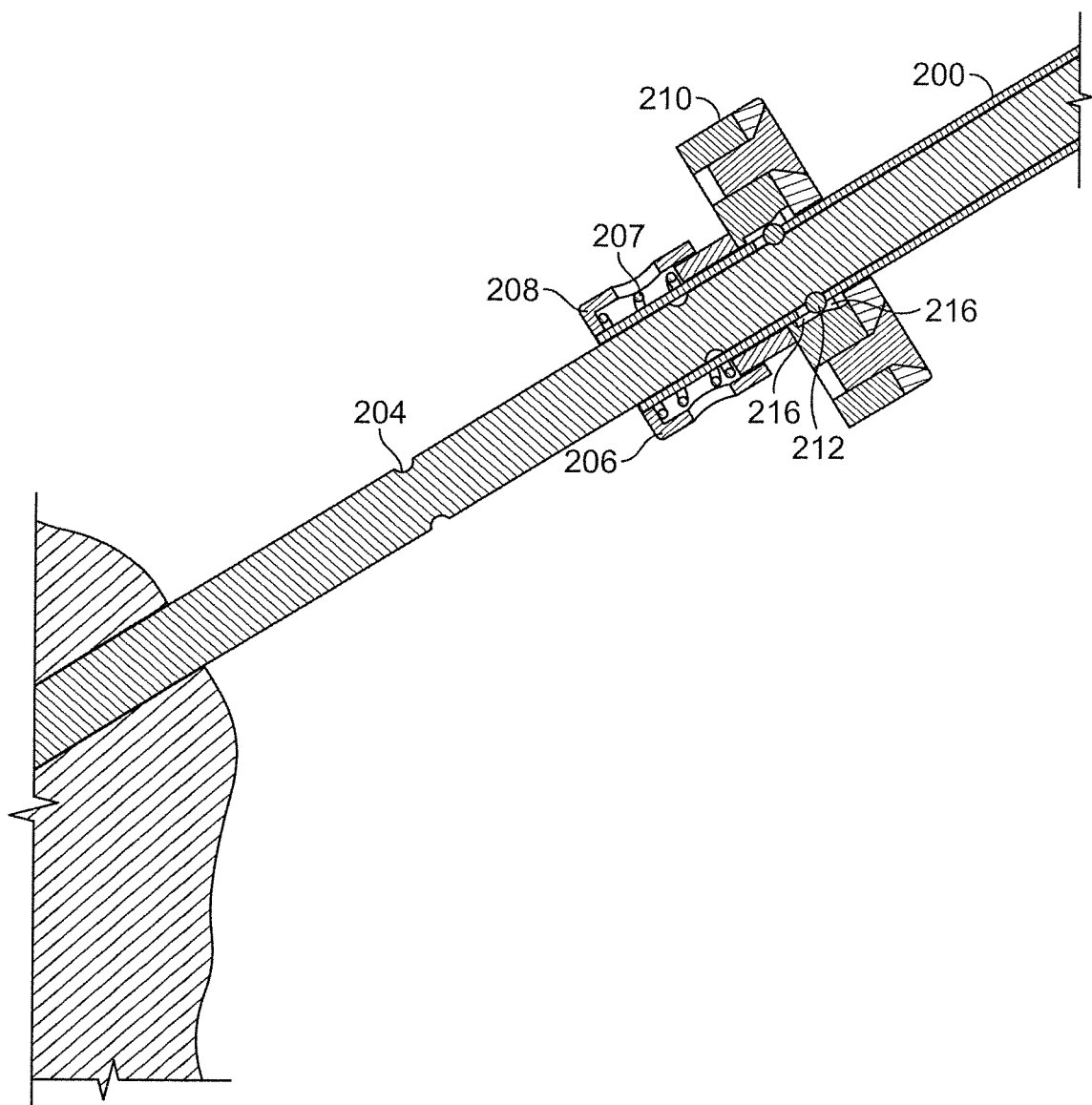
FIG. 39 is a cross section view of a positional lock shown in FIG. 36.

In FIG. 39, a ball detent version of the positional lock 202 is illustrated in a cross-sectional view. Integral to the locking sleeve 200 is a near collar 206 which houses a biasing member 208 and which compresses against a far collar 210 slidingly mounted on locking sleeve 200. Within the far collar 210 is one or more detent balls 212, riding in holes or recesses 214 within the locking sleeve 200, and which ride on the clamping bar 192. As the biasing member 208 pushes against the far collar 210, a lock ridge 216 compresses or pushes the detent ball 212 radially in the positional recess 204 therein locking the locking sleeve 200 in place. When the user overcomes the biasing member 208 by pressing together the near collar 206 and the far collar 210, the detent balls are able to ride in the unlock ridge 218 thereby falling out of the positional recess 204 and enabling the locking sleeve 200 to be slid to a different positional recess 204. The clamping bar or locking sleeve may include stops, in the form of bosses, ridges, c-clips, or setscrews for example, to limit the range of movement of the locking sleeve 200 to the desired positional recess 204.

As illustrated, the sleeve 200 extends down along the clamping bar 192 from the upper collar 206 down through the lower collar 210 which can slide thereon. The coils 207 of the spring biasing member 208 extend about the bar out from the upper collar 206 with the spring 208 connected to the lower collar 210 at the lower end of the spring 208. The lock ridge is a recess annular surface of a diameter slightly larger than that of the clamping bar 192 and extending generally axially and parallel relative to the outer surface thereof. The detent balls of a diameter that is larger than the gap between the annular surface and the bar surface so that the detent balls are normally urged into the locking recesses or annular grooves 204 formed along the clamp bar 192.

Below the lock ridge annular surface, the unlock ridge tapers away from the clamp bar as can be seen in FIG. 39. Accordingly, when the surgeon wishes to shift the lock, they simply pull up the lower collar toward the upper collar against the spring bias so as to bring the tapered surface into radially alignment with the balls allowing them to shift out of the clamp bar groove in which they reside and ride up or down along the clamp bar as the surgeon shifts the lock to the desired axial position therealong.

Figure 43:
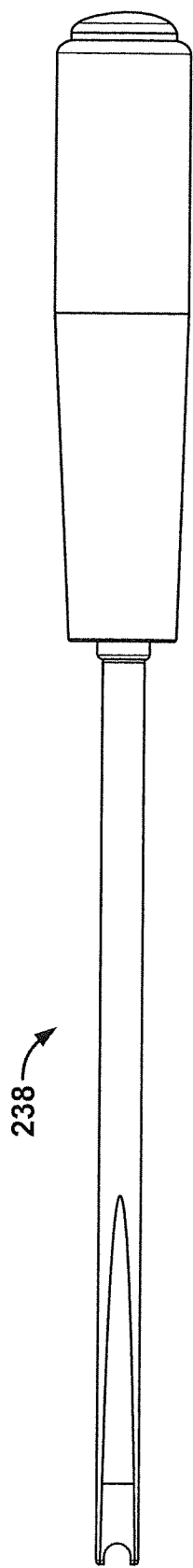
FIG. 43 is a side view of a pusher.

To assist the surgeon in positioning the connecting member 26, a pusher 238 shown in FIG. 43 may enter through the short slot yoke manipulator 102 (the distal manipulator assembly 141) to hold the rod into position as the rod inserter 140 moves the connecting member from "position 1" to "position 2." For example, by using the pusher 238 in the short slot manipulator 102 to control member rod 26, while the member rod 26 is still connected to the rod inserter 140, the surgeon has sufficient control over the rod member 26 to facilitate correct positioning. Before the sleeve 200 is moved from "position 1" the guide handles 156 may be spread open. The pusher member 238 does not lock, but instead allows the surgeon to apply force to the member 26 at the surgical site.

Figure 44A:
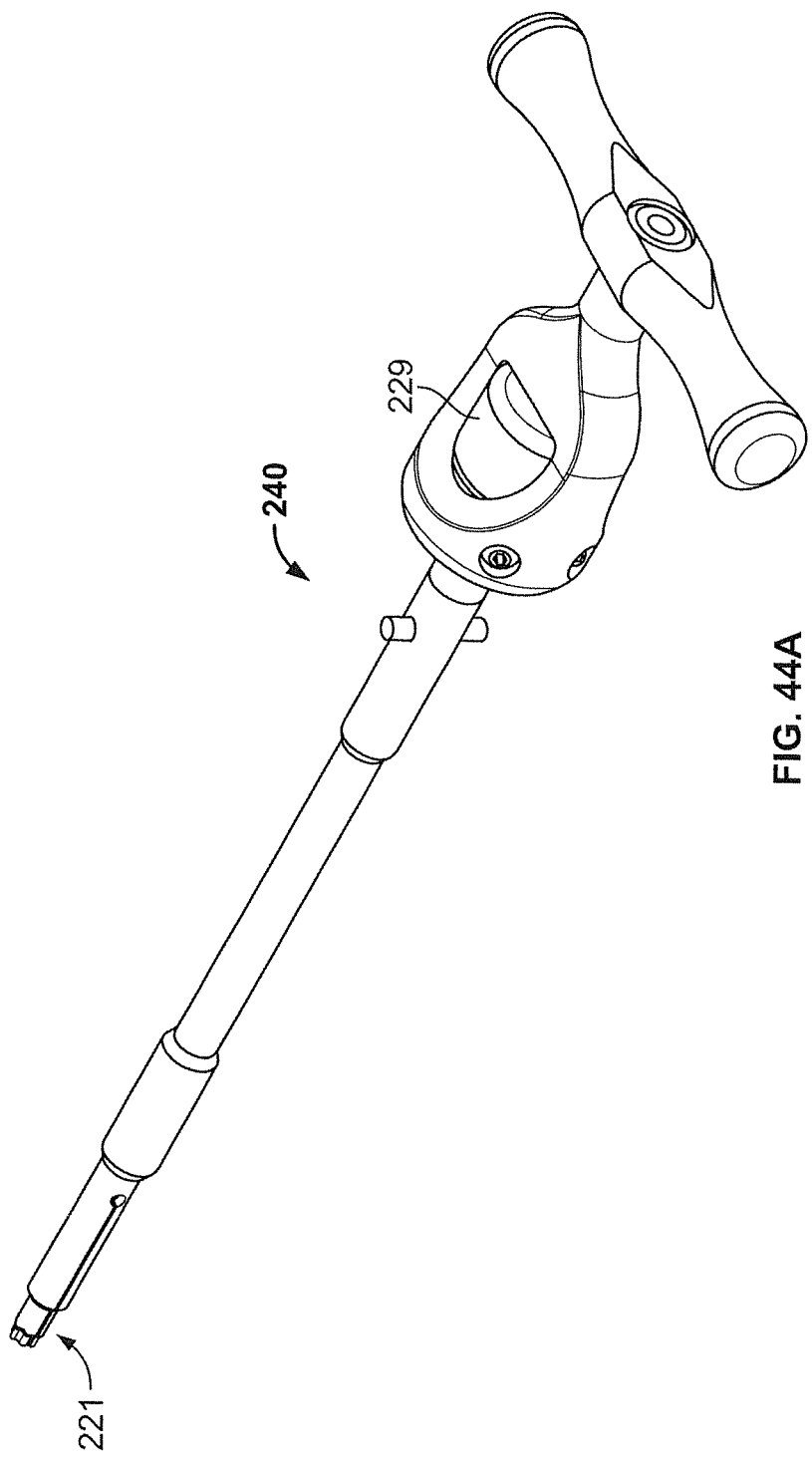
FIG. 44 A is a perspective view of a cap inserter.
Figure 44B:
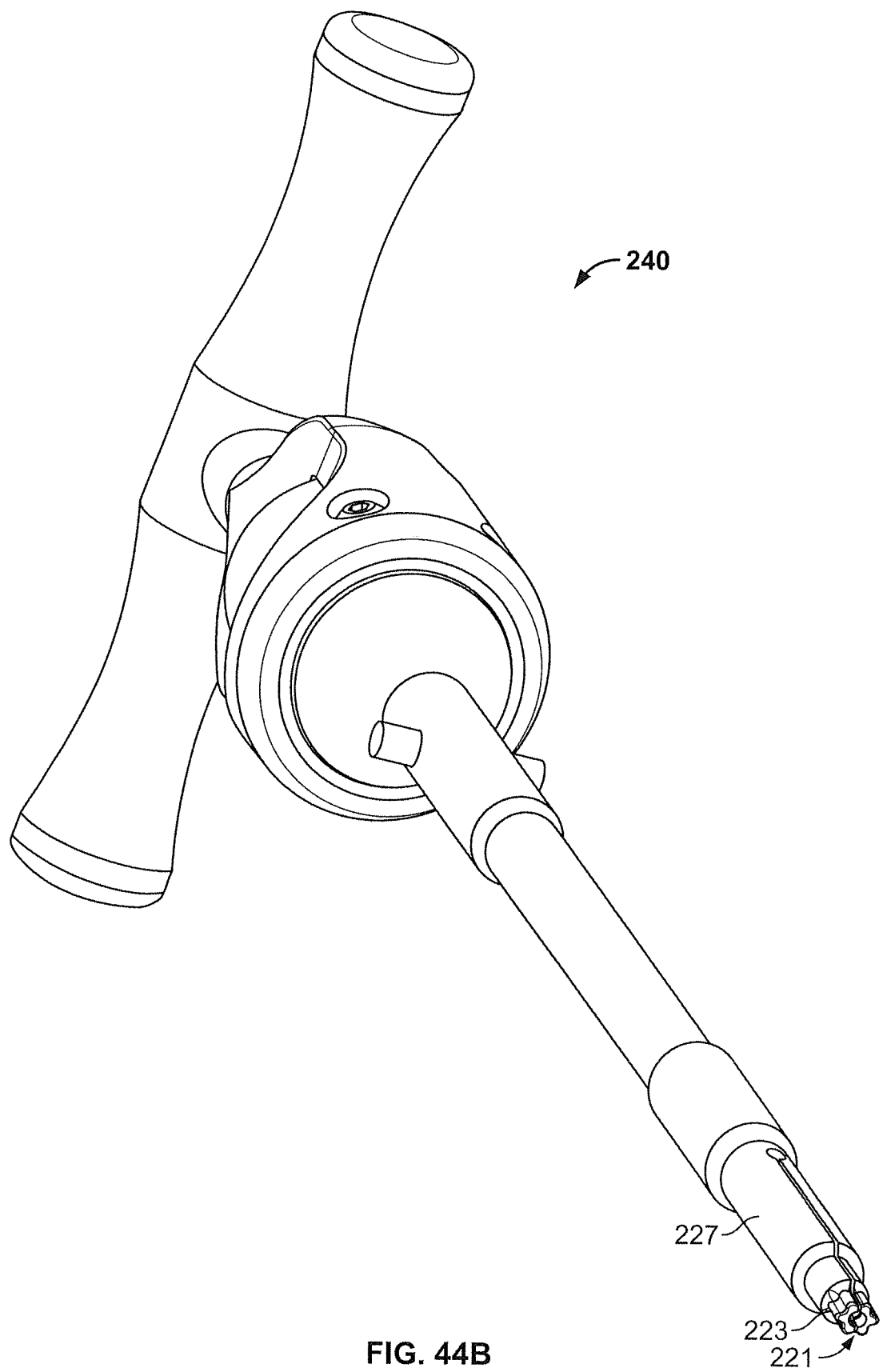

Once the connecting member 26 is properly situated in the yoke 22, a cap inserter 240 may be used to rotate the cap 24 to retain the connecting member 26 in the yoke 22. One embodiment of the cap inserter 240 is shown in FIG. 44 A. The cap 24 is positioned in the long slot yoke manipulator 124, and then the rod inserter 140 and guide 142 can be removed from the manipulators.

The cap 24 is placed into position using the cap inserter, FIGS. 44 A and B. To avoid accidental release of the cap 24 during the insertion procedure, instruments such as the cap inserter 240 and rod persuader 220 may include a retention mechanism 221 to releasably retain the cap 24. A retention mechanism 221 is located on the driving end of these instruments and may include a male driving portion 223 that mates with a female drive recess 225 in the cap 24. The male driving portion 223 is split into one or more flexible arms 227. A dial 229 at the handle end of the instrument 240 activates a plunger at the male driving portion 223 with the flexible arms 227 so that it can secure the cap to the instrument. To release the cap the dial 229 is derotated causing the plunger to retract wherein the flexible arms 227 can constrict and release the cap 24 as it is positioned in the yoke 22.

Figure 42:
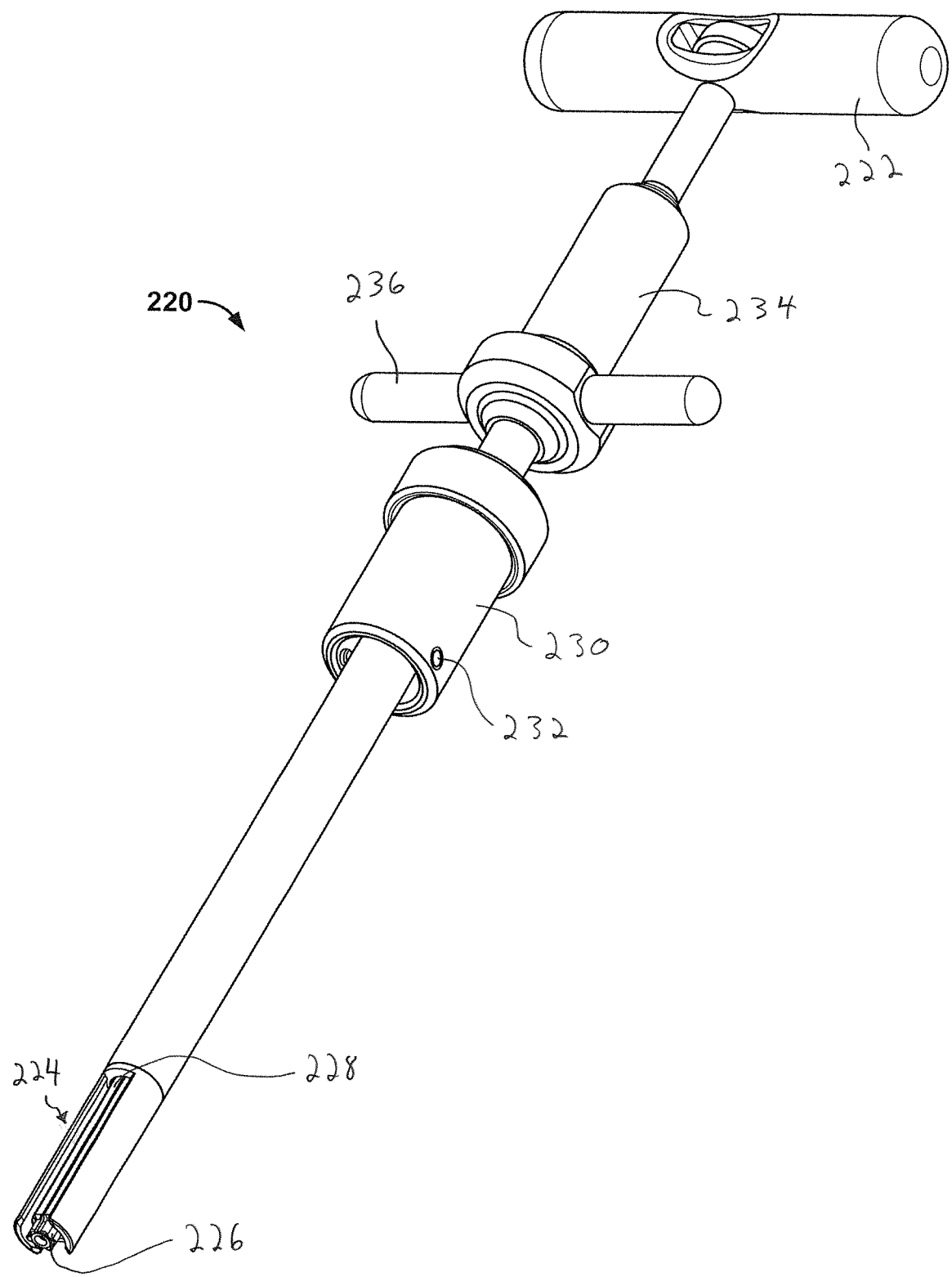
FIG. 42 is a perspective view of a rod persuader.

However, there are times when the member 26 will need to be forced into the yoke 22 in order to rotate the enclosure cap 24 thereby capturing it within the yoke 22. The MIS rod persuader 220 (FIG. 42) may be used not only to force down the rod, but also to rotate the closure cap 24. Typically, the rod persuader 220 is only used with the short slot yoke manipulator 102 when the surgeon is having difficulty positioning the connecting member 26 in the yoke 22. First, a rod driver handle 222 is derotated wherein the cap driver 226 is backed up into the window 224. The closure cap 24 is then loaded on the persuader 220 by mating the cap driver 226 within the drive surface of the closure cap 24 with the cap flanges 25 resting within the window 224. The driver rod 228 is led down the center of the yoke manipulator assembly 141 until the restraint cup 230 rests over the top of the restraint 114. The restraint cup 230 may include a lock 232 wherein a rotation of the restraint cup 230 moves the lock 232 into the retraction structure 122 to hold the persuader 220 and cap 24 within the yoke manipulator assembly 141. Other connections may be used to hold the yoke manipulator assembly 141 to the persuader 220 such as a threaded connection.

Figure 45:
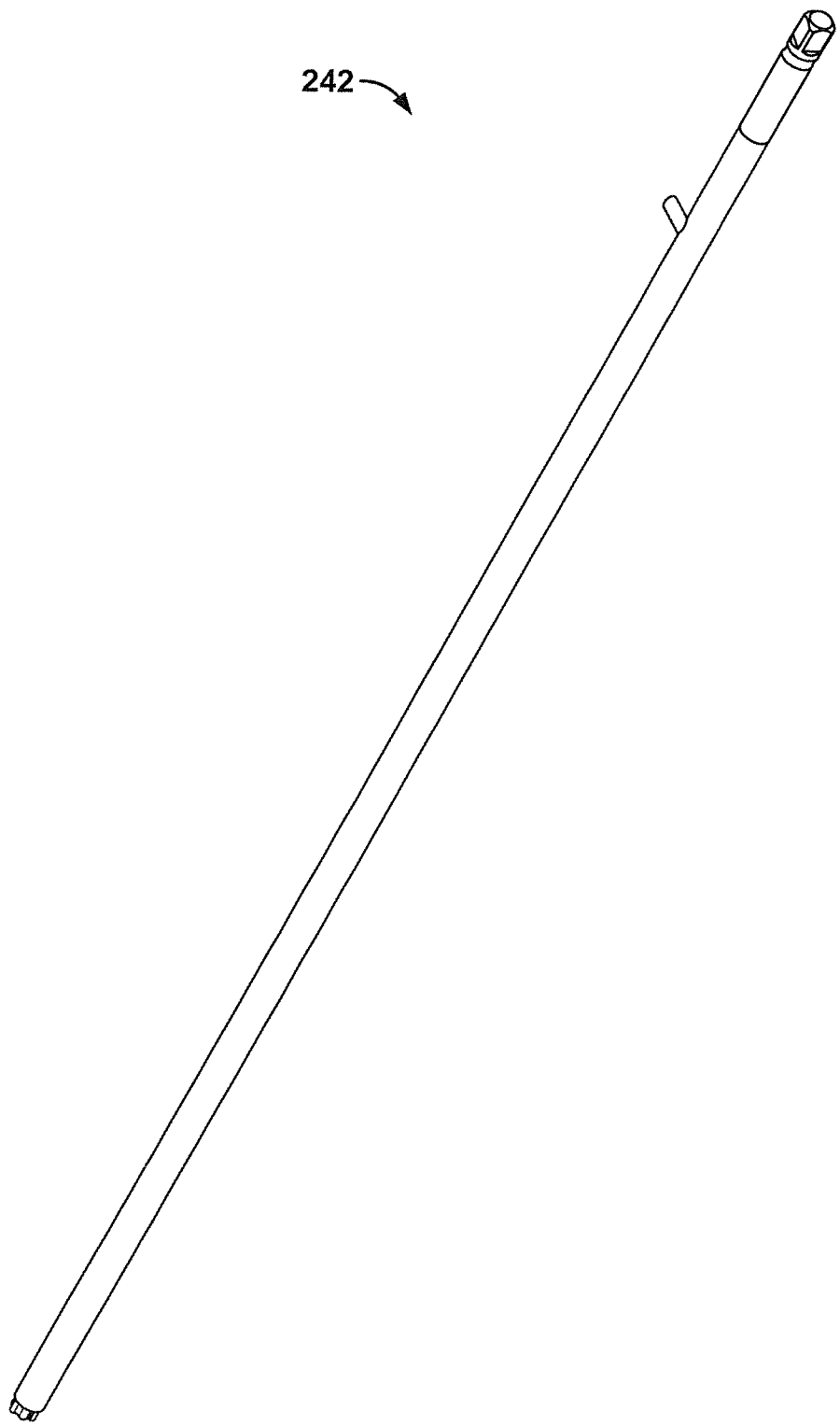
FIG. 45 is a perspective view of a final locking instrument.

The driver rod 228 maintains a threaded connection with a body 234 wherein rotation of the rod driver handle 222 will advance the driver rod 228 down through the window 224 thereby advancing the cap 24 and thus the connecting member 26 into the yoke 22 to a predetermined depth. The cap driver handle 236 is then rotated which in turn causes a rotation of the cap driver 226 and a capture of the closure cap 24 in the yoke 22. The rod driver handle 222 is then derotated to withdraw the cap driver 226 from the closure cap 24. The restraint cup 230 can then be derotated from the yoke manipulator assembly 141 for persuader removal. The persuader 220 may perform final tightening on the closure cap 24, or a final locking instrument 242 and a torque tube 254 may be used. Typically, the persuader only rotates 45 degrees and then the final locking instrument 242, shown in FIG. 45, is used to rotate the cap 24 to its final locking position. The final locking instrument 242 is generally used to finally tighten the caps in the yokes held by both the long and short slot manipulators 102, 124.

Figure 46:
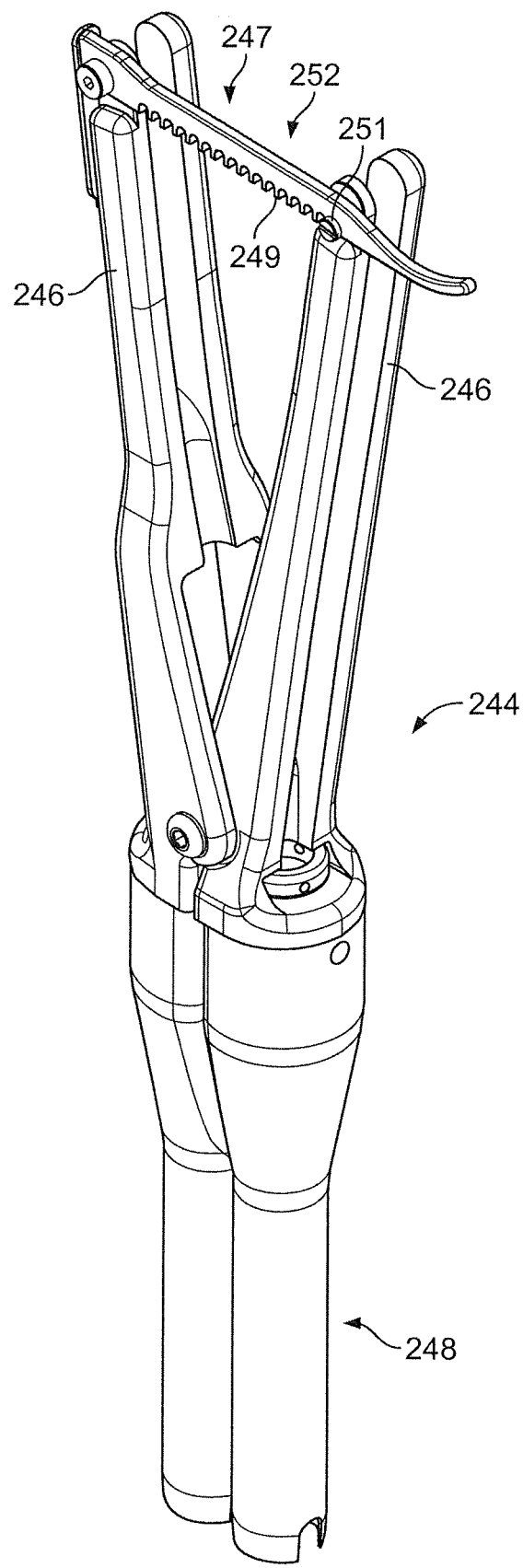
FIG. 46 is a perspective view of a compression tool with tubes attached thereto.
Figure 47:
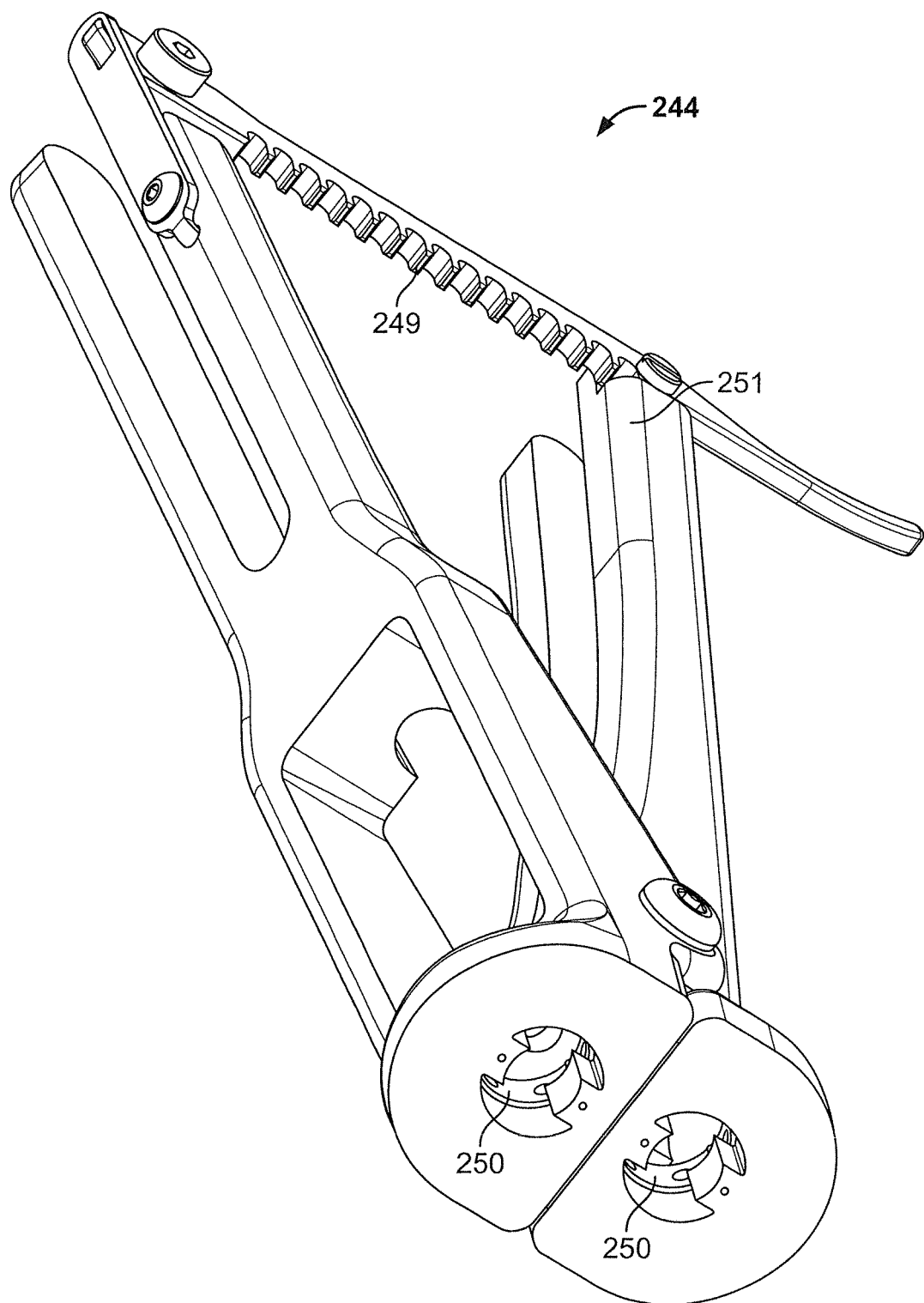
FIG. 47 is a perspective view of a compression tool without the tubes attached.

However, before the final locking instrument 242 fully tightens the cap 24, a compression tool 244 can be utilized to move the yoke manipulators 102, 124 and thereby the bone anchors 20 closer or further apart. As shown in FIGS. 46 and 47, The compression tool 244 has two handles 246. A pair of tubes 248 are slid over the yoke manipulators 102, 124. End apertures 250 open to the bottom transverse flange of the handles slide over the compression tubes 248. Then, by moving the handles 246, the surgeon can move the yoke manipulators 102, 124. The locking mechanism 252 located on the compressor 244 secures the compressor and the manipulators 102, 124 into position, such that the caps 24 can be finally tightened into position. Then, the final rotation is accomplished by the final locking instrument 242 as it is fed down through the tubes 248 of the compressor 244. Use of the compression tool 244 is based on patient needs and there are times when the compression instrument 244 will not be necessary.

More particularly, the handles 246 can be pivotally connected toward their lower flanged ends to provide relatively long lever arms for the compressor tool. This enables the surgeon to more easily distract or compress the adjacent vertebra in which the pedicle screw assemblies are implanted. One of the handles has a rack member 247 including spaced teeth 249, and the rack 247 is pivotally attached to its proximal end. The other handle has a projection 251 at its proximal end for fitting in a selected one the spaces between adjacent teeth. Accordingly, the rack 247 and projection 251 cooperate to form the illustrated and preferred locking mechanism 252 so that the handles can be fixed in a selected, locked position, relative to each other based on the distraction/compression needed for the surgical procedure.

After the connecting member 26 is locked into position, the manipulators 102, 124 may be released from the bone anchors 20. In one embodiment, removal of the manipulators involves removal of all unnecessary instrumentation from the center of the yoke manipulators 102, 124, or otherwise attached thereto. A retraction handle may be used to retract the restraint 114 from the yoke manipulator. Removal of the restraint 114 frees the arms 110, which may be formed to spring open thereby releasing the retainer recesses 136. This requires adequate clearance between the manipulator arms 110 and the inner wall of the docking sleeve 34. Now, the manipulator assembly 141 may be removed.

The surgeon may now choose to perform any final operations through the docking sleeve 34 before removal. Removing the docking sleeve requires releasing the docking fasteners 74, if employed and retracting the docking from the incision site. Appropriate wound closure techniques are then commenced.

In another embodiment, the docking sleeve 34 may include apertures, slots or other such features in the wall to permit passage of the connecting member 26 through the docking sleeve 34. As a further alternative, the fasteners 74 and docking sleeve 34 may be removed prior to the insertion of the connecting member 24. For example, the fasteners 74 and docking sleeve 34 may be removed just after the yoke manipulators 102, 124 are locked down on the yoke 22 with the restraint 114.

Another alternative would be to not use the docking sleeve 34 or the fasteners 74. In conjunction with or instead of incising the tissue along the guidewire 21, the surgeon may choose to use a single or series of progressively larger diameter obturators 36, guided by the guidewire, to stretch or open the tissues to a predetermined diameter. The surgeon may then continue the process of implanting the bone anchors 20 as described above albeit without the docking sleeve 34.

Preferably the MISS kit includes least two bone anchors or pedicle screws, which are inserted in the spinal anatomy with distal and proximal yoke manipulator assemblies 141 attached to each yoke 22. The guide cap 178 is locked on the proximal yoke manipulator assembly 141 using the bayonet connection. The guide 142 may then be positioned over the yoke manipulator assemblies 141 with the guide cap 178 seated within the proximal holder 162 and the connecting structure 120 within the distal holder 160. Locking cap 176 secures seating of the distal yoke manipulator assembly 141. The user adjusts the proximal holder 162 on the positioner 182 and may lock this position with manipulator lock 184. Proximal holder 162 is then adjusted within proximator guide 172 until the proximal and distal yoke manipulator assemblies 141 are generally parallel. The proximal lock is then applied to hold this position. The guide 142 may include etching as a quick reference for the user to choose an appropriate connecting member 26 length depending on the distance between the yoke manipulators.

The MISS connecting member 26 held in "position 1" of FIG. 33 within the rod inserter 140 and the rod inserter 140 is fed through the inserter guide 142 while the user holds both handle portions 156 adjacent to each other. The inserter 140 is fed through the slot 106 of the proximal yoke manipulator assembly 141, under the soft tissue of the patient, and into the yoke 22 of the distal pedicle screw implant as seen in FIG. 33. At this point, the rod inserter 140 is repositioned to "position 2" of FIG. 41, the handle portions 156 are permitted to be pivoted outward wherein the inserter guide no longer cradles the rod inserter 140. With the connecting rod 26 now pivotably attached to the rod inserter 140, the user guides the connecting rod 26 into the proximal yoke 22 perhaps viewing these movements through view ports 190. At this point the user preferably locks down the distal closure cap 24, then the proximal closure cap 24, using instruments and techniques described earlier. The inserter preferably is now repositioned to "position 3" of FIG. 40 and the rod inserter 140 is released from the connecting rod 26 and removed from the system. The remaining instrumentation may now be removed from the surgical site and the surgery may continue on the contralateral side if so desired.

Figure 50A:
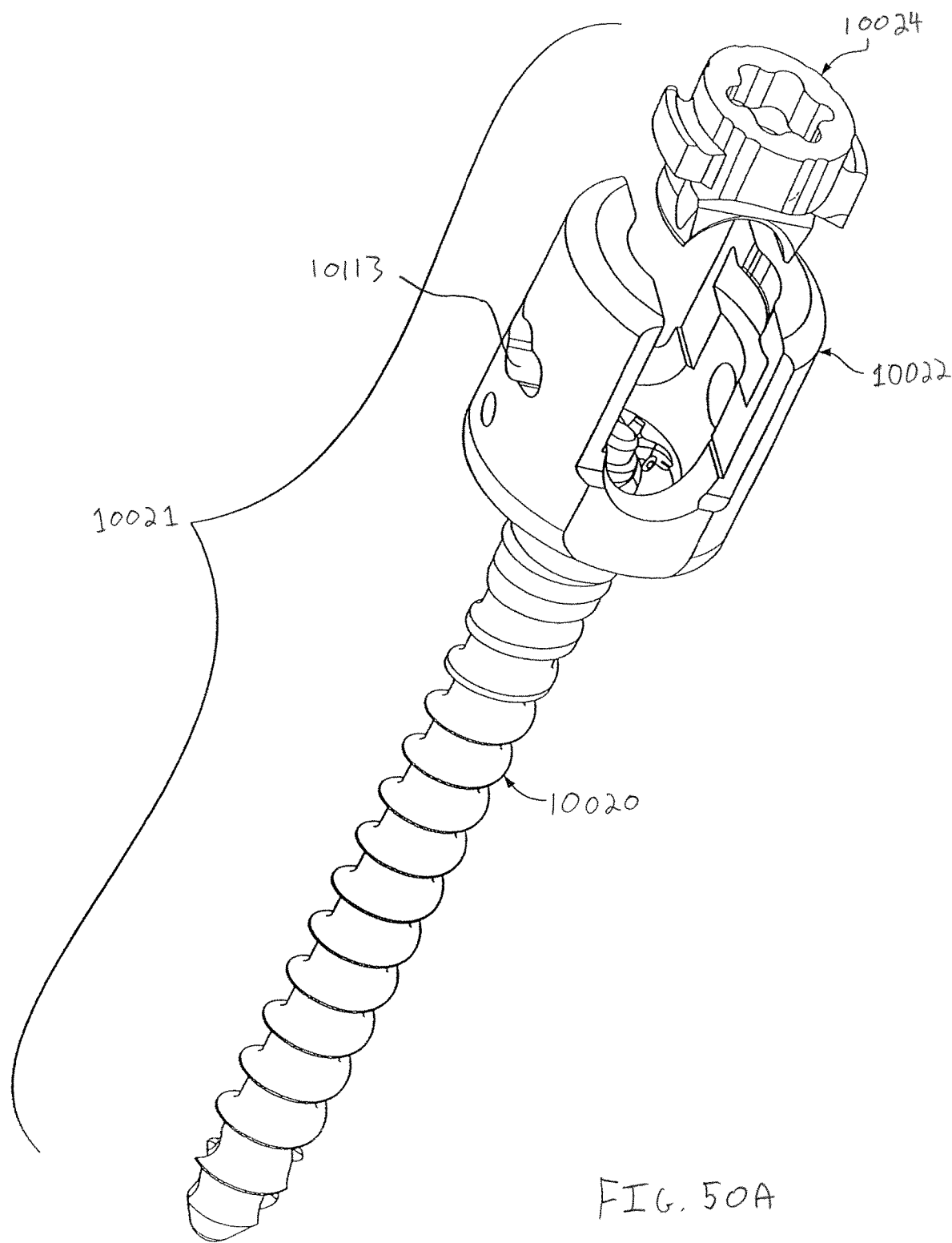
FIG. 50A is a perspective view of a bone anchor, a yoke, and a cap.
Figure 50B:
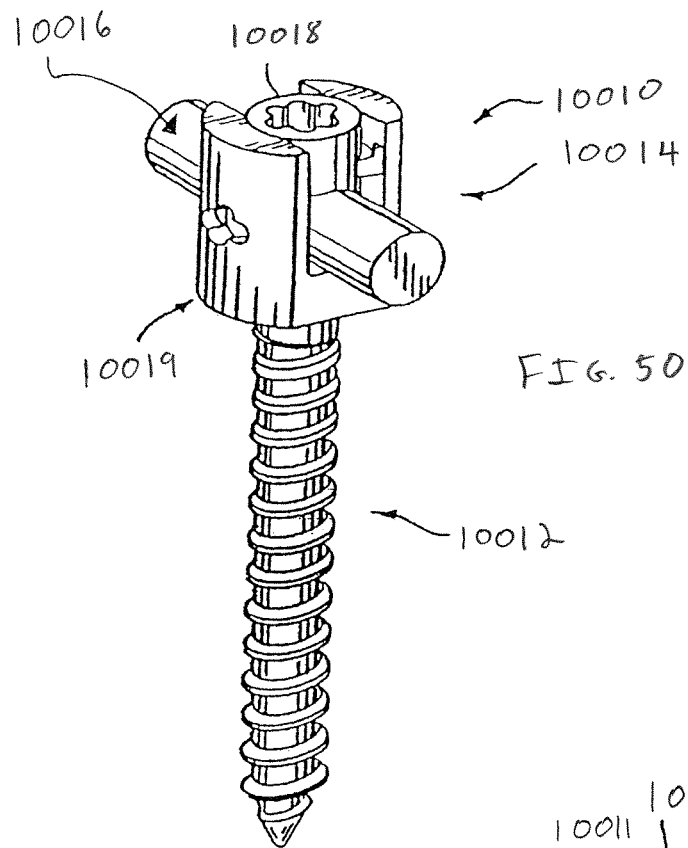
FIG. 50B is a perspective view of a spinal fixation device showing a bone screw and coupling device including a coupling member and a cam lock member for securing a spinal rod relative to the bone screw.
Figure 50C:
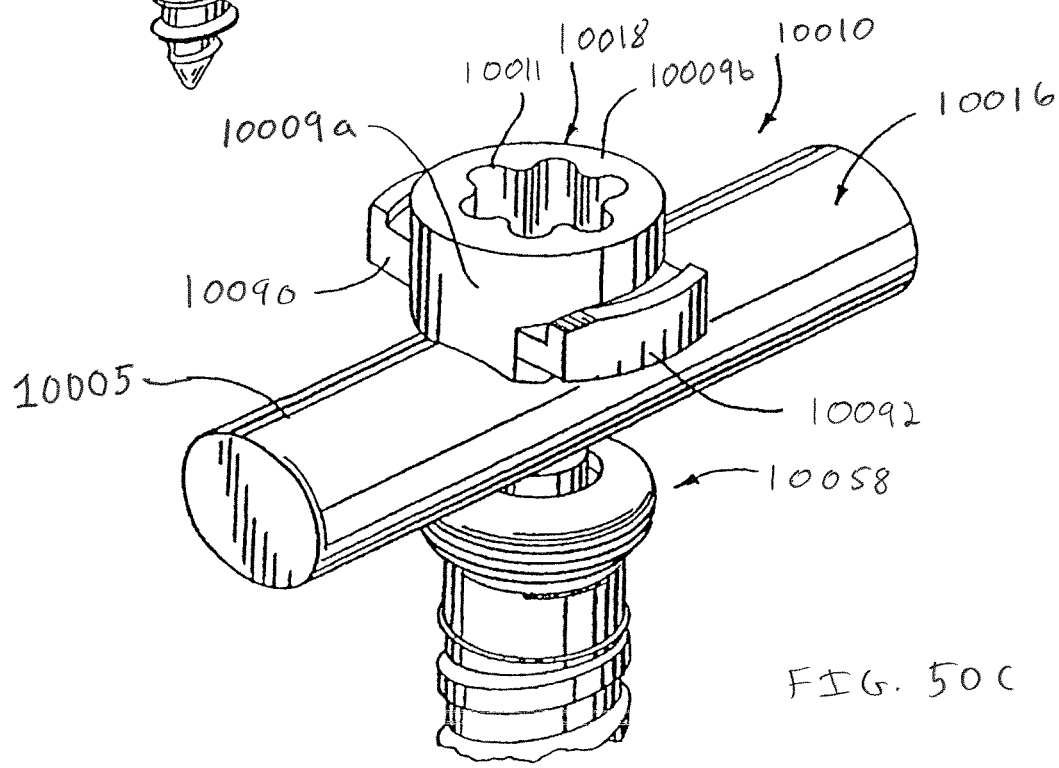
FIG. 50C is an enlarged perspective view of the spinal fixation device of FIG. 50B with the coupling member removed to better illustrate the cam lock member and to show the configuration of the head of the bone screw.
Figure 50F:
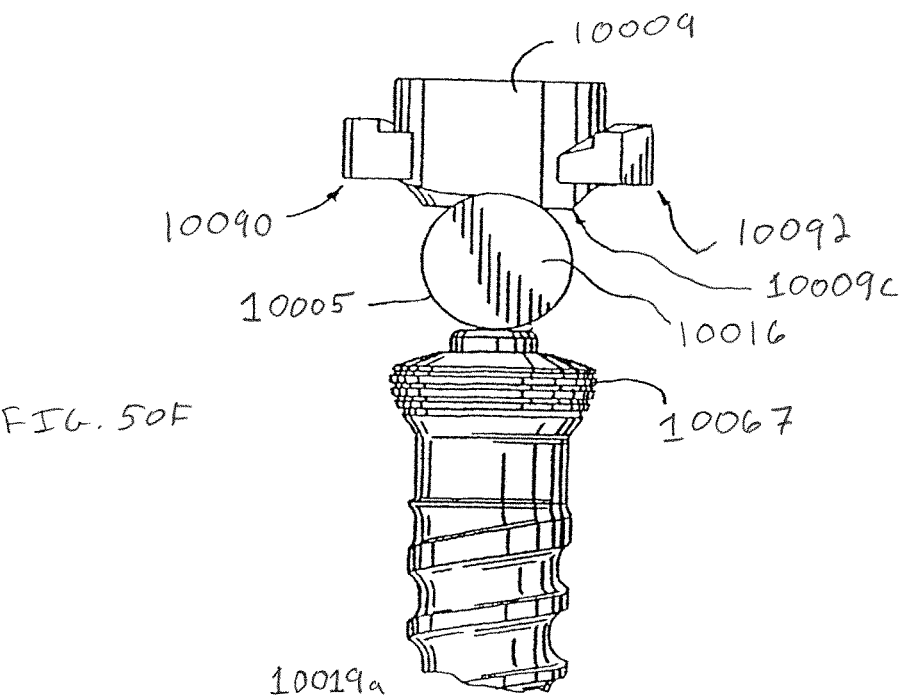
FIG. 50F is an elevational view similar to FIG. 50C with the coupling member removed to show the radial flanges on the cam lock member and a bottom cam surface thereof.
Figure 51:
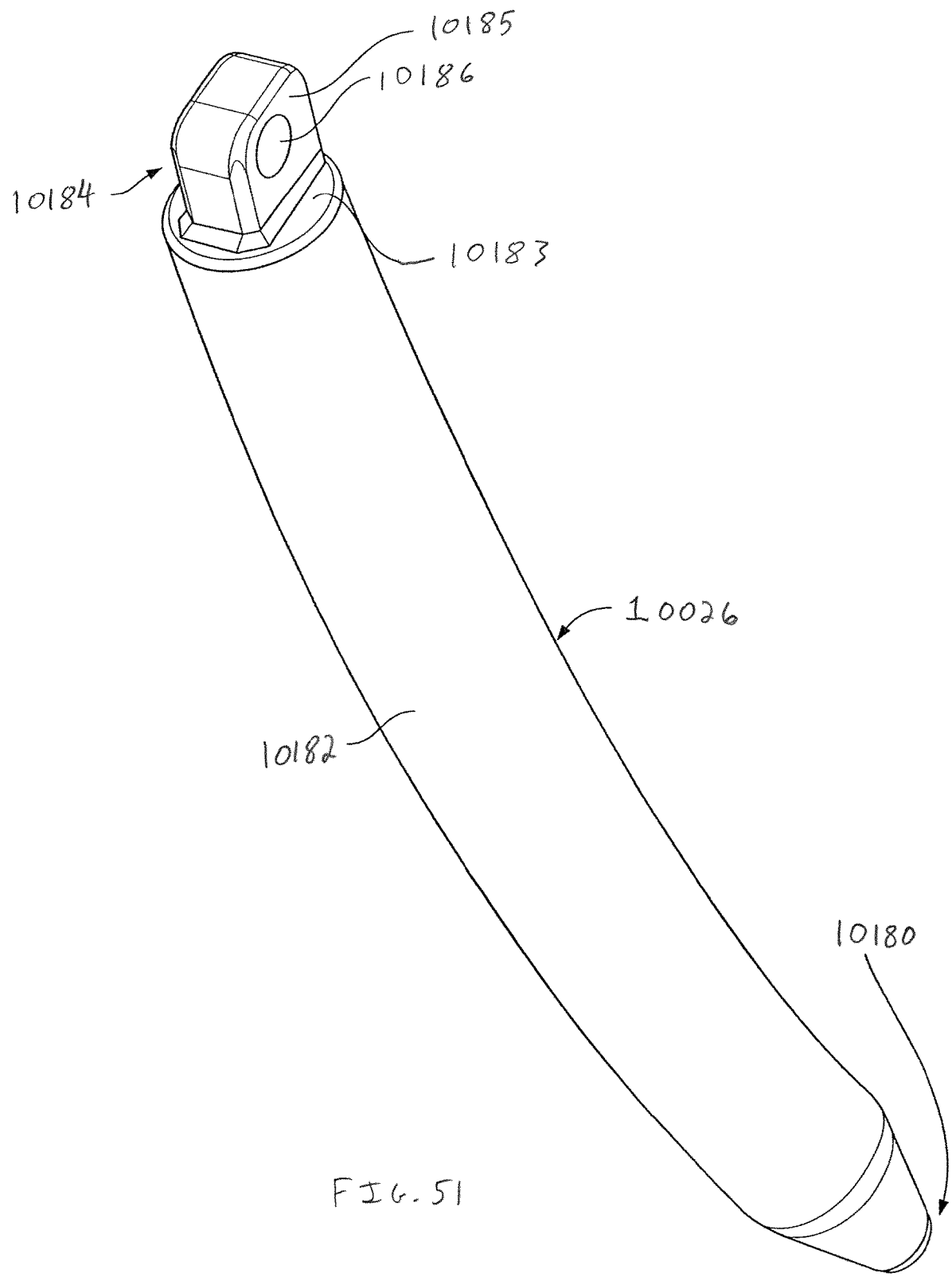
FIG. 51 is a perspective view of a connecting member.

In another approach, a minimally invasive surgical ("MIS") system can be utilized to attach an implant or fixation device to bone or bone segments. The fixation device illustrated herein is attached to the spinal column, but such a fixation device could be attached to bones other than vertebrae. The fixation device stabilizes bone or bone segments relative to one another. In one form, the fixation device includes a bone anchor or screw 10020, a yoke 10022, and a closure cap 10024, as illustrated in FIG. 50A. The cap 10024 locks into the anchor yoke 10022 such that an intermediate spinal rod or connecting member 10026 is held in position. The connecting member 10026 may be curved, as shown in FIG. 51, or it may be straight, depending upon the curvature of the patient's spine. The connecting member 10026 is seated into the yoke 10022 and secures the bone anchors 10020 relative to one another when locked by the cap 10024.

One embodiment of the fixation device includes two anchors 10020, two yokes 10022, two caps 10024, and a connecting member 10026. In another preferred embodiment, a fixation device may include three anchors 10020, three yokes 10022, three caps 10024, and one connecting member 10026. Since the bone anchors 10020, yokes 10022, and closure caps 10024 are implanted into the body, they are preferably made of biocompatible material.

An exemplary embodiment of a low profile spinal fixation system or device 10010 is shown in FIGS. 50B-50H. This spinal fixation device 10010 includes a pedicle screw assembly having a bone anchors or bone screw 10012 and the coupling device generally designated 10014. The coupling device 10014 is operable to secure an elongate member such as the connecting member or spinal rod 10016 in place relative to the bone screw 10012. The coupling device 10014 includes a compression or cam lock member or device 10018 and a coupling member 10019 that cooperate to secure the spinal rod 10016 relative to the bone screw 10012 anchored in a vertebral bone with the rod 10016 generally extending axially along the spinal column. The coupling device 10014 and specifically, the cam lock member 10018 and coupling member 10019, are provided with a compact configuration. In particular, the cam lock member 10018 and coupling member 10019 may be provided with a very low profile in a direction indicated by the axis line 10002 extending transverse and specifically orthogonally to the axis 10003 of the spinal rod 10016 fixed relative to the bone screw 10012 by the coupling device 10014, as best seen in FIG. 50E.

The low profile of the coupling device 10014 is obtained by having the cam lock member 10018 able to lock the spinal rod 10016 without needing to advance the cam lock member 10018 along the coupling member 10019. In this regard, the coupling member 10019 can be provided with a body 10004 having side openings 10004a and 10004b through which the spinal rod 10016 passes with the body 10004 free of any threading or cam surfaces that cooperate with the cam lock member 10018 for locking of the spinal rod 10016 relative to the bone screw 10012. Instead, the cam lock member 10018 is fixed against translation relative to the coupling member 10019, and preferably cooperates with the outer curved surface 10005 of the rod 10016 itself to secure it in position relative to the screw 10012 in the device 10010.

For this purpose, the cam lock member 10019 has a generally annularly configured body 10009 having a very short axial extent along turning axis 10002 thereof via annual side surface 10009*a* extending between its tip and bottom surfaces 10009*b* and 10009*c*. The top surface 10009*b* is provided with driving surface portions 10011 which cooperate to form a predetermined configuration for the receipt of a similarly configured drive tool for turning the cap member 10018 between unlocked and locked positions thereof. The bottom surface 10009*c* is programmed or contoured to provide a camming action on the curved surface 10005 of the rod 10016 when the cam lock member 10018 is turned. In another form, an intermediate clamping member in the form of a saddle member can be provided between the lock member 10018 and the spinal rod 10016. The saddle member may have an upper cam surface configured for cooperation with the lock member cam surface when the lock member 10018 is turned to its locked position so that the saddle member shifts downwardly along axis 10002 for clamping against the rod 10016 without camming thereagainst.

Similar to the cam lock member 10018, the coupling member 10019 also has a relatively small axial extent between the top and bottom surfaces 10019*a* and 10019*b* thereof. The body of the coupling member generally has a U-shaped or yoke configuration including opposing upstanding walls 10019*c*, 10019*d* spaced from each other by the rod openings 10004*a* and 1004*b* which can have an elongate configuration and be open to the top 10019*a* of the coupling member body 10004. Since the cam lock member 10018 need not be advanced down along the walls in the direction 1002, the size in this direction can be minimized.

The annular body of the cam lock member 10018 is sized to fit in the internal space of the coupling member between arcuate upstanding walls 10019*c*, 10019*d* that cooperate with the cam lock 10018 for shifting it to a locked position. The walls 10019*d*, 10019*d* are free of threading or cam surfaces that cooperate with the cam lock member 10018 for shifting it to a locked position. More particularly, the inner surface 10013 of the coupling member 10019 including arcuate surface portions 10013*a* and 10013*b* on the respective coupling walls 10019*c* and 10019*d* are sized to closely receive the outer surface 10009*a* of the cam lock member annular body 10009. These surface portions 10013*a* and 10013*b* are each free of threading or cam surface and thus only serve as guide surfaces or the like, the size of the coupling device 10014 can be kept to a minimum in the widthwise direction along the axis 10003 of the spinal rod 10016 as well.

Referring now to FIGS. 50D and 50E, the illustrated spinal fixation device 10010 has a polyaxial bone screw 10012 whose orientation can be changed such that its longitudinal axis 10012*a* extends transverse to the axis 1002 of the coupling device 10014 or is substantially aligned therewith. To this end, the coupling device 10019 is provided with a bottom throughbore 10050 that extends through the bottom wall 10052 of the coupling member 10019. The bottom wall 10052 includes an inner surface portion 10054 that tapers or curves inwardly from the surface portions 10013*a*, 10013*b* toward the center axis 10002. The diameter across the inner surface portion 10054 at it lowermost end 10056 is sized to be smaller than an enlarged head 10058 of the bone anchor screw 10012. In addition, the diameter at 10056 is sufficiently large to allow the threaded shank 10060 depending from the screw head 10058 to be advanced therethrough. In this manner, the inner surface portion 10054 serves as a seating surface from the screw head 10058. As an alternative, the diameter 10056 is threaded with a thread oversized relative to the shank, thereby allowing the screw shank 10060 to be loosely threaded through. In this instance, the diameter 10056 is sized to hold the shank 10060 from passing easily through so that the screw 10012 and coupling member 10019 may be handled by a surgeon as a single component during the operation. In addition, the oversized threads allow the screw to be polyaxial in its orientation. As a further alternative, the screw 10012 may be passed through the diameter 10056, and a c-ring or radial spring may be attached to the screw 10012 immediately adjacent to the coupling member 10019, thereby holding the two together and allowing the surgeon to utilized them as a single component during the operation.

The throughbore 10050 extends centrally through the inner surface portion 10054 and includes and enlarged lower portion 10062 formed by tapered or curved surface portion 10051 on the bottom wall 10052 of the coupling member 10019. The tapered surface 10051 extends from the smallest diameter of the bore 10050 at 10056 tapering outwardly relative to the center axis 10002 of the coupling member 10019 to the bottom surface 10019*b* thereof. The enlarged bore portion 10062 allows the screw 10012 to swivel or pivot to a variety of different orientations thereof relative to the coupling device 10014. For example, in the illustrated form, the enlarged bore portion 10062 allows the screw shank to pivot by 20 degrees on either side of the coupling device axis 10002. As the screw 10012 is pivoted, the outer arcuate surface 10053 of the screw head 10058 rides or shifts on the tapered seat surface 10054 in the coupling member 10019. Once the orientation of the coupling device 10014 relative to the bone screw 10012 fastened into a vertebral bone is determined with the spinal rod 10016 extending through the coupling member 10019 and up along the spinal column, the cam lock member 10018 is then turned to its locked position. In the locked position the cam lock member 10018 anchors the rod 10016 to the spinal column so it is fixed relative to the bone screw 10012 fastened into a vertebral bone with the bone screw head 10058 clamped against the seat 10054 thereof in the coupling member 10019 thereby fixing coupling device 10014 against shifting relative to the bone screw 10012. The outer screw head surface 10053 can be configured with concentric friction enhancing ridges or helical threads 10067 to enhance the locking action between the screw head 10058 and seat 10054.

Continuing reference to FIGS. 50D and 50E, it can be seen that in the illustrated polyaxial spinal fixation device 10010, the spinal rod 10016 is pushed downwardly for being clamped against a small anvil insert 10055. It should be noted that the previously described low profile coupling device 10014 could be employed in spinal fixation systems that are not polyaxial and/or which do not employ an insert as described hereinafter. Similarly, the present insert 10055 could be advantageously employed in systems that employ threads or cams in the coupling members thereof.

The insert 10055 has an upper anvil surface 10055*a* that engages against the underside of the spinal rod surface 10005 to maintain enhanced contact therewith over the curved surfaces of bone screw heads. The insert 10055 has an upper surface 10055*a* that may be substantially flat, may have radially oriented concave paths or valleys so that the insert 10055 rotates to the closest path to meet with the spinal rod surface 10005 or, may have a cup or peripheral ridge that deforms when compressed by the spinal rod 10016 to form a path without deforming the spinal rod. Accordingly, the insert 10055 provides at least a line of contact with the curved rod surface 10005. In other embodiments, it is anticipated that the bone anchor 10012 and the insert 10055 will have a unitary configuration.

Figure 50G:
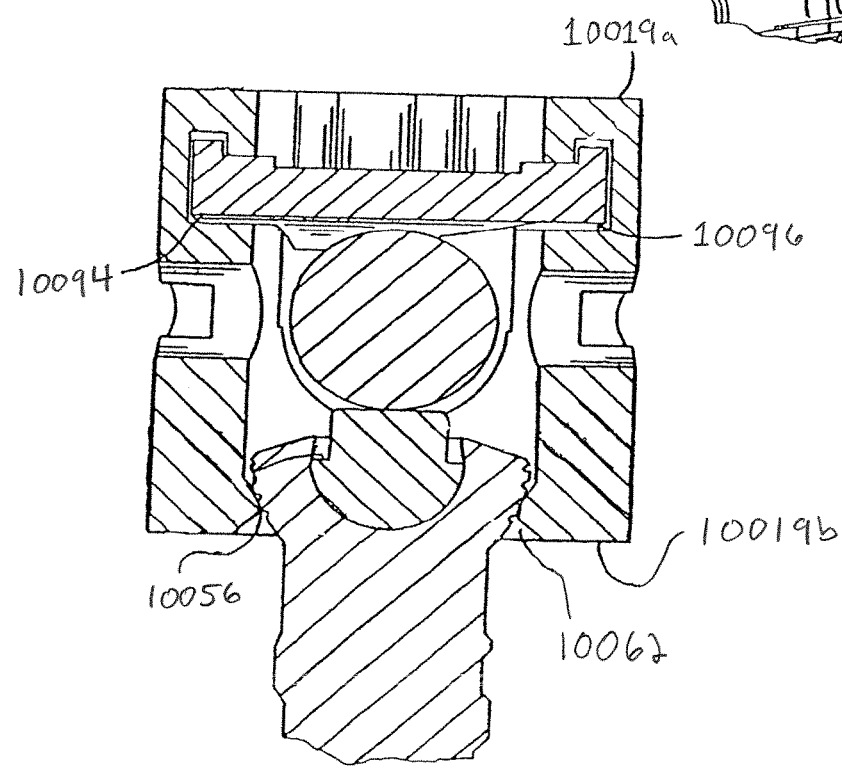
FIG. 50G is a cross-sectional view of the spinal fixation device. showing the recesses formed in the coupling member configured to receive the radial flanges on the cam lock member.
Figure 50H:
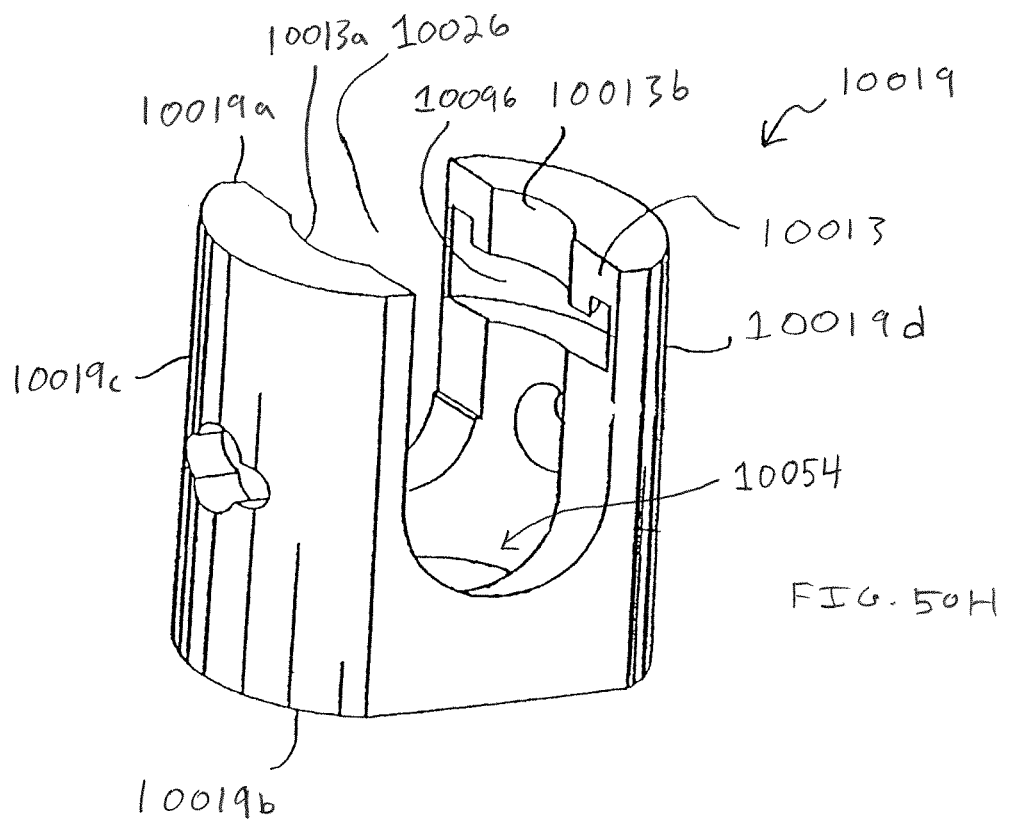
FIG. 50H is an enlarged perspective view of the yoke-shaped coupling member illustrated in FIG. 50B.

The cam lock member 10018 does not translate along the coupling member 10019 when it is turned to its locked position. In order to keep the cam member 10019 fixed against movement in the direction along axis 10002, it is provided with radial flanges 10090 and 10092 extending radially outwardly from the annular body 10009 at diametrically opposite positions thereon. The flanges 10090 and 10092 are received in correspondingly configured recesses 10094 and 10096 formed in the coupling member walls 10019*c* and 10019*d*, as can be seen in FIG. 50G. The recesses 10094 and 10096 have an arcuate configuration extending about axis 10002 as do the radial flanges 10090 and 10092 for fitting therein and allowing turning of the cam lock member 10019 between unlocked and locked positions thereof. The flanges 10090 and 10092 are received in the recesses 10094 and 10096 when the cam lock member 10018 is turned toward its locked position. With the cam surface 10009*c* camming on the rod surface 10005, the flanges 10090 and 10092 in the closely conforming recesses 10094 and 10096 prevent the cam lock member 10018 from shifting upwardly away from the spinal rod 10016 and instead forces the spinal rod 10016 down into clamping engagement with the insert 10055 which, in turn, causes the screw head 10058 and specifically outer head surface 10053 to be clamped against the seat surface 10054 in the coupling member 10019 thus fixing the coupling device 10014 relative to the bone screw 10012 and anchoring the spinal rod 10016 to the spinal column.

Figure 50I:
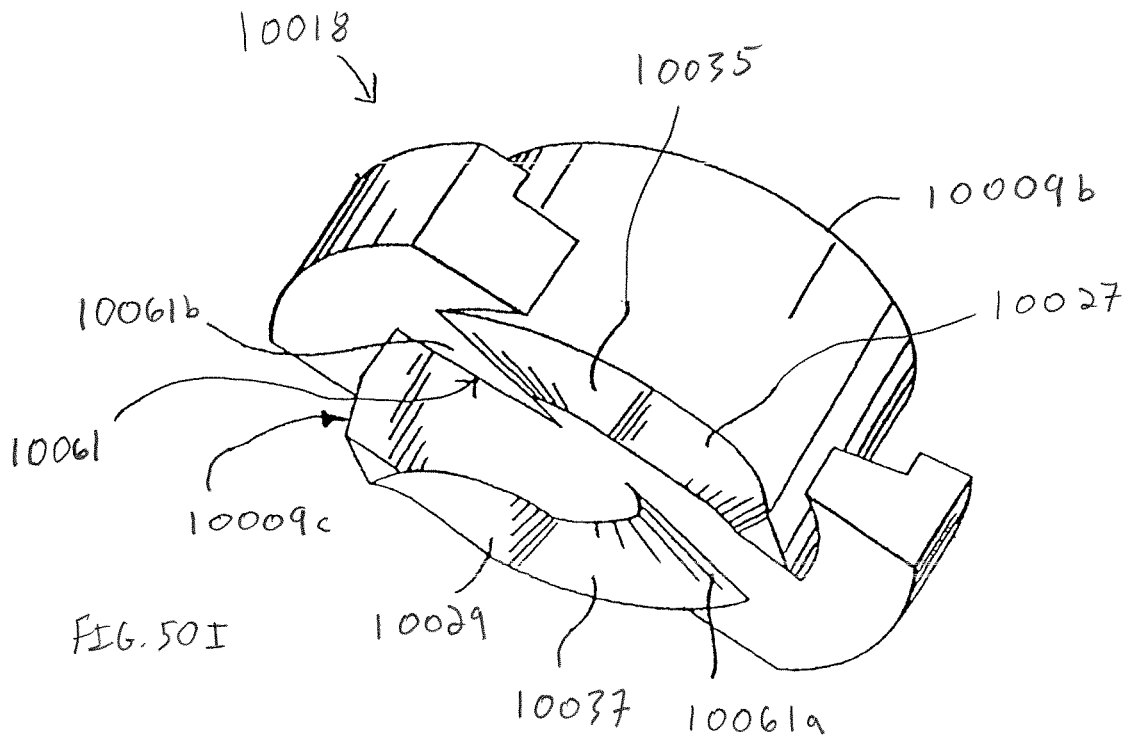
FIG. 50I is an enlarged perspective view of the cam lock member illustrated in FIG. 1B.

As previously mentioned, the cam lock member 10018 has a contoured bottom cam surface 10009*c* that cams on the curved cam surface 10005 of the spinal rod 10016. The cam surface 10009*c* is best seen in FIG. 50I. In the illustrated and preferred form, the cam surface 10009*c* is contoured to provide three distinct regions defined in relation to their action of the spinal rod 10016. A first concave region 10061 extends across the bottom 10009*c* of the cam lock member body 10009 and can be aligned with the radial flanges 10090 and 10092. Accordingly, the radial flanges 10090 and 10092 will be disposed slightly above the bottom 10009*c* of the cam lock member body 10009 to accommodate the spinal rod curved surface 10005 extending therebelow with the cam lock member 10019 in the unlocked position thereof. In this position, the flanges 10090 and 10092 are not received or fully received in the recesses 10094 and 10096 thereof.

Diametrically opposite sections 10061*a*, 10061*b* of the concave surface region 10061 are provided so that rotation of the cam lock member 10018 in the unlocked position does not cause a camming action to occur with only a slight initial turning action thereof. With the spinal rod surface 10005 aligned with the surface portions 10061*a* and 10061*b*, the spinal rod 10016 is still loosely received under the cam lock member 10018 and is not cammed thereby. The surgeon may use this position as a pre-lock configuration. Beneficially, the spinal rod 10016 is captured under the cam lock member 10018 so as to provide the surgeon with greater freedom of manipulation before finally locking the cam lock member 10018. With continued turning of the cam lock member 10018, the camming action begins at ramp regions 10035 and 10037 that are diametrically opposite to each other on the cap bottom surface 10009*c* and project downwardly from the adjacent surface sections 10061*a*, 10061*b* along direction 10002. The ramp regions 10035, 10037 are configured so that the rod 10016 is progressively pushed downward in the direction 10002 as the cam lock member 10018 is turned about the turning axis 10002 toward the locked position. Accordingly, in the unlocked position these ramp surface regions 10035 and 10037 on the bottom cam surface 10009 extend down along either side of the spinal rod 10016 so as to advantageously take up the space on either side thereof thus serving to keep the space occupied by the cam lock member 10018 in the coupling member 10019 to a minimum for providing the overall coupling device 10014 with a low profile.

Continued turning of the cam lock member 10018 toward the locked position causes the rod surface 10005 to be engaged against diametrically opposite generally flat surface regions 10027 and 10029 adjacent to the ramp surface regions 10035 and 10037 respectively. In an alternative form, the surface regions 10027 and 10029 may be a valley shape providing a depression such that the rod 10016 is received into the depression. The surface regions 10027 and 10029 are not inclined relative to the axis 10002 like the preceding ramp surfaces 10035 and 10037 and are the lowest point of engagement of the cam surface 10009*c* with the rod surface 10005. With the cam lock member 10018 turned so that the rod surface 1005 is only engaged by the surface regions 10027 and 10029, the cam lock member 10018 is in its fully locked position with the cam lock member flanges 10090 and 10092 fully received in the corresponding yoke wall recesses 10094 and 10096, as shown in FIGS. 1B and 1G. Continued turning of the cam lock member 10018 in the same direction after the fully locked position has been reached is prevented by abutment surface regions adjacent to the surface regions 10027 and 10029 respectively. These abutment surfaces extend further downwardly in direction 1002 from the surface regions 10027 and 10029.

Accordingly, in the exemplary embodiment illustrated, programmed cam surface 1009*b* provides several stages for the camming and locking action on the spinal rod 10016. As shown, the cam member 10018 can be rotated by approximately 20 degrees from the unlocked position before the rod surface 10005 reaches the ramp surfaces 10035 and 10037. At this point, the rod 10016 is cammed downwardly and the cam lock member can be turned for another approximately 60 degrees before the rod surface 10005 reaches the flat locking surfaces 10027 and 10029. The cam lock member 10018 can then be turned by another approximately 20 degrees before the rod surface 10005 abuts against the stop surfaces and then the cam lock member 10018 is in its fully locked position. Thus, in one embodiment, there is approximately 100 degrees of rotation of the cam lock member 10018 that is required from the fully unlocked position to the fully locked position with 20 degrees of play provided before the camming action begins and the camming of the rod 10016 occurring over the final 80 degrees of rotation to the fully locked position.

Figure 50K:
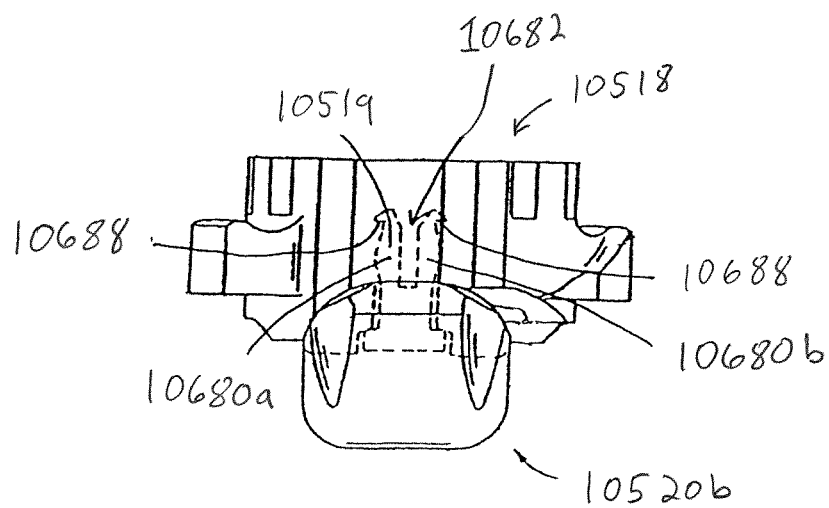
FIG. 50K is side elevational view of the cam lock member, and the clamping member in an unlocked position relative to the spinal rod.
Figure 50L:
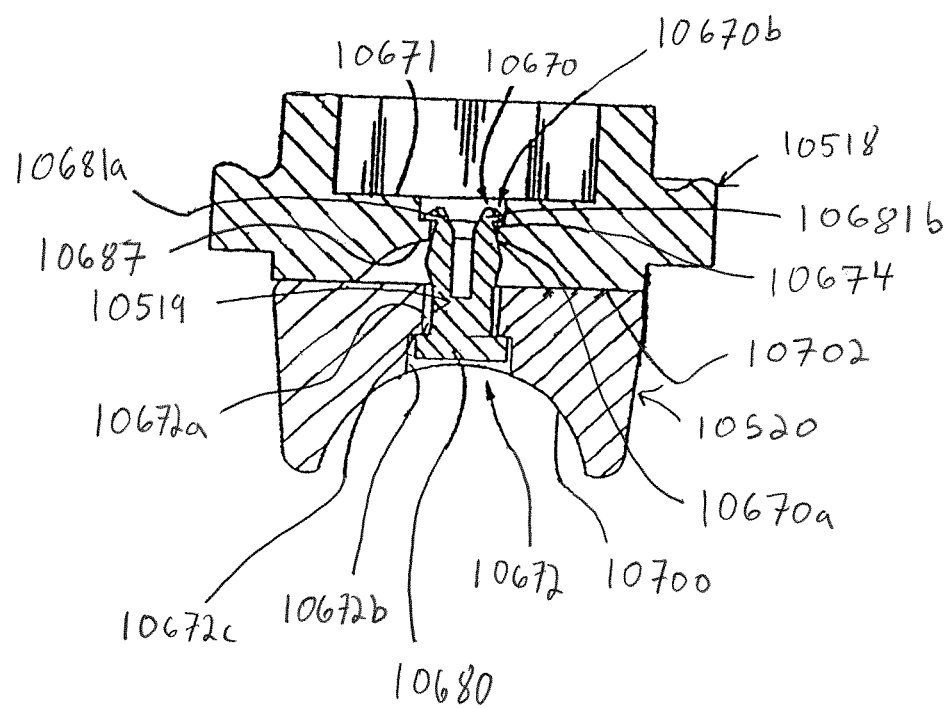
FIG. 50L is a cross sectional view of the cam lock member and the clamping member showing the clamping member shifted down along with the spring clip connecting with the cap member axially fixed and rotated to its locked position.

FIGS. 50J-50L illustrate another exemplary embodiment of a low profile spinal fixation system or device 10500 for securing a spinal rod 10016. The device 10500 includes a bone anchor member such as a screw 10502 and a coupling device for securing the spinal rod 10016 relative to the bone screw 10502. The coupling device includes a coupling member in the form of a unitary yoke 10512, an insert in the form of anvil 10516, a cam lock member in the form of a cap 10518, a connector member in the form of a spring clip 10519, and a clamping member in the form of a saddle 10520. The fixation device 10500 is similar to the embodiment of FIGS. 50A-50L in that the cap 10518 and yoke 10512 are provided with a very low profile in the direction indicated by yoke axis line 10002 extending transverse and specifically orthogonally to the axis 10003 of the spinal rod 10016 fixed relative to the bone screw 10502 by the coupling device.

The screw 10502 is directed through the yoke 10512 and attaches the yoke 10512 to a bone or bone fragment. The screw 10502 has a head 10536 with a recess 10554, and the recess 10554 receives the anvil 10516. The spinal rod 10016 is received within an internal space or channel 10601 in the yoke 10512 and is seated on top of anvil 10516. The screw 10502 is preferably a polyaxial screw, and the anvil 10516 is permitted to move within the head 10536 of the screw 10502. Accordingly, prior to the device 10500 being secured, the screw 10502 may move relative to the yoke 10512 so that the yoke 10512 and screw 10502 may be selectively positioned to assume different orientations relative to each other so that their respective axes 10002 and 10544 are not necessarily aligned with each other, and the anvil 10516 may move and pivot or rotate relative to the screw 10502 so that the anvil 10516 may be properly positioned by orienting itself with the outer surface 10005 of the rod 10016 similar to the previously described anvil 10055.

The rod 10016 is secured or locked within the yoke 10512 with the cap 10518 and saddle 10520. As will be discussed below, rotation of the cap 10518 has the dual function of securing the cap 10518 within recesses 10642 in the yoke 10512 and of forcing the saddle 10520 against the rod 10016 to lock the rod 10016 between the saddle 10520 and the anvil 10516. The saddle 10520 and cap 10518 are secured together in assembly by a distinct connector in the form of a dual-pronged, spring clip 10519.

The bone screw 10502 is preferably polyaxial, and the head 10536 is diametrically larger than the shank 10538 at the neck 10542. The polyaxial features of the screw 10502 allow the screw 10502 to be secured to a bone in a desired orientation for proper fixation to the bone while allowing the yoke 10512 to be oriented relative to the screw 10502 in an orientation desired for seating a rod 10016 therein.

The head 10536 of the screw has an arcuate or slightly ramped top surface 10550 which meets a peripheral outer surface 10552 of the screw head 10536. The peripheral outer surface 10552 of the screw head 10536 has a generally arcuate or spherical profile. The profile is interrupted with a series of concentric ridges or circular grooves cut therein. As discussed above, the screw 10502 is polyaxial so that its orientation relative to the yoke 10512 can be precisely positioned. When the coupling device is secured to the screw 10502, the grooves grip of cut into the interior of the yoke 10512 to immobilize the screw 10502 in the desired position against the yoke 10512.

The top surface 10550 includes an upwardly opening recess 10554 formed therein for receiving the anvil 10516. The recess 10554 has an arcuate or, preferably, spherical bottommost surface portion sized and configured to allow the small anvil 10516 to shift when seated in the recess 10554. To this end, the anvil 10516 has a bottom surface 10558 supported on and slidable against the bottommost surface portion. Furthermore, the recess 10554 has two pair of diametrically opposed notches, each pair perpendicularly oriented from the other pair for receiving similarly configured prongs of a driver without interfering with the anvil 10516 therein. The top surface 10550 includes a retainer or staked portion in the form of short tabs located at the opening to the recess 10554 and between each notch. Prior to disposing the anvil 10516 in the recess 10554, the tabs rise upwardly from the top surface 10550 in the axial direction so that the tabs do not hinder insertion of the anvil 10516.

Once the anvil 10516 is located in the recess 10554, the tabs are deflected over to extend radially into interference with the anvil 10516 while still allowing the anvil 10516 to move within the recess 10554 but be captured therein by the tabs. After assembly, heat or other treatment may be utilized to relieve residual stresses within the bent tabs.

The anvil 10516 has a bottom portion 10580 with a generally arcuate bottom surface 10558 which rests against the bottommost portion of the seat 10554. Accordingly, the anvil 10516 may pivot or rotate within the recess seat 10554. The anvil 10516 further includes a seat portion 10582 extending centrally upward from the anvil bottom portion 10580 to a top surface 10584 with a transverse shoulder surface 10585 between the anvil portions 10580 and 10582.

When the rod 1016 is inserted within the yoke 10512, the side surface 10005 of the rod 10016 is advanced into contact with the anvil 10516. If the bone screw 10502 is deflected or secured so that its central axis 10544 is not coincident or aligned with the yoke central axis, the anvil 10516 is initially deflected or tilted in a similar deflection. As the rod 10016 is secured and forced against the anvil 10516, the anvil 10516 pivotable in the recess 10554 will shift to require the minimized distance between the rod 10016 and the bottom surface portion of the recess 10554.

In order to have a low profile, it is preferred to minimize the height of the anvil 10516 while remaining above the top surface 10550 of the screw head 10536. The anvil top surface 10584 is sized so that, when deflected to the deflection of the bone screw 10502, at least a portion of the top surface 10584 is contact by rod 10016 being advanced toward the anvil 10516 in the yoke 10512. Accordingly, the anvil 10516 is self-righting as the rod 10016 contacting the anvil top surface 10584 forces the anvil 10516 to shift to align tangentially its minimum height, as discussed above, with the surface 10005 of the rod 10016.

As depicted in FIGS. 50K and 50L, the cap 10518 and the saddle 10520 each define central openings 10670 and 10672 respectively, through which the clip 10519 extends. The cap opening 10670 is segmented between a lower portion 10670*a* and an upper portion 10670*b* that steps open to a diameter larger than that of the lower portion 10670*a*. An annular shoulder seating surface 10674 is at the transition between the lower portion 10670*a* and the upper portion 10670*b* of the cap opening 10670. The upper portion 10670*b* also opens to a recessed bottom surface 10671 in the drive socket of the cap member 10518.

The clip 10519 includes an annular base portion 10680 and two resilient prongs or stems 10680*a*, 10680*b* projecting upward therefrom and spaced by an axially extending gap 10682 therebetween. Each stem 10680*a*, 10680*b* terminates at their free ends with flanges 10681*a* and 10681*b* including an upwardly facing cam surface that can be ramped or inclined relative to the clip axis, or have a curvature thereto. The cam surfaces aid in insertion of the clip 10519 through the openings 10670 and 10672, and a corresponding lower stop surface 10688 is provided at the prong flanged ends 10681*a* and 10681*b* extending normal to clip axis that substantially prevents unintentional removal of the clip 10519 back through the openings 10670, 10672.

The central opening 10672 of the saddle 10520 also includes an upper portion 10672*a* and a lower portion 10672*b*. The lower portion 10672*b* opens to a concave bottom 10700 of the saddle 10520 and has a larger diameter than the upper portion 10672*a* so that there is an annular shoulder surface extending therebetween. The enlarged lower portion 10672*b* is sized such that the base portion 10680 of the clip 10519 is fit and held therein in interference with the surface 10672c. Preferably, the diameter of the opening lower portion 10672b is kept to a minimum to increase the surface contact area of the saddle surface 10700 on the rod 1016. The opening upper portion 10672a can be sized to have a similar diameter as that of the smaller lower portion 10670a of the cap opening 10670.

To assemble the cap member 10518 and saddle member 10520 together, initially the spring clip member 10519 is axially inserted in saddle opening 10672 with prong free ends 10681a and 10681b first inserted in enlarged lower opening 10672b. With continued axial insertion, the cam surfaces engage and cam against shoulder surface 10672c resiliently forcing the spring prongs 10680a and 10680b toward each other to take up the gap 10682 therebetween. With the prongs 10680a and 10680b pushed together, the lateral outer edges of the cam surfaces are spaced by a distance slightly less than the opening portions 10670a and 10672a. This allows the clip member 10519 to continue to be inserted through the opening 10672 including the smaller diameter opening upper portion 10672a. Depending on the distance across the undeformed prong upper edges relative to the diameter of opening lower portion 10672b, there may also be camming against the saddle surface 10700 with some attendant prong deformation to enable the clip prongs 10680a and 10680b to fit into opening lower portion 10672b. Once the prong ends 10681a and 10681b and specifically prong surfaces 10688 thereat clear the opening upper portion 10672a, the clip prongs 10680a and 10680b return to their original undeformed state with surfaces 10688 in conforming relation with upper surface 10702 of the saddle 10520 so that absent exerting a force to bring the prongs 10680a and 10680b together, the clip member 10519 and saddle member 10520 stay assembled together.

To complete the assembly process, the prong ends 10681a and 10681b are next axially inserted in the cap opening 10670, and specifically, smaller lower portions 10670a thereof. Accordingly, cam surfaces cam against a lower surface 10687 of the cap 10518 about the central opening 10670 therein which forces the resilient stems 10680a, 10680b together taking up the gap 10682 therebetween to allow the clip prongs 10680a and 10680b to be inserted through the opening portion 10670a. Once the clip cam surfaces pass through the lower portion 10670a of the cap opening 10670, the stems 10680a, 10680b resiliently return back toward their non-flexed position. After the prongs ends 10681a and 10681b exit the opening 10670, the prongs 10680a and 10680b will return to their undeformed state, and the stop surfaces 10688 will be facing the cap surface 10671 and spaced therefrom so that there is play between the connected components, i.e., the cap 10518, the saddle 10520, and the clip 10519, as shown in FIG. 50L. Upon turning the cap 10518 to its locked position, the prong ends 10681a and 10681b reenter the opening upper portion 10670b as the saddle member 10520 is driven toward the rod 10016 shifting the spring clip member 10519 axially therewith due to engagement of the surface 10672c on the clip base 10680 with the stop surfaces 10688 brought into abutting engagement with the seating surface 10674 to substantially prevent the clip 10519 from being unintentionally pulled back through the openings 10670, 10672 of the cap is turned into its locked position.

The MIS system, described herein, can be used to implant bone fixation devices similar to the ones briefly described above. Such systems are particularly useful during spinal and neurosurgical procedures because the surgeon can need access to locations deep within the body and such access requires the surgeon to reposition or avoid vital tissues and nerves. While the MIS system is useful for performing spinal surgery, it can also be effectively used for non-spinal applications in humans and other mammals. The implants described herein are exemplary, however, and the minimally invasive instrumentation described may be used with a variety of implant forms, spinal and non-spinal, in some cases with minimal or no modification. For example, some or all of the tools described herein may be used for repairs of the hip as well as for repairs of the spine, and they may be used to implant bone screws, fusion devices, and many other prosthetic and non-prosthetic implants, or to perform non-implant repair.

The MIS system can be configured to accommodate both cannulated and non-cannulated implant placement. This allows the system to be tailored to a particular surgeon's preferences. For example, when employing guide wires, cannulated pedicle bone screws along with cannulated tools can be utilized. However, some surgeons find cannulated instruments to be less effective due to the movement constraints resulting from the presence of the guide wire.

The MIS system includes a number of instruments that the physician may use to perform the implant procedure. In sum, the MIS system provides the surgeon with tools for gaining access to the surgical site, for preparing the surgical site, attaching the fixation device, or the connecting member to the surgical site, adjusting the fixation device, and closing the surgical site. The MIS system may include: a Jamshidi needle, a guide wire, a pedicle finder, series dilators, a multistage telescoping dilation tool, a cannulated cutting instrument, obturators, a docking port or sleeve, a facing tool, an awl, a screw driver or other various locking instruments, pushers, inserters, persuaders, yoke manipulators, compression-distraction tools, and a number of other instruments. The MIS system may include all the surgical tools necessary to accomplish the procedure, or may only include the specialized surgical tools particular to the implant procedure such that the specialized tools must be supplemented by generic surgical instruments used for many different surgeries.

To begin one exemplary procedure, an incision is made and a surgeon percutaneously inserts a Jamshidi needle over the posterior spinal anatomy. The Jamshidi needle can hold the guide wire and thereby direct the guide wire into position. Correct guide wire placement is important because the surgeon can use the guide wire to direct where the implant and/or instruments are to be located. In another form, the surgeon can rely on tactile feedback to determine where the implants and various tools should be inserted, or the surgeon may employ fluoroscopic equipment to determine such placement visually. If the guide wire is used, it is driven to a predetermined depth into the target pedicle bone of the selected vertebral segment. After the guide wire is secured, the surrounding tissue is stretched using various dilation techniques. The surrounding tissue may also be incised to provide passage of the MIS system tools. Subsequent to tissue dilation and/or incision a docking port is inserted into the percutaneous opening.

The docking port is the minimally access window portal through which some steps of the surgery are performed. In one form, the docking port has an arm or handle such that it can be anchored during surgical procedures, such as to an iron intern. In another form, the docking port may have docking fasteners such that the docking port can be fixed to the bone during surgical procedures. After the docking port is secured into position, the surgeon can prepare the bone for receiving the anchor. A facing tool is sometimes used to resurface the bone to a more desired contour such as concaved, domed, flattened, or another beneficial shape. Before the anchor is inserted, an awl, or other instrument can be used to create a depression or opening on the bone surface at the location where the anchor will be set.

As briefly mentioned above, yoke manipulators are employed to assist insertion of the bone anchor with the yoke attached. Each yoke manipulator is positioned about the yoke before being inserted. The yoke manipulators have two portions, an inner sleeve that includes the portion that is arranged about the yoke and an outer sleeve or restraint that is slid down the inner sleeve to secure the manipulator around the yoke. Having the yoke manipulators and the yokes secured relative to one another allows the surgeon to correctly align the yokes after they have been inserted into the wound. Correct alignment is important because the connecting member is eventually positioned within each yoke. After the yoke manipulator has been secured to the yoke, the yoke manipulators and bone anchors are advanced down the docking port. A screw driver can also be advanced with the yoke manipulator. The screw driver rotates the anchor into position on the pedicle bone. At this point in the procedure, the docking port may be removed, although the yoke manipulator typically remains within the incision, to facilitate insertion of the connecting member. Before insertion of the connecting member, the surgeon typically repeats the procedure to insert the other bone anchor(s).

After the bone anchors, yokes, and yoke manipulators are inserted and the manipulators are aligned, the connecting member may be inserted. At least one of the yoke manipulators includes a pair of slots, one on each side of the manipulator and an opening toward the yoke, to allow for passage of the connecting member. One other yoke manipulator has at least one slot opening toward the yoke allowing for insertion of the connecting member into the yoke. The connecting member is fed between the slots of the yoke manipulators by a rod inserter. The yoke manipulators along with the rod inserter can facilitate placement of the connecting member into a position spanning the yokes, without requiring another opening or incision into the body other than the openings used to attach the anchors. After the connecting member is positioned within the yokes, a closure cap is inserted into the yoke and rotated such that the connecting member is secured into a pre-lock position such that the connecting member and yokes can move relative to one another. The yoke manipulators and bone anchors can be moved together or apart from one another along the connecting member. After positioning of the bone anchors, the caps are moved to the final-lock position. The yoke manipulators may then be removed from the bone anchors along with any other tools and instruments, such as the docking ports if not previously removed. After removal of the tools, the surgeon closes the wound. The MIS system allows for insertion of an implant without unnecessary trauma to the body, and more particularly to the tissue surrounding the implant. Further, the system provides the surgeon with guidance during the procedure without being unduly rigid.

In one form of the procedure, the surgeon first makes the incision into the skin. Such an incision could be made by a number of incising or cutting instruments. Thereafter, the surgeon proceeds by percutaneously inserting a Jamshidi needle. The Jamshidi needle and a guide wire are typically coupled together to facilitate insertion of the guide wire. The handle of the Jamshidi needle includes a click wheel. After the guide wire is inserted into the Jamshidi needle, the click wheel is advanced until a guide wire is held firmly into position. Proper implant placement is required for a successful procedure and the surgeon must correctly identify the pedicle anatomy to which the device will be attached. Therefore, the surgeon can use the Jamshidi needle over the posterior spinal anatomy to provide tactile feedback for determining guide wire placement. In another form, a fluoroscopic imaging device is used to assist the surgeon in placing the device in the proper position. Various radio-imagery may be utilized to monitor the procedure in addition to assuring proper placement of tools and components. Using imaging equipment prevents placing the tools incorrectly or driving the instruments or implants in the wrong location, or too deeply into the body tissue, as this could harm vital body tissue, nerves, etc.

After it is positioned, the guide wire is driven to a predetermined depth to firmly secure the guide wire for the remainder of the procedure. A portion of the guide wire typically extends out of the tip of the Jamshidi needle. To secure the guide wire, the handle of the Jamshidi needle is typically tapped with a mallet or other tool to thereby drive the portion of the guide wire extending from the tip of the Jamshidi needle into the bone. After the guide wire has been tapped into the bone and secured, the Jamshidi needle is removed from the incision by releasing the click wheel and leaving the guide wire secured to the bone. While the above procedure is one way the guide wire may be positioned, a number of other procedures exist. Further, use of the guide wire varies by surgeon and while some surgeons prefer to use the guide wire throughout the procedure, others prefer not to use the guide wire at all, and still others prefer to use the guide wire during only a portion of the procedure. For example, some surgeons may employ the guide wire until the bone anchors are to be inserted. Whereas, other surgeons will use the guide wire during more steps of the procedure, including during insertion of bone anchors, which may require the use of cannulated anchors that can be slid down the guide wire.

The guide wire is typically secured where the bone anchors will be attached. The guide wire is preferred to have a self-cutting and self-tapping thread, however, the thread type and insertion means vary by surgeon preference. Alternatively, the guide wire may have a non-threaded sharpened end for advancement through soft tissue and piercing the bone. Such a guide wire is preferably constructed of biocompatible metals or alloys such as stainless steel, titanium, or nitinol.

Following placement of the guide wire, the tissue surrounding the guide wire is stretched or dilated. To stretch the tissue, a number of open ended cylinders or series dilators can be used. The series dilators are tubes with one end having a sloped nose that can slowly stretch the tissue from around the guide wire. The tubes advanced into the incision incrementally increase in diameter. Thus, as each tube is inserted into the incision, the tissue surrounding the guide wire is expanding. To simplify the dilation procedure, a dilation tool such as the dilation tool disclosed in U.S. patent application Ser. No. 11/466,262, filed on Aug. 22, 2006, may be employed.

In another form, an obturator or a set of obturators can be used to dilate the tissue surrounding the surgical site. When a set of obturators is employed, the diameter of each subsequently employed obturator increases. As with many of the tools, the obturators may be used in conjunction with a guide wire if the tool is cannulated. If cannulated, the opening of the obturator is advanced down the guide wire and into the incision. The obturators have a sloped nose that when pushed into the incision will stretch the surrounding tissue to accommodate the increasing diameter of the obturator. A shaft of the obturator may be the same, reduced, or enlarged in diameter, compared to the nose. The obturator preferably includes transitional sloped or arcuate portions to ease retraction of the obturator. The obturator may also include a flange, a boss, threads, or locking pins to secure the obturator into position. In addition, the end of the obturator opposite the nose may include a handle or other structure suited for gripping the instrument to control movement of the instrument into the opening.

In yet another form, the tissue surrounding the guide wire is incised, instead of stretched, to provide access for the MIS system tools and fixation device. A scalpel or cutting instrument may expand the previous incision to accommodate the remaining MIS system procedure. A cannulated cutting tool that includes a handle, a cylindrical body, and fins may be used to increase the size of an opening. The fins may cut precise openings in the tissue surrounding the guide wire.

After the surrounding tissue has been stretched or incised sufficiently to accommodate the MIS system tooling, a docking port or sleeve 10064 may be slid down the series dilators, the telescoping tissue dilator, or other tool located within the incision. Sliding the docking port 10064 into the incision retains the surrounding tissue about the docking port 10064, which now serves as an opening or window in the tissue, large enough to accommodate the tools used during portions of the MIS procedure. In another form, the docking port 10064 may be advanced into the tissue with an obturator. If the obturator is cannulated, the obturator and docking port 10064 are slid down the guide wire.

The docking port 10064 is typically the access window through which a portion of the MIS system procedure is conducted; however, the surgeon may choose to insert the bone anchors 10020 without the docking port 10064. The docking port 10064, illustrated in FIGS. 3-6, includes a handle 10066, a cylindrical body 10068, and an angled end 10070. The handle 10066 may include channels 10072 to increase grip. An articulating arm, such as an iron intern, may attach to the handle 10066 of the docking port 10064 to secure the docking port 10064 in position. Before the docking port 10064 is secured into position for the insertion of the bone anchors 10020, the angled end 10070 of the docking port 10064 is inserted into the incision. The angled end 10070 is contoured to fit adjacent the spine. A first edge 10074 is sized to fit toward the center of the patient and a second edge 10076 is sized to face toward the side of the patient. More particularly, the first edge 10074 is positioned adjacent to the transverse process. The edges 10074, 10076 come together at tip 10078 which is slightly off-set from the center of the cylindrical body to facilitate a better fit with the spine. In one preferred form, the inner diameter of the docking port 10064 is about 0.646 inches, the outer diameter is about 0.721 inches, the distance from the center of the cylindrical body 10068 to the tip of the handle 10066 is about 2.622 inches, and the length of the cylindrical body 10068 is 5.326 inches. Further, the docking port 10064 is made of biocompatible material. In one preferred form, the material is polyetheretherketone or PEEK. This allows the docking port 10064 to provide a working channel, to electrically shield the bone anchor 10020, and further, if the docking port 10064 is PEEK, and therefore radiolucent, the docking port 10064 will not interfere with fluoroscopy.

After the docking port 10064 is positioned adjacent to the vertebrae and secured into position, a number of various instruments can prepare the implant site. For example, to prepare the implant site, the surgeon may need to remove an osteophyte overlying the area where the anchor 10020 will be seated. A surgeon can remove such interfering structures using a facing tool. The facing tool can be used to smooth or refine the bone surface, thereby creating a flattened area suitable for seating implants. The facing tool may also be cannulated to accommodate the guide wire or may not be cannulated, having other structure to facilitate position of the tool within the docking port 10064.

In one embodiment, the facing tool includes a generally flat cutting surface with cutting edges that remove boney material. The cutting edges remove bone as the tool is rotated and a recess or a bone chip reservoir that provides a space where the removed material may accumulate. In addition to a flat cutting surface, the cutting surface may also have another contour such as convex or concave. The facing tool typically includes a handle to grip the tool and a depth stop, typically a stop collar that engages the docking port 10064 or other instruments. The depth stop helps prevent the tool from being advance too far into the bone. In addition, the facing tool includes a positioning member or centering portion. The centering portion of the facing tool is sized to be received inside the docking port 10064. Centering the facing tool ensures correct placement of the smoothed site and further prevents the cutting surface and cutting edges from wearing against the docking port 10064.

In another form, an awl may prepare the implant site by perforating the cortex of the bone overlying the pedicle. A cannulated awl may be used over the guide wire by sliding the cannulated awl down the guide wire into the docking port 10064 and toward the implant site. If the guide wire is not employed, the awl can be visually placed at the implant site or the awl may include a centering portion that guides the awl to the implant site. The awl is driven into the bone by tapping on the end projecting out from the docking port 10064 with a mallet. After the cortex of the bone is breached and a depression or opening is made, the awl can be removed from the docking port 10064. If the surgeon chooses, the depression can be created by rotating the awl instead of tapping on the end.

In another form, a pedicle finder or another drilling tool can be used to prepare the implant site. The pedicle finder is advanced down the docking port 10064 toward the bone. Once positioned adjacent the bone, the pedicle finder can create a pilot hole for the bone anchor 10020. The surgeon must take care not to make the hole too deep. Whether or not the surgeon taps a pilot hole often depends on the type of bone anchor 10020 and the surgeon's preference.

Whether a pilot hole is tapped by the pedicle finder or a depression is made by the awl, the surgeon may also wish to use a probe to assess the position of the hole or depression to ensure that it has not veered into an unintended or unsafe location. Some surgeons have found that verifying the hole or depression position can be difficult when employing a guide wire because the instruments and the bone anchors 10020 are constrained to the guide wire. As suggested earlier, the guide wire can be removed before insertion of the bone anchor 10020 and is preferred by many surgeons because an improperly placed guide wire can cause incorrect implant placement, which can have potentially harmful results.

After the implant site has been prepared, the surgeon may now insert the anchor 10020 into position. A number of methods and instruments are available for delivering the bone anchor 10020 and yoke 10022 to the surgical site. Each bone anchor 10020 is mated to one yoke 10022 and the two are advanced into position together. The yoke 10022 and the bone anchor 10020 may be a fixedly or polyaxially connected. The methods and instruments can be used in varying combinations. The tools used to seat the bone anchors 10020 are typically advanced through the docking port 10064.

Figure 56:
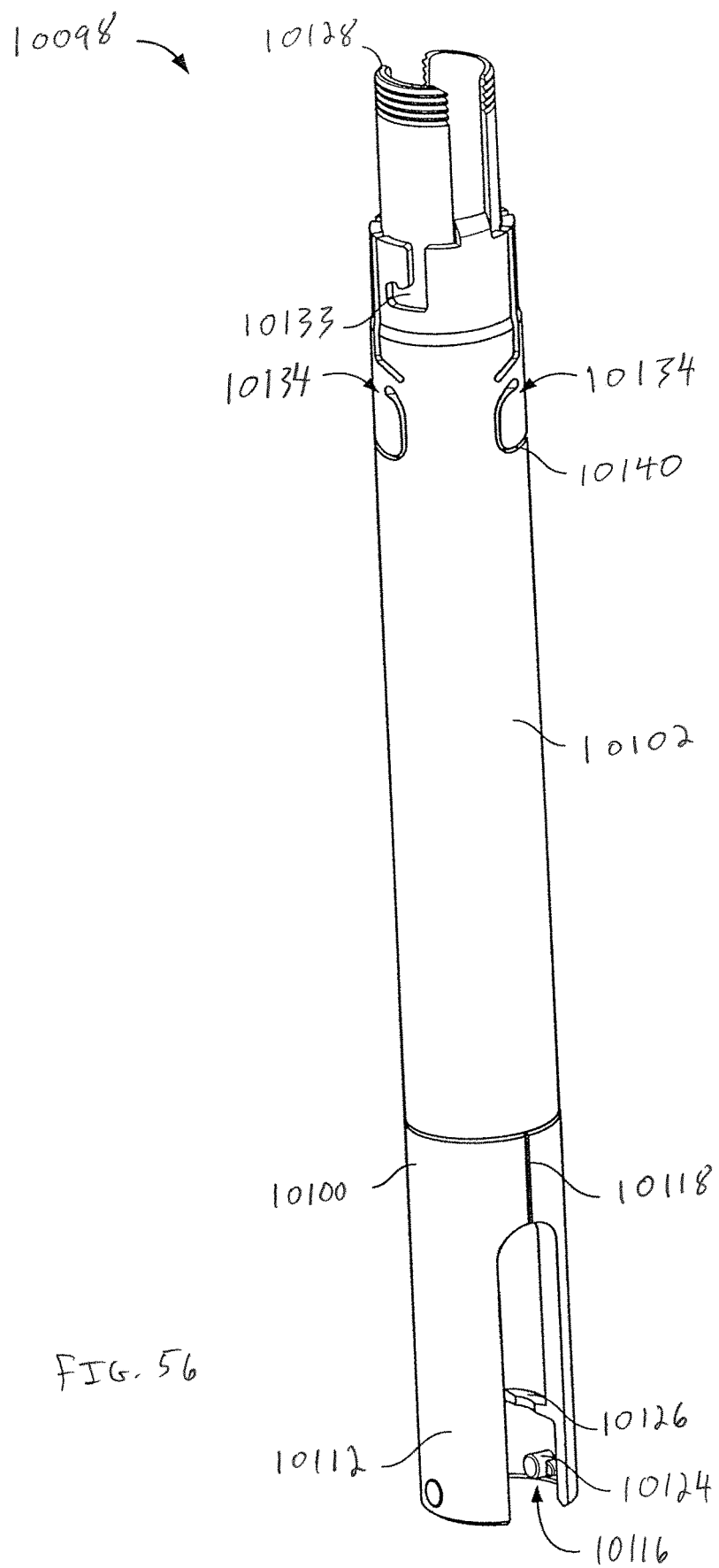
FIG. 56 is a perspective view of a short slot yoke manipulator.
Figure 57:
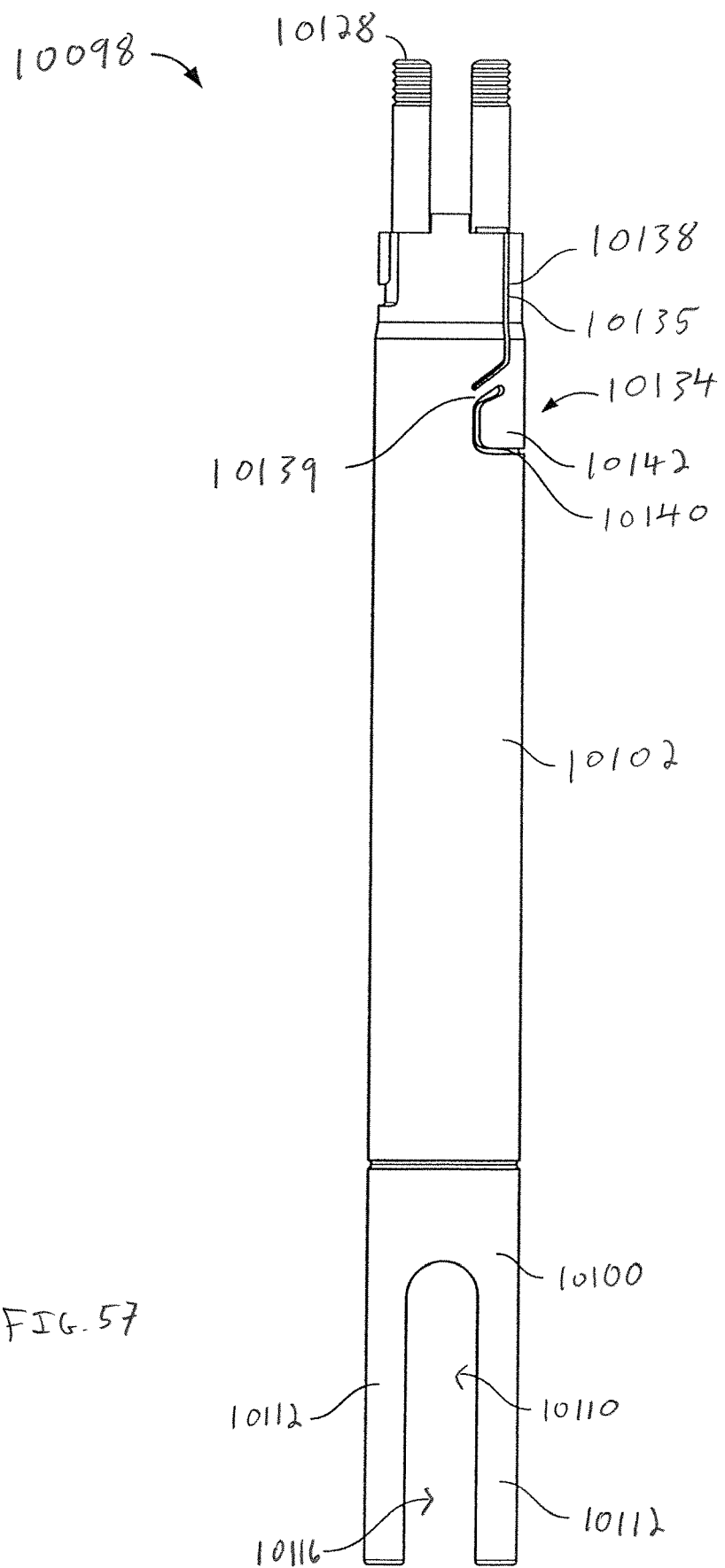
FIG. 57 is a front view of the yoke manipulator of FIG. 7.
Figure 58:
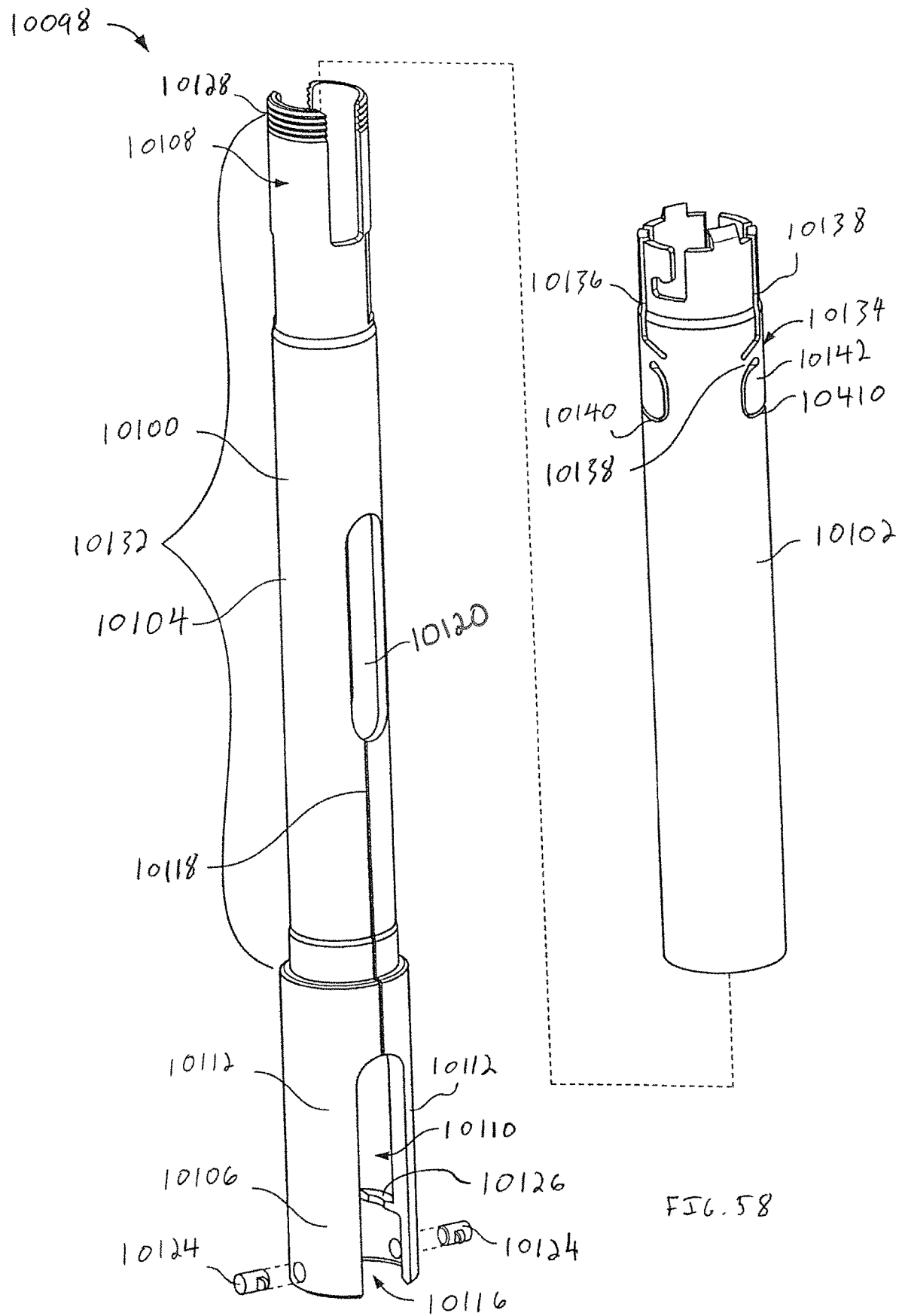
FIG. 58 is an exploded view of the yoke manipulator of FIG. 7.
Figure 59:
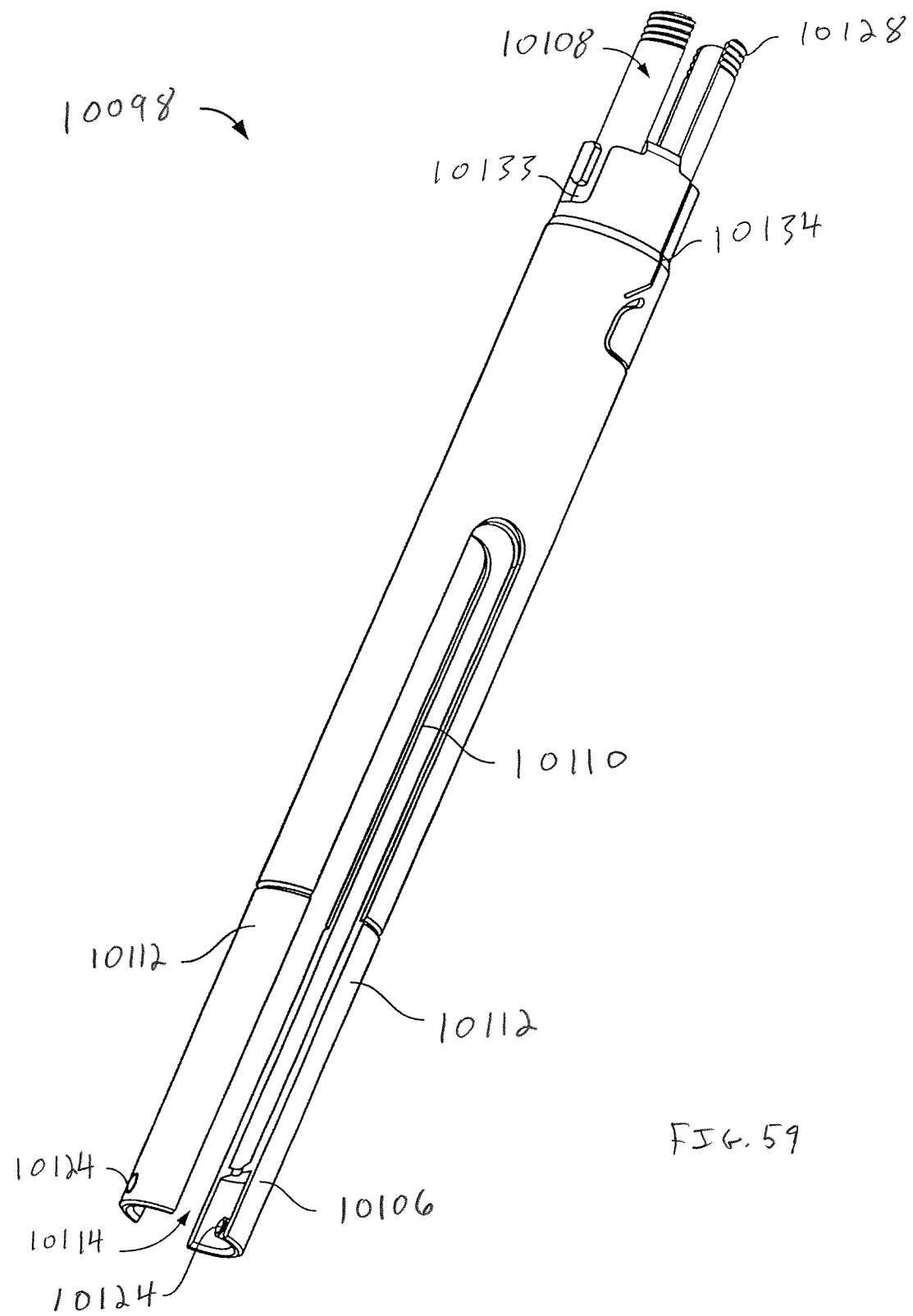
FIG. 59 is a perspective view of a long slot yoke manipulator.
Figure 60:
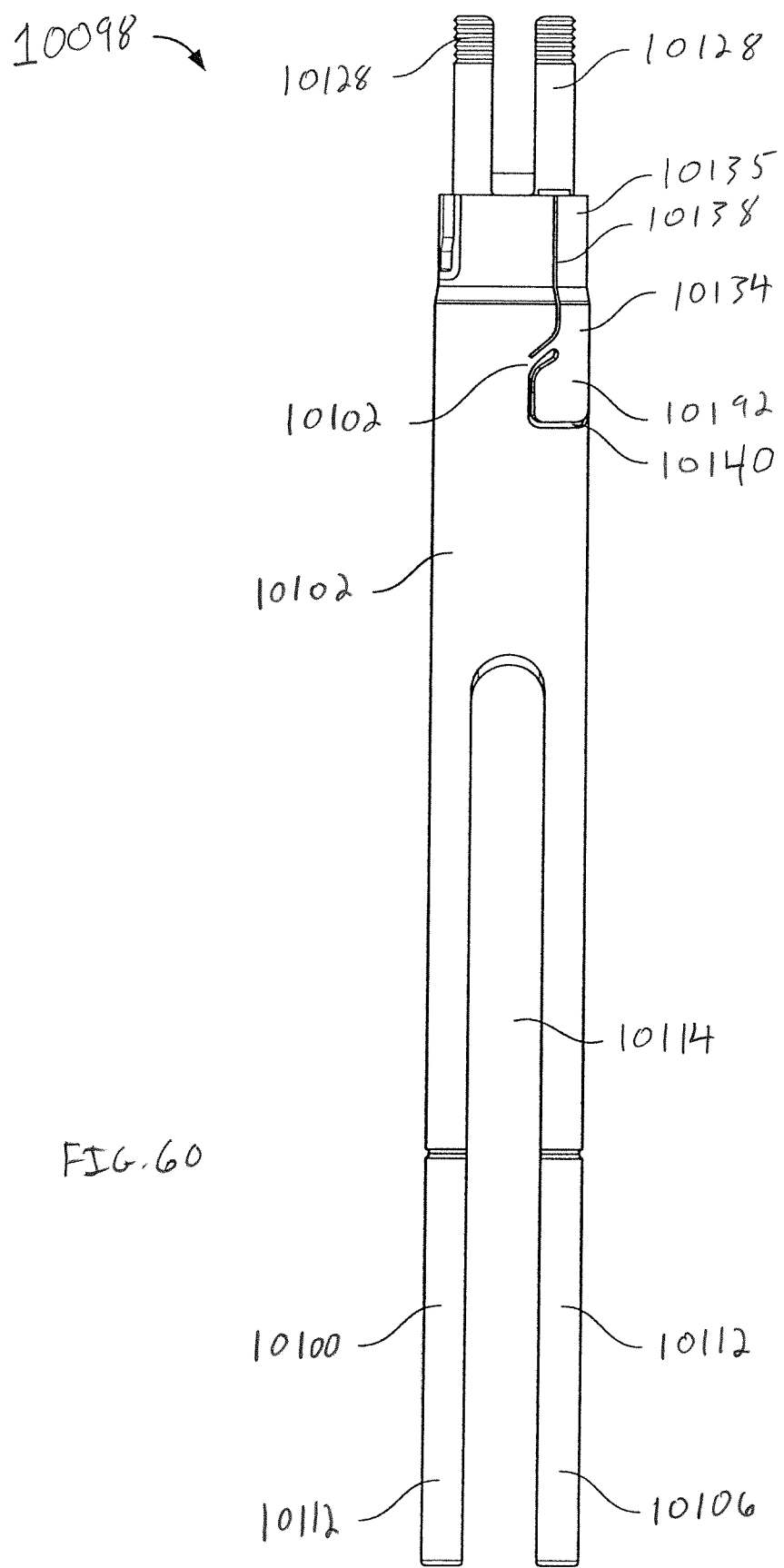
FIG. 60 is a front view of the yoke manipulator of FIG. 59.
Figure 61:
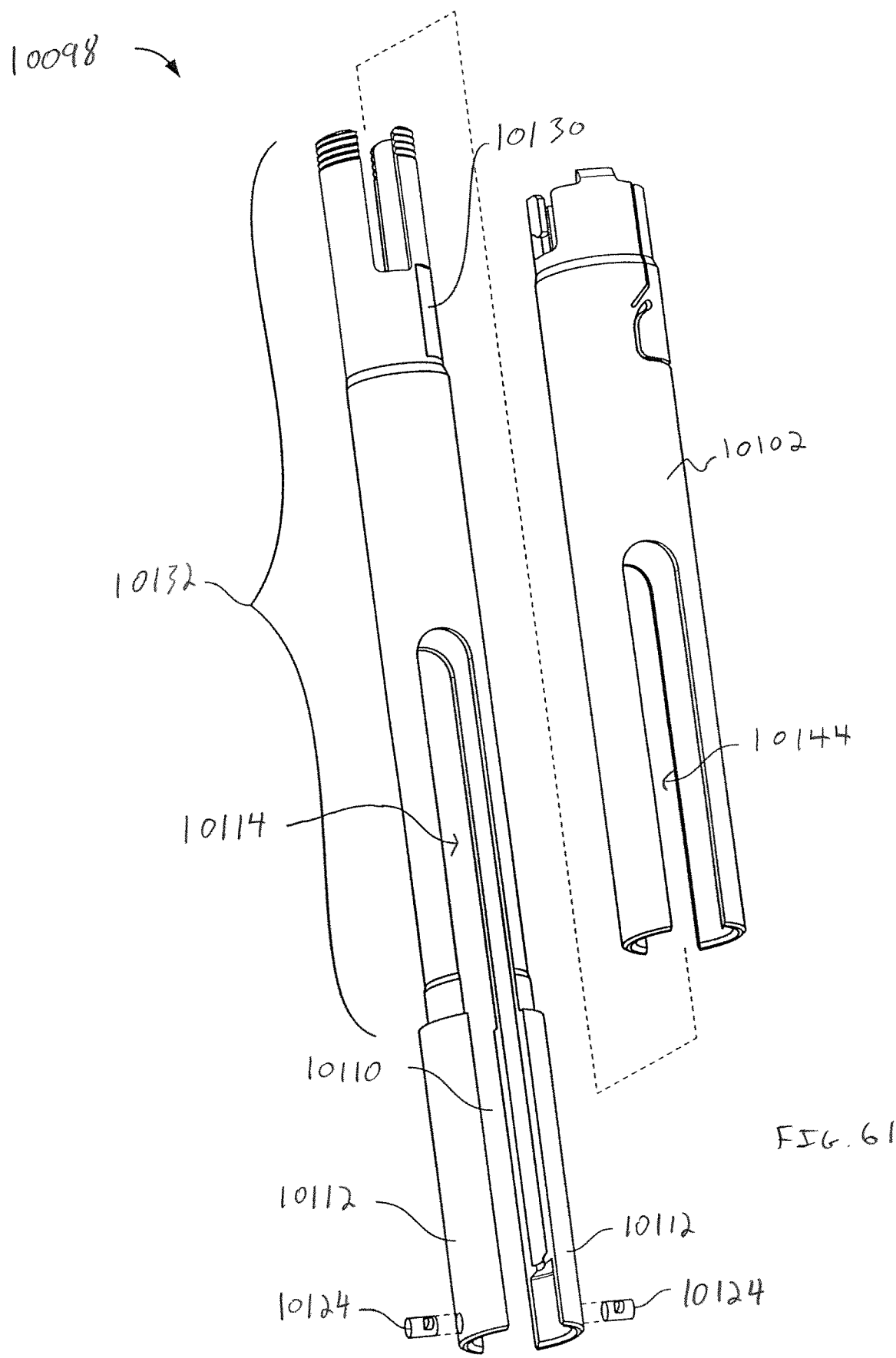
FIG. 61 is an exploded view of the yoke manipulator of FIG. 59.

In one form, the bone anchor 10020 is delivered to the surgical site with a yoke manipulator 10098. As shown in FIGS. 58 and 61, the yoke manipulator 10098 is comprised of two cylindrical sleeves 10100 and 10102. The inner cylindrical sleeve 10100 includes a main shaft body 10104 having a first end 10106 that is inserted into the incision and a second end 10108. The first end 10106 includes two shaft slots 10110 that create two shaft arms or prongs 10112. The two shaft slots 10110 can vary in length. FIGS. 59-61 illustrate a long slot 10114 that begins at the first end 10106 and extends down the shaft pass the midpoint of the sleeve 10100. FIGS. 56-58 illustrate a short slot 10116. The manipulators 10098 having short slots 10116 also typically include a channel 10118 leading to an internal slot 10120. The material used for the manipulator 10098 can impact the length of the slots 10110 that can be made. The manipulators 10098 may have a number of slot lengths. In another form, instead of using a long slot 10114 and a short slot 10116, a medium length slot 10110 may also be used and further both slots 10110 may be the same length. The slots 10110 allow for some movement of the prongs 10112. In addition, the slots 10110 provide for clearance for manipulation of the connecting member 10026, as described below. The prongs 10112 are typically placed around a portion of the yoke 10022. After the prongs 10112 are positioned around the yoke 10022, the outer cylindrical sleeve 10102 is slid into position over the inner cylindrical sleeve 10100 thereby securing the yoke 10022 and bone anchor 10020 relative to the yoke manipulator 10098.

The portions of the prong 10112 that surround a portion of the yoke 10022 typically include a boss, recess, flange, or other retainer to engage a complementary structure on the yoke 10022. In one embodiment depicted in FIGS. 56-61, each of the prongs 10112 includes a boss or pin 10124 located on the inside surface of the prongs 10112 and located relatively close to the end of the inner cylindrical sleeve 10100. The pins 10124 help prevent the yoke 10022 and anchor 10020 from prematurely separating from the manipulator 10098. In one form, as shown in FIGS. 58 and 61, the pins 10124 include a centrally located cylinder shape flanked by two semi-ovals. The somewhat irregular shape can create a more secure connection between the yoke and the inner cylindrical sleeve 10100. The inside surface of the prongs 10112 further may include a radially inward extending flange 10126 to provide a stop limiting axial movement of the yoke 10022 within the sleeve. On the second end 10108, the inner sleeve 10100 includes a connecting structure 10128, such as threads, flanges, slots, or bosses, to connect other tools or instruments such as a screw drive assembly and a guide bar, among others. In addition, the second end 10108 includes a mating structure such as a flat 10130, to mate with structure on the outer sleeve 10102.

The inner sleeve 10100 has a recessed section 10132 that accommodates the outer cylindrical sleeve 10102. The recessed section 10132 begins at the second end 10108 and extends down the shaft body 10104 toward the prongs 10112. The outer cylindrical sleeve 10102 serves as a restraint on the movement of the inner sleeve 10100, more particularly the prongs 10112 that are secured about the yoke 10022. As suggested above, the outer sleeve 10102 prevents or limits the movement of the prongs 10112 when the sleeve 10102 is mated with the inner sleeve 10100. The outer sleeve 10102 includes a positioner 10133 such as a slot, flange, boss or recess for engagement of an instrument. In addition, this positioner 10133 can mate the outer sleeve 10102 with other instruments. After the outer sleeve 10102 is slid over the inner sleeve 10100, the two sleeves mate together by a spring 10134 of the outer sleeve 10102. When the spring 10134 is depressed, elastic deformation of the outer sleeve 10102 allows the sleeve 10102 to be removed from around the inner sleeve 10100 by raising a finger portion 10135 of the spring 10134 away from a flat 10130 of the inner sleeve 10100. In one form, the spring 10134 is comprised of three separate channels 10136, 11038, 11040 in the outer sleeve 10102. As shown in FIGS. 57-58, the channels or slits 10136 and 10138 define a finger 10135 and the generally U-shaped slit 10140 defines a tab 10142. A gap 10139 is located between the channel 10140 and the slit 10136, 11038. The tab 10142 functions as a lever, and when the tab 10142 is depressed the finger 10135 raises and disengages from the flat 10130 of inner sleeve 10100.

As shown in FIGS. 59-61, the outer sleeve 10102 that mates with the longer slot 10114 manipulator may also have a slot 10144 similar to the slot 10110 in the inner sleeve 10100. The slots 10110, 11044 allow for passage of the connecting member 10026 during the implant procedure. In a preferred form, one yoke manipulator 10098 is used for each bone anchor 10020. Therefore, if the procedure requires two anchors 10020, then two yoke manipulators 10098 are used and if the fixation device has three bone anchors 10020, then three yoke manipulators 10098 are employed. Since the slots 10110 and 10144 allow for passage of the connecting member 10026, the manipulators 10098 and slots 10110, 11044 are preferably aligned. Structure facilitating alignment of the manipulators 1098 can be on the inner and outer sleeves 10100, 10102.

After the bone anchors 10020 are positioned adjacent to the bone, the bone anchors 10020 are typically driven into the bone by rotating a screw driver. The screw driver is sized to fit within the yoke manipulator 10098. The screw driver includes a shaft, with a positioning structure preferably in the form of a pin, boss, flange, or other structure complementary to the yoke manipulator 10098. In addition, the screw driver includes a head with a set of prongs that mate with the anchor 10020 such that when the screw driver is rotated, the anchor 10020 advances into the bone. The screw driver may also include a removable capture, such as a sleeve with internal threads, for mating the screw driver and the manipulator 10098, and thus the prongs are more easily engaged with the head of the bone anchor 10020. In one form, the capture is comprised of threads, but another connection, such as a bayonet style connection can be used. Opposite the prongs, the screw driver includes an end that can mate with a removable handle, ratchet, or other attachment. Further, the shaft of the screw driver may include a guide portion that centers the screw driver within the yoke manipulator 10098. The screw driver can be inserted into the incision with the yoke manipulator 10098 or can be advanced down the yoke manipulator 10098 after the anchor 10020 has been positioned in the pilot hole. After the bone anchor 10020 has been seated in the bone, the screw driver is removed from the yoke manipulator 10098.

After the anchors have been driven into the bone, the spinal rod or connecting member 10026 is inserted to span between the yokes 10022. During the insertion of the connecting member 10026, the manipulators 10098 and slots 10110 and 10112 are aligned relative to one another. Alignment of the manipulators ensures that the yokes 10022 are aligned such that the connecting member 10026 can be positioned within the yokes 10022. The alignment is typically accomplished with a strut or guide bar 10160. However, the connecting member 10026 could be inserted without the use of a guide bar 10160. The guide bar 10160 has structure that, when mated with the yoke manipulators 10098, facilitates alignment of the yoke manipulators 10098 relative to one another.

Figure 62:
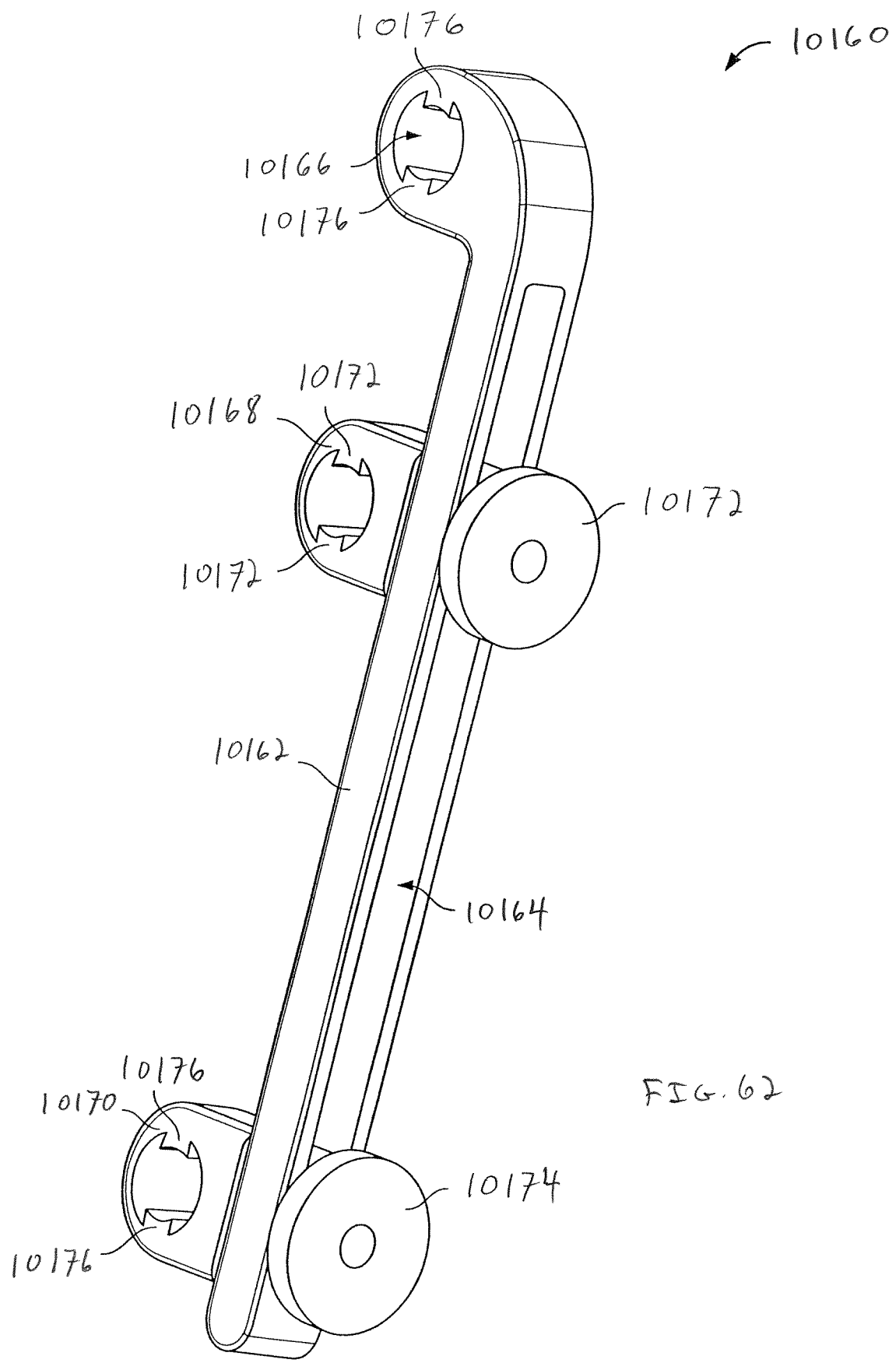
FIG. 62 is a perspective view of a guide bar.
Figure 63:
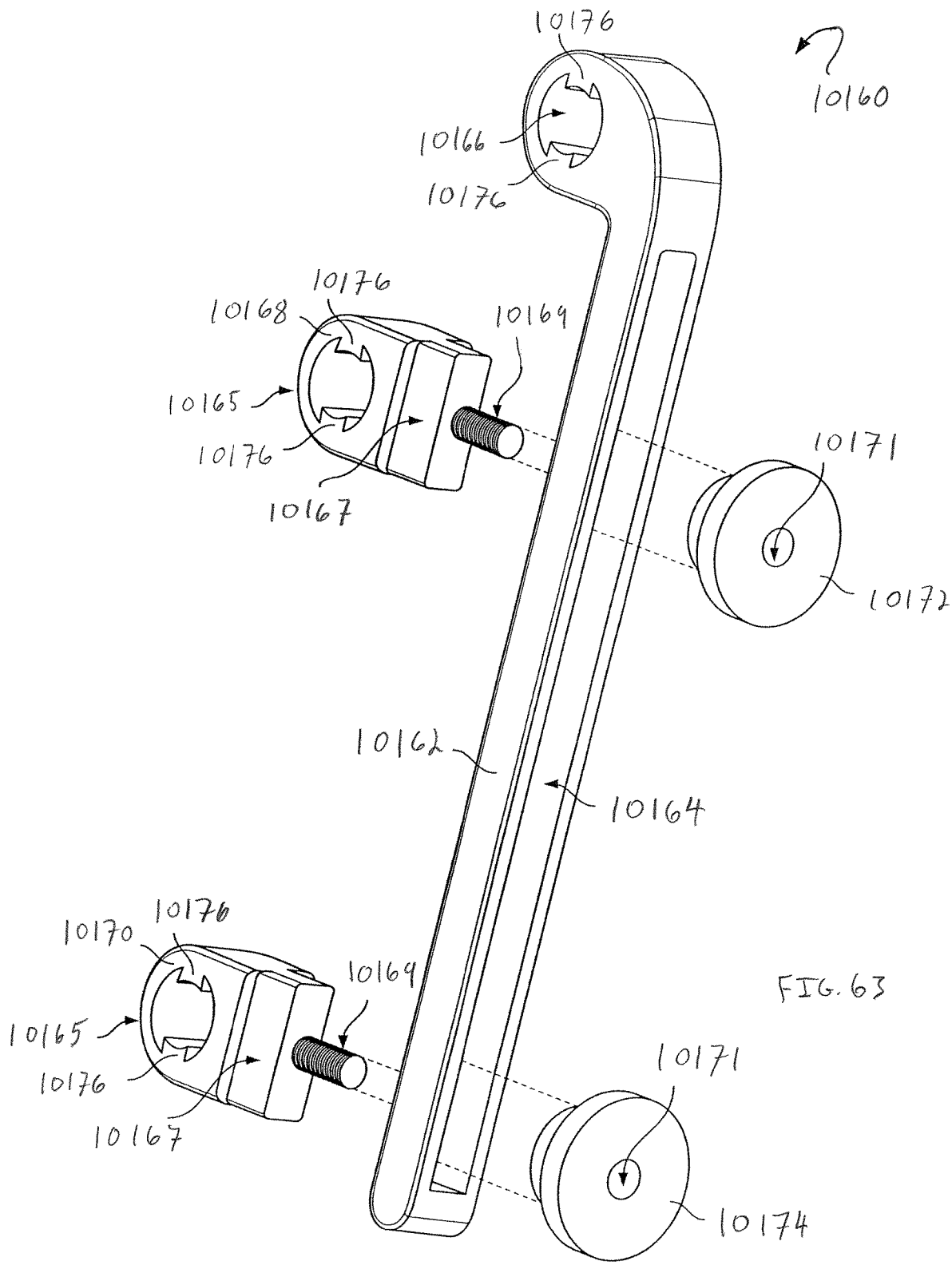
FIG. 63 is an exploded view of the guide bar of FIG. 62.

As shown in FIGS. 62 and 63, the guide 10160 typically includes a guide body 10162 having a horizontal slot 10164 and an end opening 10166. Within the horizontal slot 10164 are located sliding attachment brackets 10168 and 10170 oriented within a slide body 10165, which can be secured into position by set nuts 10172 and 10174. The slide body 10165 includes a reduced portion 10167 that fits within the horizontal slot 10164. Attached to the reduced portion 10167 of the slide 10165 is a threaded portion 10169. The threaded portions 10169 engage threaded openings 10171 in the set nuts 10172, 11074. The openings 10168, 11070 are movable with respect to opening 10166 to accommodate the spinal anatomy of different patients. The opening 10166 and attachment brackets 10168, 10170 are generally circular with two projections 10176 to secure the connection between the guide 10160 and the yoke manipulators 10098 that are mated with the guide 10160. The projections 10176 can fit within the connecting structure 10128 on the second end 10108 of the manipulator 10098 illustrated in FIGS. 56-61. Therefore, the physician can align the slots on the first end 10106 of the inner sleeve 10100 by aligning the connecting structure 10128 on the second end 10108. In one preferred embodiment, the guide body 10162 includes etch marks so that the physician can determine what length connection member 10026 is required. To adjust the position of the attachment brackets 10168, 10170, the nuts 10172, 10174 are unscrewed and then the attachment brackets 10168, 10170 can move within the horizontal slot 10164.

Figure 64:
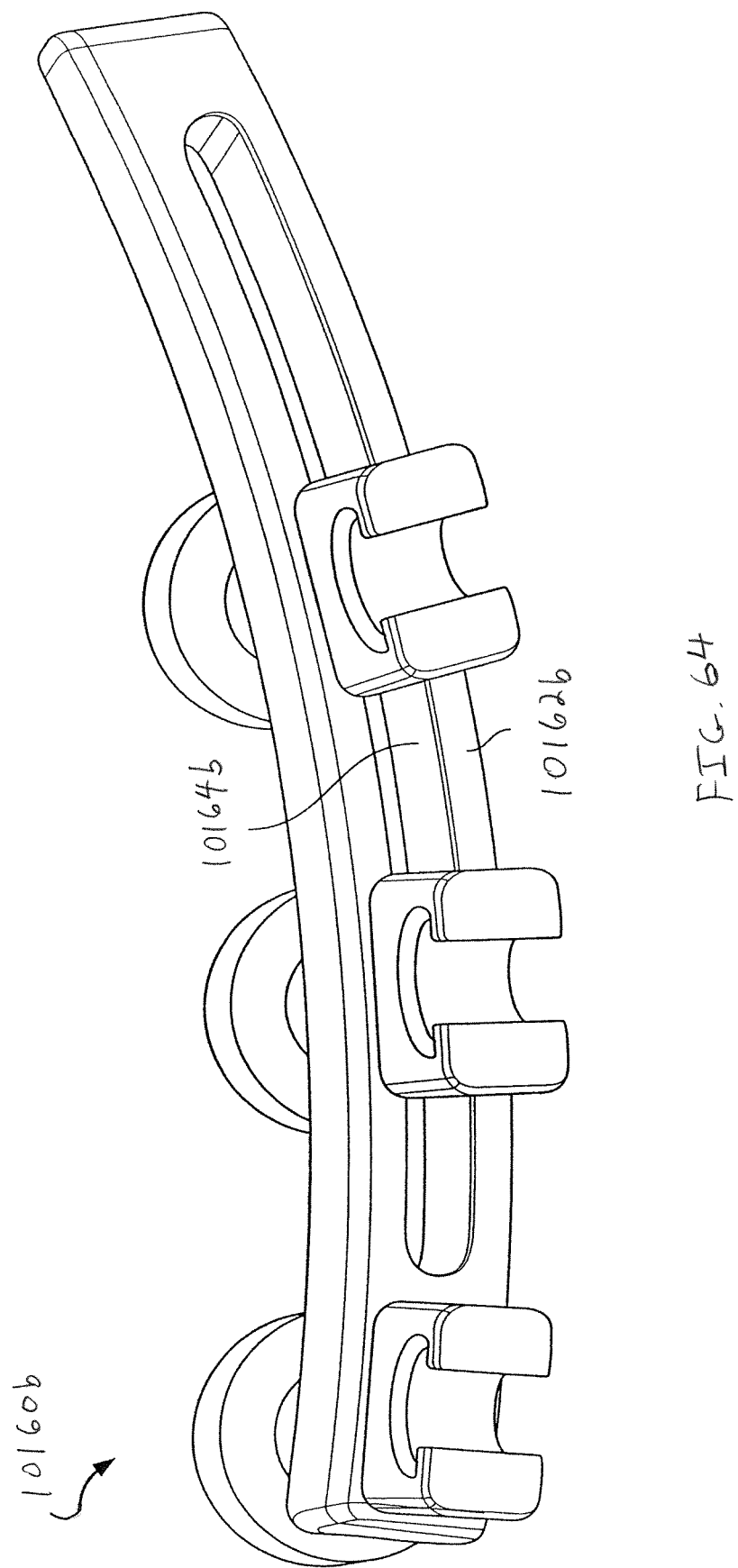
FIG. 64 is a perspective view of another guide bar.
Figure 65:
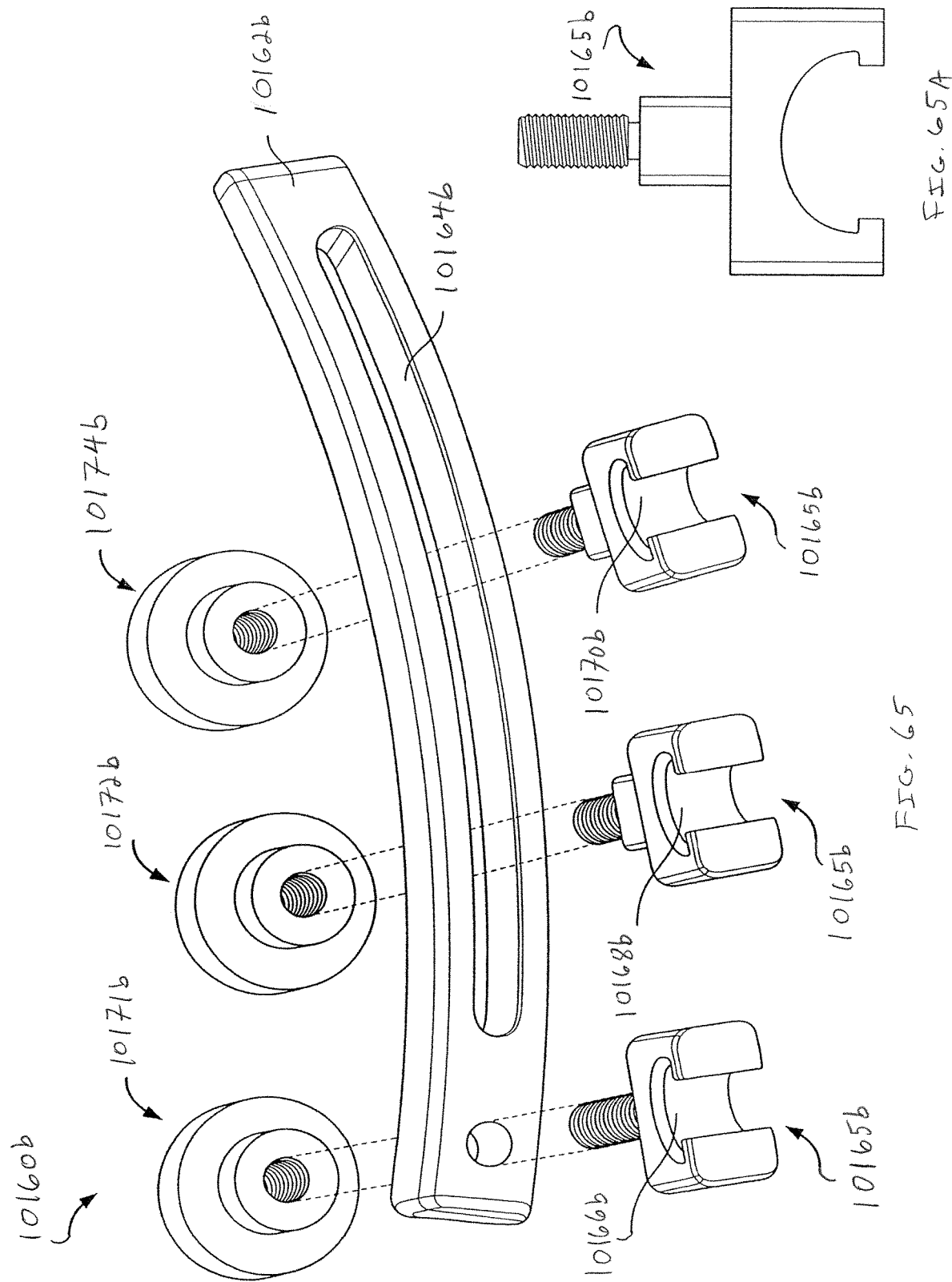
FIG. 65 is an exploded view of the guide bar of FIG. 64.
Figure 66:
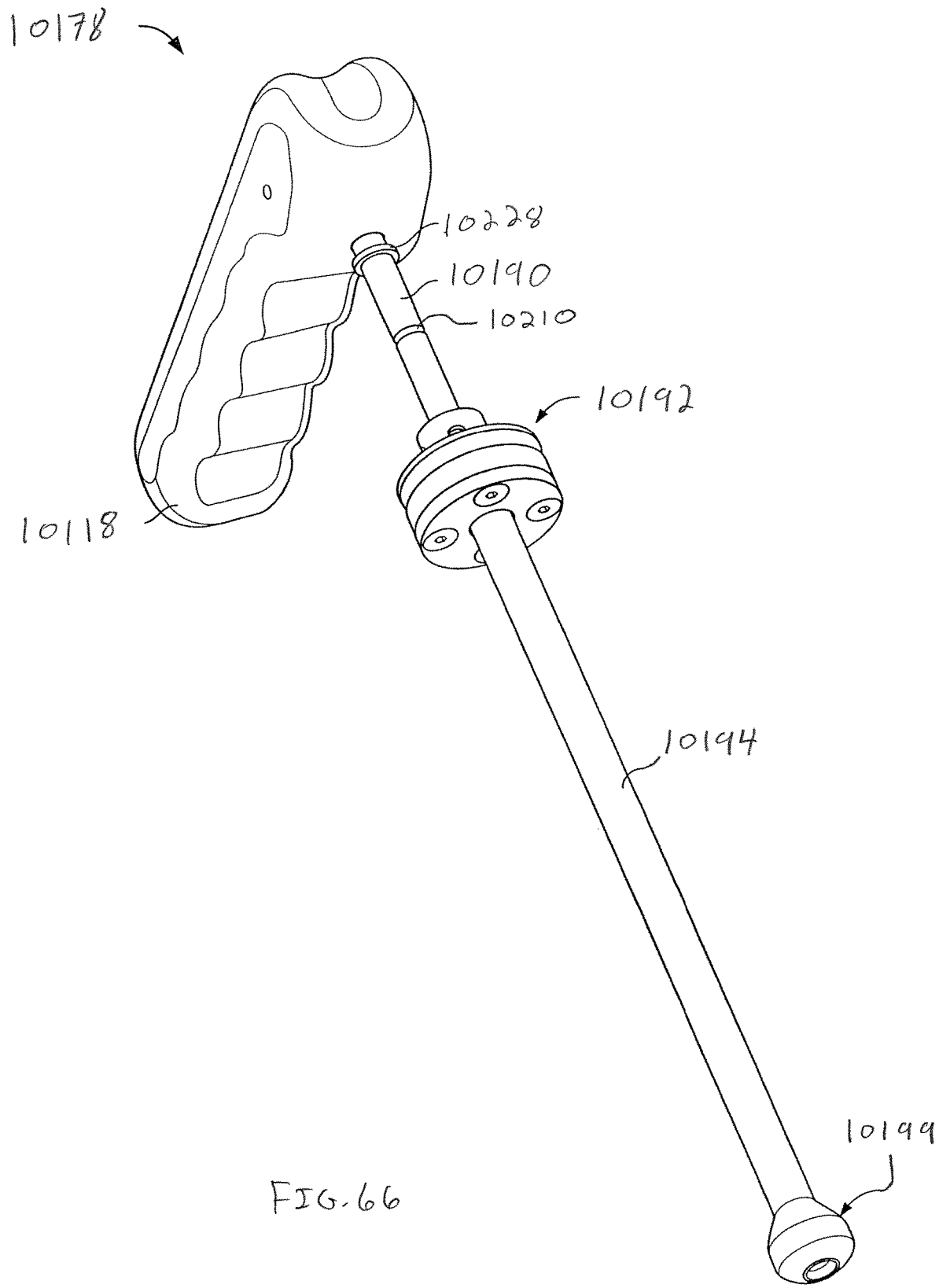
FIG. 66 is a perspective view of a rod inserter having an outer sleeve in a first stage of rod insertion.
Figure 67:
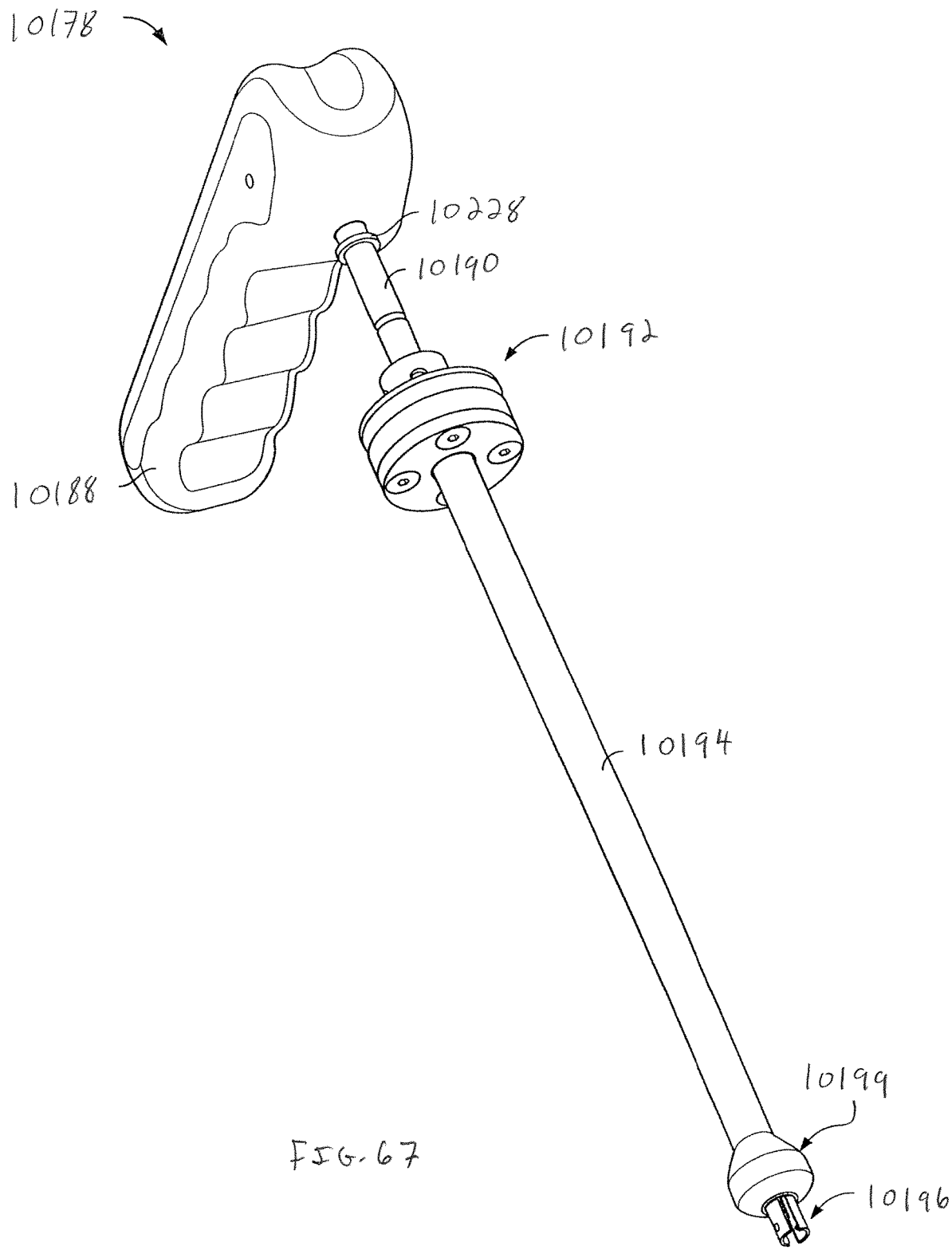
FIG. 67 is a perspective view of the rod inserter of FIG. 66 having the outer sleeve in a second stage of rod insertion.
Figure 68:
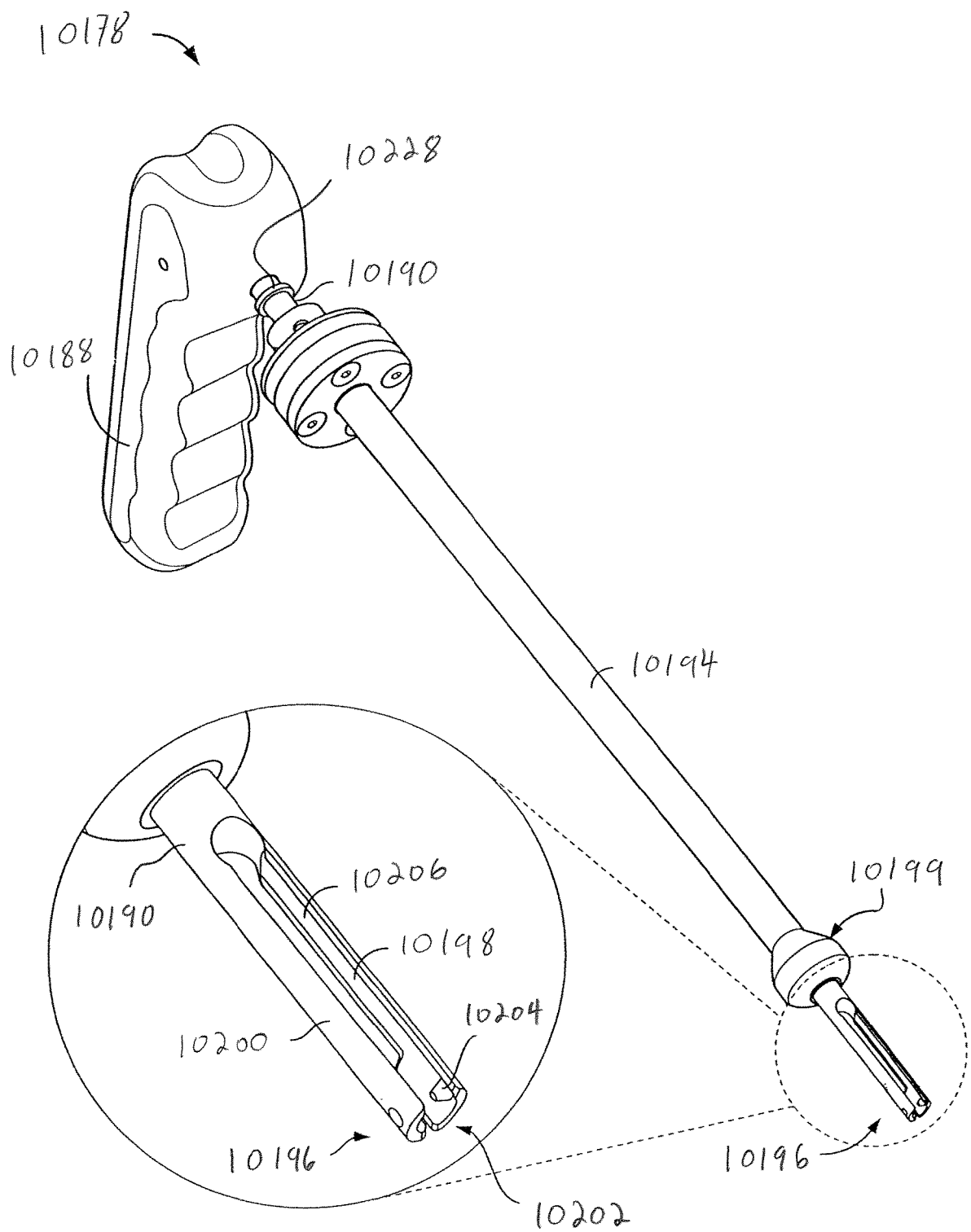
FIG. 68 is a detailed perspective view of the rod inserter of FIG. 66 having the outer sleeve in a third stage of rod insertion.
Figure 69:
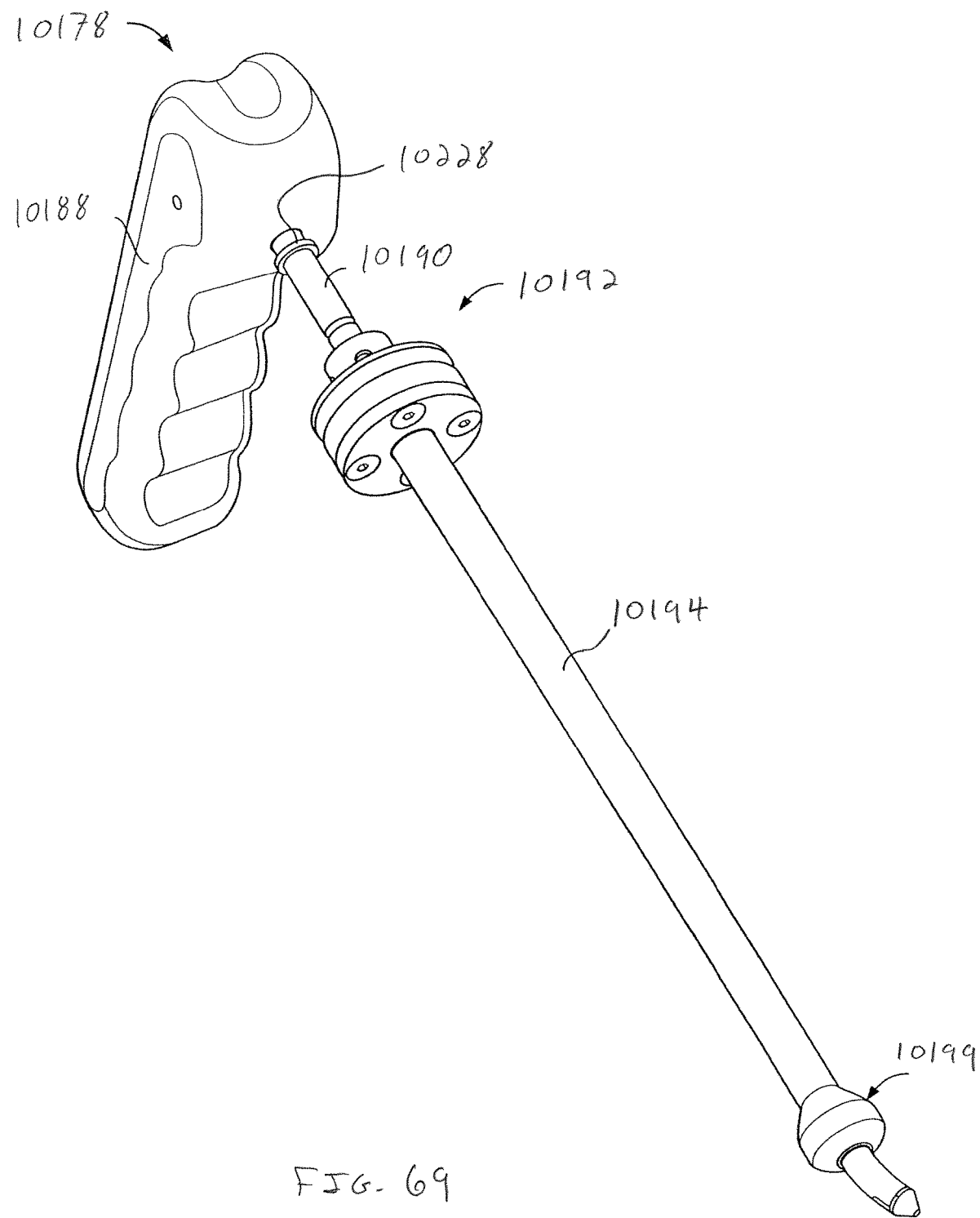
FIG. 69 is a perspective view of the rod inserter of FIG. 66 having the outer sleeve in a first stage and a connecting member mounted thereto.
Figure 70:
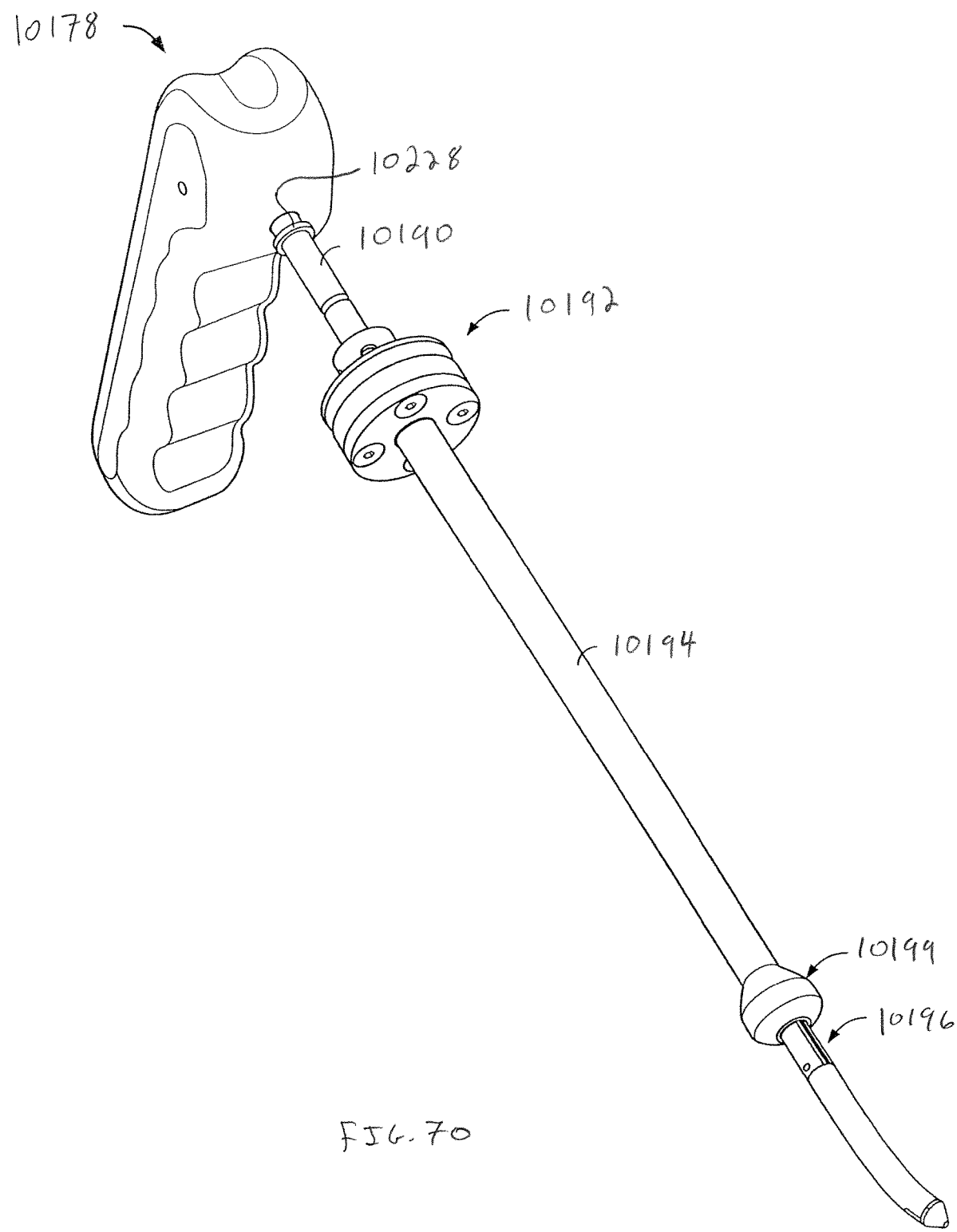
FIG. 70 is a perspective view of the rod inserter of FIG. 66 having the outer sleeve in a second stage and a connecting member mounted thereto.

In another form, illustrated in FIGS. 64 and 65, a guide 10160*b* may have a curved guide body 10162*b* with a curved slot 10164*b*. The curvature of the guide 10160*b* correlates to the curvature of the spine and connecting member 10026 to be implanted along the spine. Using the curved guide 10160*b* can facilitate insertion of the connecting member 10026 if the connecting member 10026 that is implanted is curved. A pair of sliding attachment brackets 10168*b* and 10170*b*, oriented within a slide body 10165*b*, can be secured into position by set nuts 10172*b*, 10174*b*. In addition, the slide body 10165*b* with opening 10166*b* is held into position with set nut 10171*b*.

To insert the connecting member 10026 into the yokes 10022, a rod inserter 10178 is typically used. The rod inserter may be used in conjunction with the guide 10160 and yoke manipulators 10098. If desired, a path through the surrounding tissue may be created by first using a muscle splitter to facilitate insertion of the connecting member 10026. The features of the connecting member 10026 may include a nose portion 10180 with a rounded, chamfered, or reduced diameter tip, a body 10182 having a round constant diameter, and an attachment end 10184. The connecting member 10026 may be straight or bent depending on the profile of the patient and the surgeon's preference. The nose 10180 is preferably shaped to ease the passage of the connecting member 10026 through the soft tissue, the yoke manipulators 10098, various other MIS system instrumentation, and into the yoke 10022. The attachment end 10184 is used to hold the member 10026 and steer it into position within the yoke 10022. The end 10184 may include connecting structure 10186 such as a bore, boss, flats, capture, groove, ridge, or other distinct structure that would serve to securely hold the member 10026 to the rod inserter 10178 during the insertion procedure. As shown in FIG. 51, the attachment end 10184 includes a flat surface 10183 transverse to the body 10182 of the connecting member, and a projection 10185. The projection 10185 includes the connecting structure 10186 shown as a bore, and may also be shaped to limit the movement of the connecting member 10026 when it is connected to the rod inserter 10178. For example, the projection 10185 may be offset from the center of the connecting member 10026 or the projection 10185 or connecting structure 10186 may be a number of different shapes or sizes.

To begin the insertion procedure, the connecting member 10026 is secured to the rod inserter 10178. The rod inserter 10178 functions to hold and guide the connecting member 10026 into position within the yoke 10022. As shown in FIGS. 66-71, the rod inserter 10178 includes a handle 10188, an inner shaft 10190, a shift assembly 10192, and a locking sleeve 10194. The inner shaft 10190 includes an attachment end 10196 that attaches the connecting member 10026. The attachment end includes two slots 10198. Preferably the prongs 10200 flex such that the two prongs can be arranged about a portion of the connecting member 10026. Each of the prongs 10200 preferably includes connecting structure 10202 that securely grips corresponding structure 10186 on the connecting member 10026. The connecting structure 10202 can include a recess or boss 10204, shown in FIG. 68 on the inside surface of the prongs 10200. This boss 10204 can facilitate a secure connection between the connecting member 10026 and the rod inserter 10178. In addition, the prongs 10200 include a flat or shelf 10206 to limit the rotational movement of the connecting member 1026 during the insertion procedure as described below. This flat 10206 can limit the movement by contacting the projection 10185 or other structure of the connecting member 10026. Opposite the attachment end, the rod inserter includes the handle 10188, the handle may be fixed by a fixation pin 10195, or threads, compression fit, bonded or otherwise affixed to the inner shaft 10190. The handle 10188 is typically mounted substantially perpendicular to the inner shaft 10190 and is preferably sized and shaped for optimal manual control.

The rod inserter 10178 goes through several stages during the insertion procedure. During one stage, the locking sleeve 10194 is slid down the inner shaft 10190 into the fully extended configuration. The fully extended configuration positions the locking sleeve 10194 to surround the inner shaft 10190 and the prongs 10200. The connecting member 10026 is held between the prongs 10200 and when the locking sleeve 10194 is slid down the inner shaft 10190 into the fully extended configuration, the connecting member 10026 is secured between the prongs 10200. Such an arrangement limits the movement of the connecting member 10026 with respect to the rod inserter 10178. During a second stage, the locking sleeve 10194 is moved to expose the entire connecting member 10026 allowing the connecting member 10026 to pivot relative to the rod inserter 10178. The connecting member 10026 remains attached to the rod inserter 10178 via the connecting structure 10202. The connecting structure 10202 keeps the connecting member 10026 attached to the rod inserter 10178 during the second stage by preventing the prongs 10200 from splaying outward away from the connecting member 10026. When the prongs 10200 splay outward the connecting structure 10202 of the rod inserter 10178 disengages with the connecting structure 10186 of the connecting member 10026. Therefore, during a third stage, the locking sleeve 10194 is moved to sufficiently expose the slots 10198 such that the prongs 10200 can splay and disengage with the connecting member 10026.

During use of the rod inserter 10178, the movement of the locking sleeve 10194 is controlled by the shift assembly 10192. The shift assembly 10192 locks the sleeve 10194 into position. To do this, the shift assembly includes a ball and detent mechanism 10208 that provides a releasable lock for securing the sleeve 10194 into position. The inner shaft 10190 includes recesses 10210 that engage ball detents 10212 in the shift assembly 10192. Since there are three stages the rod inserter 10178 undergoes during insertion of the connecting member 10026, there are three separate locking sleeve 10194 positions. In this regard, the inner shaft 10190 includes three recesses 10210 that engage the detent balls 10212 in the shift assembly 10192. The position of the recesses 10210 correlate to the three locking sleeve 10194 positions and to the different insertion stages.

In one embodiment of the shift assembly 10192, as shown in FIGS. 66-72, the assembly 10192 includes a spring housing 10214 with a spring 10216, a ball housing 10218, and a cover plate 10220. The spring housing 10214 is located away from the ball housing 10218, which is adjacent to the cover plate 10220. The spring housing 10214 is secured or welded to the locking sleeve 10194. The locking sleeve 10194 includes radially inward facing angled cutouts 10222. The ball detents 10212 reside within the angled cutouts 10222 and a stepped-opening 10224 in the ball housing 10214. When the sleeve 10194 is secured in one of the three positions, the angled cutouts 10222 align with recesses 10210 on the inner shaft 10190. To move the sleeve 10194 from one of the three locked positions, the ball housing 10218 and plate 10220 are moved toward the spring housing 10214. The housings 10214 and 10218 are biased away from one another by compression spring 10216. When the ball housing 10218 and plate 10220 are moved the ball detents 10212 are able to move into the larger aperture of the stepped-opening 10224. Having the ball detents 10212 in the larger aperture allows the detents 10212 to disengage from the recess 10210 on the inner shaft 10190 such that the inner shaft 10190 and the locking sleeve 10194 can move relative to one another. The plate 10220 bounds the ball detents 10212 in the ball housing 10218 and the plate 10220 is secured to the housing 10218 by screws 10226. In addition to the recesses 10210, the inner shaft 10194 may optionally also include a hard stop 10228, or the handle 10188 may be used as a stop.

During the various stages of rod insertion, the rod inserter 10178 and the connecting member 10026 have three relative configurations: rigid attachment where the locking sleeve 10194 surrounds a substantial portion of the prongs 10200 limiting or blocking the pivoting movement of the connecting member 10026, pivoting or articulating attachment where the pivot connection between the inner shaft 10190 and the connecting member 10026 is unblocked and pivoting is permitted, and disengagement from attachment where the locking sleeve 10194 is moved up the inner shaft 10190 such that the prongs 10200 splay away from one another and release from the connecting member 10026. To move the locking sleeve 10194 from one position to another, a selectively engageable lock, such as the shift assembly 10192, may be used to prevent undesired shifting of the locking sleeve 10194 from the rigid attachment to the pivoting attachment. When the connecting member is rigidly attached to the rod inserter 10178, the locking sleeve 10194 covers the pivot connection or the pivot axis is blocked to restrict the pivoting of the spinal rod or connecting member 10026 about the pivot axis. When the locking sleeve 10194 is moved upward toward the handle 10188 and uncovers the pivot connection, the connecting member 10026 is free to pivot about the pivot connection. To limit the rotational movement of the connecting member 10026 to movement in one direction, a stop may be provided on the inner shaft.

Figure 71:
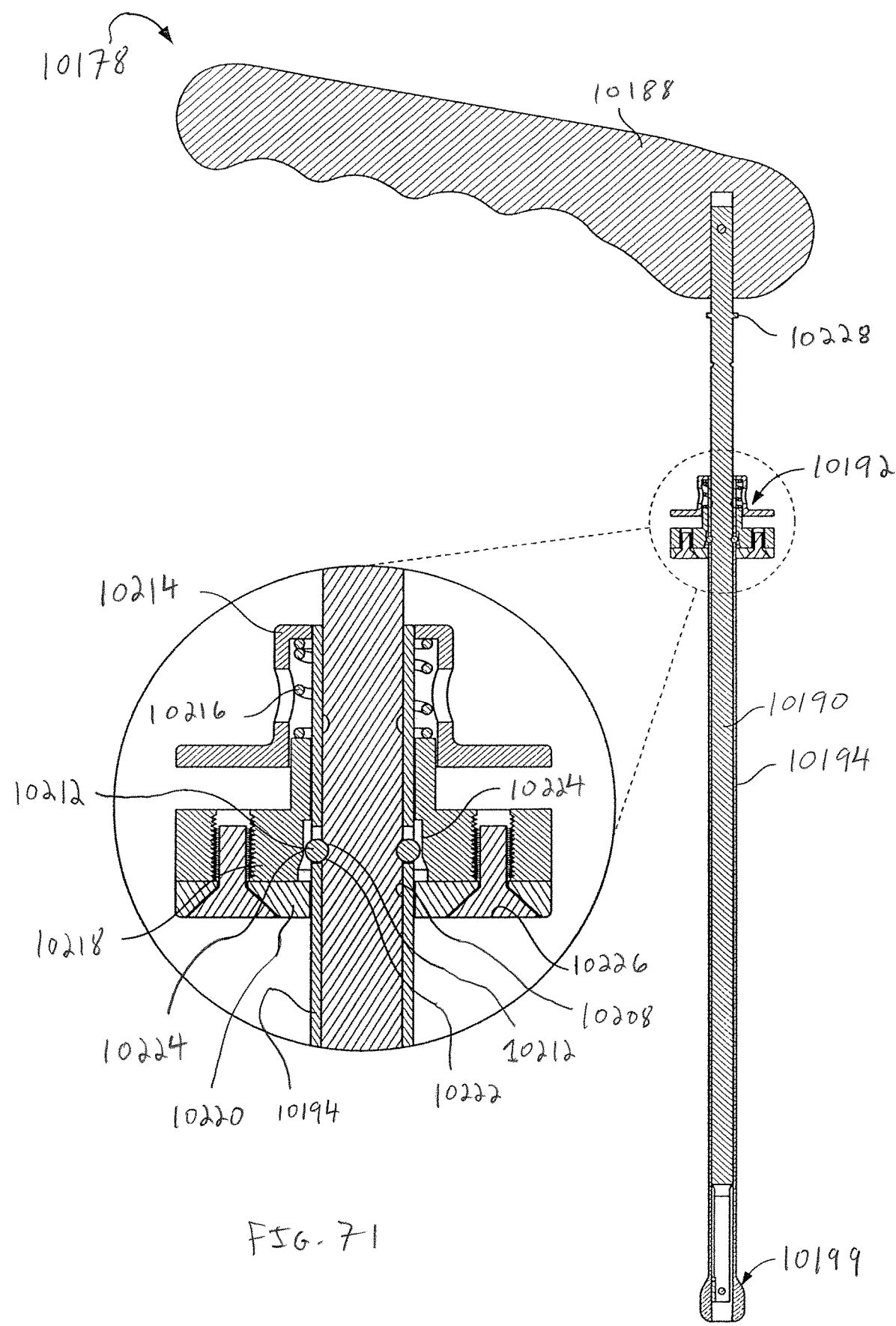
FIG. 71 is a cross-sectional view of the rod inserter of FIG. 66 having the outer sleeve in the first stage of rod insertion.
Figure 72:
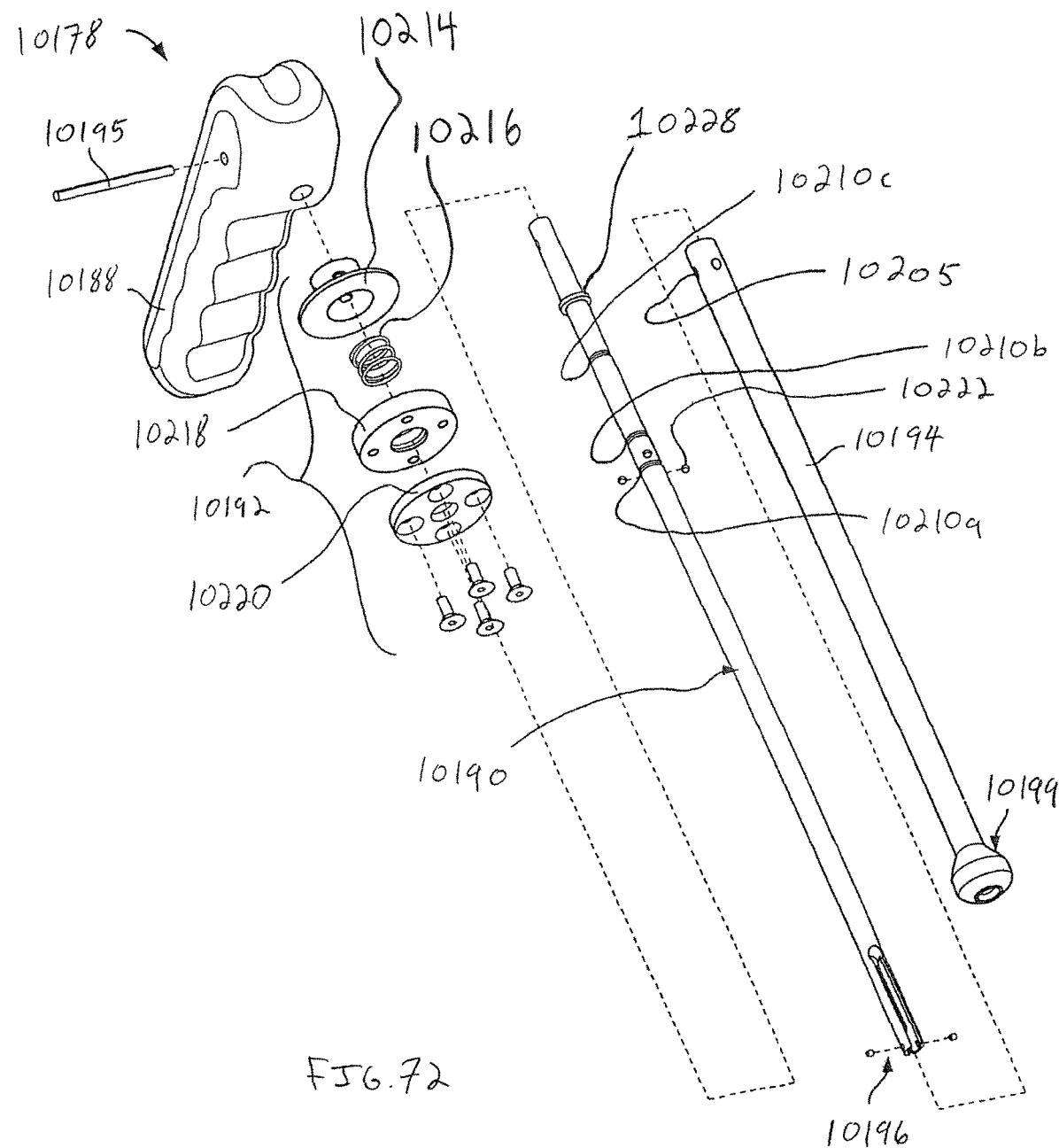
FIG. 72 is an exploded view of the rod inserter of FIG. 66.
Figure 73:
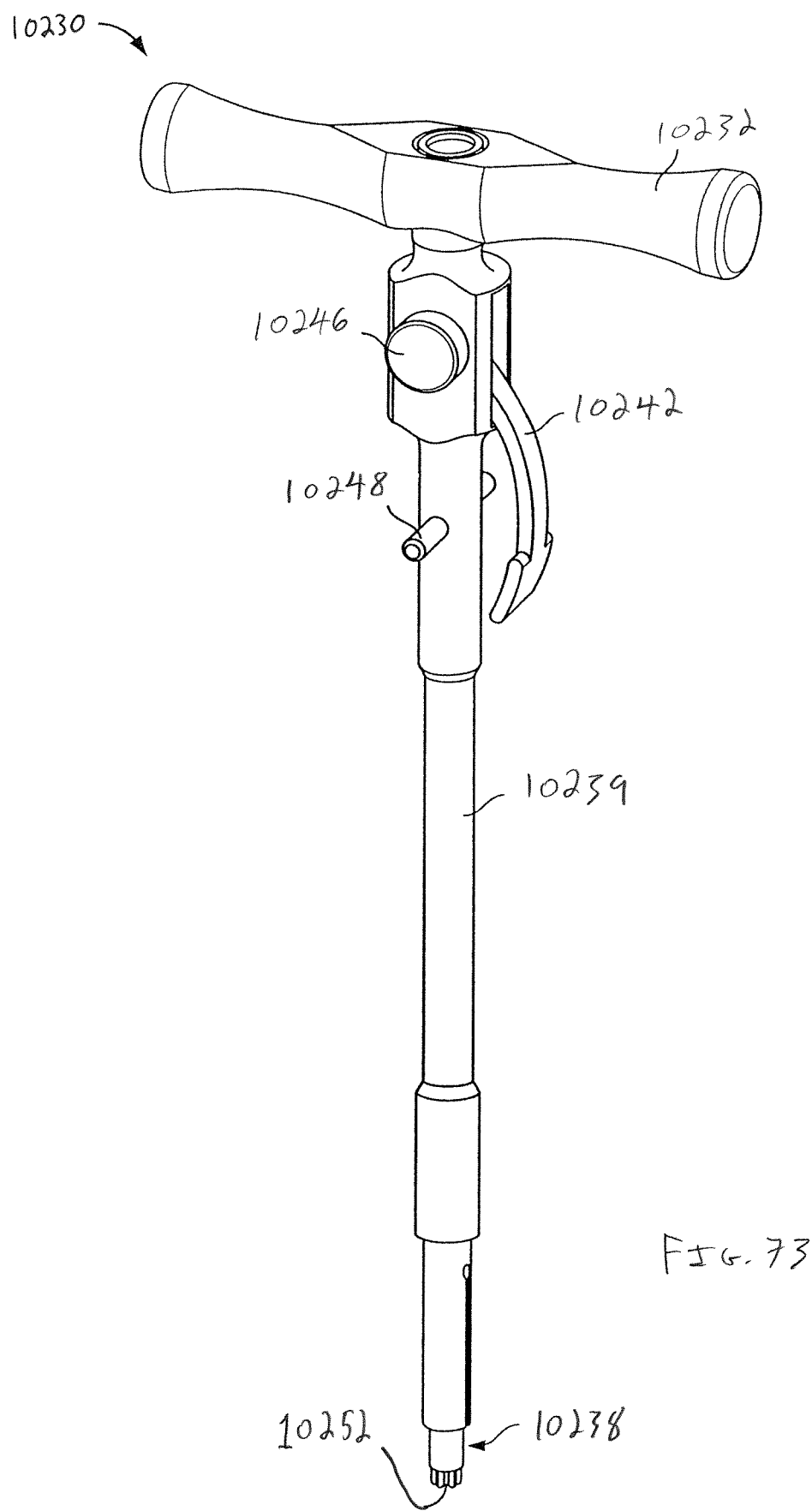
FIG. 73 is a perspective view of a cap inserter having a lever in the lowered position.
Figure 74:
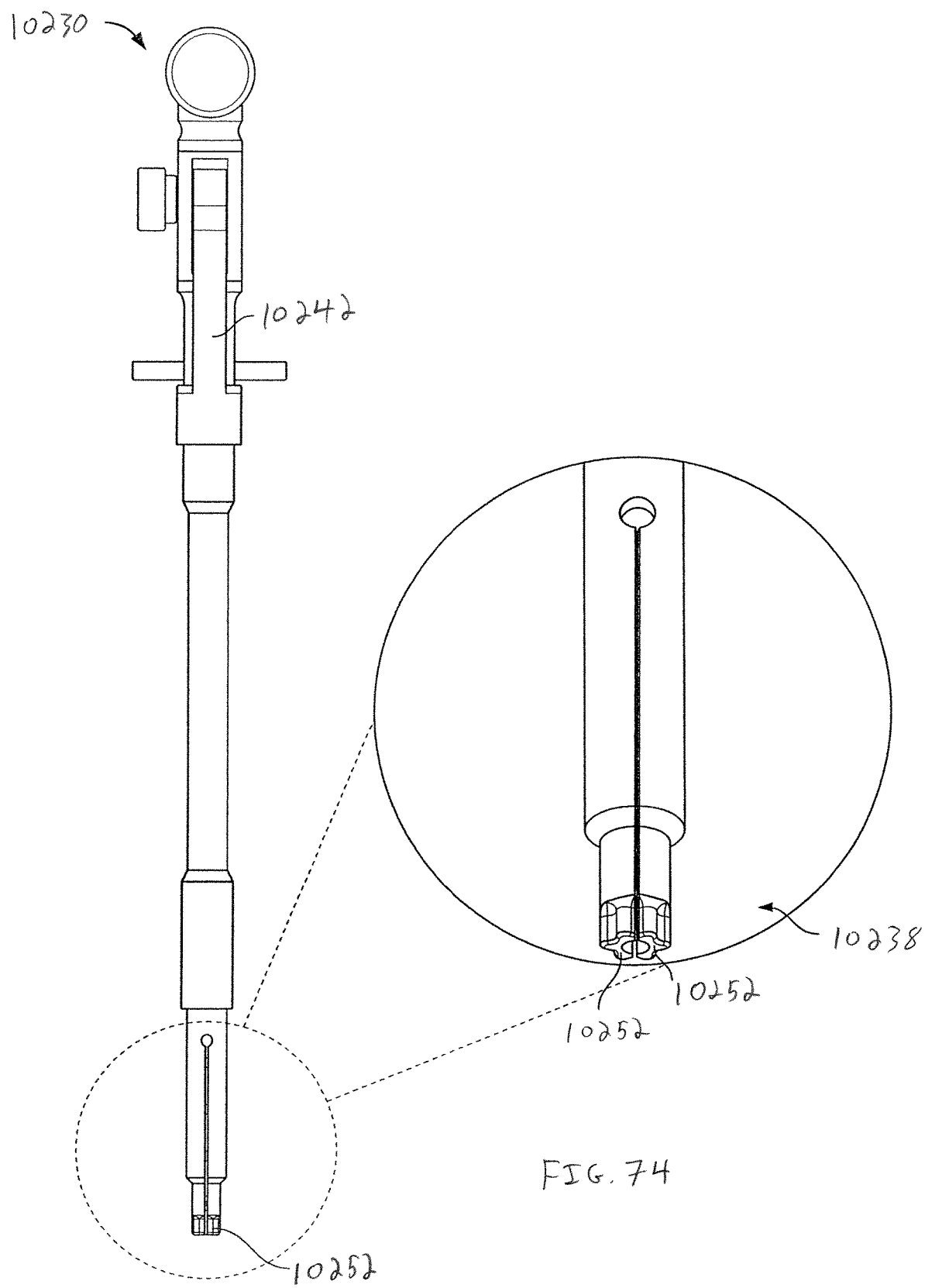
FIG. 74 is a side elevation view of the cap inserter of FIG. 73.
Figure 75:
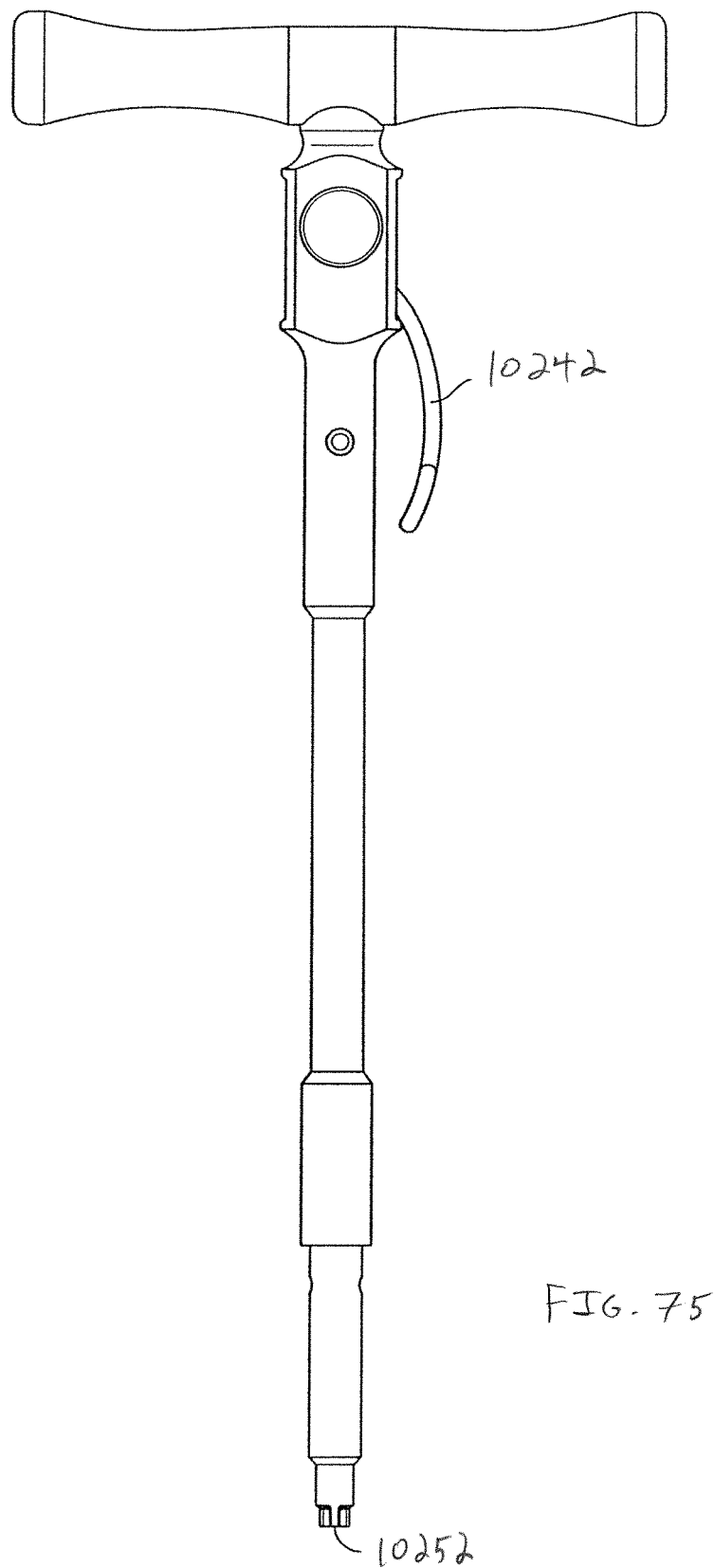
FIG. 75 is a front elevation view of the cap inserter of FIG. 73.

Turning to more of the detail of the shift assembly 10192, and more particularly the shift assembly 10192 positioning during the rod insertion procedure, the selectively engageable lock includes at least one locking member or detent 10212 that is positionable in the aperture 10222 of the locking sleeve 10194 and one of the recesses 10210 at the inner shaft 10190. As shown in FIG. 72, the inner shaft 10190 has three recesses 10210a, 10210b, and 10210c. The shift assembly 10192 as shown in FIG. 71, has an internal slot or stepped-opening 10224 facing the locking sleeve 10194, the stepped-opening 10224 having a narrow portion and a wide portion with an inclined ramp extending therebetween. When the locking member or detent 10212 is positioned in the narrow portion of the stepped-opening 10224 adjacent one of the recesses 10210, shifting of the locking sleeve 10194 is limited or prevented. Depending on which recess 10210a, 10210b, 10210c, the rod inserter 10178 will be secured into a different configuration. When the detent 10212 is positioned between the opening 10222 of the locking sleeve 10194 and the recess 10210a, the locking sleeve 10194 is positioned such that the pivoting movement of the connecting member 10026 is limited or blocked. When the detents 10212 are engaging the blocking recess 10210a, the locking sleeve 10194 is positioned to prevent pivoting. The unblocking recess 10210b is located between the blocking recesses 10210a and the release recess 10210c. When the detents 10212 of the shift assembly 10192 are positioned in the unblocking recesses 10210b, the locking sleeve 10194 allows the connecting member 10026 to pivot about the pivot connection but not disengage from the rod inserter 10178. When the detents 10212 are positioned in the release recesses 10210c, the prongs 10200 splay outwardly allow the connecting member 1026 to disengage from the inner shaft 10190. To move the shift assembly 10192 from one recess 10210 to another recess 10210, a portion of the shift assembly 10192 that is biased toward the pivot axis is moved from the biased position such that the detents 10212 previously captured between the narrow portion of the stepped-opening 10224 and the recess 10210 are able to move into the wide portion of the stepped-opening 10224 such that the locking member or detent 10212 disengages from the recess 10210a, 10210b, 10210c.

After the connecting member 10026 is inserted into the yokes 10022, the caps 10024 are positioned and pre-locked within the yokes 10022. There are a number of ways to seat and pre-lock the caps 10024. Seating the caps 10024 can vary in difficulty, depending on the patient's spinal structure, the number of caps, and the order with which the caps are seated. In one preferred embodiment, a cap inserter 10230 is used to position and pre-lock the cap 10024. The cap 10024 locks the connecting member 10026 into position. The cap 10024 can be configured in a number of positions. In one embodiment, the pre-lock configuration rotates the cap 10024 such that the cap 10024 is within the yoke 10022, but the connecting member 10026 can be axially moved relative to the yoke 10022. In one form, the pre-lock is about 45 degrees of rotation between the cap 10024 and the yoke 10022. The cap inserter 10230 may be limited to 45 degrees of rotation by a set of pins 10248 that engage a counter torque tube 10352 described herein. The final lock configurations of the cap 10024 position the cap 10024 within the yoke and prevent the connecting member 10026 from moving relative to the yoke 10022.

Figure 76:
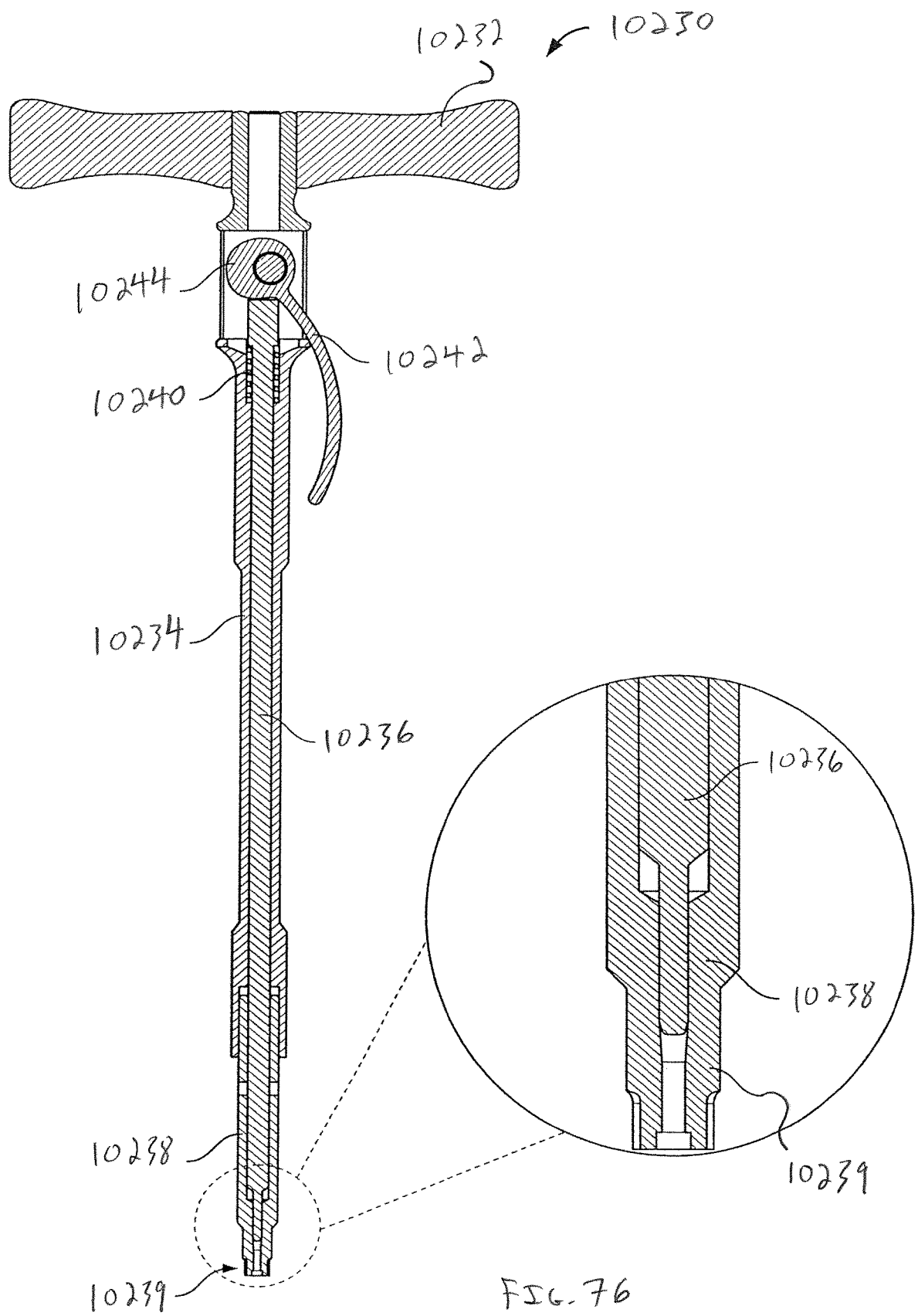
FIG. 76 is a detailed cross-sectional view of the cap inserter of FIG. 73.
Figure 77:
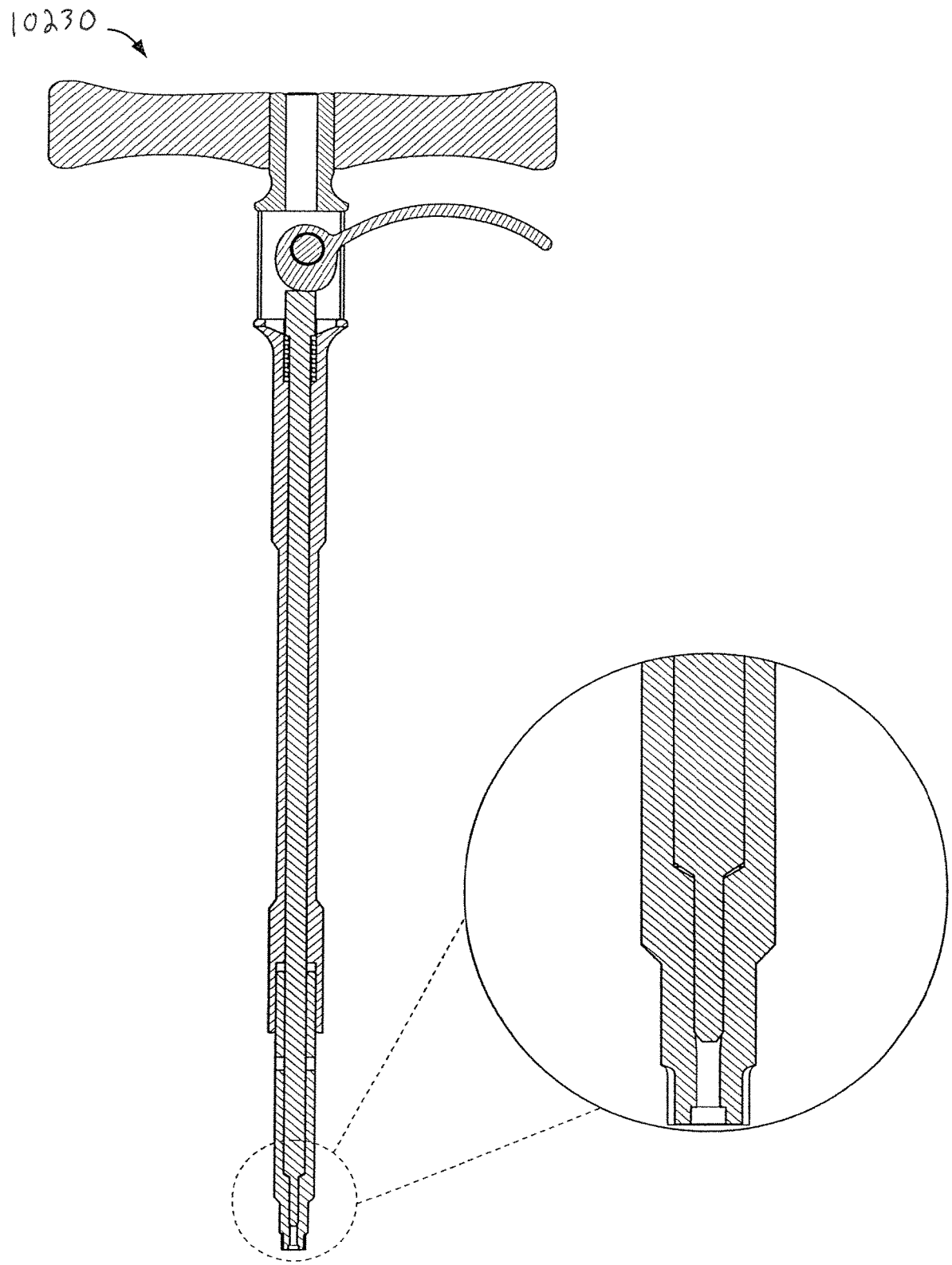
FIG. 77 is a detailed cross-sectional view of the cap inserter of FIG. 73 having the lever in the raised position.
Figure 78:
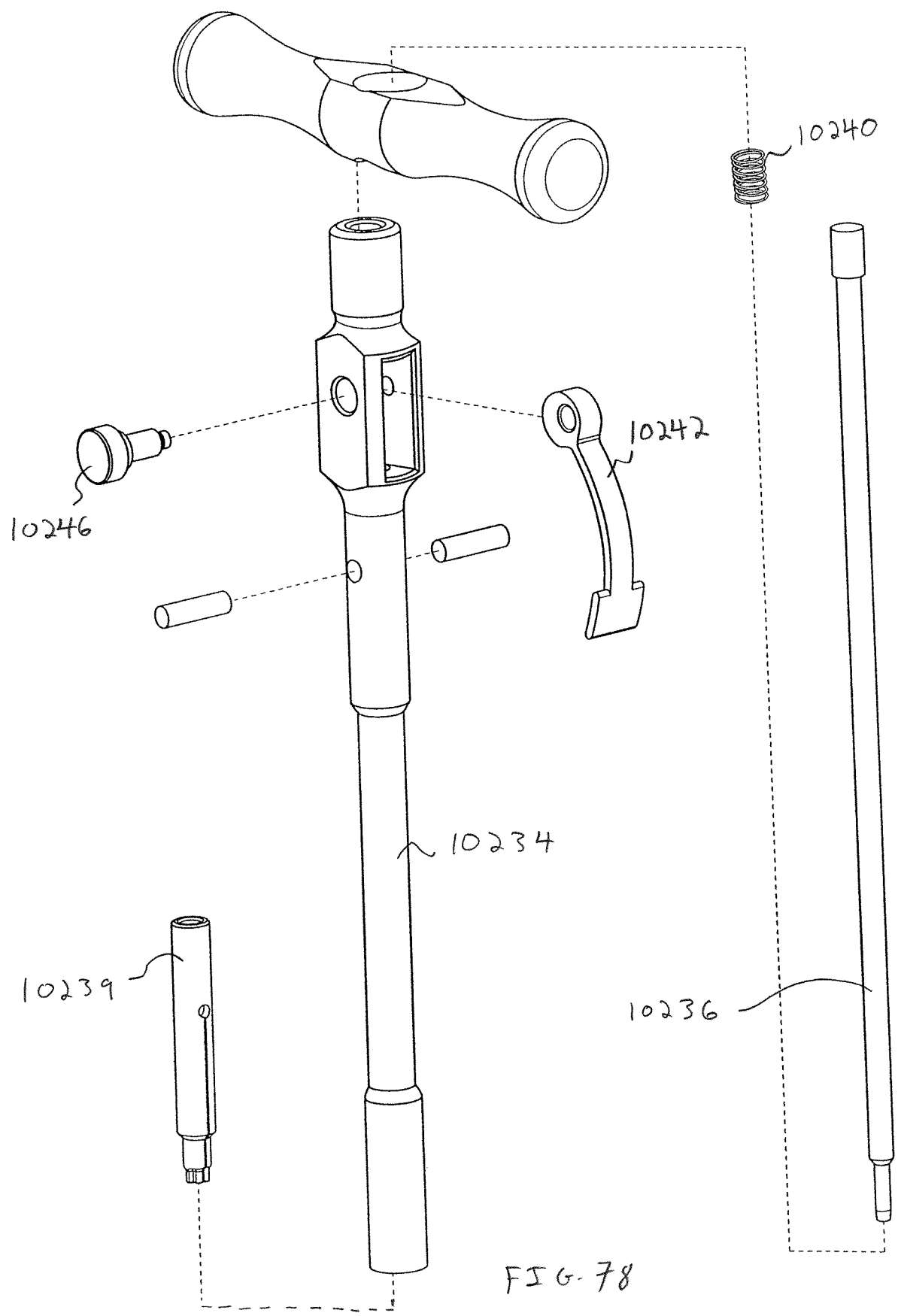
FIG. 78 is an exploded view of the cap inserter of FIG. 73, as configured in accordance with the various embodiments of the invention.
Figure 79:
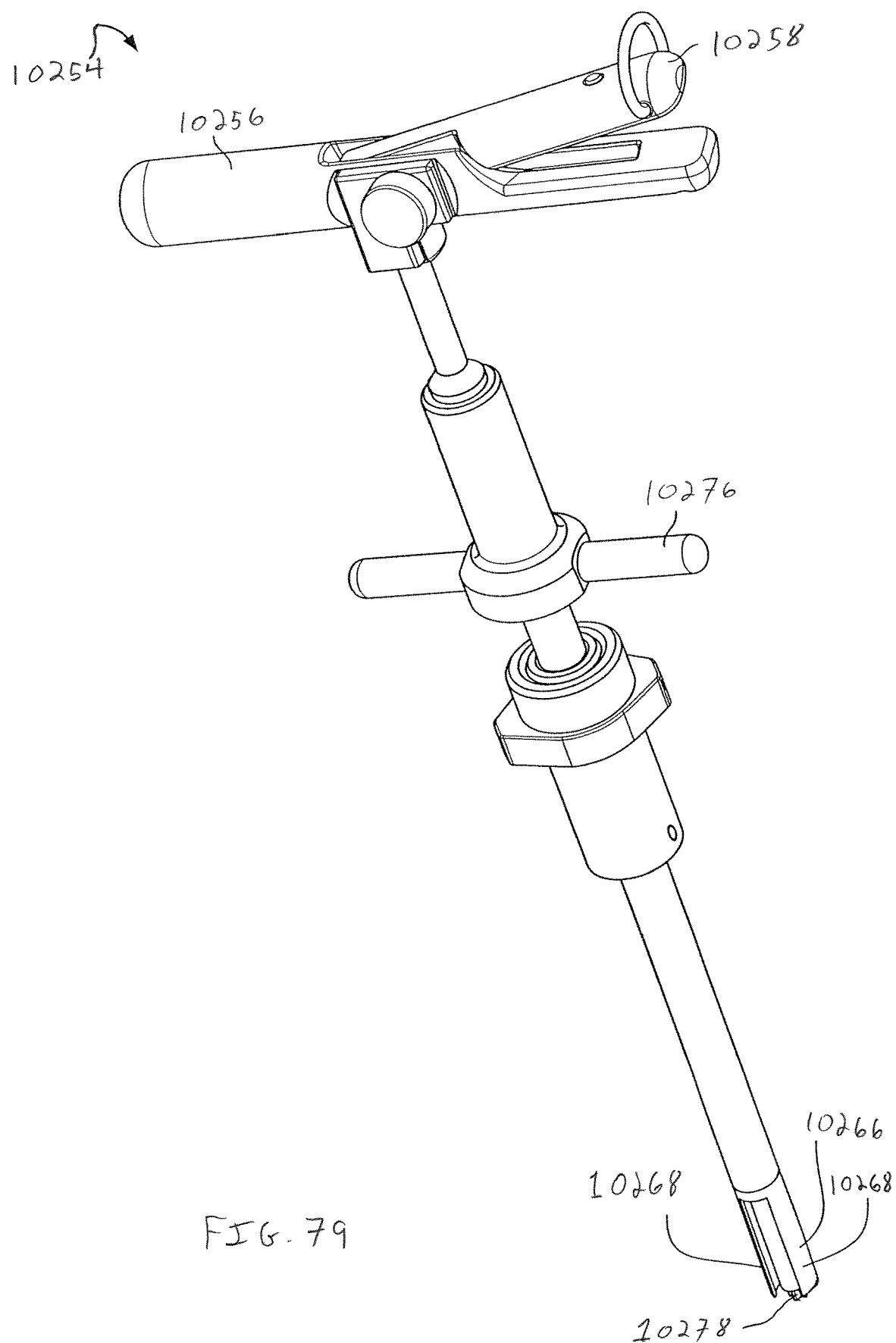
FIG. 79 is a perspective view of a rod persuader.

The cap inserter 10230 includes a handle 10232, a shaft body 10234, cap inserter rod 10236, shaft tip 10238, spring 10240, lever 10242 with camming mechanism 10244, thumb screw 10246 and grip rods 10248. As shown in FIG. 76, the cap inserter rod 10236 is housed within the shaft body 10234 and the shaft tip 10238 is attached to an end of the shaft body 10234. The spring 10240 biases the inserter rod 10236 to an upward position. When the lever 10242 is rotated up, the camming mechanism 10244 pushes the cap inserter rod 10236 down such that an end 10239 of the shaft tip 10238 is splayed outward. The shaft tip 10238 includes split star portions 10252. The star shape prevents the cap inserter 10230 from rotating relative to the cap 10024. Thus, when the cap inserter 10230 and the cap 10024 are engaged with one another, the movement of the cap inserter 10230 is transferred to the cap 10024. When the inserter rod 10236 splays the split star portions 10252, the shaft tip 10238 engages a star portion of the cap 10024. Therefore, the cap 10024 is secured to the cap inserter 10230. The cap inserter 10230 with the secured cap 10024 is fed down the manipulator 10098. After the cap 10024 is positioned within the yoke 10022, the cap inserter 10230 is rotated 45 degrees to position the cap 10024 in the pre-lock position.

The cap inserter 10230 can be disassembled for cleaning. To assemble the inserter 10230, the spring 10240 is placed around the inserter rod 10236 and the inserter rod 10236 is fed down the shaft body 10234. The shaft tip 10239 is press fit, threadingly connected, welded, or otherwise attached to the shaft body 10234. The lever 10242 is secured into position by the thumb screw 10246, which is positioned within an opening within the lever 10242. The thumb screw 10246 may be threaded or otherwise connected to the shaft body 10234.

In another form, a rod persuader 10254 can be used to position and pre-lock the cap 10024. The persuader is typically used to attach subsequent caps 10024 to the respective yokes 10022 and seat the connecting member 10026 after the initial cap 10024 has been positioned. The rod persuader 10254 includes an upper handle 10256 with a lever 10258, and a draw shaft 10260 inside a drive shaft 10262, both of which are inside a cannula 10264 and an outer sleeve 10266. The rod persuader 10254 is operated in a number of steps.

Figure 80:
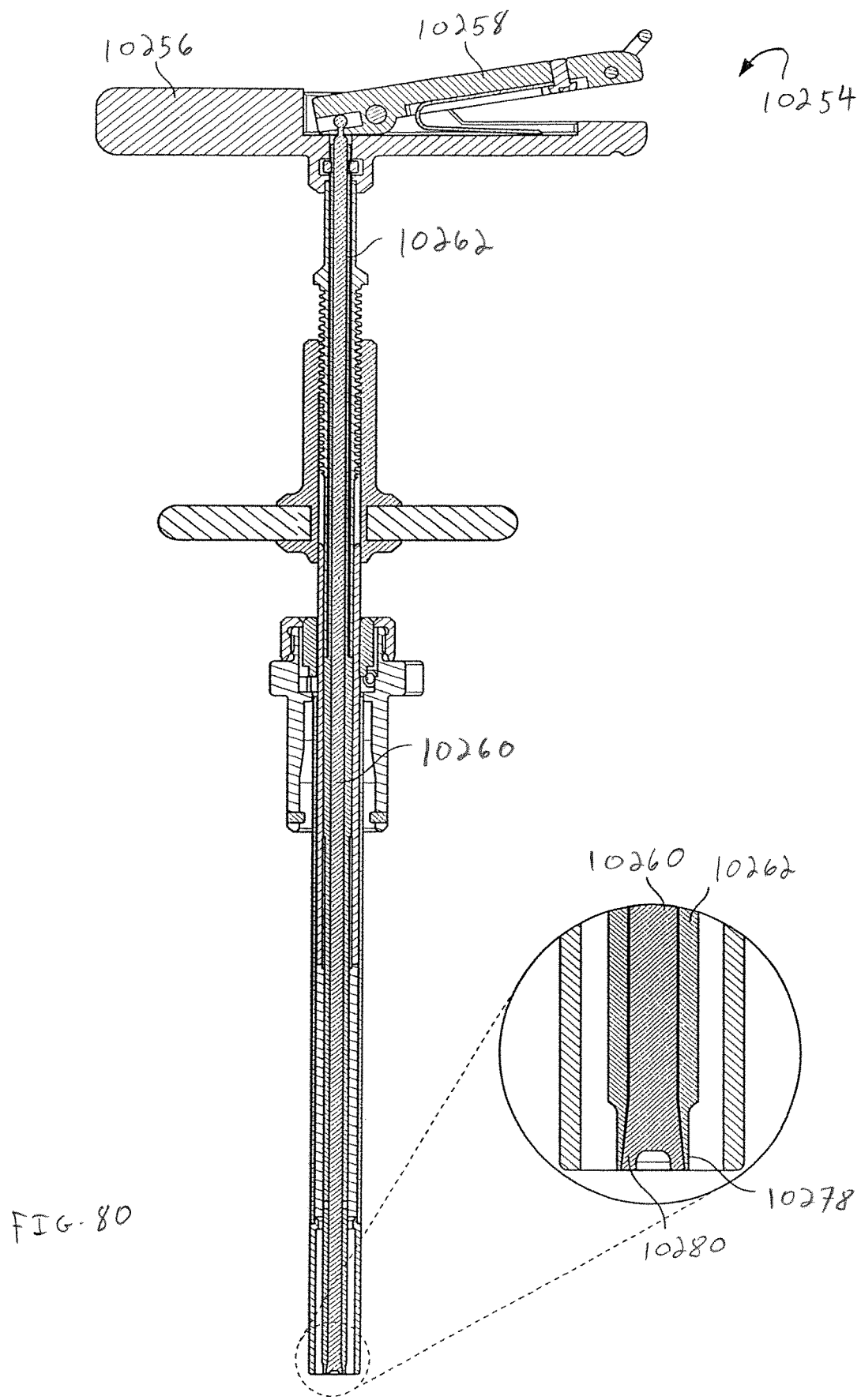
FIG. 80 is a detailed cross-sectional view of the rod persuader of FIG. 79 having a lever raised.
Figure 81:
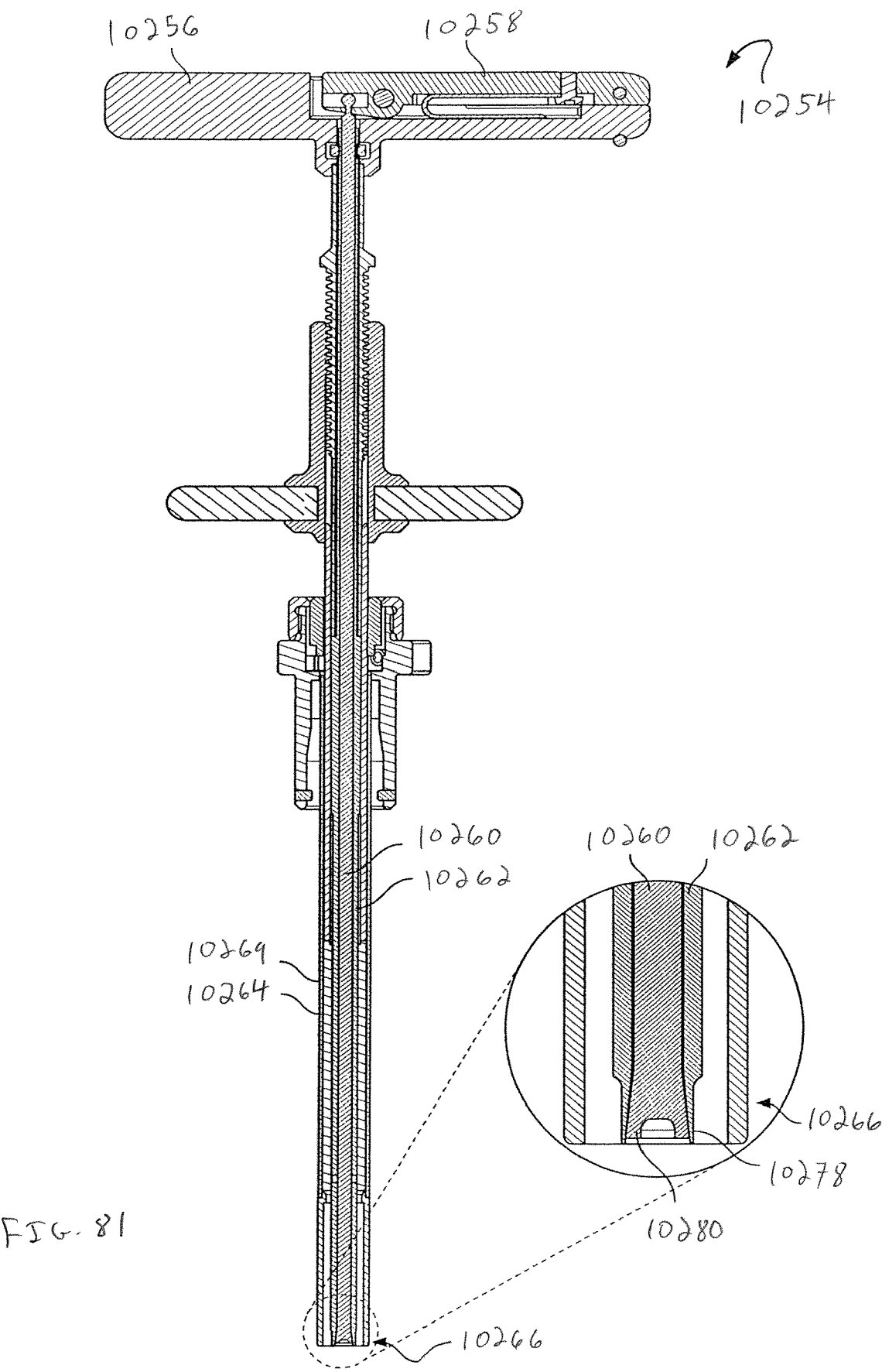
FIG. 81 is a detailed cross-sectional view of the rod persuader of FIG. 79 having the lever lowered and locked, as configured in accordance with the various embodiments of the invention.

First, the drive shaft 10262 is fully extended, such that a portion of the drive shaft 10262 is extended from a tip of the outer sleeve 10266 of the cannula 10264 so that the cap 10024 can be attached to the rod persuader 10254. The tip of the outer sleeve 10266 is comprised of two prongs 10268. The drive shaft 10262 is driven downward by rotating the upper handle 10256. As can be seen in the cross-sectional FIGS. 80-82, by rotating the upper handle 10256, a plurality of threads 10270 on a sleeve 10262' located around the drive shaft 10262 engage threads 10272 on the drive assembly 10274. The drive assembly 10274 includes the lower handle 10276.

After the drive shaft 10262 is extended, the cap 10024 must be attached to the rod persuader 10254. Therefore, with the drive shaft 10262 in the extended position, a star tip 10278 of the drive shaft 10262 can be splayed to engage the cap 10024. The draw shaft 10260, inside the drive shaft 10262, has an expanded end 10280 opposite a joint end 10282. By raising the draw shaft 10260, the two portions of the star tip 10278 are splayed when the sloped inner surface of the drive shaft 10262 is forced outward by the expanded end 10280. The joint end 10282 includes a ball 10290 and a reduced diameter portion 10292. To move the draw shaft 10260, the lever 10258 is lowered. The lever 10258 is secured into the lowered position by rotating a ring lock 10284 down around upper handle 10256. The joint 10282 pivots about the thumb screw 10288 such that when the lever 10258 is lowered, the joint end 10282 raises to pull the draw shaft 10262 upward. The lever 10258 is biased to the raised position by a leaf spring 10286.

Figure 82:
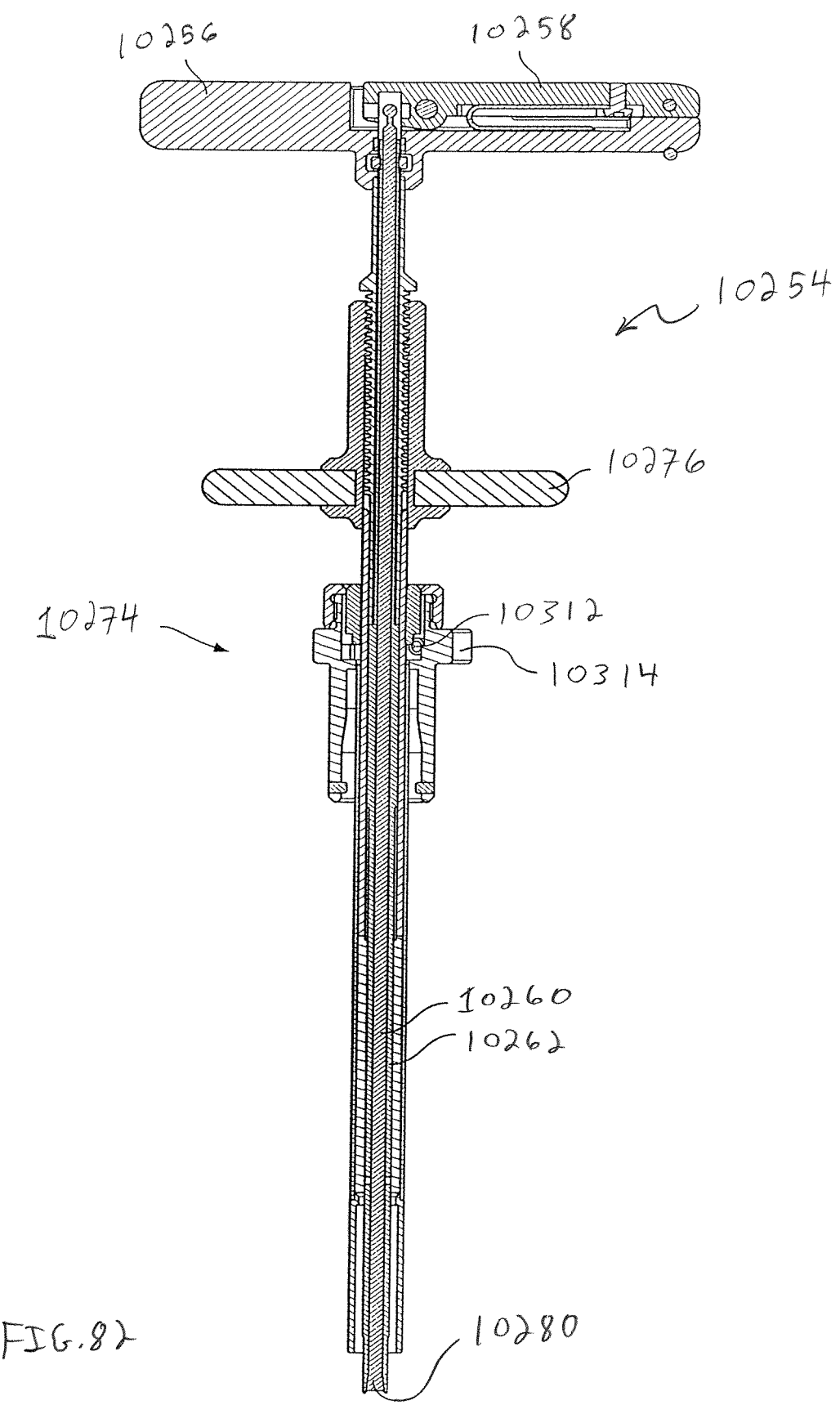
FIG. 82 is a cross-sectional view of the rod persuader of FIG. 79 having a drive shaft and a draw shaft in an extended position, as configured in accordance with the various embodiments of the invention.

The thumb screw 10288 also attaches the lever 10258 to the upper handle 10256. The thumb screw 10288 passes through an opening 10294 in a plate 10296. The plate 10296 fits in an angled cut-out in the handle 10256. When assembled, the thumb screw 10288 also passes through openings 10298, 10300 and an opening 10302 in the lever 10258. The plate 10296 includes a projection 10304 that passes through an opening 10306 in handle 10256 and engages a reduced diameter portion 10308 of the drive shaft 10262. By engaging the reduced diameter portion, the movement of the handle 10256 translates to the drive shaft 10262. As shown in FIG. 82, the drive shaft 10262 can be rotated down such that the tip 10278 is exposed at the end of the cannula 10264. The rotation of the drive shaft 10262 is limited by a shelf 10310 located on the outer sleeve 10265 that engages the drive assembly 10274.

After the cap 10024 is attached to the persuader 10254, the persuader 10254 is advanced down the manipulator 10098. The cap 10024 is sometimes backed up into the tips 10266, by rotation of the upper handle 10256, for insertion into the manipulator 10098. The upper handle 10256 is rotated until the cap 10024 is within the yoke 10022. Then, the lower handle 10276 can be rotated 45 degrees to move the cap into the pre-lock position. Rotating the lower handle 10276 rotates the drive shaft 10262 and star tip 10278. In addition, after the upper handle 10256 has been rotated such that the threads 10270 and 10272 are completely engaged, continuing to rotate the upper handle 10256 may also produce the required rotation of the drive shaft 10262.

Figure 83:
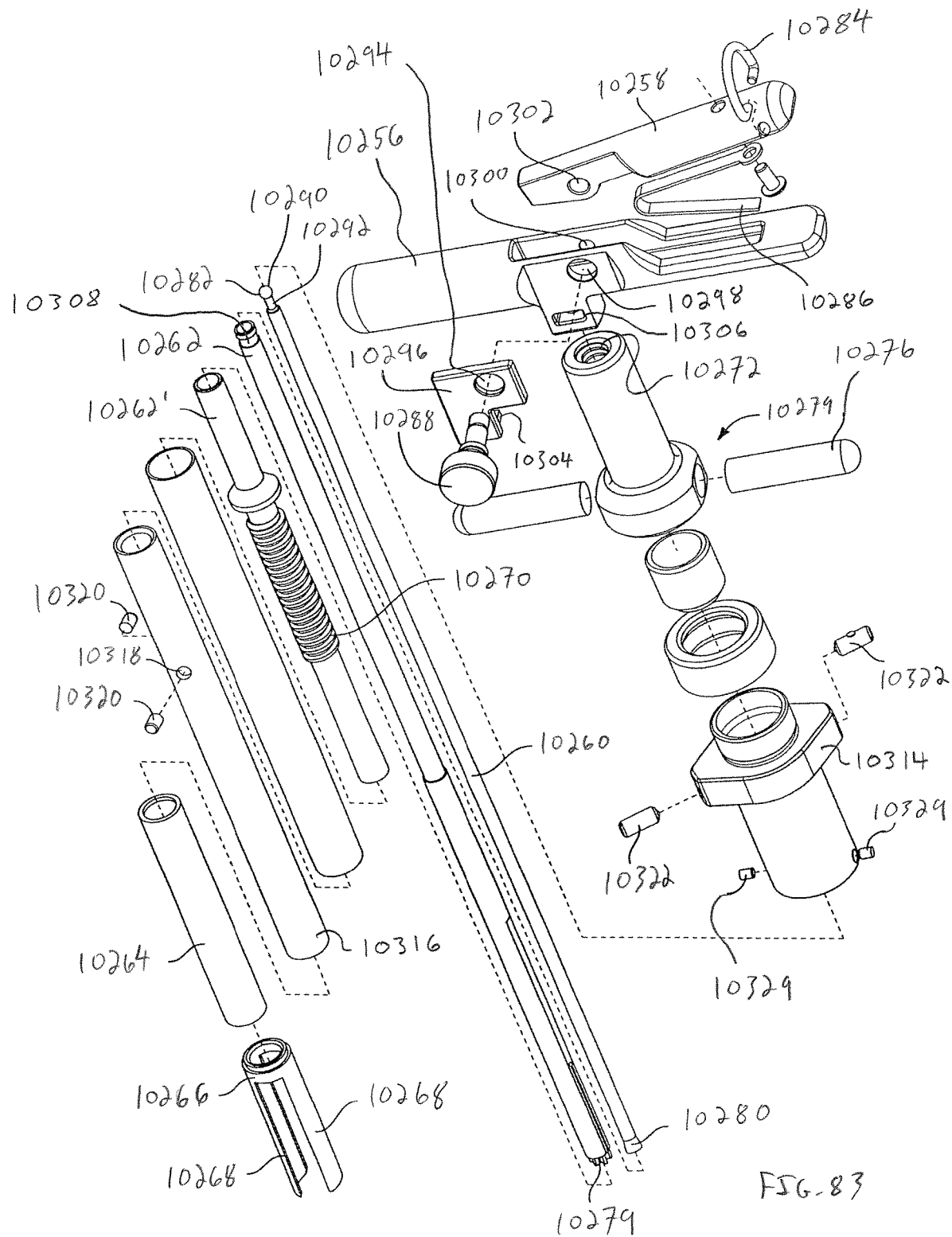
FIG. 83 is an exploded view of the rod persuader of FIG. 79, as configured in accordance with the various embodiments of the invention.
Figure 84:
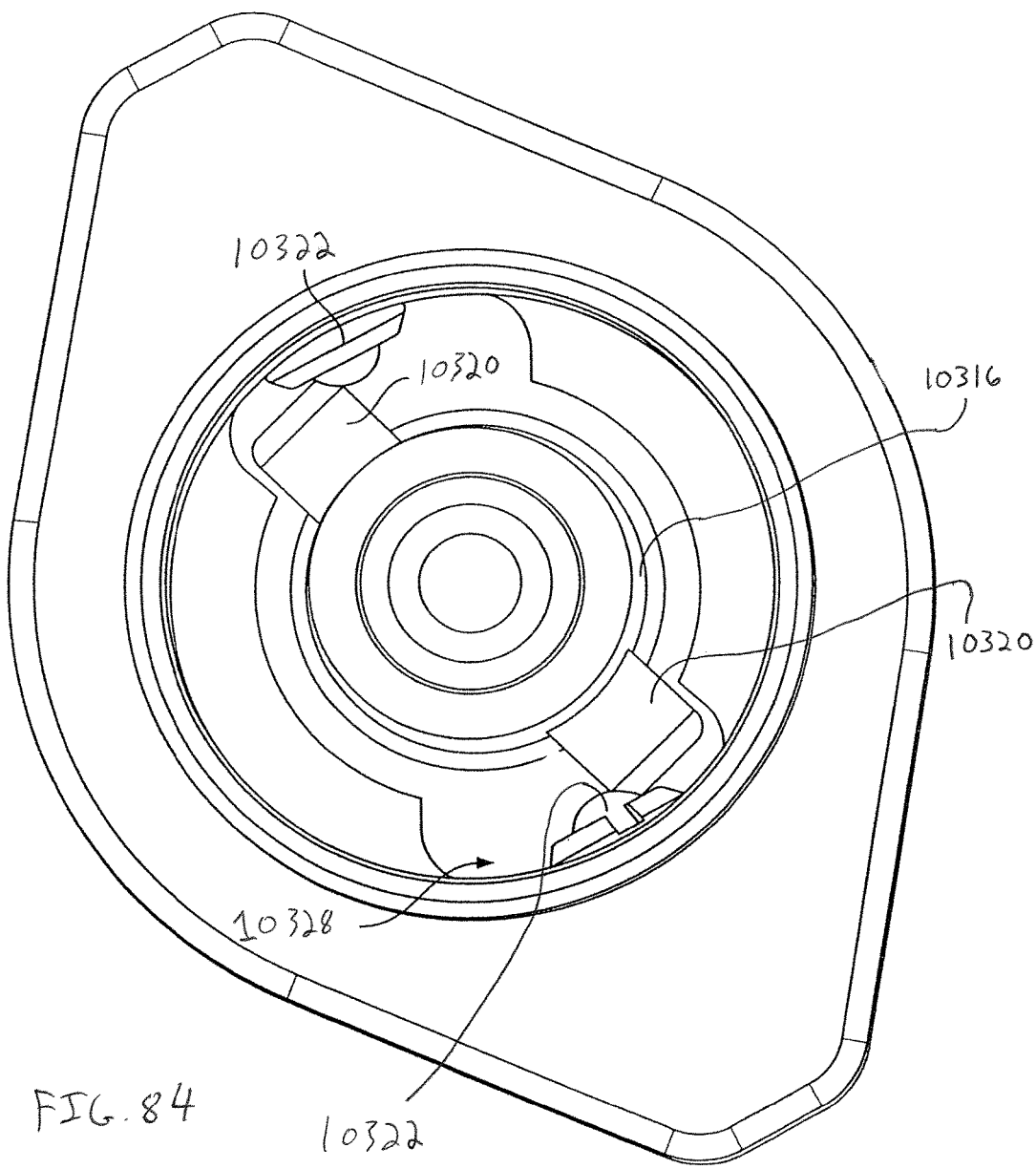
FIG. 84 is an enlarged view of a portion of the rod persuader of FIG. 79, as configured in accordance with the various embodiments of the invention.

The rod persuader 10254 includes structure to help rotate the cap 10024 to the 45 degrees pre-lock position. Below the drive assembly 10274, the persuader 10254 includes a ball and detent mechanism 10312 for walking the cap 10024 into the yoke 10022. The ball and detent mechanism 10312 is located in housing 10314 and is secured relative to the lower handle 10276. A drive tube 10316 surrounds a portion of the drive shaft 10262. The drive tube 10316 includes openings 10318 that house at least one pin 10320 that engage at least one plunger 10322 located within openings 10324 in the housing 10314. The housing 10314 also includes an aperture 10326 with a groove 10328 within which the pins 10320 can move until abutting internal walls thereof, which function as a stop. As stated above, rotating either handle 10256, 10276 can rotate the star tip 10278 and also rotates drive tube 10316 and the pins 10320. The ball and detent mechanism 10312 provides the surgeon with tactile feedback such that the surgeon can feel when the drive tube 10316 and the star tip 10278 have been rotated 45 degrees. As suggested earlier, 45 degrees may be the pre-lock position for the caps 10024. The housing 10314 also includes a set of pins 10329 that can mate with the yoke manipulators 10098 connecting structure, shown as a bayonet connection in FIG. 83.

After the cap 10024 is configured in the pre-lock position, the cap 10024 is released from the persuader 10254 by disengaging the ring lock 10284 such that lever 10258 raises and thus, the star tip 10278 disengages from the cap 10024. Then, the rod persuader 10254 may be removed from the system.

Figure 85:
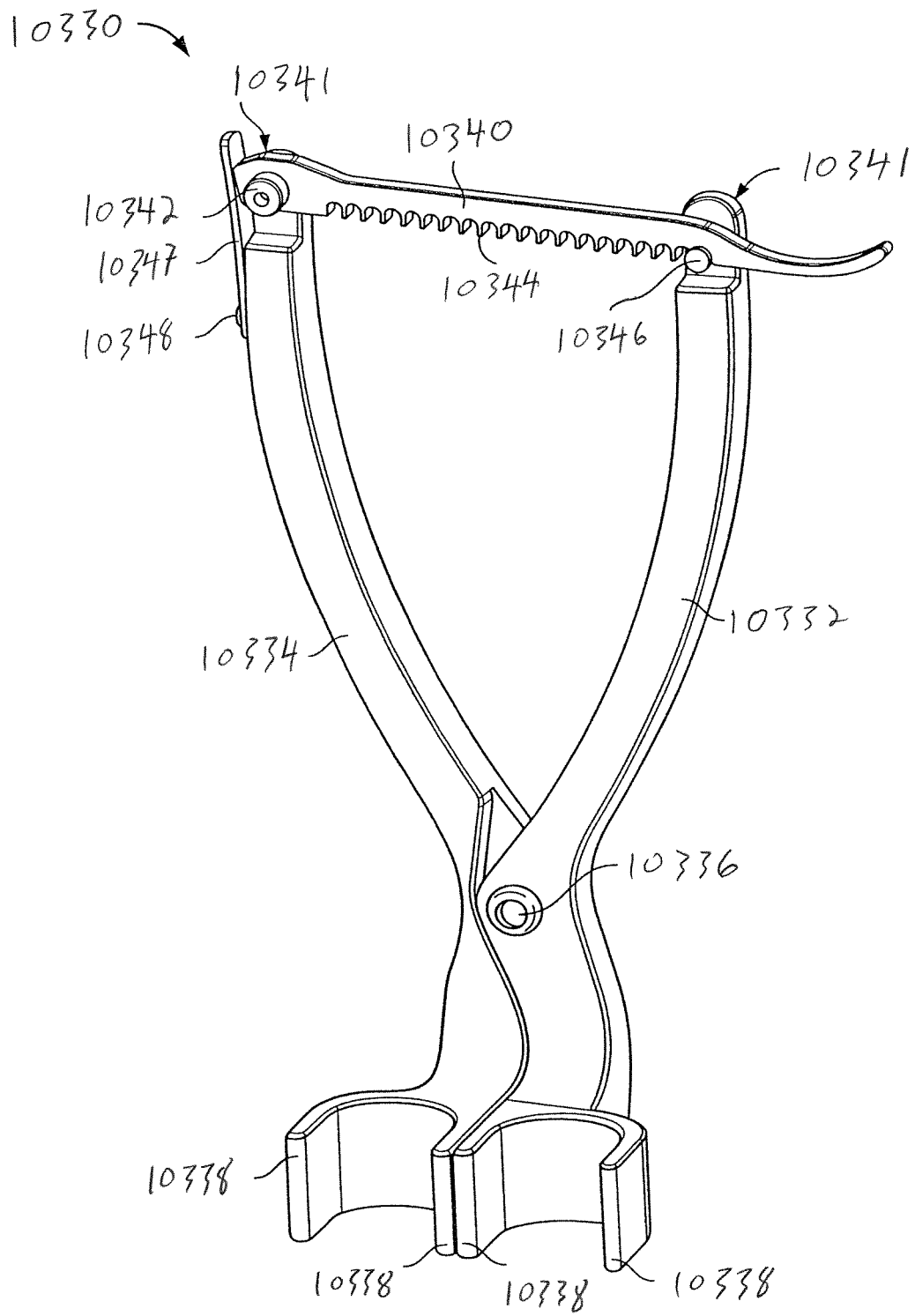
FIG. 85 is a perspective view of a compression-distraction tool, as configured in accordance with the various embodiments of the invention.

Before the caps 10024 are moved to the final-lock position, a compression-distraction tool 10330 can be used to adjust the distance between the vertebrae. Before the compression-distraction tool 10330 is employed, the surgeon may wish to slide a counter torque tube 10352 down the yoke manipulators 10098 to facilitate a more secure engagement between the compression-distraction tool 10330 and the bone anchors 10020. As shown in FIG. 85, the compression-distraction tool 10330 includes two handles 10332, 10334, pivotally connected together by a screw 10336. Each of the handles has a set of engagement arms 10338 that are placed around the counter torque tube 10352 or yoke manipulators 10098. The engagement arms 10338 have flat surfaces that engage the flats 10376 on the counter torque tube 10352. Opposite the engagement arms 10338, a ratchet end 10341 of the compression-distraction tool 10330 includes a rack member 10340 that is pivotally attached to one handle by a screw 10342. The rack member 10340 includes spaced teeth 10344 that engage a projection or latch pin 10346 on the handle without the screw 10342. The compression-distraction tool 10330 further includes a spring 10347 attached to one handle by a screw 10348. The surgeon can slide the engagement arms 10338 around the counter torque tube 10352 or the yoke manipulators 10098. The surgeon can move the handles 10332, 10334 apart thereby bringing the counter torque tubes 10352 closer together or the handles 10332, 10334 can be spread farther apart, thereby moving the counter torque tube 10352 closer together. By moving the yoke manipulators 10098, the vertebras are moved closer or farther apart. Such movement is facilitated by having the pivot point of the compression-distraction tool 10330 correlate with the radius of curvature of the connecting member 10026.

After the final position of the bone anchors 10020 are set with respect to the connecting member 10024, the caps 10024 may be moved to the final-lock position. A number of tools are available to set the caps 10024 in the final-lock position. In one embodiment, the final-lock configuration for the cap 10024 is generally just over 100 degrees in total. Therefore, the second stage of the locking rotates the cap 10204 an additional 55 degrees from the pre-lock position. A final locker 10350 is often used along with a counter torque tube 10352. The counter torque tube 10352 has connecting structure 10378 that limits how much the final locker 10350 can rotate. The dowels 10366 of the final locker 10350 can move within the connecting structure 10378, but the structure 10378 functions as a stop to prevent over-rotation and over-tightening of the cap 10024. However, the rod persuader 10254 or cap inserter 10230 may also be used.

Figure 86:
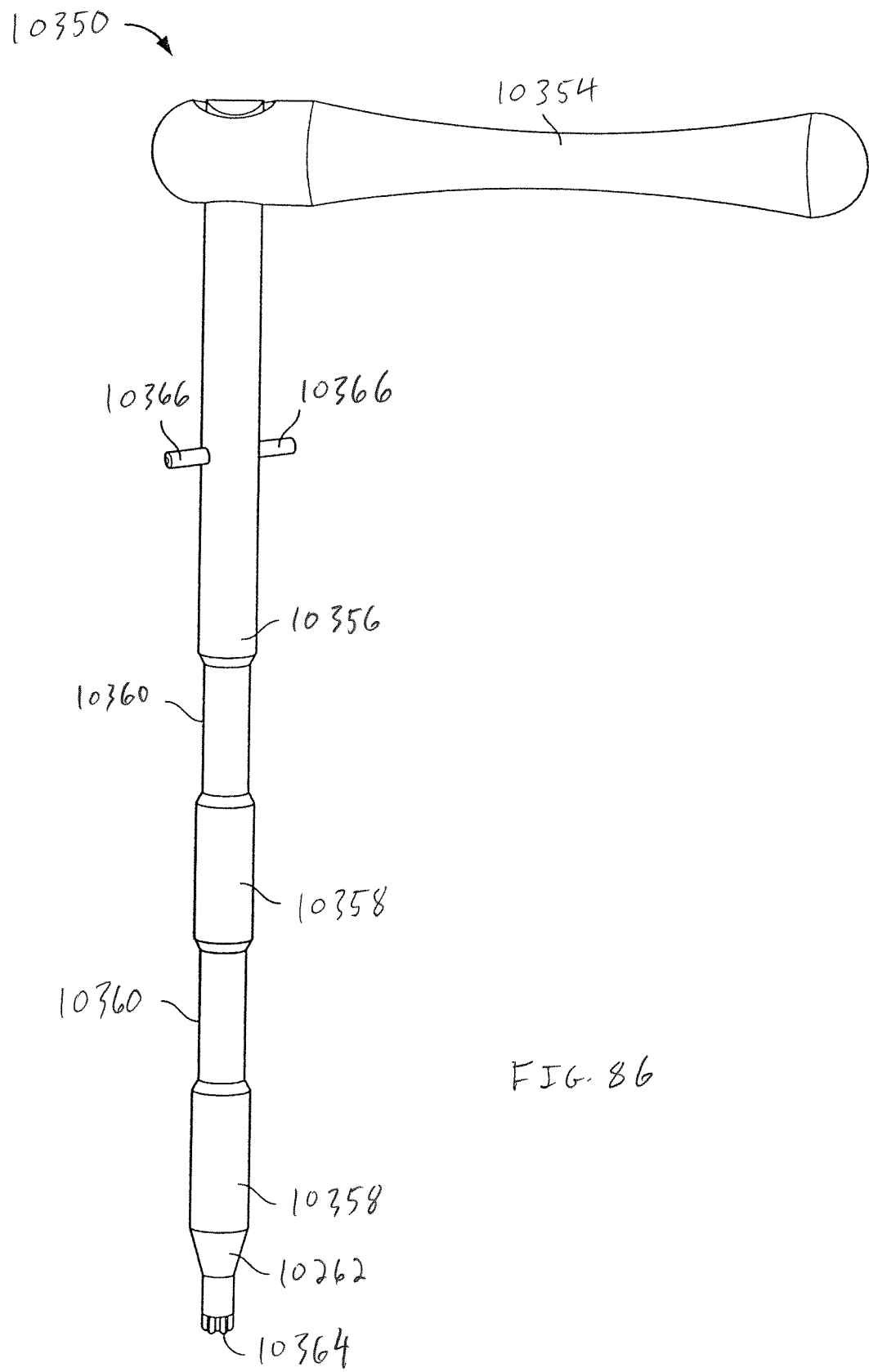
FIG. 86 is a front elevation view of a final locking instrument, as configured in accordance with the various embodiments of the invention.
Figure 87:
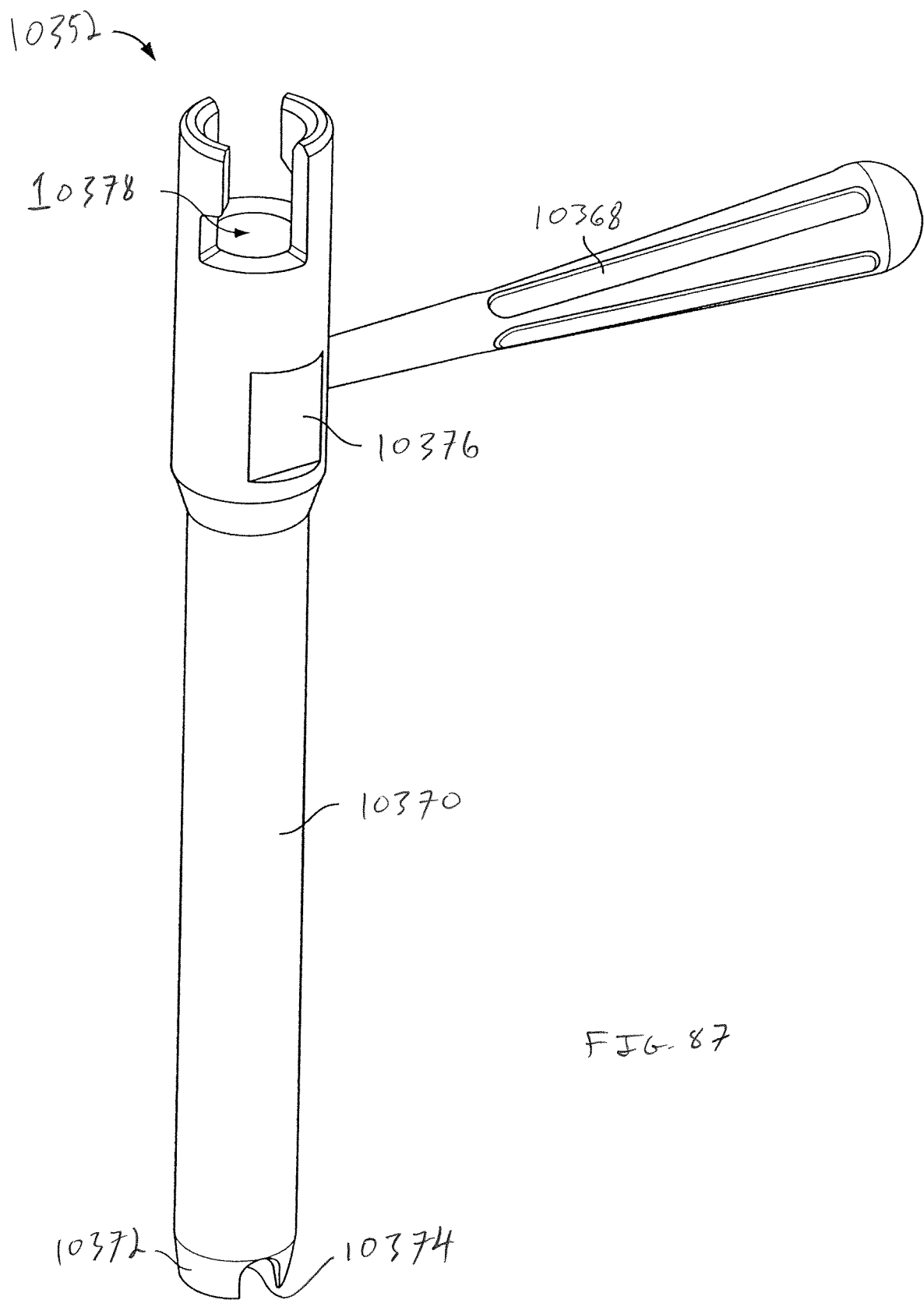
FIG. 87 is a perspective view of a counter torque tube, as configured in accordance with the various embodiments of the invention.
Figure 88:
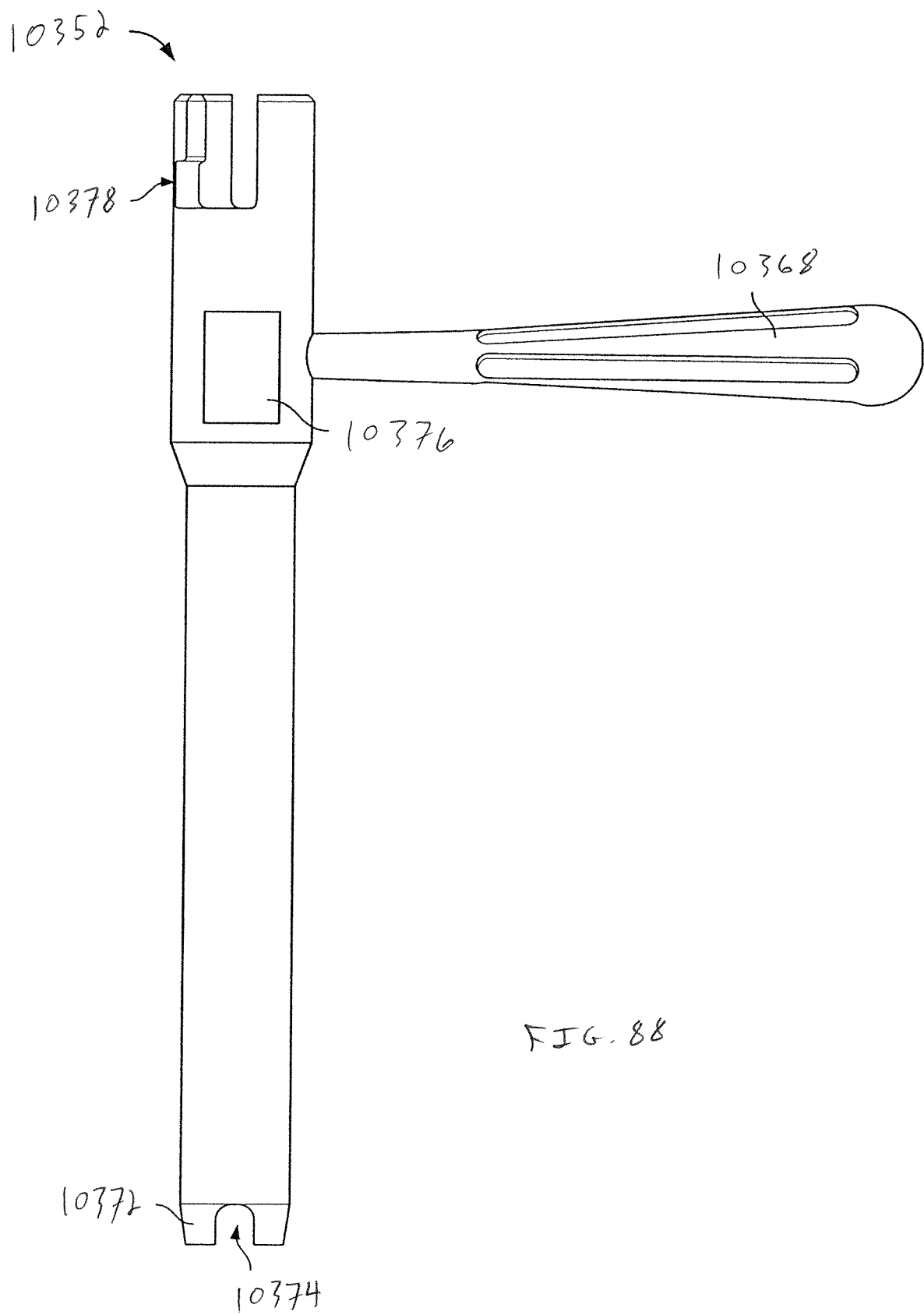
FIG. 88 is a side elevation view of the counter torque tube of FIG. 87, as configured in accordance with the various embodiments of the invention.

As shown in FIG. 86, the final locker 10350 includes a handle 10354, a shaft 10356, centering portions 10358, cutout portions 10360, tapered portions 10362, and an engagement end 10364. The engagement end 10364 is sized to fit within the cap 10024 and engage the star shape to rotate the cap 10024 into the final-lock position. The final locker 10350 also includes pins 10366. The centering portions 10358 help guide the final locker 10350 into the cap 10024, while the cutout portions 10360 limit the amount of friction experience between the final locker 10350 and the counter torque tube 10352. To ensure that the cap 10024 can be rotated without the yoke 10022 also rotating, the counter torque tube 10352 can be placed within the docking port 10064. The counter torque tube 10352 includes a handle 10368, a sleeve 10370, tapered portion 10372, curved cutouts 10374, flats 10376, and connecting structure 10378. In addition, the counter torque tube 10352 includes dowel pins 10380 located on the inside of the sleeve 10370. The dowel pins 10380 can be used to orient the counter torque tube 10352 with the yoke manipulator 10098 that it slides around.

Figure 90:
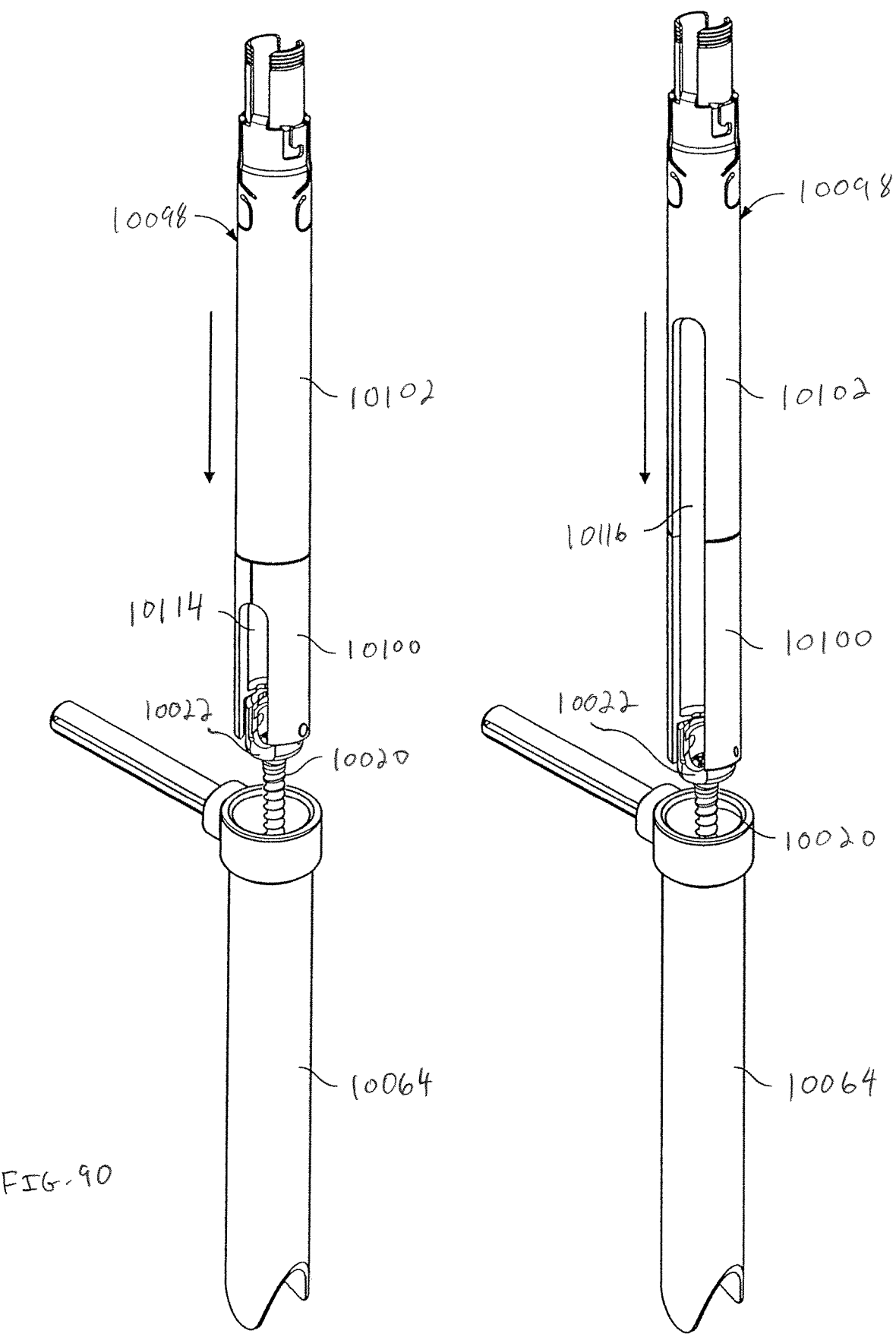
FIG. 90 is a perspective view of two yoke manipulators, two bone anchors with yokes mated therewith, and two docking ports.
Figure 91:
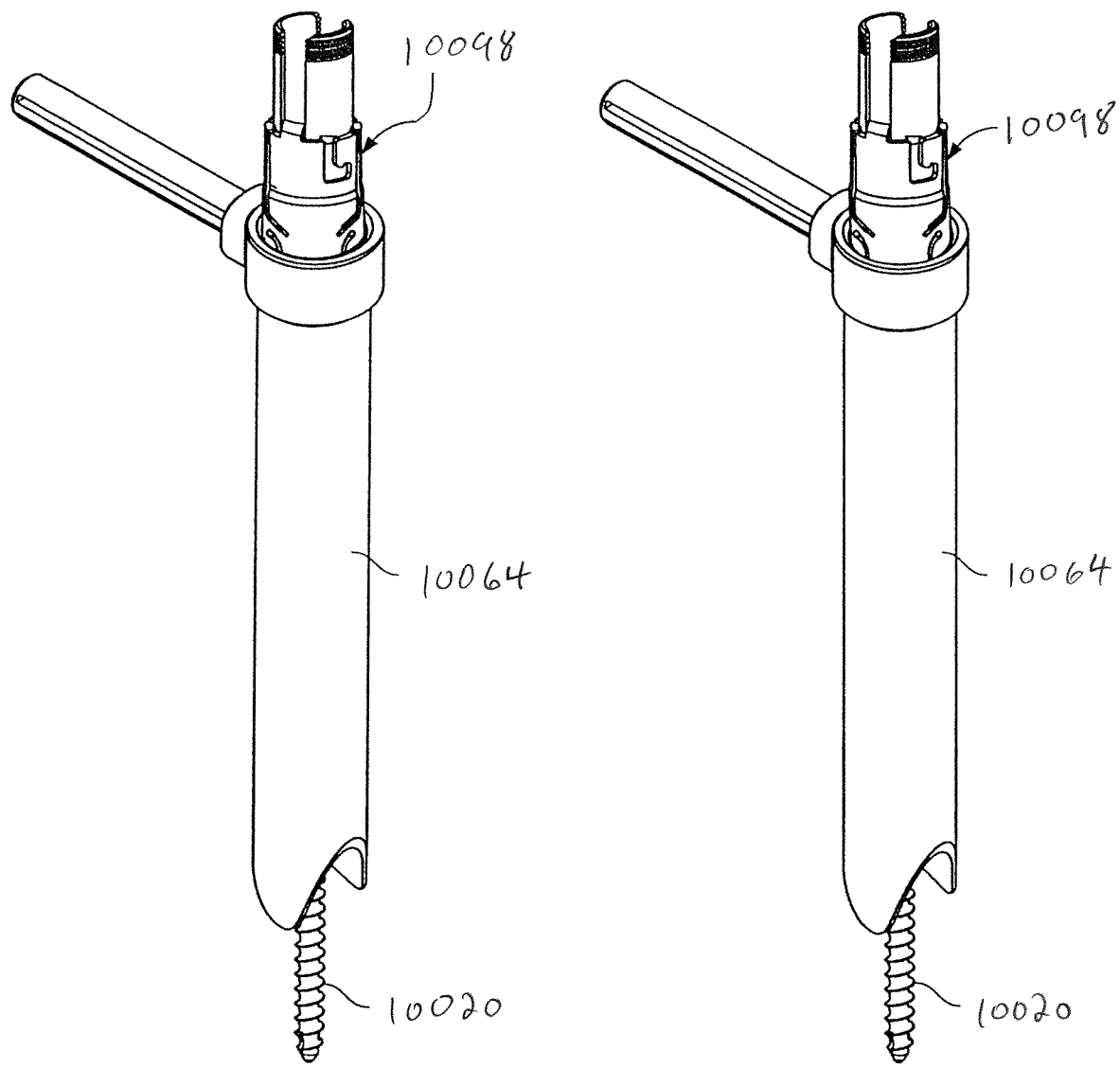
FIG. 91 is a perspective view of two yoke manipulators, two bone anchors with yokes mated therewith, and two docking ports after the bone anchors have been secured to the bone.
Figure 92:
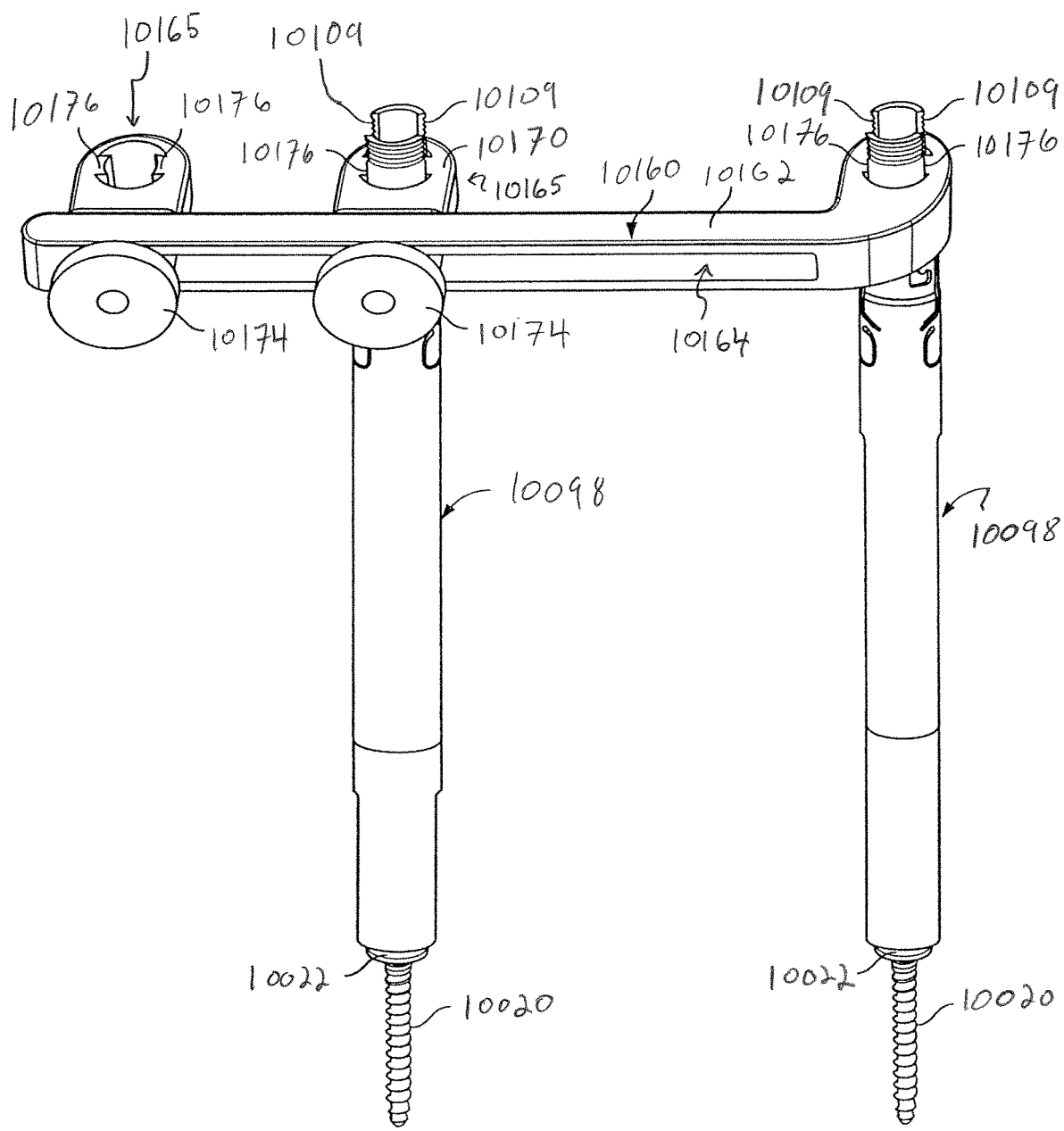
FIG. 92 is a perspective view of two yoke manipulators with the yokes and bone anchors mated therewith, and a guide bar.
Figure 93:
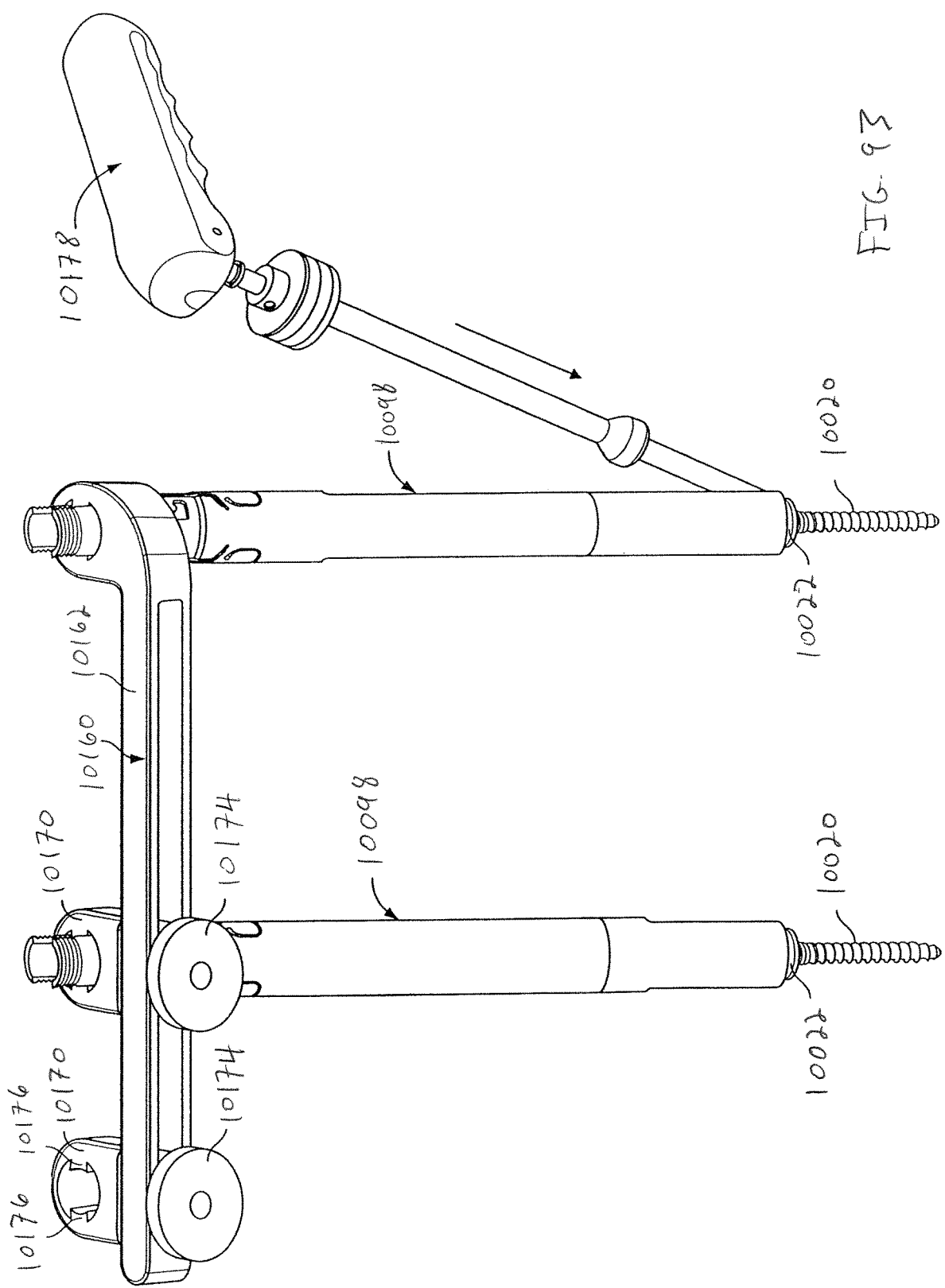
FIG. 93 is a perspective view of two yoke manipulators with the yokes and bone anchors mated therewith, a guide bar, and a rod inserter.
Figure 94:
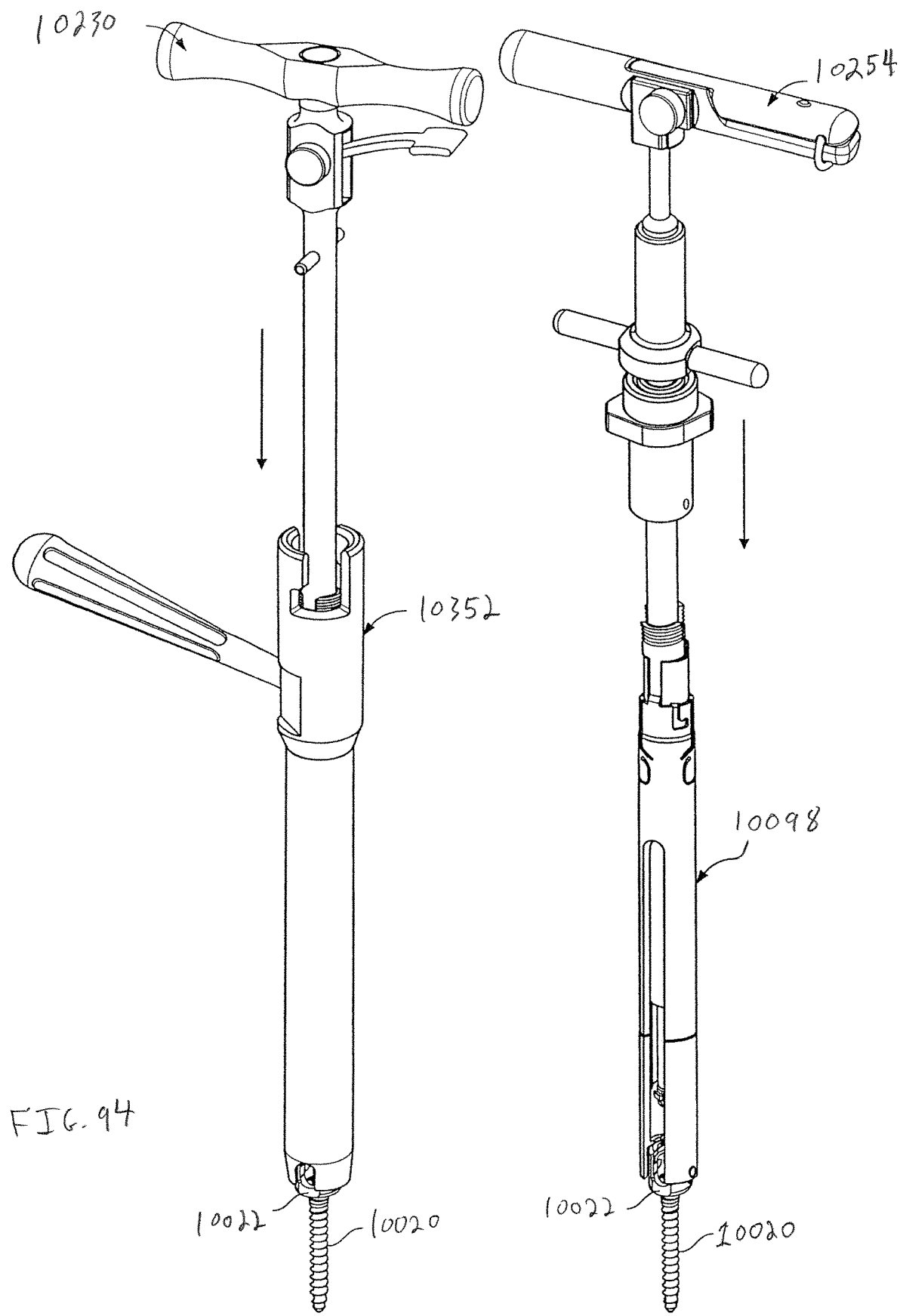
FIG. 94 is a perspective view of two yoke manipulators with the yokes and bone anchors mated therewith, a guide bar, a cap inserter and a rod persuader.
Figure 95:
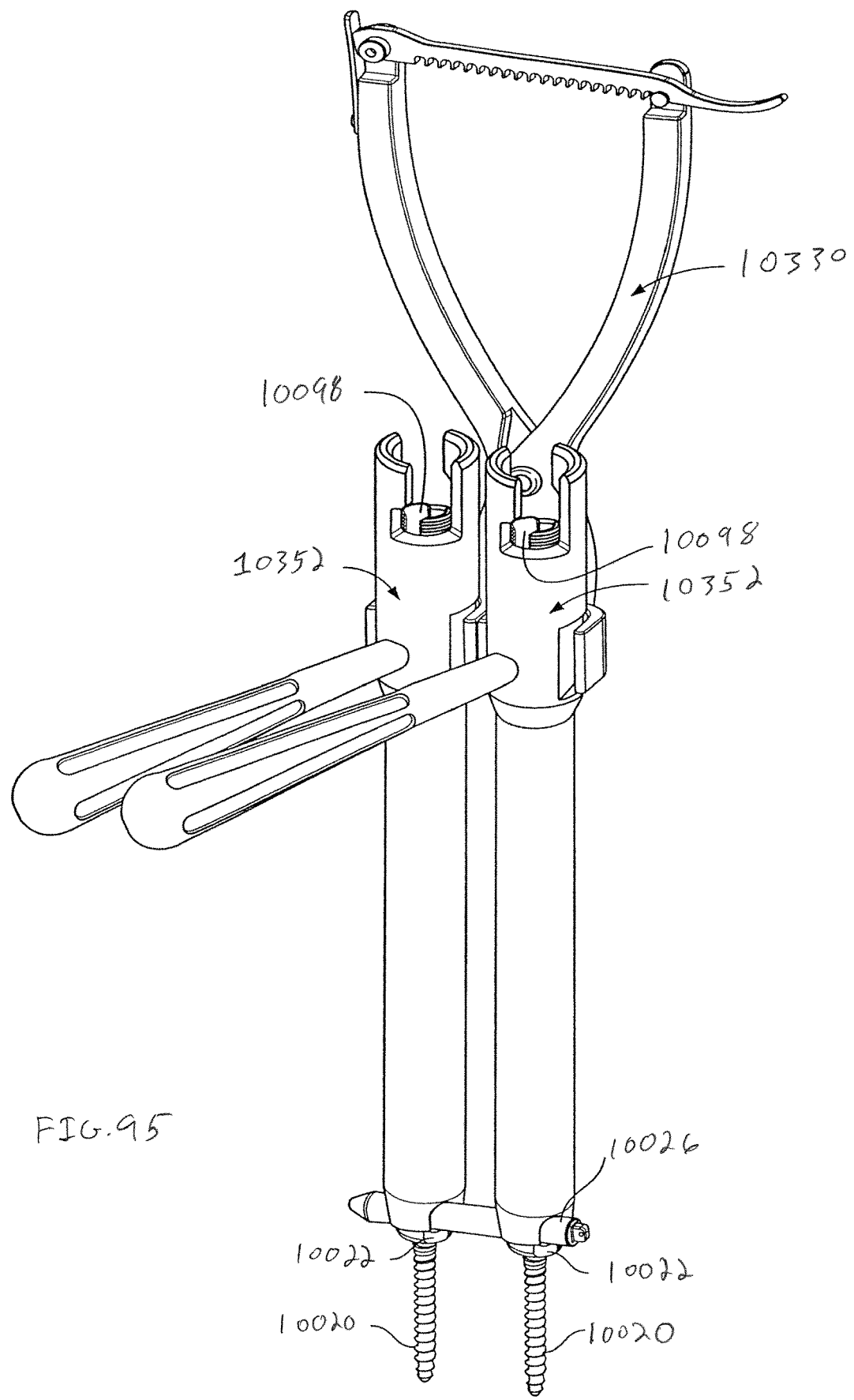
FIG. 95 is a perspective view of two yoke manipulators with the yokes and bone anchors mated therewith, two counter torque tubes, and a compression-distraction tool.

Demonstrative arrangements of the MIS system tools are depicted in FIGS. 90-96. As shown in FIG. 90, the yoke manipulators 10098 are placed within the docking ports 10064 having the bone anchors 10020 and the yokes 10022 attached thereto. To attach the yokes 10022 to the yoke manipulators 10098, an opening 10113 on the yoke 10022 is mated with the connecting structure 10124 of the inner sleeve 10100 of the yoke manipulator 10098. After the yoke 10022 and the inner sleeve 10100 are mated, the outer sleeve 10102 is slid down the inner sleeve 10100 and the two are mated together. Mating the two sleeves 10100, 10102 together secures the engagement between the inner sleeve 10100 and the yoke 10022. As shown in FIG. 91, the yoke manipulators 10098 are advanced through the docking port 10064 where the bone anchors 10020 are then rotated through the bone. After the bone anchors 10020 have been seated in the bone, the guide 10160 may be attached to the yoke manipulators 10098, to ease insertion of the connecting member 10026. As shown in FIG. 92, the projections 10176 of the slide body 10165 of the guide bar 10160 mate with a pair of slots 10109 on the second end 10108 of the yoke manipulators 10098. As discussed previously, the slide body 10165 can move within the horizontal slot 10164 such that the guide bar 10160 can accommodate differently sized patients and can also be moved during the subsequent compression or distraction stage. As shown in FIG. 93, the rod inserter 10178 is advanced down one manipulator 10098, preferably the longer slot manipulator 10098 if one is present. Then, the rod inserter 10178 is advanced through the stages such that the connecting member 10026 is seated within the yokes 10022. After the connecting member 10026 is seated within the yokes 10022, the caps 10024 are positioned within the yoke 10022. As discussed previously, the caps 10024 are delivered to the yokes 10022 by the cap inserter 10230 or rod persuader 10254. The rod persuader 10254 having a mechanical advantage such that the caps 10024 inserter second in time can be more easily seated. The caps 10024 are delivered to the yokes 10022 by splaying the insertion end of the tool and creating a secure engagement between the insertion tool and the cap 10024. After the caps 10024 are positioned within the yokes 10022, the caps 10024 are rotated to the pre-lock configuration. This allows the bone anchors 10020 and yokes 10022 to move relative to the connecting member 10026. After the caps are in the pre-lock position, the compression-distraction tool 10330 can be used to move the bone anchors 10020 together as shown in FIG. 95 or apart from one another. Finally, the final locking tool 10350 is used to move the caps 10024 from the pre-lock position to the final lock position. After the caps 10024 are in position, the tools can be removed from the system.

In one example of the procedure, the patient is placed in the prone position on an operating table. For operative fluoroscopy to be most successful, the table may be radiolucent. A guide wire can be placed using a Jamshidi needle and fluoroscopy equipment to establish the position and orientation of the guide wire on the pedicle. The Jamshidi needle is advanced slightly further than the planned length of the bone anchor 10020. If the bone resists, the Jamshidi needle may be driven into position by pushing on the handle and using a twisting motion. The shoulder of the tool will permit over-advancement of the tool into the bone. If the bone completely resists the attempts to manually penetrate the bone, the Jamshidi can be used as a drill guide. After penetrating the bone, the guide wire may be placed into the bore of the Jamshidi needle and gently tapped into the bone. The Jamshidi needle is removed and the guide wire is left in position.

Subsequent to the positioning of the guide wire, the tissue surrounding the guide wire is dilated. The dilation tools can be selected from various options. For example, if the series dilators are used, four dilators are used to create a path through the fascia and muscle to establish a working portal. The smallest diameter tube enters the tissue first, followed by increasingly larger diameters, until all four tubes are employed. Preferably the tubes are pushed down far enough for each of the tips to contact bone.

After the tissue is stretched, the docking sleeve or port 10064 can be positioned around in situ tissue dilators with the acute angle of the tip facing the spinous process, and the obtuse angle of the tip facing the transverse process. In one form, the docking port 10064 may have an orientation direction etched on the outside of the tube to aid in placement. The docking port 10064 should be advanced until it rests against the facet and transverse process, and can restrict soft tissues from encroaching. The series dilation tools or other dilation tools used can be removed from the system, leaving the guide wire in place.

The pedicle where the bone anchor 10020 is seated is next prepared. After which, the bone anchor 10020 is placed and aligned. The prongs 10112 of the yoke manipulators 10098 are splayed to place around the yoke 10022 such that the pins 10024 engage openings 10113. Then, the outer sleeve 10102 is slid down the inner sleeve 10100 to secure the yoke 10022 to the yoke manipulator 10098. The screw driver is then fed down the yoke manipulator 10098 and mated with the bone anchor 10020. The screw driver may include a separate handle that is attached to the driver before the driver is inserted into the yoke manipulator 10098. Then the bone anchor 10020, yoke 10022, yoke manipulator 10098 and screw driver are advanced to the bone. The bone anchor 10020 is placed at the attachment site. The slots 10114 and 10116 of the yoke manipulators 10098 can be oriented in the cephalad/caudal direction. To ensure correct depth placement of the bone anchors 10020, the depth can be radiographically examined. In addition, the yoke manipulator 10098 may include a ring. If the ring is driven below the top of the docking port 10098, then the bone anchors 10020 may have been driven too far. After the bone anchors 10020 are driven into position, the screw driver is removed from the system. The other bone anchors 10020 are driven into the bone in the same manner described above.

The yokes 10022 are then aligned such that they can receive the connecting member 10026. The guide bar 10160 or 10160b may be attached to the yoke manipulator 10098. The attachment brackets 10172, 10174 or 10171b, 10172b, and 10174b are moved until the yoke manipulators 10098 are parallel or in another desired alignment. Then each of the sliding bodies is tightened into position.

After the yoke manipulators 10098 are positioned, the connecting member 10026 is inserted. Initially, the connecting member 10026 is attached to the rod inserter 10178. To do this, the locking sleeve 10194 is slid backwards such that the connecting member 10026 can be placed within the prongs 10200. The pins 10204 are aligned with the bore 10186 of the connecting member 10026. Then the locking sleeve 10194 is moved forward to secure the connecting member 10026 to the rod inserter 10178.

The connecting member 10026 insertion is primarily controlled by the surgeon. The surgeon aims the rod inserter 10178 between the slots 10114, 10116 in the yoke manipulators. The nose 10180 of the connecting member 10026 is placed in the caudal-most slot of the yoke manipulators 10098. The connecting member 10026 is pushed then down to the level of the yoke 10022. If the connecting member 10026 is too high, the surgeon may need to compress excess soft tissue.

The connecting member 10026 is pushed into both yokes 10022. The position within the yokes 10022 can be verified by looking down the yoke manipulators 10098. The position can also be verified radiographically. The nose 10180 of the member 10026 preferably extends past the yoke 10022 such that the full diameter body 10182 of the connecting member 10026 is within the yoke 10022.

After the connecting member 10026 is positioned within the yokes 10022, the counter torque tube is deployed over one yoke manipulator 10098. The pins 10380 of the counter torque tube 10352 are aligned with slots on the second end 10108 of the yoke manipulator 10098. Then the cap 10024 is inserted using the cap inserter 10230 and counter torque tube 10352. Two cross pins 10248 on the cap inserter 10230 can indicate depth and orientation. The counter torque tube 10253 also may include etchings to ensure proper depth and positioning. Typically, the cap inserter 10230 is turned clockwise to seat the cap 10024 and therefore, it may be beneficial to begin the procedure as far counter-clockwise as the tools will allow. The surgeon typically may use tactile feed back to feel the cap 10024 seat atop the connecting member 10026. The cap inserter 10230 is released from the cap 10024 and pulled straight up to avoid loosening the cap. The rod persuader 10254 is used in a similar manner to seat subsequent caps 10024. The cap 10024 can be loaded by latching the ring 10284 and then the cap 10254 is advanced down toward the yoke 10022.

After the caps 10024 are seated, the distance between the bone anchors 10020 can be adjusted using the compression-distraction tool 10330. After the bone anchors 10020 are positioned, the caps 10024 are tightened to the final-lock position. After final locking, the tools are removed and the incision closed.

The MIS system may include a number of alternative or additional tools such that a surgeon can further customize the implantation procedure. As previously indicated, the implant and the implant procedure are chosen based on the condition of the patient, the anatomy of the patient, and the preferences of the surgeon. Thus, by providing additional options for implant insertion, the surgeon can chose tools and devices that are more suited to a particular patient or are more suited to the surgeon's preferences.

As shown in FIG. 51, the connecting member 10026 includes the body portion 10182 and an attachment end 10184 that may have a reduced portion or other structure for securing the connecting member 10026 to the rod inserter 10178. Positioning the attachment end 10187 in the yoke 10022 can be problematic the cap 10024 may not properly secure the connecting member 10026 within the yoke 10022. The preferred positioning having the attachment end 10184 outside of the yoke 10022 of the pedicle screw assembly 10021. In addition to positioning of the attachment end 10184 outside of the yoke 10022, the nose or tip 10180 of the connecting member 10026 should be kept in the far yoke 10022.

The rod inserter 10178 may include a bulbous portion 10199 to limit how closely the rod inserter 10178 can be to the yoke manipulator 10098 and also how far the tool can advance into the wound. Depending on a surgeon's particular preference, such further advancement may provide needed flexibility.

One of the alternative instruments that may address some of these concerns is the rod insertion tool 11078, illustrated in FIGS. 97A-97D, which, like the rod inserter 10178, may be used to guide and position the spinal rod or connecting member 10026 into the yokes 10022. The rod insertion tools 10178, 11078 can be used in conjunction with the yoke manipulators 10098 to position the body 10182 of the connecting member 10026, which has a generally constant diameter body 10182, within the yokes 10022. The rod inserter 11078 of FIGS. 97A-97D differs from the rod inserter 10178 of FIGS. 66-72 in that it includes an adjustment sleeve 11091 and a latch 11102.

Figure 97A:
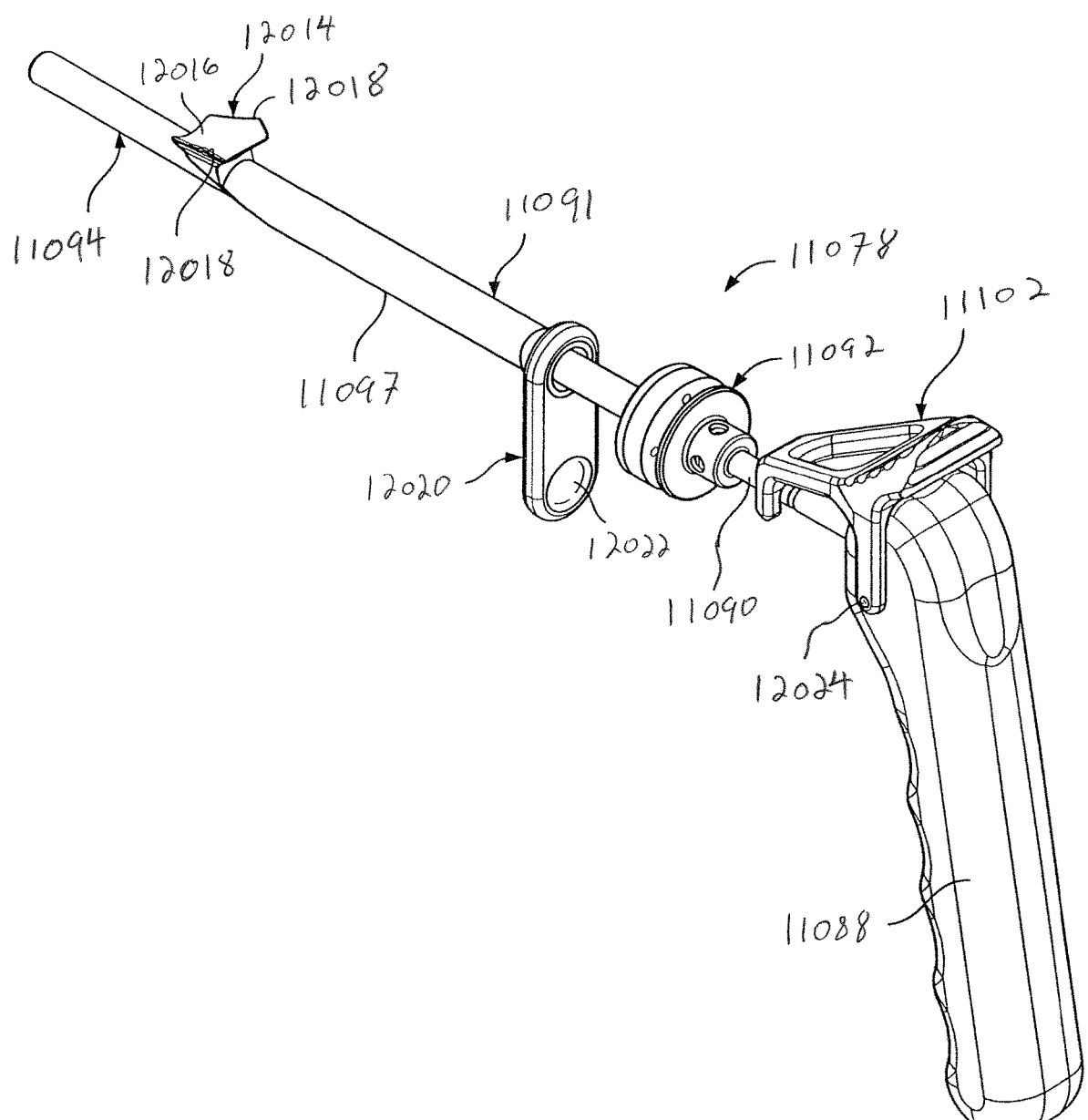
FIG. 97A is a perspective view of an alternative rod inserter having an adjustment sleeve for verifying the positioning of the inserted rod.
Figure 97B:
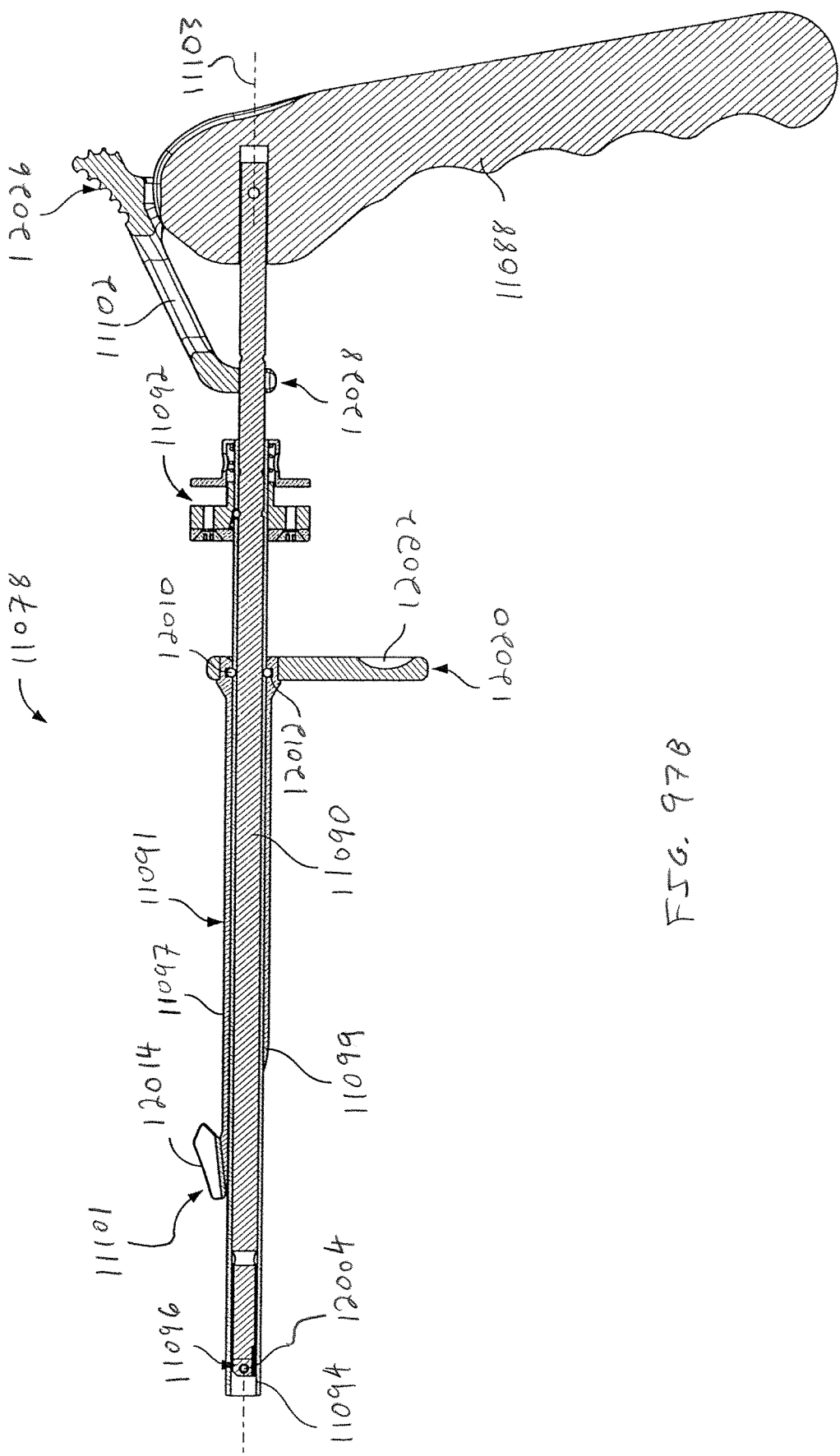
FIG. 97B is a cross-sectional view of the rod inserter of FIG. 97A showing the coaxial arrangement of an inner shaft, a locking sleeve, and the adjustment sleeve.

In the embodiment illustrated in FIGS. 97A-97B, the adjustment sleeve 11091 that may be employed to verify positioning of the connecting member 26 and correct its placement if necessary. Specifically, the adjustment sleeve 11091 may be used to pull the attachment end 10184 of the connecting member 10026 outside of the yoke 10022. The adjustment sleeve 11091 of FIG. 97A includes structure, described below, that generally keeps the surgeon from pulling the tip 10180 of the connecting member 10026 out of the yokes 10022 by over-rotating the inserter 11078 such that the inserter 11078 is directly adjacent to the yoke manipulator 10098.

Figure 48:
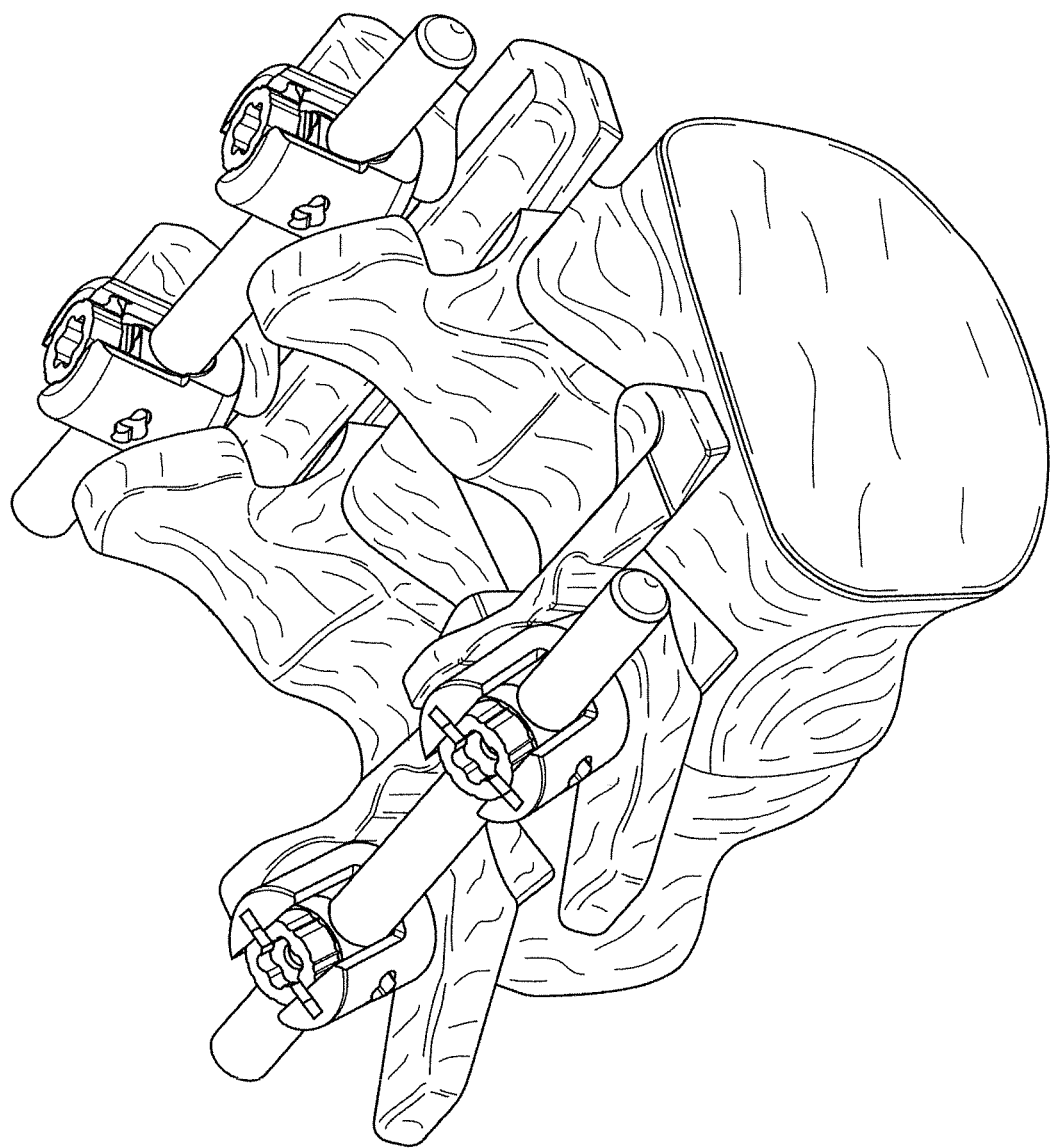
FIG. 48 is a perspective view of another embodiment of an MISS implant.
Figure 49:
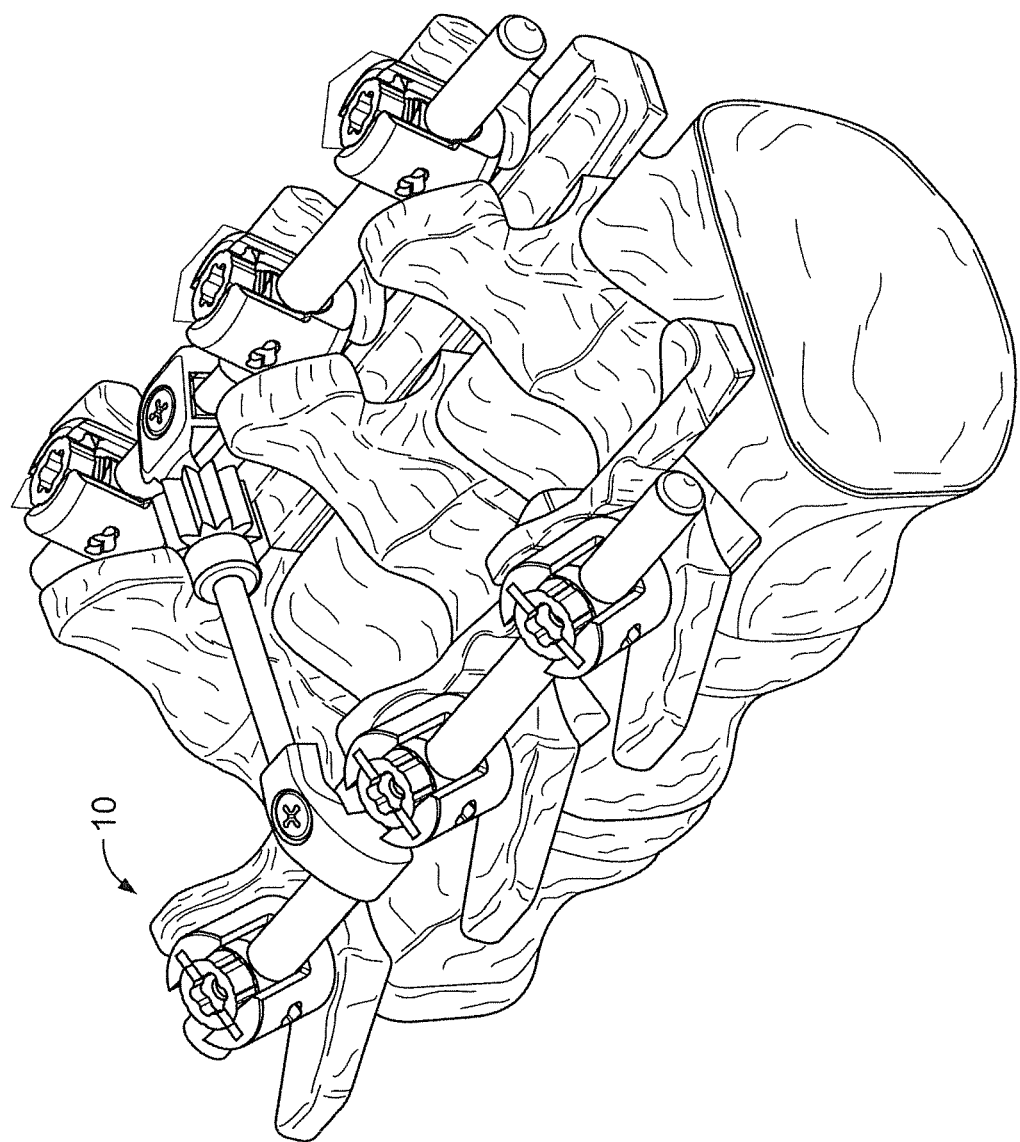
FIG. 49 is a perspective view of another embodiment of an MISS implant including a crosslink.

The adjustment sleeve 11091 is positioned over the outer locking sleeve 11094 and has a friction member 12010 so that the adjustment sleeve 11091 remains where it is positioned after being released by the surgeon. In one preferred embodiment, the friction member 12010, as shown in FIG. 48B, is a resilient O-ring member, such as a silicon O-ring, positioned between the outer locking sleeve 11094 and a groove 12012 inside the adjusting sleeve 11091 to project radially inward therefrom and to frictionally engage with the outer locking sleeve 11094. The adjustment sleeve 11091 further includes a shaft 11097 having an insertion end 11099 that is slanted such that only a projecting portion 11101 of the end 11099 is inserted into the patient. The slanted edge 11099 extends obliquely to the tool axis 11103 to minimize having the edge 11099 catch on tissue as the tool is inserted into the wound.

The insertion end 11099 of the adjustment sleeve 11091 also includes a wedge 12014 that facilitates correct placement of the rod member 10026 in the yokes 10022. When the adjusting sleeve 11091 is pushed down toward the wound, the wedge 12014 becomes positioned between the rod inserter 11078 and the yoke manipulator 10098. Thus, the connecting member 10026 will be pulled out such that the attachment end 10184 thereof is not within the yoke 10022. The wedge 12014 also can prevent misplacement of the rod inserter 11078 directly adjacent the manipulator 10098 to thereby keep the surgeon from pulling the tip 10180 out of the far yoke 10022. The wedge 12014 has a central portion 12016 that is connected to the sleeve 11091 and two projecting sides 12018 that curve outward from the sleeve 11091 to form a seat where the yoke manipulator 10098 received thereagainst. The adjusting sleeve 11091 and wedge 12014 are employed after the connecting member 10026 has been generally positioned between the yokes 10022 and the wedge 12014 creates a distance between the yoke manipulator 10098 and rod inserter 11078 such that the attachment end 10184 of the connecting member 10026 is not within the near or proximate yoke 10022 so that the closure cap 10024 will be seated atop the body 10182 of the connecting member 10026. Opposite the insertion end 11099, the sleeve 11091 includes a radially or laterally extending tab 12020 which can be used to move the adjustment sleeve 11091 about the outer locking sleeve 11094 of the rod inserter 11078. The tab 12020 has a depression 12022 to provide a gripping surface.

Figure 98A:
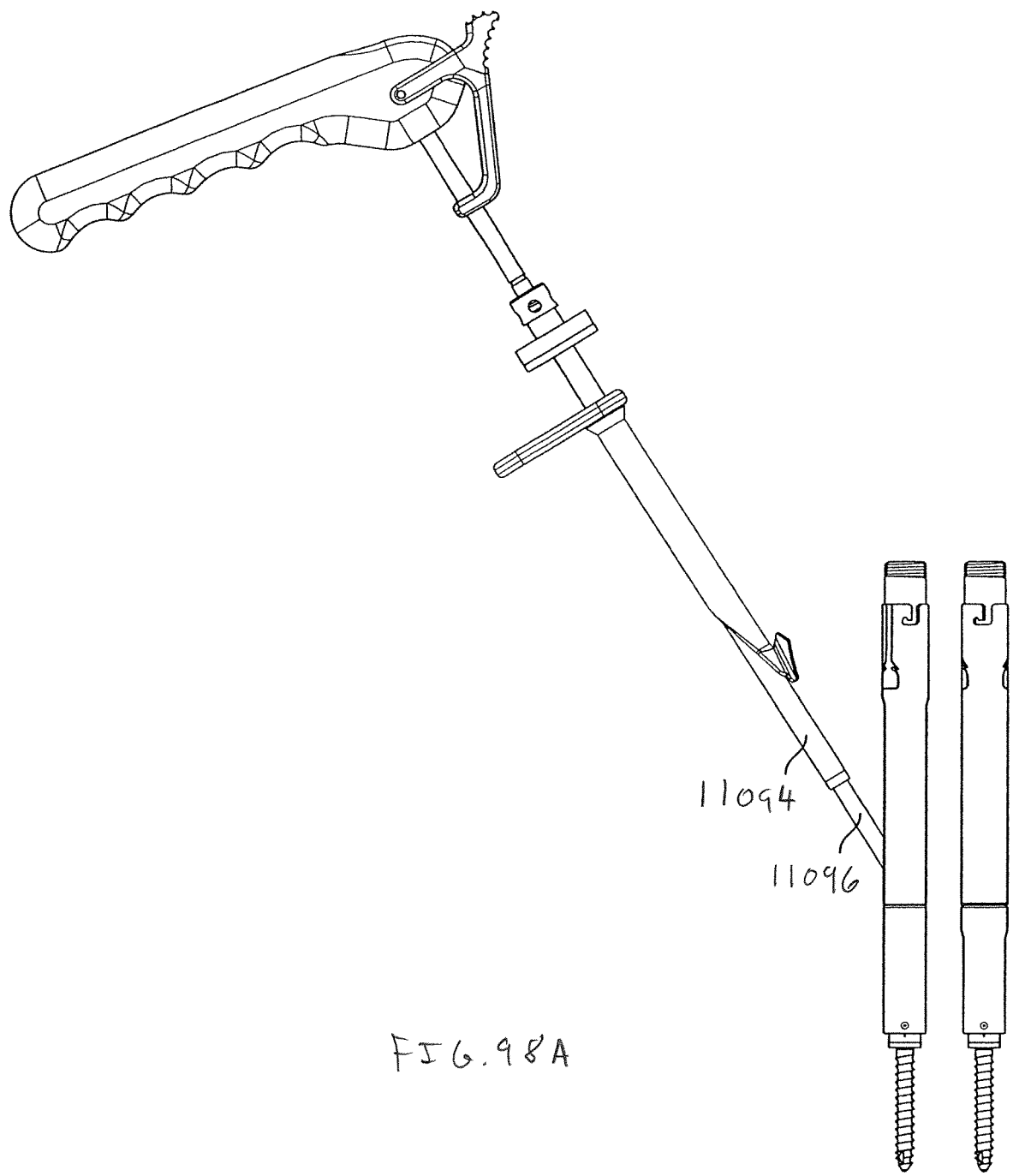
FIG. 98A is a side view of the rod inserter of FIG. 97A, the yoke manipulators of FIGS. 56-61, and the pedicle screw assemblies of FIG. 50 at an initial stage of the rod insertion procedure.
Figure 98B:
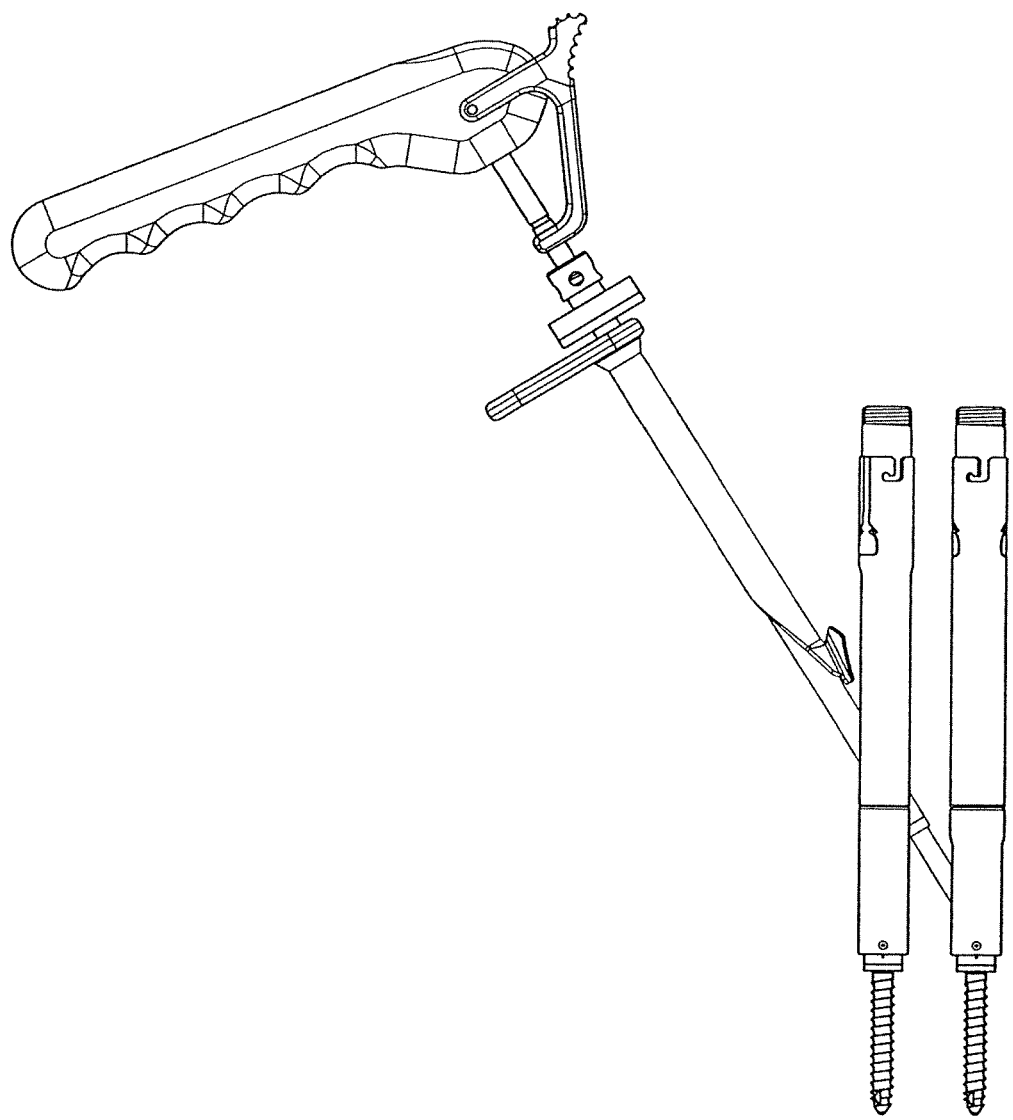
FIG. 98B is a side elevation view of the tools of FIG. 98A in a first intermediate stage of the rod insertion procedure.
Figure 98C:
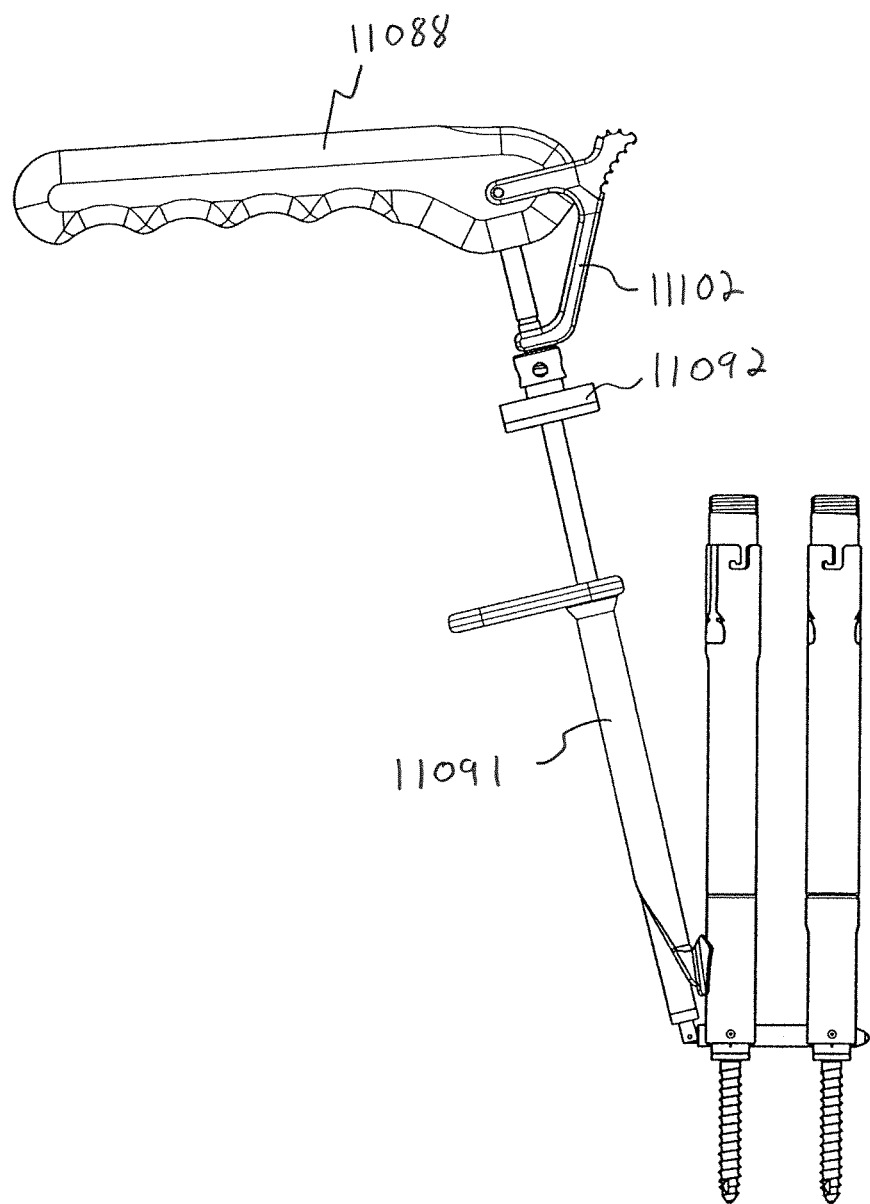
FIG. 98C is a side elevation view of the tools of FIG. 98A in a second intermediate stage of the rod insertion procedure with the nose of the connecting member in the yoke of the far pedicle screw assembly.
Figure 98D:
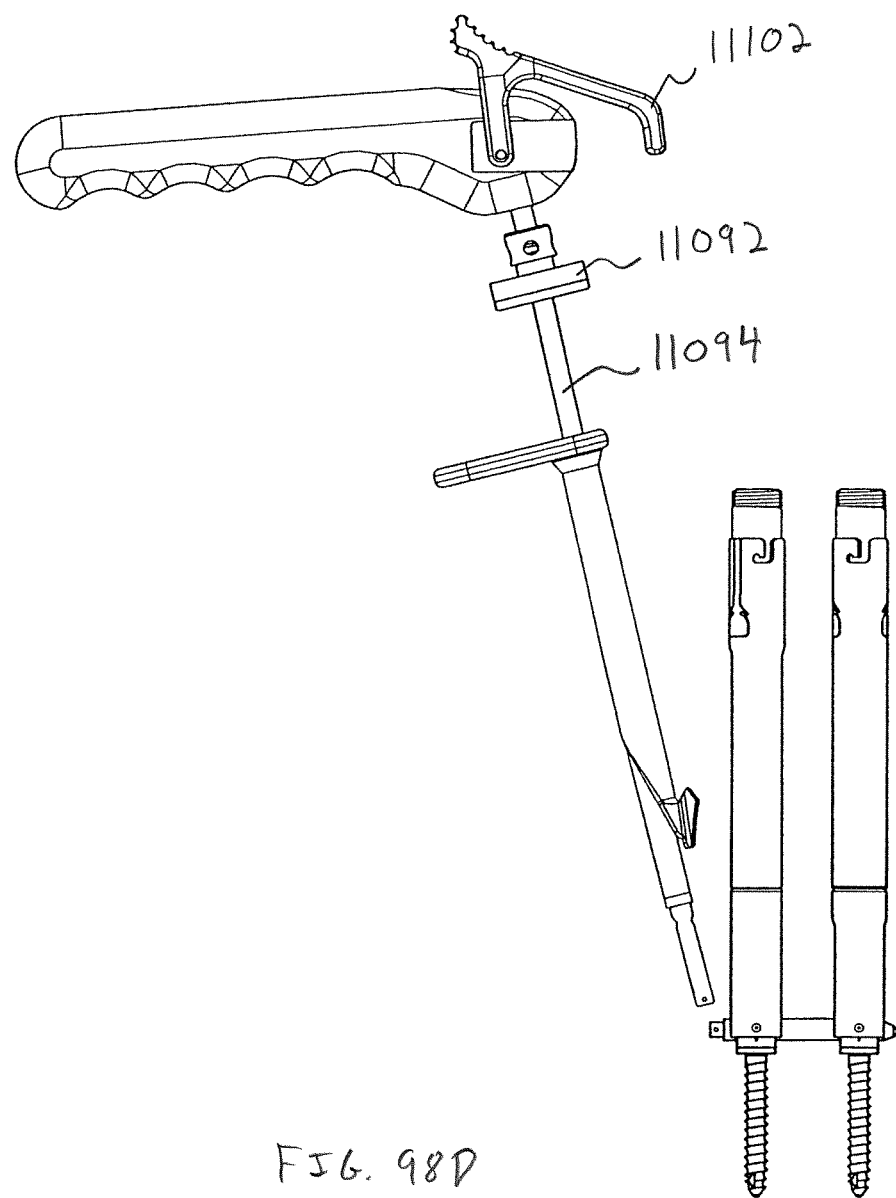
FIG. 98D is a side elevation view of the tools of FIG. 98A in a final stage of the rod insertion procedure with the connecting member within the yokes of the pedicle screw assemblies.

The rod inserter 11078 further includes a latch 11102 for limiting the movement of the shift assembly 11092 and the locking sleeve 11094. If the locking sleeve 11094 is inadvertently advanced too far up the inner shaft 11090 during the MIS procedure, the connecting member 10026 may be prematurely released from the rod inserter 11078 by allowing the prongs 12000 to splay. The latch 11102 is attached to the handle 11088 by two pins 12024. A safety position shown in FIGS. 98A-98C limits the surgeon from moving the shift assembly 11092 and locking sleeve 11094 too far up the inner shaft 11090 and the shift assembly 11092. The latch 11102 can rotate about the pins 12024 from the safety position (FIGS. 98A-98C) to the disengaged position (FIG. 98D) by engaging a finger portion 12026. The latch 11102 includes a stopper 12028 with a U-shaped portion 12030 that engages the inner shaft 11090 in the safety position. When the latch 11102 is in the safety position, the movement of the shift assembly 11092 is constrained from moving too close toward the handle 11088. This is so that when the surgeon is moving the shift assembly 11092 toward the handle 11088 the shift assembly 11092 will abut the stopper 12028 before the locking sleeve 11094 has released the prongs 12000 from the connecting member 10026. Accordingly, in the latched or safety position, the latch member 11102 limits accidental removal of the connecting member 10026 from the rod inserter 11078. The latch 11102 is pivoted to the disengaged position when the shift assembly 11092 needs to be advanced farther up the inner shaft 11092 to disengage the connecting member 10026 from the rod inserter 11078 as shown in FIG. 98D.

Figure 97D:
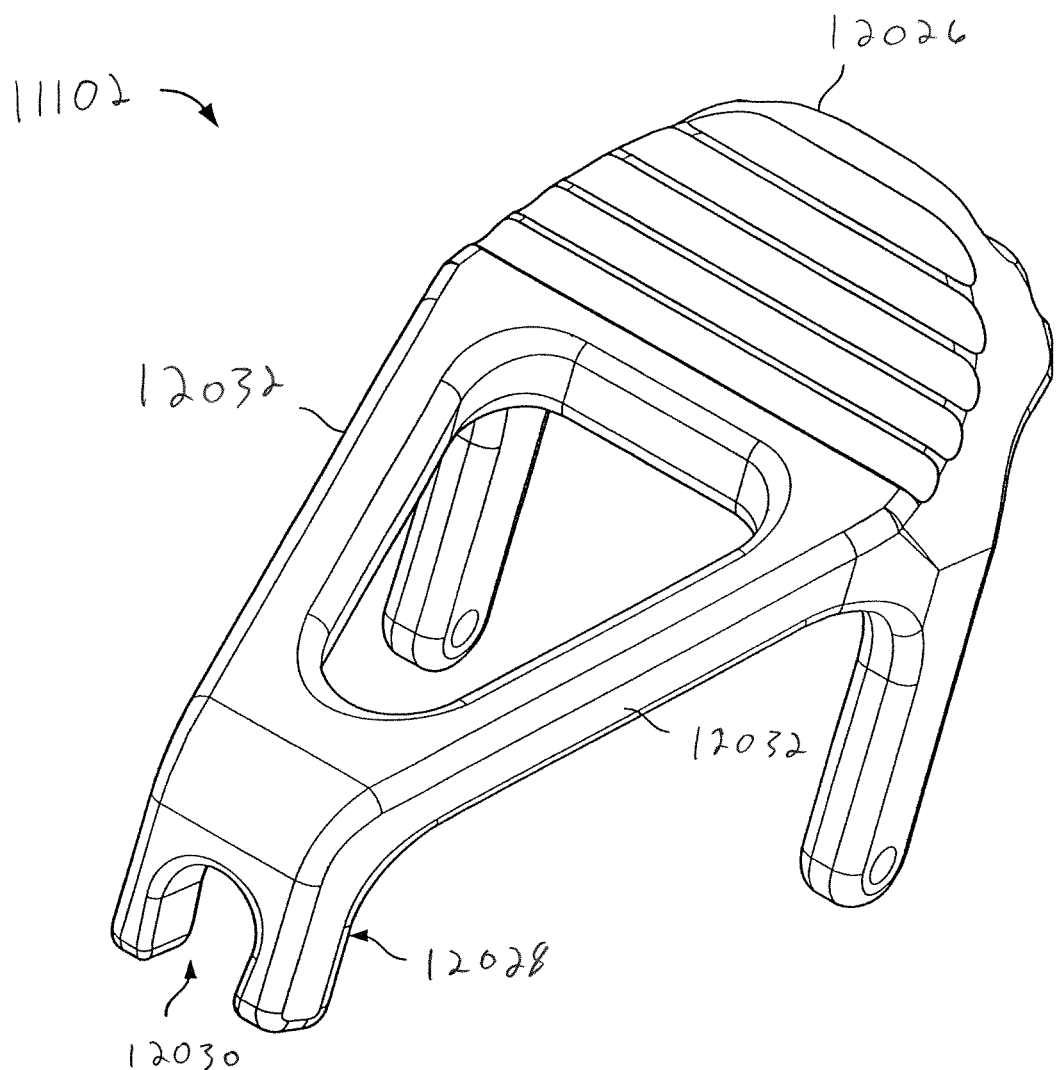
FIG. 97D is a perspective view of a latch portion of the rod inserter of FIG. 97A used for limiting the movement of the locking sleeve.

As shown in FIG. 97D, the latch 11102 includes two connecting arms 12032 that extend from the stopper 12028 to the finger portion 12026; however, it is contemplated that the latch 11102 may be unitary. The latch 11102 is comprised of black radel although other suitable materials can be used. Similar to the inner shaft 11190 of rod inserter 11178, the inner shaft 11090 may have etchings or grooves that indicated where the shift assembly 11092 should be positioned to inform the surgeon of the configuration of the end of the tool that is inserted into the wound. For example, the inner shaft 11090 may include characters or depictions to indicate the unlock, articulate, and lock positions.

To position the spinal rod or connecting member 10026 into the yokes 10022 of the pedicle screw assemblies 10021, the connecting member 10026 is pivotably connected to the attachment end 11096 of the inner shaft 11090 about a pivot axis. Before the connecting member 10026 is advanced through the slots 10114, 10112 of the yoke manipulators 10098, the outer locking sleeve 11094 is positioned over the pivot axis to limit or block pivoting of the connecting member 10026 about the pivot axis. After securing the connecting member 10026 to the rod inserter 11078, the connecting member 10026 is advanced through the long slot 10114 of the proximal yoke manipulator 10098 and then a first portion or nose 10180 of the connecting member 10026 is inserted into the far yoke 10022 of one of the pedicle screw assemblies 10021. The outer locking sleeve 11094 is then moved to an unblocking position exposing the pivot axis to thereby permit pivoting of the connecting member 10026 about the pivot axis. The pivoting movement of the connecting member 10026 may be limited such that the connecting member 10026 may pivot in one direction while limiting or restricting the pivoting in the opposite direction when the locking sleeve 11094 is in the unblocking position. While in the pivoting position, the rod inserter 11078 can be manipulated to place a portion of the connecting member 10026 is a second closer or proximal yoke 10022 of another of the pedicle screw assemblies 10021. Finally, to disconnect the connecting member 10026 from the inner shaft 11090, the outer locking sleeve 11094 may be advanced sufficiently away from the pivot axis to allow the prongs 12000 of the inner shaft 11090 to be disengaged from the connecting member 10026. The locking sleeve 11094 may be secured relative to the inner shaft in each of the release, unblocking, and blocking positions. Further, the locking sleeve 11094 may be unlocked to move between the release, unblocking, and blocking positions.

The different configurations between the connecting member 10026 and the rod inserter 11078 are used in the various stages of rod insertion. As illustrated in FIG. 98A, the pivot connection between the connecting member 10026 and the inner shaft 11090 is covered such that the pivoting movement of the connecting member 10026 is blocked or prevented. In this configuration, the surgeon may direct the connecting member 10026 through the proximal yoke manipulator 10098 having the long slot 10114 toward the far yoke manipulator 10098 having the short slot 10116. The surgeon then guides the tip 10180 of the connecting member 10026 into and/or just past the yoke 10022, as illustrated in FIG. 98B. When the tip 10180 of the connecting member 10026 is positioned at the far yoke 10022, the inserter 11078 is adjusted to the articulating position by pulling back on the shift assembly 11092. The surgeon also moves the locking sleeve 11094 by pulling the shift assembly 11092 upward toward the latch 11102. As discussed above, the movement of the shift assembly 11092 is limited by the latch 11102. When the locking sleeve 11094 is pulled back such that the shift assembly 11092 is adjacent the latch 11102, the pivot connection is unblocked or exposed such that the connecting member 10026 may articulate. In this configuration, the connecting member 10026 is pivoted or rotated downward such that the end 10184 opposite the tip 10180 can be positioned within the proximal yoke 10022 attached to the yoke manipulator 10098 having the long slot 10114. As shown in FIG. 98C, the latch 11102 limits the surgeon from pulling the shifting assembly 11092 too far upwards toward the handle 11088. After the connecting member 10026 has been rotated into position between the yokes, the surgeon may ensure that the attachment end 10184 is not located within the proximal yoke 10022 by moving the inner shaft 11090 of the inserter 11078 nearly parallel to the yoke manipulator 10098 and thereby pulling the attachment end 10184 out of the yoke 10022. However, depending on the surgeon, the rod inserter 11078 may already be adjacent the yoke manipulator 10098 and the surgeon may employ the adjustment sleeve 11091 as a wedge to pull the attachment end 1184 out of the proximal yoke 10022. The latch 11102 may rotated upward, as illustrated in FIG. 98D, to allow the shift assembly 11092 and the locking sleeve 11094 to be moved to expose a substantial portion of the opposing prongs 12000 such that the prongs 12000 splay outward and disengage or release the connecting member 10026.

Turning to more of the details of the construction, the rod inserter 11078, like inserter 10178, includes a handle 11088 to which an inner elongate rod or shaft 11090 is attached, for example, by welding, threaded engagement, pins, screws, and adhesive, among others. The inner shaft 11090 having a shift assembly 11092 and an outer control sleeve or a locking sleeve 11094 mounted thereon. The inner shaft 11090 and the locking sleeve 11094 are configured as a shaft assembly having a longitudinal axis. The inner shaft 11090 of the rod inserter 11078 including an attachment end portion 11096 having connecting structure, such as a pivot connection, configured to mate with the attachment end 10184 of the connecting member 10026. For example, the attachment end 11096 may be adapted to pivotably engage the spinal rod or connecting member 10026 about a pivot axis. To aid in the attachment of the connecting member 10026, the inner shaft 11090 of the rod inserter 11078, includes two slots 11098 at the attachment end 11096 that separate two opposing prongs 12000 from each other. During the MIS procedure, the prongs 12000 may be situated about portions of the connecting member 10026 similar to the configuration previously discussed with respect to inserter 10178. As discussed below, the outer locking sleeve 10094 of the shaft assembly may be moved relative to the inner shaft 10090 to prevent or block the connecting member 10026 from pivoting.

The opposing prongs 12000 may include connecting structure 12002 that mates with corresponding structure 10186 of the connecting member 10026. The connecting structure 12002, shown in FIG. 97C such as a pivoting connection, and may include a recess, a boss or a projection, such as protuberances or frustoconical projections 12004 that project inward from the inwardly facing surfaces of the opposing prongs 12000. As shown in FIG. 51, the connecting structure 10186 may be a recess or a through-bore, but may also include a boss, flat, capture, groove, or ridge, among others, configured to engage corresponding structure present on the rod inserter 10178, 11078. It is also contemplated that the projections or protuberances be located on the connecting member 10026 and the recesses located on the inwardly facing surfaces of the pair of opposing prongs 12000.

Once the connecting structure 12002 of the prongs 12000 is mated with corresponding structure 10186 on the connecting member 10026, a pivot connection about a pivot connection is established between the connecting member or rod 10026 and the inserter tool 11078. By sliding the locking sleeve 11094 down the inner shaft 11090, the opposing prongs 12000 of the inner shaft 11090 are secured into position about the connecting member 10026 thereby clamping the connecting member 10026 between the prongs 12000. The locking sleeve 11094 may be slid down along the inner shaft 11090 to at least partially secure the prongs 12000 around the attachment end 10184 of the connecting member 10026 in a similar fashion to rod inserter 10178. To keep the connecting member 10026 generally rigidly attached to the inserter tool 11078 during the beginning of the rod insertion procedure, the locking sleeve 11094 is slid down such that the locking sleeve 11094 surrounds at least a substantial portion of the inner shaft 11090. By having the locking sleeve 11094 surround the pivot axis and connection between the connecting member 10026 and the inner sleeve 11090, the member 10026 is blocked from pivoting and is secured rigidly to the rod inserter 11078. Such a rigid connection is used during the MIS procedure to direct the connecting member 10026 through the slots 10114, 10116 and into the yokes 10022. After the nose or tip 10180 of the connecting member 10026 is positioned in the far yoke 10022, the connecting member 10026 is allowed to pivot such that the attachment end 10184 pivots downward toward the proximal yoke 10022. The locking sleeve 11094 of the rod inserter 11078 is moved upward toward the handle such that the pivot connection is exposed and the pivoting is no longer blocked. In the pivoting configuration, the locking sleeve 11094 remains positioned close enough to the pivot connection to keep the opposing prongs 12000 engaged with the attachment end 10184, but the locking sleeve 11094 is not surrounding the pivot connection and does not prevent or block the connecting member 10026 from pivoting. After the connecting member 10026 has been seated in each of the yokes 10022, the connecting member 10026 can be released from the rod inserter 11078 by shifting the locking sleeve 11094 from the pivoting or unblocking position to the release position whereby the locking sleeve 11094 is sufficiently spaced from the opposing prongs 12000 of the inner shaft 11090 to permit the prongs 12000 to flex outwardly relative to each other to release the connecting member 10026. Before the connecting member 10026 is released from the rod inserter 11078, the latch 11102 is pivoted to the disengaged position such that the locking sleeve 11094 can be moved to the disengage position.

After the connecting member 10026 is generally laterally positioned within the yokes 10022 as described previously, the member 10026 is sufficiently seated within the yokes 10022 such that the closure caps 10024 can fit within the yokes 10022 to secure the connecting member 10026. Depending on the patient's anatomy, the connecting member 10026 may extend at an upward incline to such a degree such that the closure cap 10024 cannot fit within the yoke 10022. In such a circumstance, the connecting member 10026 must be pushed into the yoke 10022. The rod persuader 10254, along with the closure cap 10024 may be used to seat the connecting member 10026 and to secure the closure cap 10024 into position by rotating the caps 10024. However, the rod persuader 10254 may encounter a number of limitations depending on the patient anatomy and the preferences of the surgeon.

If the patient has a significantly displaced vertebra, the force required to reduce the connecting member 10026 to its seated position in the yoke 10022 may be quite significant and such large loads may be problematic. Seating of the connecting member 10026 may require one vertebra to be adjusted relative to another vertebra; a significant amount of force can be required for the persuader 10254 to move the vertebra via the closure cap 10024 and yoke manipulator 10098. The persuader 10254 may encounter several problems when employed on patients having significantly displaced vertebra: the cap 10024 may be pushed onto the tip of the persuader tool 10254 too tightly and could become difficult to disengage from the persuader 10254; the connection between the inner and outer sleeves 10100, 10102 of the yoke manipulator 10098 could fail under the large loads; and the prongs 10112 of the yoke manipulator 10098 that attach to the yoke 10022 could splay and disengage from said yoke. Such disengagement of the prongs 10112 is especially problematic with manipulators 10098 having the long slots 10114.

The rod persuader 10254 includes a portion that applies axial downward force against the cap 10024, engaged with the connecting member 10026 to urge the connecting member 10026 into the yoke 10022, while the persuader 10254 uses the yoke manipulator 10098 to hold the yoke 10022 relative to the cap 10024. This axial downward force could force the cap 10024 onto the persuader too tightly to be easily or conveniently disengaged. Further, in one exemplary embodiment, the rod persuader 10254 connects to the outer sleeve 10102 of the yoke manipulator 10098 via a bayonet connection illustrated as including a set of pins 10329 in FIG. 83. However, the inner sleeve 10100 is the portion of the yoke manipulator 10098 that attaches to the yoke 10022. Thus, the inner sleeve 10100 and outer sleeve 10102 of the yoke manipulator 10098 typically need to be secured relative to one another to transfer the forces of the rod persuader 10254 to the yoke 10022.

Referring to FIGS. 56-61, the bone anchor 10020 and the yoke 10022 of the pedicle screw assembly 10021 are delivered to the vertebra by the yoke manipulator 10098, which includes two cylindrical sleeves 10100, 10102. The inner sleeve 10100 includes two shaft slots 10110 that create two shaft arms or prongs 10112, which are positioned around portions of the pedicle screw assembly. The outer sleeve 10102 is slid over the inner cylindrical sleeve 10100 to secure the yoke manipulator 10098 to portions of the pedicle screw assembly to prepare the assembly to be delivered to the bone. In one exemplary embodiment, the inner sleeve 10100 and the outer sleeve 10102 are secured to one another via a spring 10134, as shown in FIGS. 56-61. The spring 10134 operates such that when it is depressed, the outer sleeve 10102 deforms to allow the sleeve 10102 to be removed from around the inner sleeve 10100. The persuader 10254 seats the cap 10024 and the connecting member 10026 by transferring force from the persuader 10254 to the outer sleeve 10102, which transfers the force to the inner sleeve 10100, and then to the yoke 10022. Such a configuration requires a secure connection between the inner and outer sleeves 10100, 10102 in order to seat the connecting member 10026 and cap 10024 with the persuader 10254. The spring 10134 employs elastic deformation to allow the outer sleeve 10102 to be removed from around the inner sleeve 10100 by raising the finger portion 10135 of the spring 10134 away from the flat 10130 of the inner sleeve 10100, as shown in FIGS. 57 and 58. Thus, if the force needed to seat the connecting member 10026 is excessively large, the spring 10134 may encounter problems such as disengagement of the spring 10134 from the flat 10130. The axial force may be significant enough to permanently deform the spring 10134. Whether permanent deformation results, the force may nonetheless be large enough to buckle the spring 10134 thereby permitting the proximal edge of the spring 10134 to move past the corresponding ledge of the inner sleeve thereby disengaging the inner and outer sleeves 10100, 10102.

To address the problems arising when large forces are required to seat a connecting member 10206, a surgeon may prefer to use a convincing tool 12100 instead of the rod persuader 10254 to seat the connecting member 10026 into the yokes 10022. The convincing tool 12100 can be positioned around outside of the yoke manipulator 10098 (as opposed to the rod persuader 10254 that is advanced down the center bore of the yoke manipulator 10098), thereby avoiding having the prongs of the manipulator 10098 splaying outwardly. Since the convincing tool 12100 is outside the yoke manipulator 10098, the closure cap 10024 may be delivered to the yoke 10022 in a procedure separate from the procedure that seats the rod. Thus, the closure cap 10024 is delivered with another tool, e.g., cap inserter 10230, when the convincing tool 12100 is employed, as opposed to having the cap 10024 inserted and the connecting member 10026 seated by the persuader 10254. This allows the connecting member 10026 to be seated and the closure cap 10024 delivered into position within the yoke 10022 without using the same tool and thereby avoiding having the closure cap 10024 pushed to tightly onto the tip of the persuader 10254.

Figure 99A:
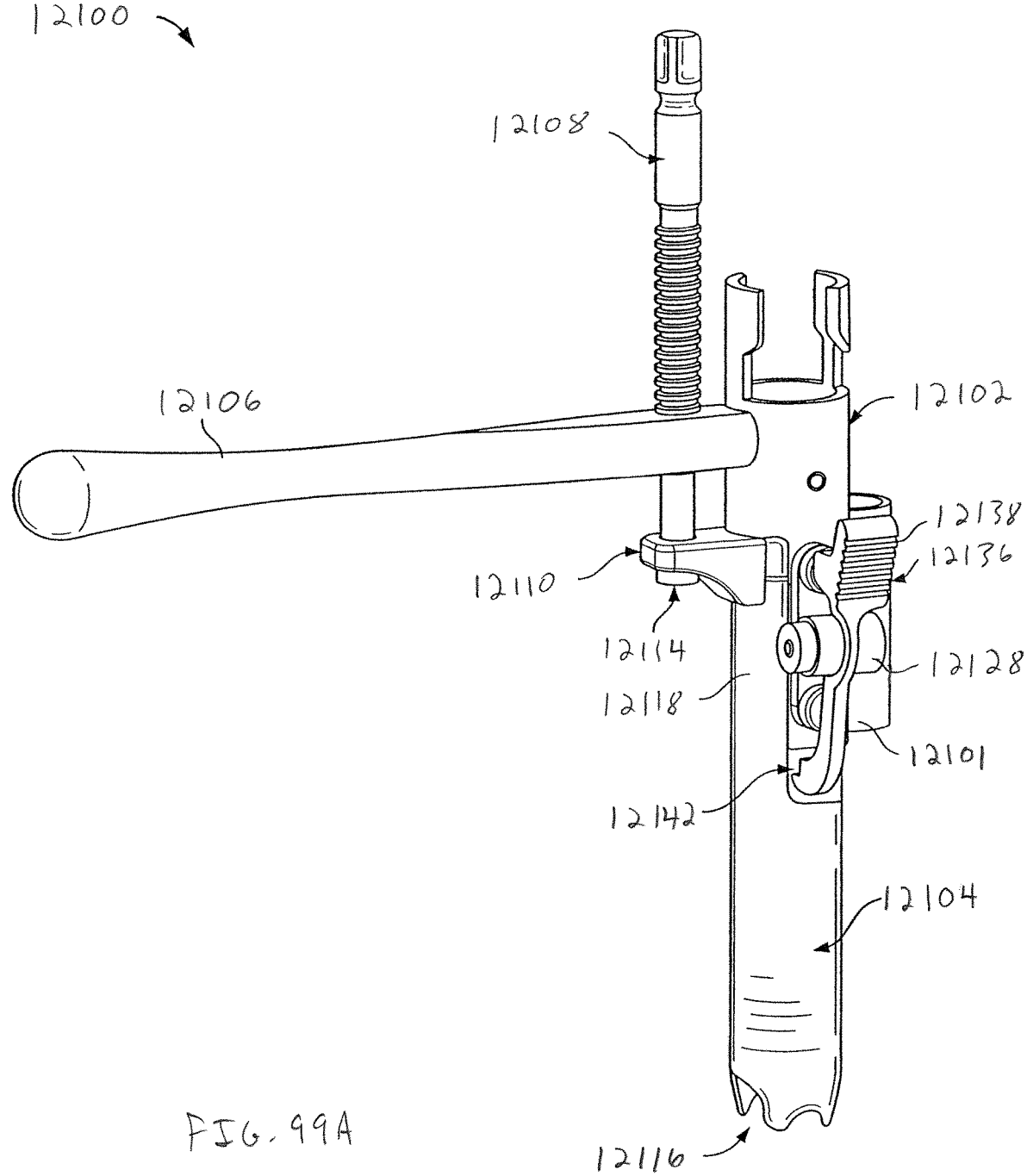
FIG. 99A is a perspective view of a convincing tool having a tool housing, a translation tube, and a latch for engaging the inner sleeve of the yoke manipulator of FIGS. 59-61.

As illustrated in FIG. 99A, the convincing tool 12100 includes a tool housing 12102, a translation tube 12104, a handle 12106, and a drive 12108 that rotatably is supported by a pivot housing 12110. The translation tube 12104 has a lower insertion end 12116 and an upper attachment end 12118 at which the pivot housing 12110 is attached. A shoulder bolt 12114 secures the drive 12108 to the housing 12110 as shown in FIG. 99C. The pivot housing 12110 is secured to the translation tube 12104 through a housing pin 12112. Since the drive 12108 is rotatably offset from the translation tube 12104, as shown in FIG. 99A, a slot 12142 allows the movement of the drive 12108 to be transferred to the translation tube 12104 and allows the pivot housing 12110 to ride upwards and downwards relative to the housing 12102.

Figure 99B:
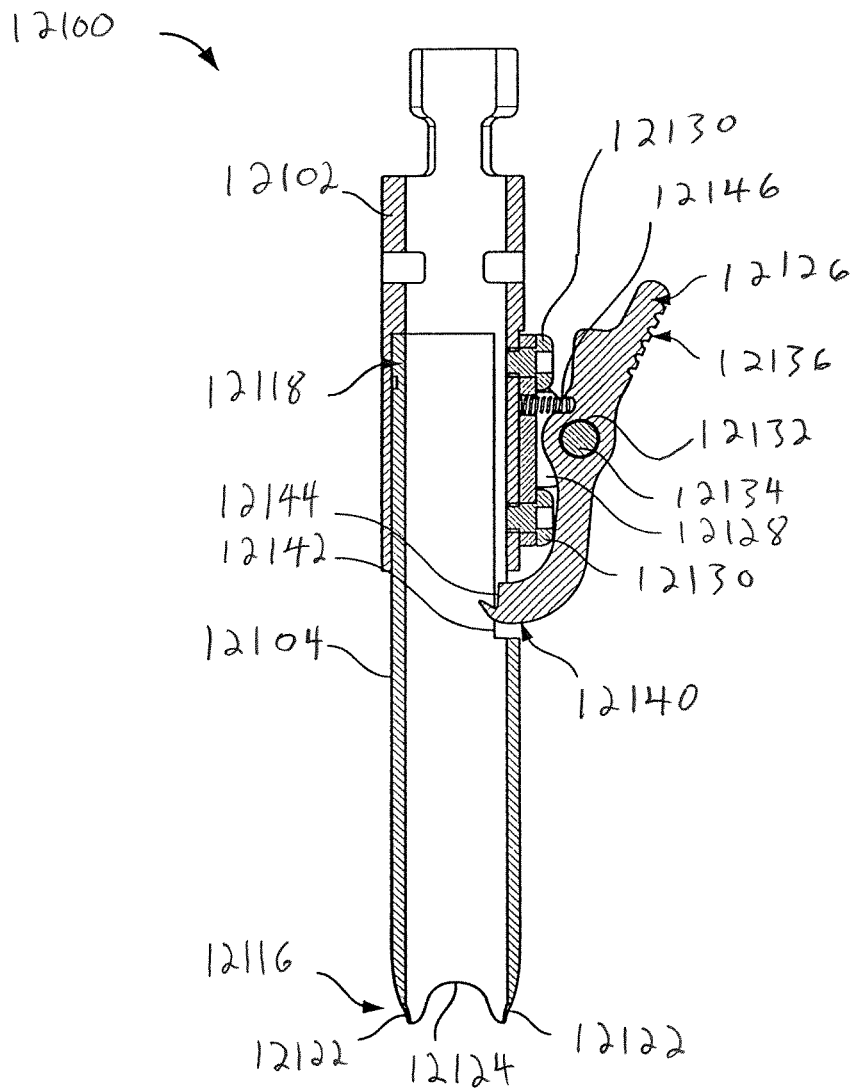
FIG. 99B is a cross-sectional view of the convincing tool of FIG. 99A showing the configuration of the tool housing, the driver, the rotatably offset translation tube, and the latch.
Figure 99C:
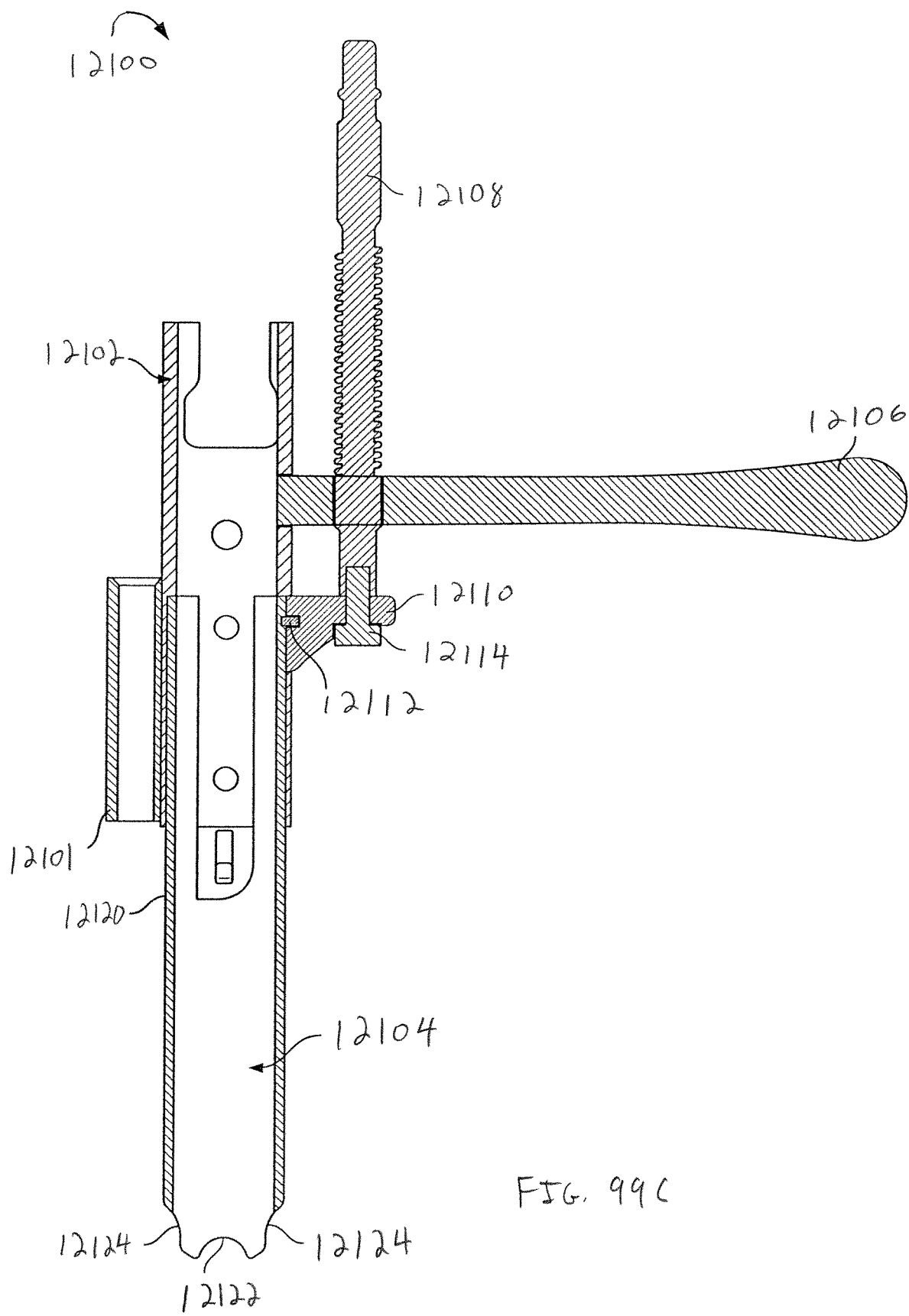
FIG. 99C is another cross-sectional view of the convincing tool of FIG. 99A showing the tool housing, the driver, and the rotatably offset translation tube.
Figure 99D:
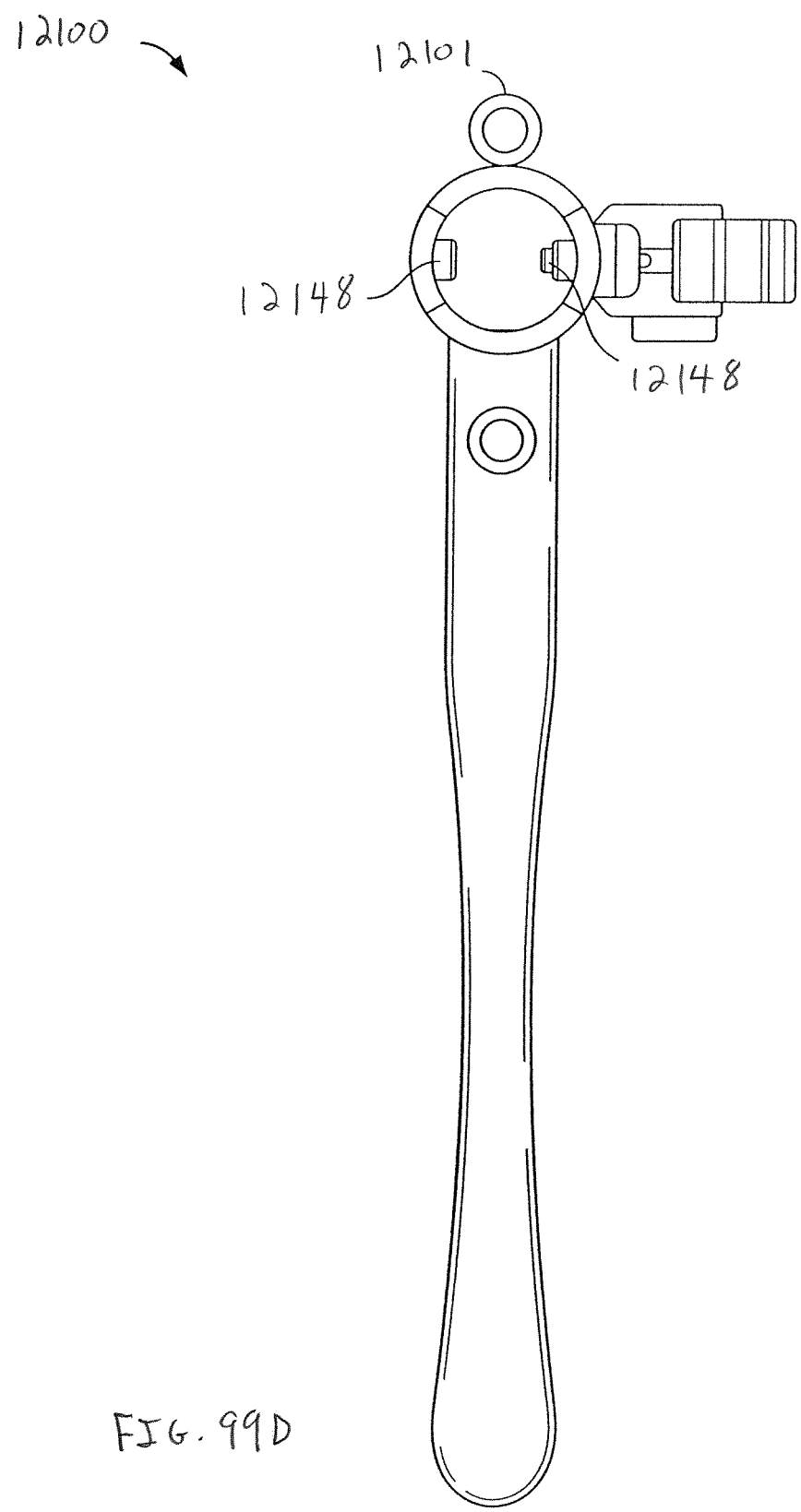
FIG. 99D is a top plan view of the convincing tool of FIG. 99A showing the tool housing, the handle, and the latch.
Figure 99E:
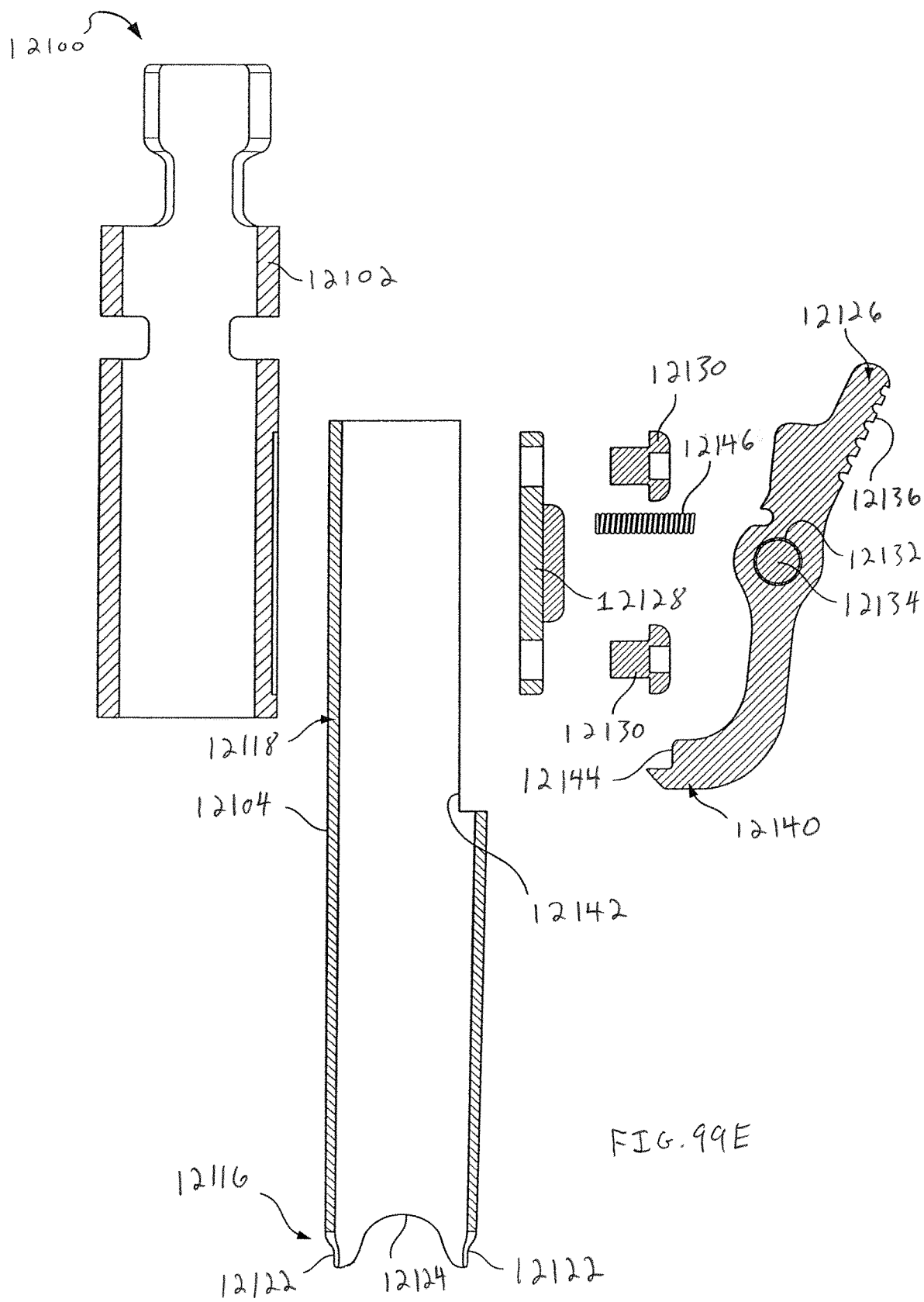
FIG. 99E is an exploded perspective view of the convincing tool of FIG. 99C.
Figure 99F:
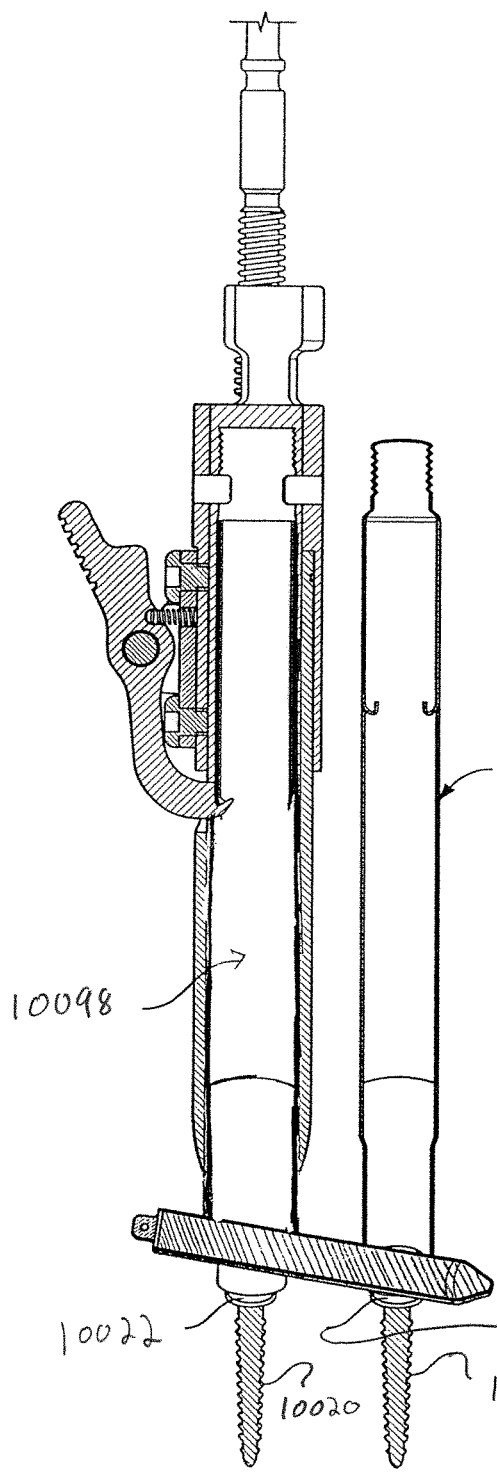
FIG. 99F is a side elevation view of the convincing tool of FIG. 99A, the yoke manipulators of FIGS. 56-61, the connecting member of FIG. 51, and the pedicle screw assemblies of FIG. 50 showing an initial stage rod positioning with the yokes.
Figure 99G:
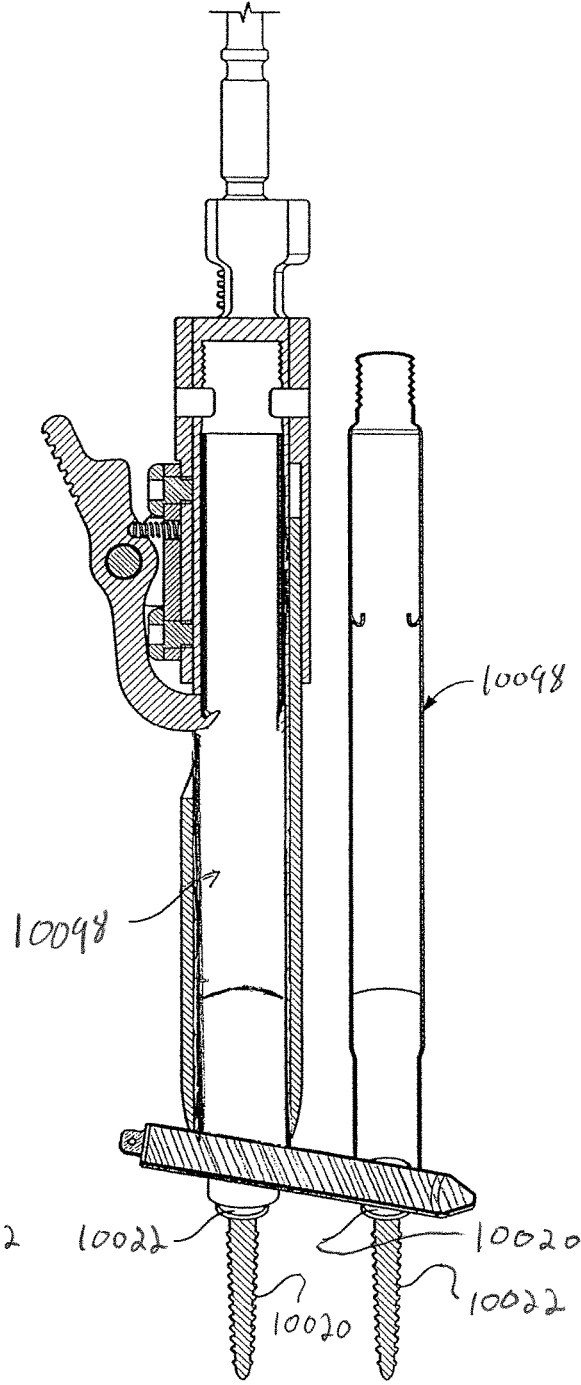
FIG. 99G is a side elevation view of the tools of FIG. 99F in an intermediate stage of rod positioning.
Figure 99H:
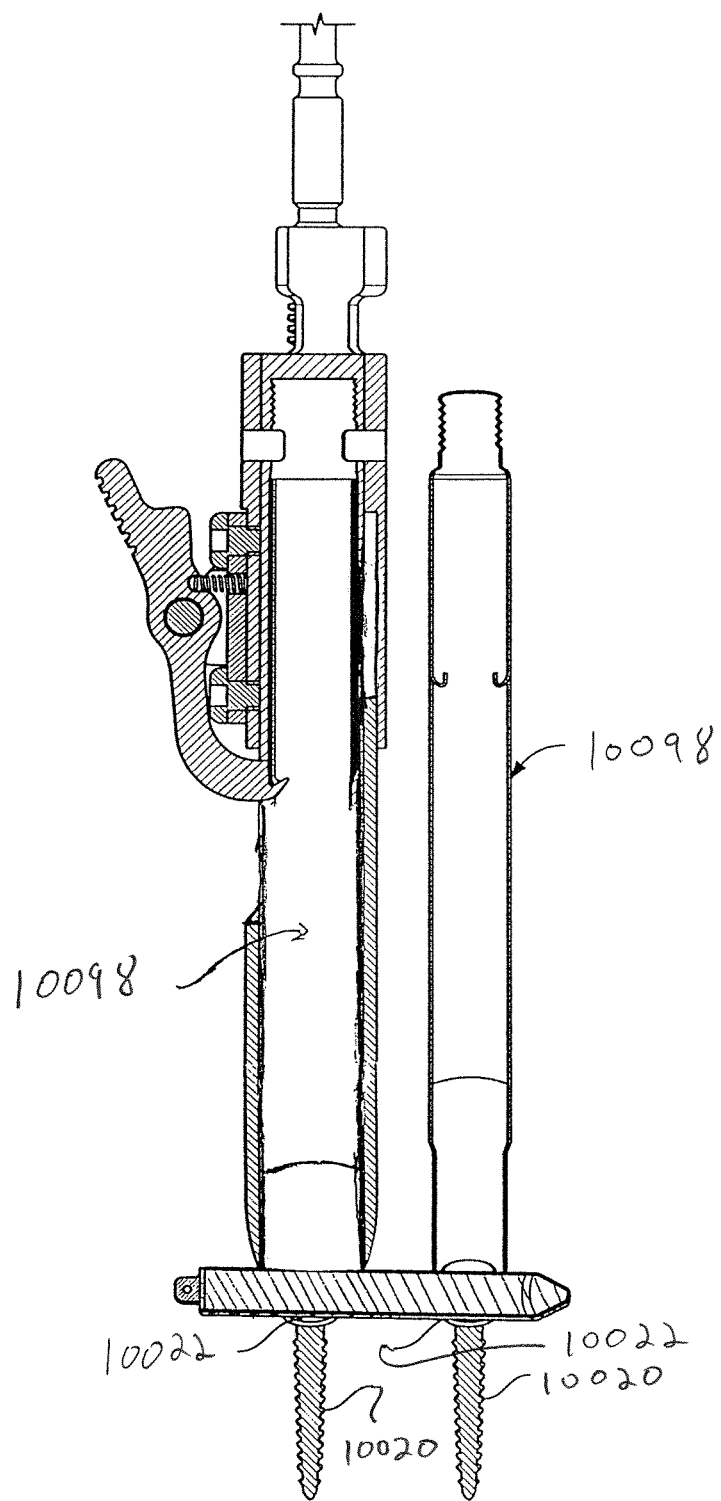
FIG. 99H is a side elevation view of the tools of FIG. 99F in a final stage of rod positioning.

To assist with seating the connecting member 10026, the translation tube 12104 has opposing rod cutouts 12122 and opposing interference cutouts 12124 spaced ninety degrees from, the rod cutouts 12122 about the bottom 12116 of the tube 12104, as shown in FIGS. 99B and 99C. The rod cutouts 12122 are of a smaller size than the interference cutouts 12124. The rod cutouts 12122 are located transverse to the handle 12106. The rod cutouts 12122 are sized to engage the connecting member 10026 and position the connecting member 10026 into the yokes 10022. As discussed below in greater detail, the convincing tool 12100 seats the connecting member 10026 by pushing down on the member 10026 while holding the yoke 10022 against shifting by having the housing 12102 retain the yoke manipulator 10098. The interference cutouts 12124 provide clearance between the translation tube 12104 and various portions of the spinal processes. The insertion end 12116 has a tapered configuration to ease insertion of the convincing tool 12100 into the surgical site.

The connecting member 10026 is seated by having the translation tube 12104 push downward on the connecting member 10026 while the tool housing 12102 keeps the yoke 10022 vertically stationary. To seat the connecting member 10026 into the yoke 10022, the convincing tool 12100 not only pushes on the connecting member 10026, but also attaches to the long slot 10114 of the inner sleeve 10100 yoke manipulator 10098. By securing to the inner sleeve 10100 of the yoke manipulator 10098 to which the yoke 10022 is mated, the yoke 10022 is retained in position while the connecting member 10026 is pushed downward and seated therein. Therefore, the connecting member 10026 is pushed down relative to the yoke 10022 via the yoke manipulator 10098 by having the translation tube 12104 advanced into the wound by turning the driver 12108.

To secure to the inner sleeve 10100, the tool housing 12102 of the convincing tool 12100 includes a latch 12126, as shown in FIGS. 99A and 99B. The latch 12126 secures to the long slot 10114 of the yoke manipulator 10098 while the translation tube 12104 pushes on the connecting member 10026. Securing the tool housing 12102 via the latch 12126 to the yoke manipulator 10098 allows the translation tube 12104 to move the connecting member 10026 relative to the yoke manipulator 10098 and the yoke 10022. The latch 12126 pivots about a hinge 12128 that is attached to the housing 12102 by a pair of fasteners 12130, such as cap screws. The latch 12126 has an opening 12132 through which a pivot 12134, such as a shoulder screw, extends. In addition, the latch 12126 includes a finger tab 12136 with ribs 2138 for added friction. Opposite the finger tab 12136, the latch 12126 includes a toothed projection 12140 that extends through a slotted opening 12142 located in the translation tube 12104. The toothed projection 12140 includes a flat 12144 that provides clearance for the outer sleeve 10102 of the yoke manipulator 1098. Thus, since the toothed projection 12140 extends only a small distance past the flat 12144 that may engage the outer sleeve 10102, the toothed projection 12140 will not extend significantly into the tubular opening of the yoke manipulator 10098. Therefore, the convincing tool 12100 will not extend into the opening and interfere with the delivery of tools, devices, implants, or portions thereof that may be delivered down the center bore of the yoke manipulator 10098, such as the closure cap 10024. Instead, the toothed projection 12140 extends through the outer sleeve 10102 and engages the long slot 10114 of the inner sleeve 10100, which is attached to the yoke 10022, without excessively protruding past the inner sleeve 10100.

As shown in FIG. 99B, the latch 12126 may have a curved geometry extending from the hinge structure 12128 in order to provide clearance for one of the fasteners 12130 and engage the tool with the inner sleeve 10100 through the slotted opening 12142 that is located on the other side of the fastener 12130 from the pivot 12134. The convincing tool 12100 further includes a spring 12146 that biases the toothed projection 12140 into engagement with the inner sleeve 10100 and simultaneously biases the finger portion 12136 outward from the housing 12102. Since the convincing tool 12100 grabs the inner sleeve 10100 of the yoke manipulator 10098 instead of the outer sleeve 10102, the force does not have to be transferred to the inner sleeve by the spring 10134. This creates a more robust attachment to the yoke 10022 and lessens the chance the connection between the two sleeves may fail.

Figure 89:
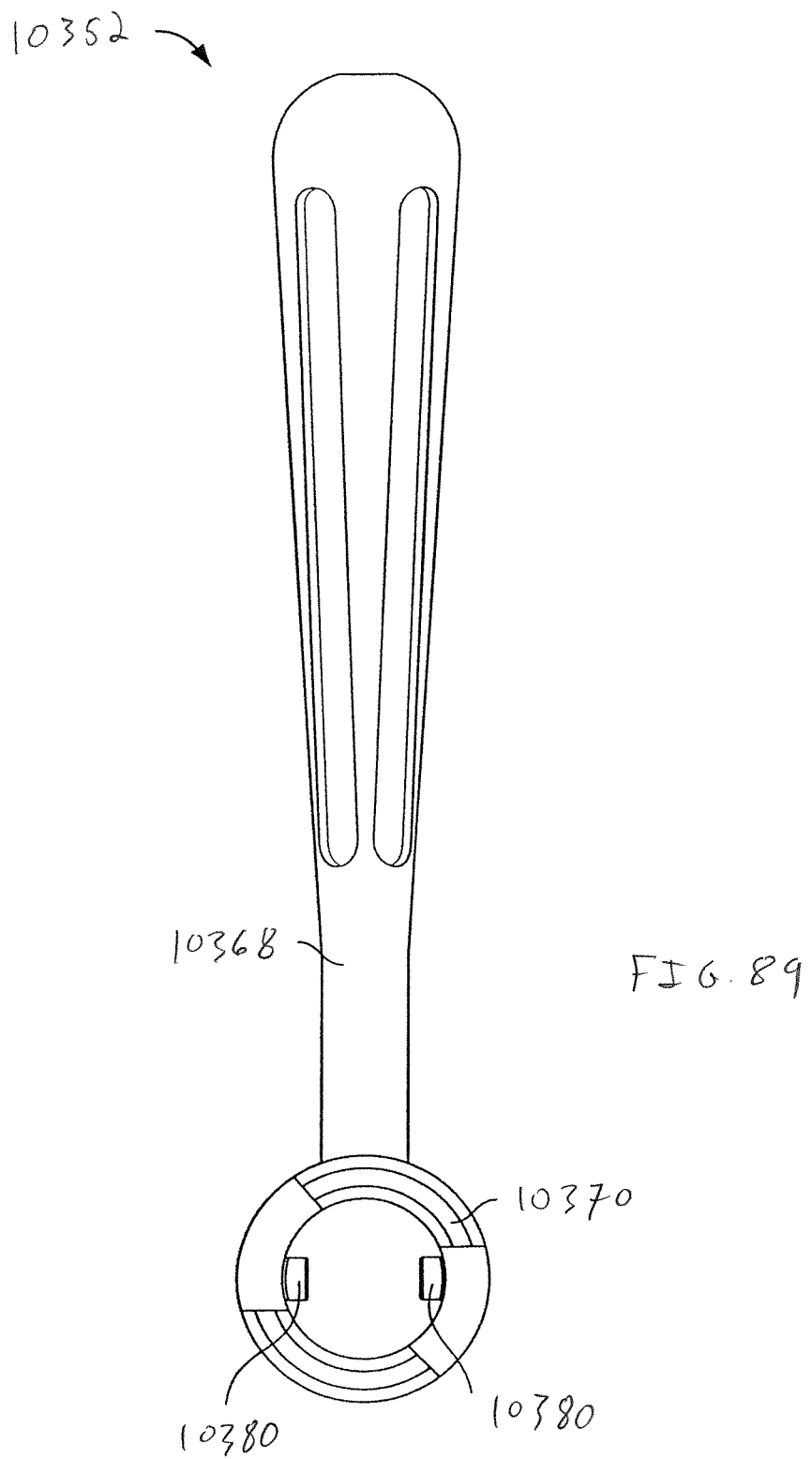
FIG. 89 is a top elevation view of the counter torque tube of FIG. 87, as configured in accordance with the various embodiments of the invention.

The convincer tool 12100 also includes two internal pins 12148 that extend into the tool housing 12102 and are slid down corresponding structure on the yoke manipulator 10098 to keep the two tools aligned. The internal pins 12148 are similar to those located in the counter torque tube 10352, as shown in FIG. 89. Proper tool alignment may assists with correct positioning of the cap 10024 relative to the yoke 10022 and misalignment of the cap 10024 may prevent it from seating within the yoke 10022. In addition, the convincer 12100 includes a side tube 12101 to be used for compression or distraction as discussed later.

Figure 100A:
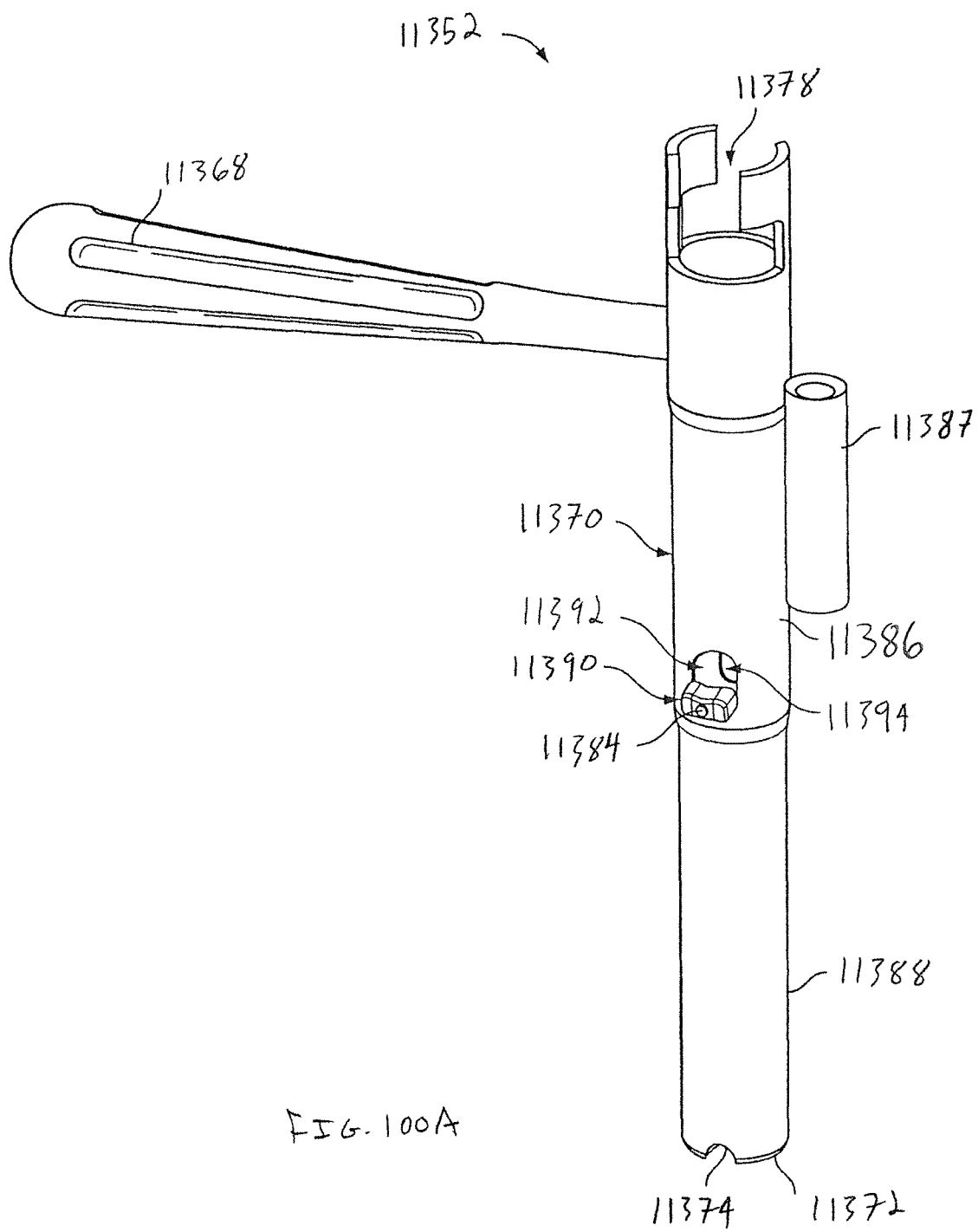
FIG. 100A is a perspective view of an alternative counter torque tube having a fulcrum and an opening for use in seating the connecting member.
Figure 100B:
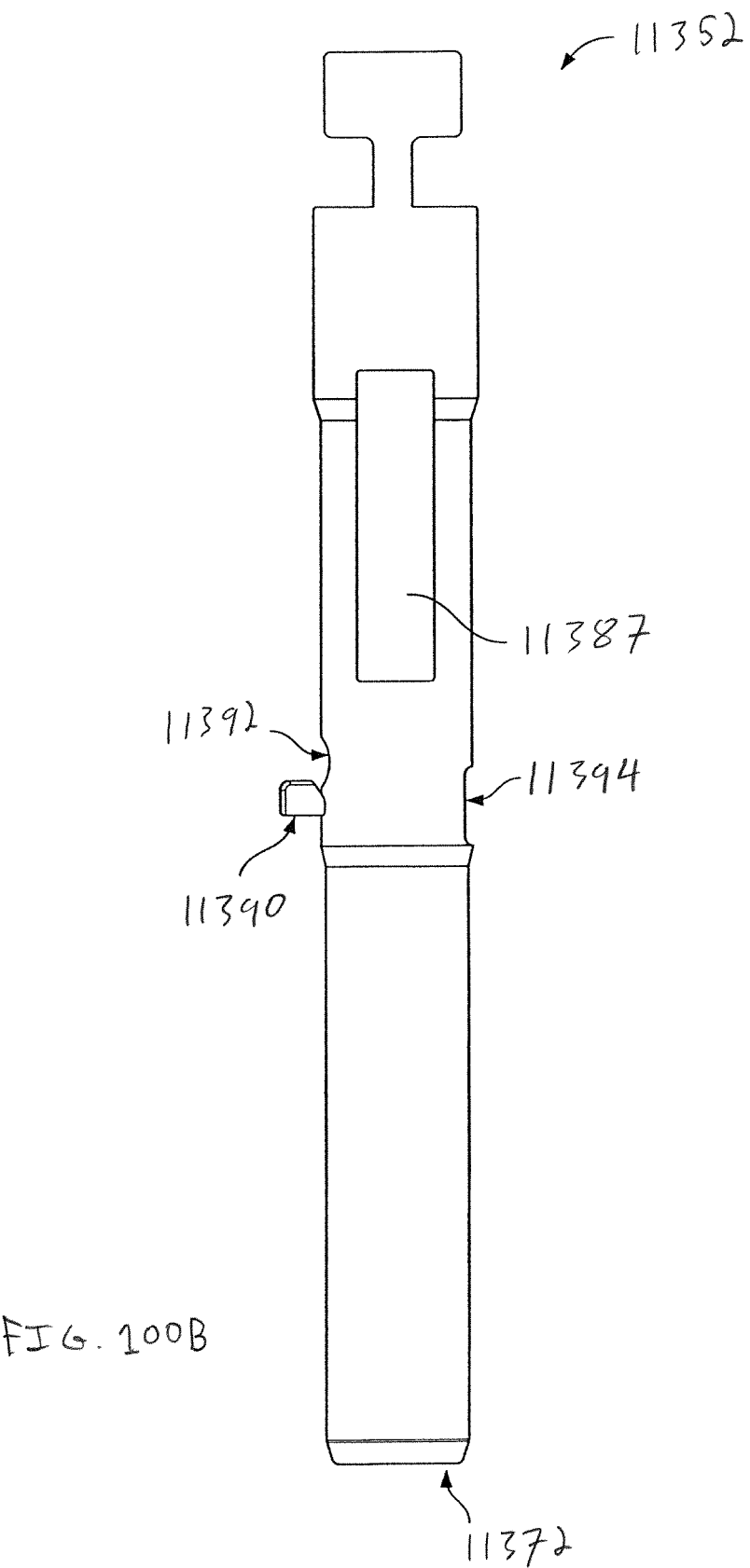
FIG. 100B is a side elevation view of the alternative counter torque tube of FIG. 100A.
Figure 100C:
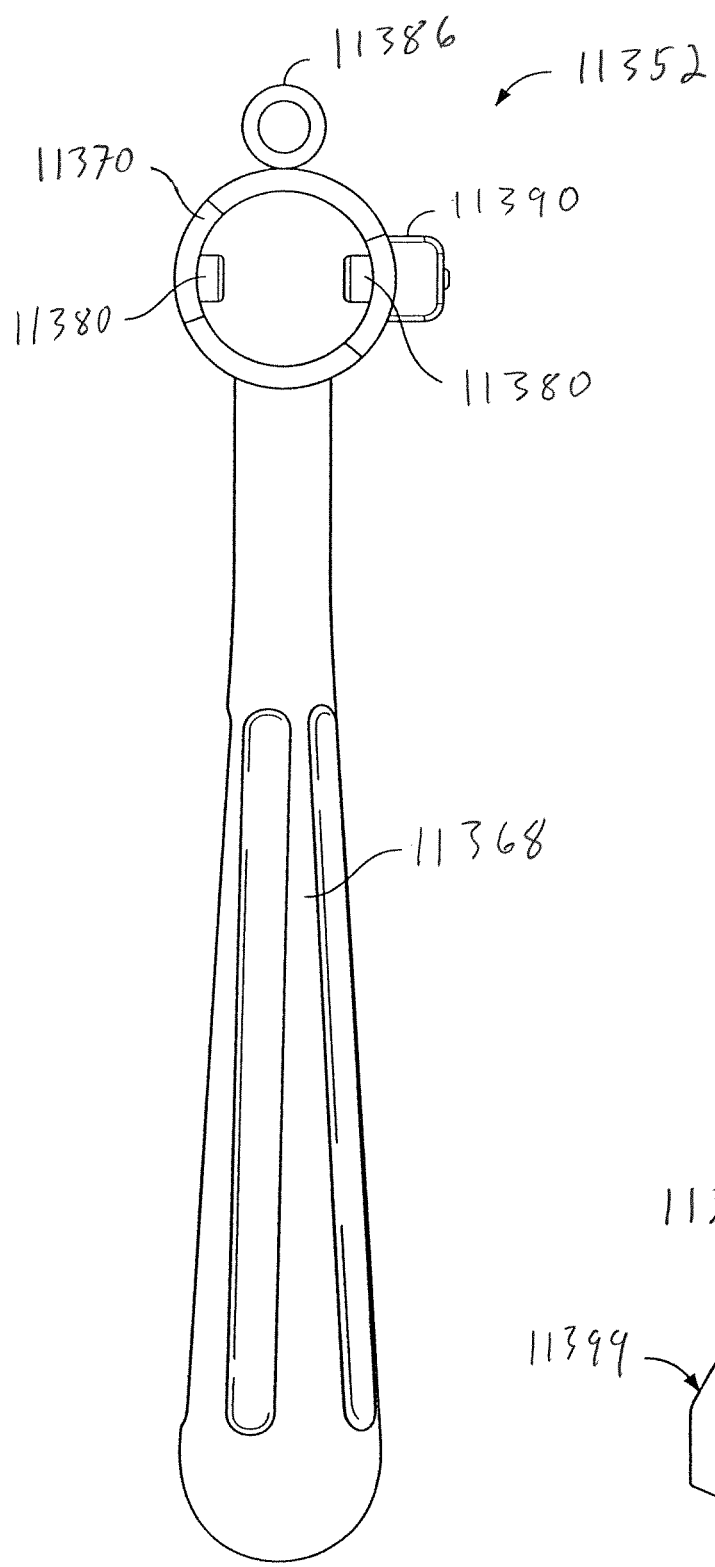
FIG. 100C is a top plan view of the alternative counter torque tube of FIG. 100A.
Figure 100D:
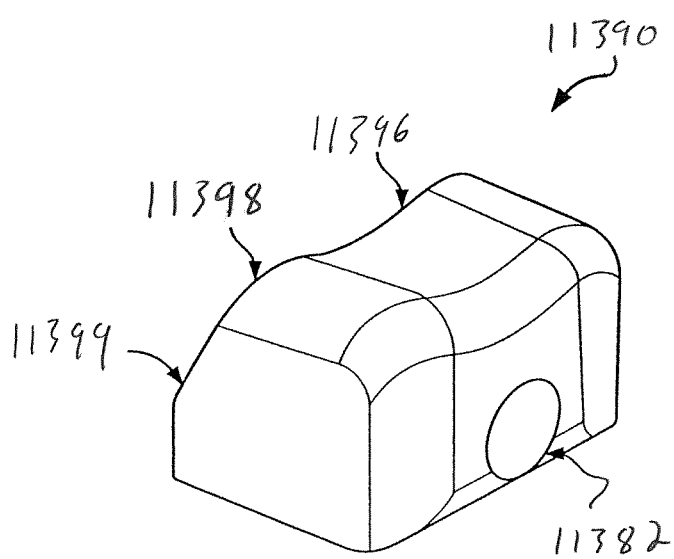
FIG. 100D is a perspective view of a fulcrum portion of the counter torque tube of FIG. 51A.

Another alternative tool is the counter torque tube 11352 as shown in FIGS. 100A and 100B. Similar to counter torque tube 10352, the counter torque tube 11352 is positioned around the yoke manipulator 10098 and includes a handle 11368 and a body 11370. However, the counter torque tube 11352 is slightly longer than tube 10352. The body 11370 has a larger diameter portion 11386 and a smaller diameter portion 11388. The smaller diameter portion 11388 is the lower portion of the tube 11352 and is the portion that is inserted into the wound. The smaller diameter portion 11388 extends to a tapered end 11372 that has curved cutouts 11374. The curved cutouts 11374 are sized so snugly engage the connecting member 10026. In addition, the counter torque tube 11352 may include cutouts (not shown) to provide clearance from the various spinal structures. The counter torque tube 11352 also has connecting structure 11378 that limits the movement of the final locker 11350, however, unlike connecting structure 11378 of tube 11352, the connecting structure 11378 allows for more rotation of the final locker 11350 and therefore allows the surgeon to fully lock the closure cap 10024. A pair of dowel pins 11380 also extends into the center of the counter torque tube 11352 and may be used to mate the counter torque tube 11352 with the yoke manipulator 10098. The counter torque tube 11352 may also have a side tubes 11387 that allow the tool to be mated with the compression-distraction tool 11330 discussed below.

In one embodiment, the counter torque tube 11352 includes a fulcrum 11390 in the larger diameter portion 11386 just below an opening 11392. After the counter torque tube 11352 is seated atop the connecting member 10026, a lever 11400, discussed in greater detail below, may be inserted through the opening 11392 and may engage the long slot 10114 on the yoke manipulator 10098. Then, the lever 10400 can be rotated around the fulcrum 10390 to move the long slot 10114 and thus, the yoke manipulator 10098, upwards. By pulling upwards on the yoke manipulator 10098, the yoke 10022 is pulled upward while the connecting member 10026 is being pushed downward by the tapered end 11372 of the counter torque tube 11352 helps seat the connecting member 10026 and may be useful if the surgeon encounters soft tissue that prevents the member 10026 from seating in the yokes 10022.

The fulcrum 11390 includes middle indentation 11396 having geometry to guide the lever 11400 to the opening 11392. The fulcrum 11390 has a sloped portion 11398 on the side adjacent the counter torque tube 11352. The opening 11392 of the counter torque tube 11352 is located slightly lower than upper surface of the fulcrum. Thus, a shoulder or ledge 11399 is created on the fulcrum 11390 since the opening 11392 extends below the upper surface of the fulcrum. The ledge 11399 allows the lever 11400 to pivot above the bottom of the opening 11392 and this positioning allows the surgeon to provide more force to reduce the connecting member 10026 into the yoke 10022. In addition, the fulcrum 11390 includes a through opening 11382 which may accommodate a pin 11384 that attaches the fulcrum 11390 to the body 11370 of the counter torque tube 11352.

The counter torque tube 11352 further includes an opening 11394 located opposing opening 11392 and fulcrum 11390. The opening 11394 may accommodate the fulcrum 11390 of an adjacent counter torque tube 11352. Thus, the opening 11394 is slightly lower relative to opening 11392 to accept the fulcrum 11390, which sits below opening 11392 of an adjacent tube 11352. In one preferred embodiment, the surgeon will employ one counter torque tube 11352 for each bone anchor 10020 implanted into the patient. If the connecting member 10026 is relatively short and the compression-distraction tool 11330 is used to shorten the distance between the bone anchors 10020, the fulcrum 11390 may abut adjacent counter torque tubes 11352. Thus, by adding an opening 11394, one counter torque tube 11352 has clearance for an adjacent tube 11352. Thus, the opening 11394 allows the compression-distraction tool 11330 to be used to adjust the bone anchors 10020 more closely to one another with interference of the fulcrum with the body 11370.

Once the counter torque tube 11352 and the lever 11400 are used to seat the connecting member 10026, the tools can remain in position while the closure cap 10024 is seated. Since the counter torque tube 11352 allows the surgeon to overcome the soft tissue positioned around the implant, the counter torque tube 11352 should not be removed from the system until after the connecting member 10026 and closure cap 10024 have been secured into position.

Figure 101:
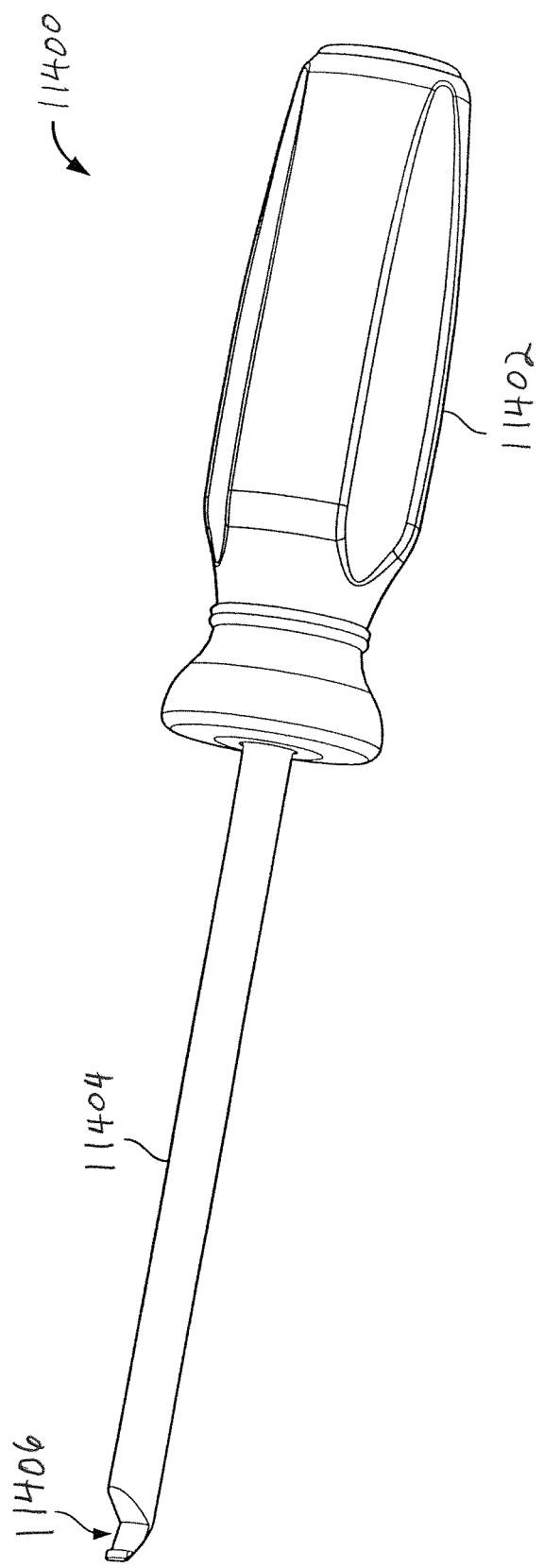
FIG. 101 is a perspective view of a lever for use with the counter torque tube of FIG. 51A to use with the fulcrum to seat the connecting member.

As shown in FIG. 101, the lever 11400 has a handle 11402 with a rod 11404 attached thereto. The rod 11404 had a hook-shaped end 11406 that is able to pass through the opening 11392 of the counter torque tube 11352 to engage the yoke manipulator 10098. The hook-shaped end 11406 is sized with a tapered geometry such that the tip fits easily within the opening 11392. In one preferred embodiment, the closure cap 10024 will be inserted through the yoke manipulator 10098 and then the lever 11400 will be employed such that the portion of the lever 11400 that extends into the central opening of the yoke manipulator 10098 will not interfere with the delivery of the closure cap 10024.

Figure 102:
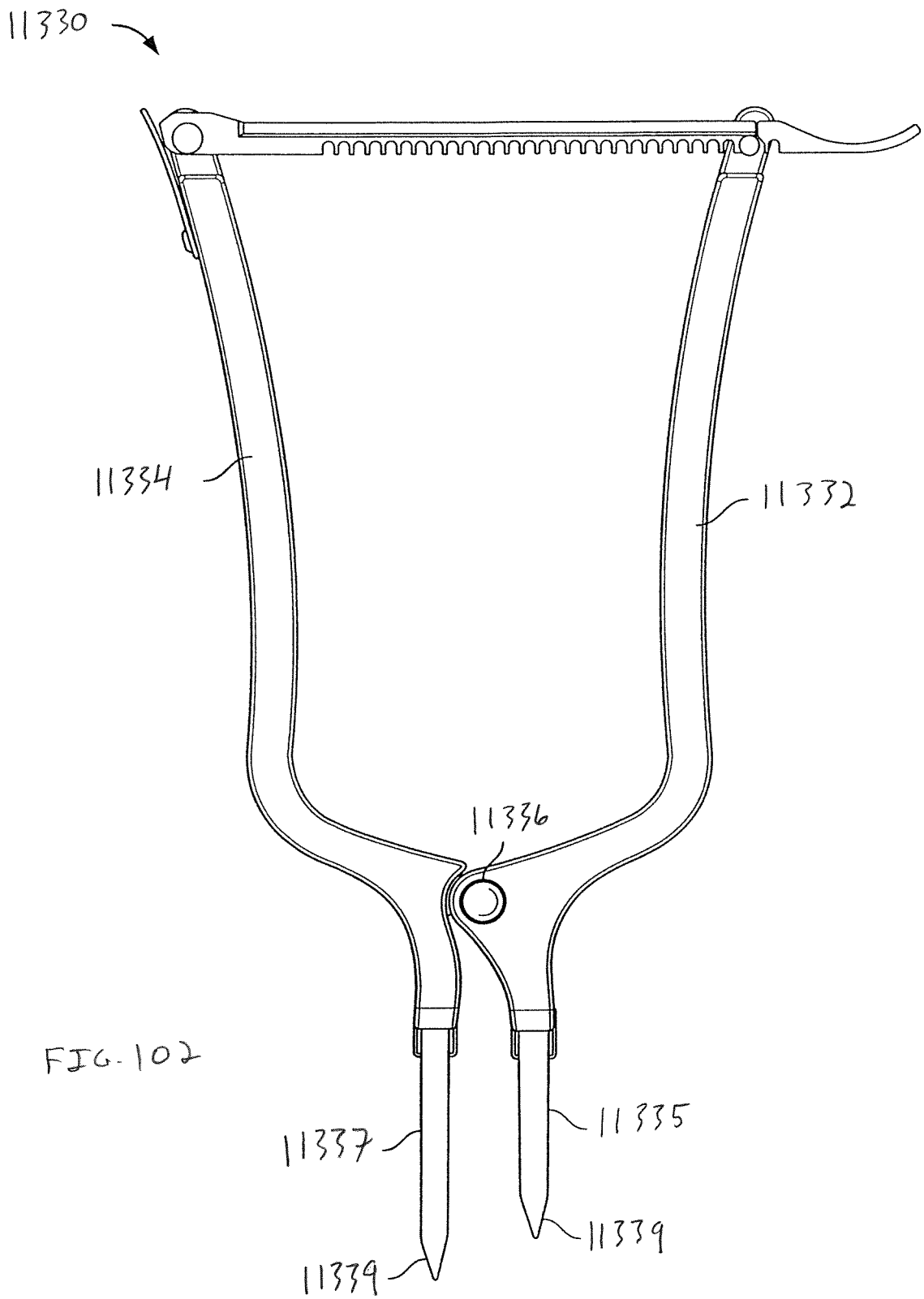
FIG. 102 is a front elevation view of an alternative compression-distraction tool for use in adjusting the distance between vertebrae.

As discussed above, the surgeon can compress or distract the position of the bone anchors 10020 to adjust the distance between the vertebrae. The compressor-distraction tool 11330, similar to tool 10330, includes two handles 11332 and 11334 connected together by pivot pin 11336. As shown in FIG. 102, the arms or handles 11332, 11334 are slightly longer than those of tool 10330. The longer handles 11332, 11334 provide additional mechanical advantage. Instead of engagement arms 10338 as employed by the tool 10330 shown in FIG. 85, the handles 11332, 11334 attach to pins 11335, 11337. The arms 10338 engaged flats located on the various MIS tools while the pins 11335, 11337 engage sleeves on the sides of the various MIS tools. The pin 11335 is slightly shorter than the pin 11337 to accommodate their insertion into openings one at a time. The pins 11335, 11337 further include tapered tips 11339 also provide for easier insertion. Since in one preferred embodiment, the connecting members 10026 are pre-bent to a radius of 7 inches, the center pivot point of the tool 11330 is 7 inches away from the connecting member 10026 to avoid a binding effect. The compression-distraction tool 11330 may be used with the convincing tool 12100 and the counter torque tube 11352.

Another tool a surgeon may desire to incorporate into the MIS procedure is the tissue dilation tool disclosed in U.S. Provisional Patent Application No. 60/813,628 filed on Aug. 22, 2006 and hereby incorporated by reference. Such a tool may be employed to stretch the tissue around an initial incision. This way a smaller incision can be maximized to accommodate larger various tooling and implants without requiring a larger incision by stretching the tissue.

In addition to the minimally invasive surgical procedure described herein, many of the described tools are used in a procedure that may require the surgeon to increase the size of the opening into the patient beyond what is normally considered a minimally invasive procedure. While the MIS system uses a stab wound opening to insert each bone anchor 10020 and closure caps 10024 and also uses one of those openings to insert the connecting member 10026, the mini-open procedure has an opening that extends the distance between where the bone anchors 10020 are seated. During a typical MIS procedure, a relatively small incision is made at the surgical side through which the pedicle screw assemblies 10021 and connecting member 10026 are advanced. A confined guideway created by the incision allows that delivery of the implant with the view of the implant site being obstructed. The mini-open procedure preferably uses a retractor to stretch the wound to accommodate various tools. While MIS system is the least invasive procedure, the full open procedure can be the most invasive and requires that the wound be sized large enough to accommodate the procedure without relying on the tissue dilators or retractors. Since the mini-open procedure provides the surgeon less space to operate than the full open, the tools are configured to avoid having to fully open the surgical wound. Such a slit opening in a mini-open surgery may be used based on the patient's anatomy or surgeon preferences.

Figure 103A:
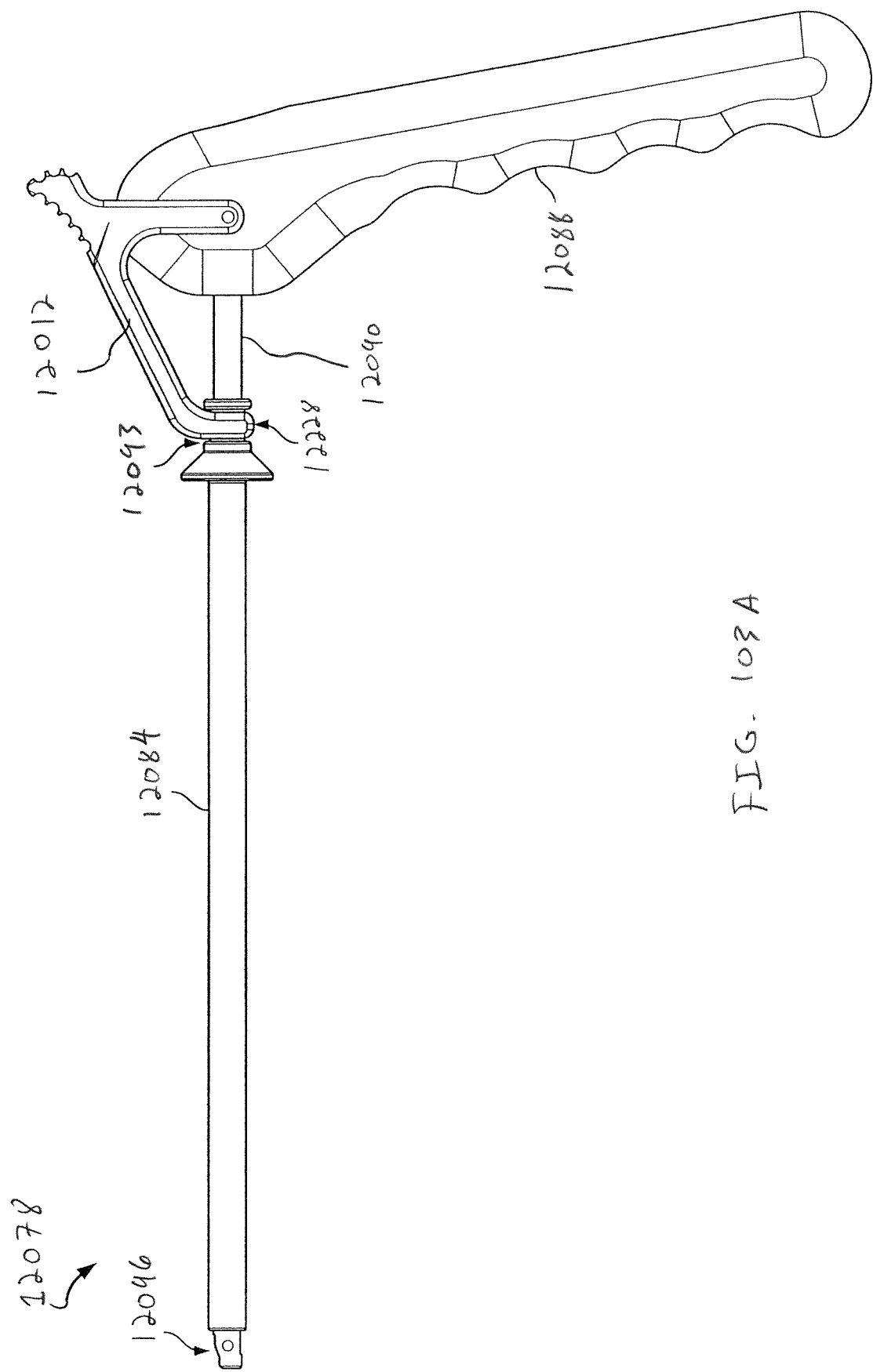
FIG. 103A is a side elevation view of an alternative rod inserter for use in a minimally open procedure to position the spinal rod within the pedicle screw assemblies.

In a mini-open procedure, a rod inserter 12078 may be used to seat the connecting member 10026 as illustrated in FIG. 103A. Unlike the rod inserters 10178 and 11078, the connecting member 10026 can only be configured two ways relative to the inserter 12078: secured such that the connecting member is approximately 100° relative to the inner shaft 12090 and disengaged such that the rod inserter 12078 may be removed from the surgical site after rod insertion. The attachment end 12096 is configured to secure the member 10026 approximately 90-100° relative to the shaft 12090 and locking sleeve 12094 such that the tip 10180 of the connecting member 10026 is slightly lower than the attachment end 10184 during the insertion procedure. The attachment end 12096 is also configured to either secure the member 10026 to the inserter 12078 or to release the member 10026, unlike inserters 10178 and 11078 that have an articulating position such that the member 10026 may rotate relative to the inserters 10178, 11078.

As shown in FIG. 103A-103C, the rod inserter 12078 includes a handle 12088, a latch 12102, inner shaft 12090, and a locking sleeve 12084. However, instead of a shift assembly the locking sleeve 12084 has a connecting structure 12093 that engages the latch 12102. The rod inserter 12078 having only two relative positions does not require a mechanism to shift the tool from a variety of configurations. The inner shaft 12090 includes an attachment end 12096 having two prongs 12105. The prongs 12105 have connecting pins 12103 that can mate with corresponding structures on the connecting member 10026 to secure the two relative to each other. The latch 12102 includes a stopper 12228 with a u-shaped portion 12230. When the latch 12102 is in the safety position as described above, the u-shaped portion engages a recess 12084a located on the locking sleeve 12084. The recess 12084a has two raised portions 12084b on either side. The locking sleeve 12084 also includes an expanded portion 12084c that may be easily engaged by the fore finger and middle finger. After the connecting member 10026 has been positioned between the yokes 10022, a finger portion 12226 of the latch 12102 may be engaged to shift the latch 12102 to the disengaged position. Then, the expanded portion 12084c of the locking sleeve 12084 may be engaged to pull the locking sleeve 12084 back and allow the attachment end 12096 to disengage from the connecting member 10026.

Figure 104:
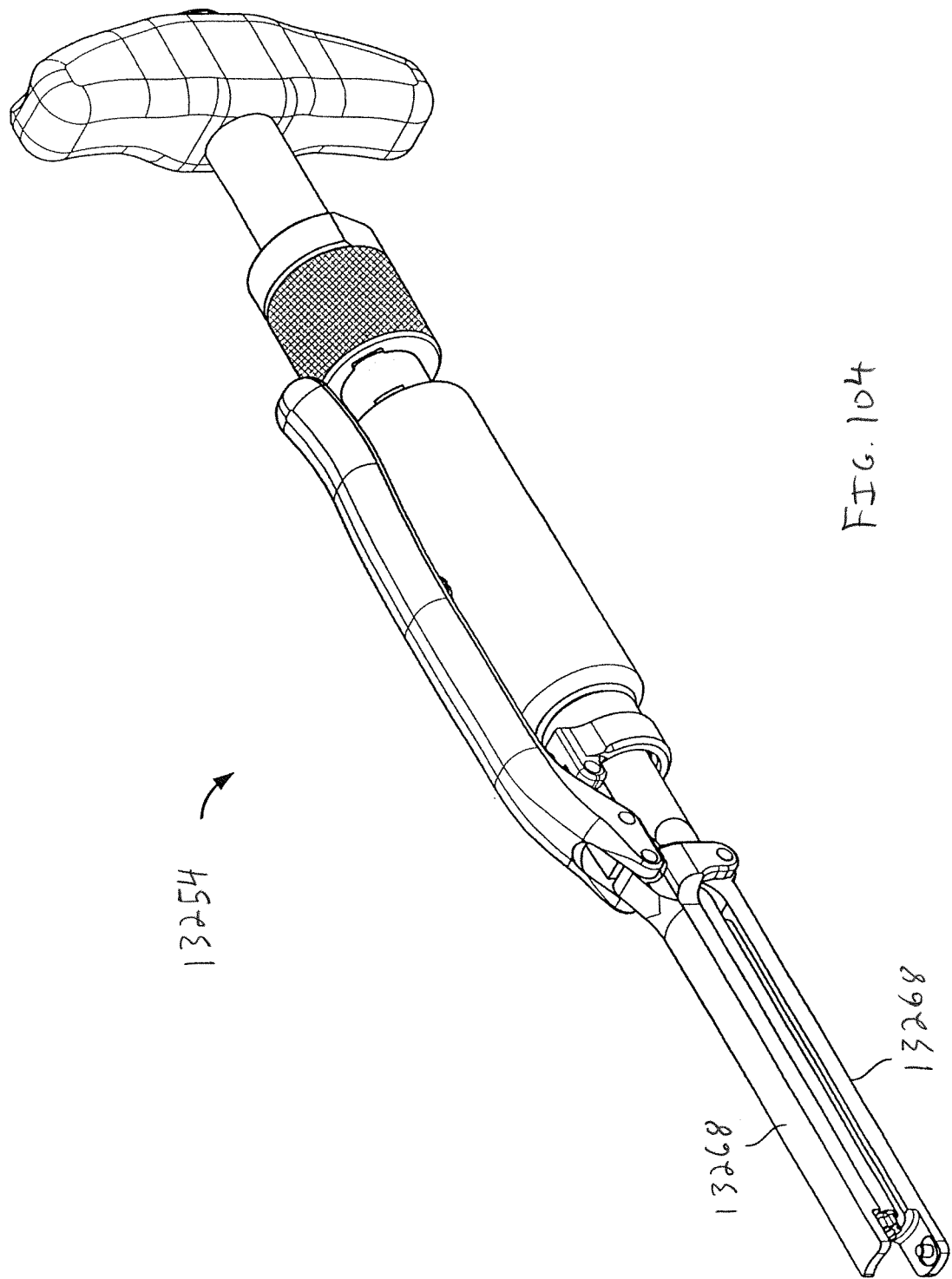
FIG. 104 is a perspective view of an alternative rod persuader for use in urging the spinal rod into the yoke and for securing the cap to the yoke.

For the mini-open procedure, a rod persuader 10254 similar to the persuader tool disclosed in U.S. Provisional Patent Application No. 60/889,494, filed on Feb. 12, 2007 and U.S. patent application Ser. No. 10/973,659, filed Oct. 26, 2004, both of which are herein incorporated by reference, may be used to insert the closure cap 10024 and seat the connecting member 10026 sufficiently in the yokes 10022. FIG. 104 illustrates an example of such a rod persuader. However, in one preferred embodiment, the jaw arms or prongs 13268 are longer to accommodate delivery of the closure cap 10024 to the yoke 10022 in a mini-open procedure. The longer arms 13268 allow for more clearance with the retractor that is often used in mini-open procedures.

Figure 105A:
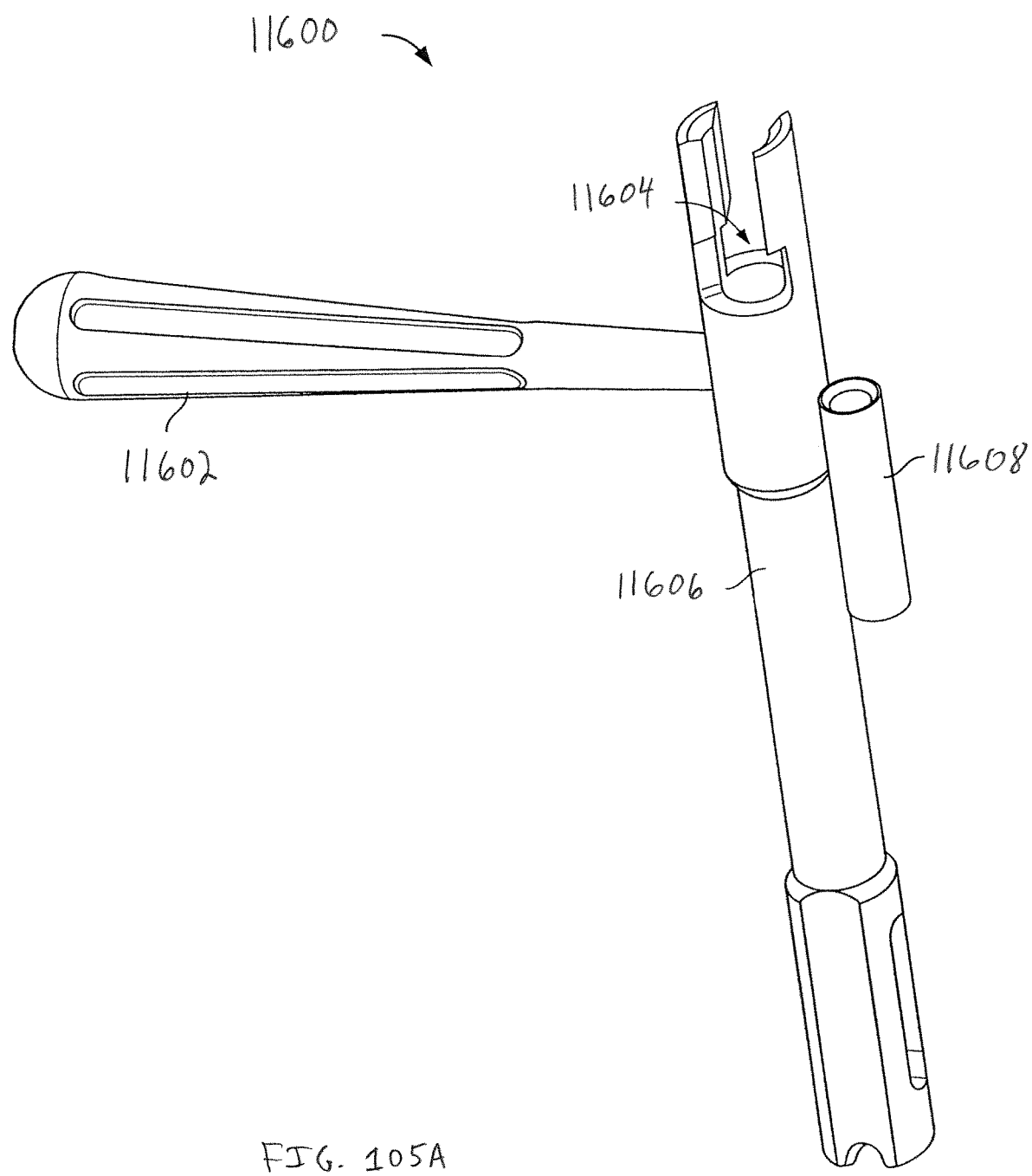
FIG. 105A is a perspective view of a stabilization tube for use during insertion of the cap.

Another tool that may be used in a mini-open procedure is the stabilization tube 11600, as shown in FIGS. 105A and 105B. The stabilization tool 11600, like the counter torque tube 11352, may include a handle 11602, connecting structure 11604, a shaft 11606 and a side tube 11608 to mate with the compression-distraction tool 11330. However, the stabilization tool 11600 is narrower than the counter torque tube because in the mini-open procedure, the yoke manipulator 10098 is not employed or has been removed at this stage. Since the opening spans the distance between the bone anchors 10020, the surgeon does not have to struggle with soft tissue that might prevent the connecting member 10026 from seating within the yokes 10022. Thus, the stabilization tube 11600 is employed to retain the yoke 10022. To retain the yoke 10022, the inner geometry of the stabilization tube 11600 includes flats 11610 that retain two sides of the yoke 10022. In addition, it is contemplated that the inner geometry 11612 will include structure corresponding to the cross-section of the closure cap 10024 so that the cap 10024 is properly oriented during delivered into the yoke 10022. However, such inner geometry may not be necessary depending on what tools are used to deliver the closure cap 10024 into the yoke 10022.

While there have herein been illustrated and described with respect to specific examples, including presently preferred modes of carrying out the invention, those skilled in the art will appreciate that there are numerous variations and permutations of the above-described apparatus that fall within the scope and spirit of the invention as set forth in the appended claims. Further, those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept.

What is claimed is:

1. A method of inserting a spinal rod into yokes of first and second pedicle screw assemblies that have been anchored to bones, the method comprising:
   pivotally connecting a spinal rod and a distal end portion of a spinal rod inserter;
   advancing a distal end portion of the spinal rod through an entrance opening of a first yoke manipulator associated with the first pedicle screw assembly, into an interior space of the first yoke manipulator, and through an exit opening of the first yoke manipulator while maintaining the spinal rod inserter distal end portion outside of the first yoke manipulator;
   advancing the spinal rod distal end portion from a space between the first yoke manipulator and a second yoke manipulator toward the second yoke manipulator and through at least an entrance opening of the second yoke manipulator, the second yoke manipulator associated with the second pedicle screw assembly;
   pivoting the spinal rod inserter relative to the spinal rod to position the spinal rod in the yoke of the first pedicle screw assembly while the spinal rod extends through the entrance opening of the second yoke manipulator; and
   configuring the distal end portion of the spinal rod inserter to a blocking configuration that inhibits pivoting of the spinal rod inserter relative to the spinal rod,
   wherein advancing the distal end portion of the spinal rod through the entrance opening, into the interior space, and through the exit opening of the first yoke manipulator includes keeping the spinal rod inserter distal end portion in the blocking configuration to inhibit pivoting of the spinal rod inserter.

2. The method of claim 1, wherein advancing the distal end portion of the spinal rod through the entrance opening of the first yoke manipulator includes advancing the distal end portion of the spinal rod while the spinal rod and the spinal rod inserter distal end portion have an orientation relative to one another; and
   wherein pivoting the spinal rod inserter relative to the spinal rod to position the spinal rod in the yoke of the first pedicle screw assembly includes changing the orientation of the spinal rod and the spinal rod inserter distal end portion relative to one another.

3. The method of claim 1, further comprising reconfiguring the distal end portion of the spinal rod inserter from the blocking configuration to a clearance configuration to facilitate pivoting of the spinal rod inserter relative to the spinal rod.

4. The method of claim 1, wherein the spinal rod includes an attachment member and the spinal rod inserter distal end portion includes arm portions; and
   wherein pivotally connecting the spinal rod and the spinal rod inserter comprises engaging a protrusion and an opening of the spinal rod attachment member and the spinal rod inserter arm portions.

5. The method of claim 1, wherein pivotally connecting the spinal rod and the distal end portion of the spinal rod inserter comprises forming a pivot connection therebetween; and wherein advancing the distal end portion of the spinal rod from the space between the first and second yoke manipulators and through at least an entrance opening of the second yoke manipulator comprises positioning the pivot connection between the entrance openings of the first and second yoke manipulators.

6. The method of claim 5, wherein pivoting the spinal rod inserter relative to the spinal rod to position the spinal rod in the yoke of the first pedicle screw assembly comprises moving the pivot connection across the interior space of the first yoke manipulator and through the entrance opening of the first yoke manipulator.

7. The method of claim 1, wherein advancing the distal end portion of the spinal rod through the entrance opening of the first yoke manipulator includes advancing the distal end portion of the spinal rod obliquely downward relative to a longitudinal axis of the first yoke manipulator.

8. The method of claim 1, wherein advancing the spinal rod distal end portion from the space between the first and second yoke manipulators and through at least the entrance opening of the second yoke manipulator includes advancing the spinal rod distal end portion while maintaining the spinal rod inserter distal end portion outside of the first yoke manipulator.

9. The method of claim 1, further comprising inserting the first yoke manipulator through a first incision and inserting the second yoke manipulator through a second incision and the advancing of the spinal rod is performed without requiring another incision other than the first and second incisions.

10. The method of claim 1, further comprising advancing the spinal rod distal end portion along a path outside of the first yoke manipulator to the entrance opening of the first yoke manipulator while keeping the connected spinal rod inserter and the spinal rod mechanically disconnected from the first and second yoke manipulators.

11. A method of inserting a spinal rod into yokes of first and second pedicle screw assemblies that have been anchored to bones, the method comprising:

pivotally connecting a spinal rod and a distal end portion of a spinal rod inserter;

advancing a distal end portion of the spinal rod through an entrance opening of a first yoke manipulator associated with the first pedicle screw assembly, into an interior space of the first yoke manipulator, and through an exit opening of the first yoke manipulator while maintaining the spinal rod inserter distal end portion outside of the first yoke manipulator;

advancing the spinal rod distal end portion from a space between the first yoke manipulator and a second yoke manipulator toward the second yoke manipulator and through at least an entrance opening of the second yoke manipulator, the second yoke manipulator associated with the second pedicle screw assembly; and pivoting the spinal rod inserter relative to the spinal rod to position the spinal rod in the yoke of the first pedicle screw assembly while the spinal rod extends through the entrance opening of the second yoke manipulator, wherein pivotally connecting the spinal rod and the spinal rod inserter comprises:

positioning a reduced thickness attachment member of the spinal rod between arm portions of the spinal rod inserter distal end portion;

shifting a sleeve of the spinal rod inserter and the clamp arms relative to one another to a first configuration wherein the sleeve urges the arm portions together about the spinal rod attachment member; and wherein the sleeve and the arm portions in the first configuration thereof permit the spinal rod to pivot relative to the arm portions.

12. The method of claim 11, further comprising shifting the sleeve and arm portions relative to one another to a second configuration wherein the sleeve extends about the spinal rod and inhibits pivoting of the spinal rod relative to the arm portions.

13. A method of inserting a spinal rod into yokes of first and second pedicle screw assemblies that have been anchored to bones, the method comprising:

positioning an attachment member of a spinal rod between portions of an elongate shaft of a spinal rod inserter;

shifting an inner shaft and an outer sleeve of the elongate shaft of the spinal rod inserter relative to one another to secure the portions of the spinal rod inserter elongate shaft to the spinal rod attachment member;

advancing a distal end portion of the spinal rod through a portion of an entrance opening of a first yoke manipulator associated with the first pedicle screw assembly, into an interior space of the first yoke manipulator, and through a portion of an exit opening of the first yoke manipulator closer to the yoke of the first pedicle screw assembly than the portion of the entrance opening while maintaining the spinal rod inserter outside of the first yoke manipulator;

advancing the distal end portion of the spinal rod from outside of the portion of the exit opening of the first yoke manipulator toward a second yoke manipulator and through at least an entrance opening of the second yoke manipulator, the second yoke manipulator associated with the second pedicle screw assembly; and moving the secured portions of the spinal rod inserter elongate shaft and the attachment member of the spinal rod downward toward the yoke of the first pedicle screw assembly to position the spinal rod in the yoke of the first pedicle screw assembly while the spinal rod extends through the entrance opening of the second yoke manipulator; and locking the outer sleeve and the inner shaft relative to one another and keeping the outer sleeve and the inner shaft locked relative to one another during the advancing the distal end portion of the spinal rod and the moving the secured portions of the spinal rod inserter elongate shaft and the attachment member of the spinal rod.

14. The method of claim 13, wherein shifting the inner shaft and outer sleeve relative to one another to secure the portions of the spinal rod inserter elongate shaft to the spinal rod attachment member includes clamping the spinal rod attachment member between the portions of the spinal rod inserter elongate shaft.

15. The method of claim 13, wherein the portions of the spinal rod inserter elongate shaft include arm portions of the inner shaft; and wherein shifting the inner shaft and outer sleeve relative to one another to secure the portions of the spinal rod inserter elongate shaft to the spinal rod attachment member includes positioning the inner shaft and the outer sleeve in a blocking configuration wherein the outer sleeve extends around a least a portion of the arm portions and inhibits separation of the arm portions from the spinal rod attachment member.

16. The method of claim 15, further comprising shifting the outer sleeve and the inner shaft relative to one another to a clearance configuration wherein the outer sleeve is spaced from the at least a portion of the arm portions to permit the spinal rod to be disconnected from the spinal rod inserter shaft.

17. The method of claim 13, wherein shifting the inner shaft and outer sleeve to secure the portions of the spinal rod inserter shaft and the spinal rod attachment member includes connecting the spinal rod and spinal rod inserter elongate shaft so that the spinal rod and the spinal rod inserter elongate shaft have a first angle relative to one another; and
    wherein advancing the distal end portion of the spinal rod through the entrance opening, interior space, and exit opening of the first yoke manipulator includes keeping the connected spinal rod and spinal rod inserter shaft at the first angle relative to one another.

18. The method of claim 13, wherein the inner shaft and the outer sleeve are straight.

19. The method of claim 13, wherein the portions of the spinal rod inserter elongate shaft include arm portions; and
    wherein shifting the inner shaft and outer sleeve relative to one another to secure the portions of the spinal rod inserter elongate shaft to the spinal rod attachment member includes clamping the spinal rod attachment member between the arm portions.

\* \* \* \* \*